(12) United States Patent
Saha et al.

(10) Patent No.: US 7,241,812 B2
(45) Date of Patent: Jul. 10, 2007

(54) METHODS AND COMPOSITIONS FOR MODULATING SPHINGOSINE-1-PHOSPHATE (S1P) RECEPTOR ACTIVITY

(75) Inventors: Ashis K. Saha, Stow, MA (US); Malcolm J. Kavarana, Burlington, MA (US); Ghotas Evindar, Waltham, MA (US); Alexander L. Satz, Needham, MA (US); Barry Morgan, Franklin, MA (US)

(73) Assignee: Praecis Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 11/204,266

(22) Filed: Aug. 12, 2005

(65) Prior Publication Data

US 2006/0135786 A1 Jun. 22, 2006

Related U.S. Application Data

(60) Provisional application No. 60/646,436, filed on Jan. 21, 2005, provisional application No. 60/601,232, filed on Aug. 13, 2004.

(51) Int. Cl.
*A61K 31/167* (2006.01)
(52) U.S. Cl. ............... 514/626; 514/357; 514/438; 546/337; 549/77; 564/194
(58) Field of Classification Search ............ 514/357, 514/438, 626; 546/337; 549/77; 564/194
See application file for complete search history.

(56) References Cited

U.S. PATENT DOCUMENTS

| | | | |
|---|---|---|---|
| 2,406,366 A | 8/1946 | Graef | |
| 2,423,579 A | 7/1947 | Buren | |
| 5,604,229 A | 2/1997 | Fujita et al. | |
| 5,719,176 A | 2/1998 | Fujita et al. | |
| 5,948,820 A | 9/1999 | Fujita et al. | |
| 5,952,316 A | 9/1999 | Fujita et al. | |
| 6,004,565 A | 12/1999 | Chiba et al. | |
| 6,187,821 B1 | 2/2001 | Fujita et al. | |
| 6,214,873 B1 | 4/2001 | Adachi et al. | |
| 6,372,800 B1 | 4/2002 | Fujita et al. | |
| 6,437,165 B1 | 8/2002 | Mandala et al. | |
| 6,969,692 B2 | 11/2005 | Brady et al. | |
| 7,064,217 B2 | 6/2006 | Macdonald et al. | |
| 2002/0042358 A1 | 4/2002 | Spiegel | |
| 2002/0072502 A1 | 6/2002 | Ho | |
| 2002/0137916 A1 | 9/2002 | Loughran et al. | |
| 2003/0027800 A1 | 2/2003 | Miller et al. | |
| 2003/0096022 A1 | 5/2003 | Sabbadini | |
| 2004/0034075 A1 | 2/2004 | Smith et al. | |
| 2004/0048857 A1 | 3/2004 | Pan et al. | |
| 2004/0122236 A1 | 6/2004 | Lynch et al. | |
| 2004/0254222 A1 | 12/2004 | Kohno et al. | |
| 2005/0222422 A1 | 10/2005 | Lynch et al. | |
| 2006/0166940 A1 | 7/2006 | Buehimayer et al. | |

FOREIGN PATENT DOCUMENTS

| | | |
|---|---|---|
| EP | 1602660 A1 | 12/2005 |
| WO | WO 9848794 A1 * | 11/1998 |
| WO | WO-02/18395 A1 | 3/2002 |
| WO | WO-02/29001 A2 | 4/2002 |
| WO | WO-02/064616 A2 | 8/2002 |
| WO | WO-02/076995 A2 | 10/2002 |
| WO | WO-03/029205 A1 | 4/2003 |
| WO | WO-03/061567 A2 | 7/2003 |
| WO | WO-03/062252 A1 | 7/2003 |
| WO | WO-03/097028 A1 | 11/2003 |
| WO | WO-2004/010949 A2 | 2/2004 |
| WO | WO-2004/010987 A2 | 2/2004 |
| WO | WO-2004/024673 A1 | 3/2004 |
| WO | WO-2004/026817 A1 | 4/2004 |
| WO | WO-2004/058149 A2 | 7/2004 |
| WO | WO-2004/061107 A1 | 7/2004 |
| WO | WO-2004/096752 A1 | 11/2004 |
| WO | WO-2004/096757 A1 | 11/2004 |
| WO | WO-2004/103279 A2 | 12/2004 |
| WO | WO-2004/110979 A2 | 12/2004 |
| WO | WO-2005/000833 A1 | 1/2005 |
| WO | WO-2005/041899 A2 | 5/2005 |
| WO | WO-2005/054215 A1 | 6/2005 |
| WO | WO-2005/085179 A1 | 9/2005 |
| WO | WO-2005/115150 A2 | 12/2005 |
| WO | WO-2005/118523 A1 | 12/2005 |
| WO | WO-2006/009092 A1 | 1/2006 |
| WO | WO-2006/010379 A1 | 2/2006 |
| WO | WO-2006/010544 A2 | 2/2006 |
| WO | WO-2006/047195 A2 | 5/2006 |
| WO | WO-2006/052723 A2 | 5/2006 |
| WO | WO-2006/058316 A1 | 6/2006 |
| WO | WO-2006/063033 A2 | 6/2006 |
| WO | WO-2006/064757 A1 | 6/2006 |

OTHER PUBLICATIONS

Albert, Rainer et al, "Novel Immunomodulator FTY720 Is Phosphorylated in Rats and Humans to Form a Single Stereoisomer. Identification, Chemical Proof, and Biological Characterization of the Biologically Active Species and Its Enantiomer," *J. Med. Chem.*, vol. 48:5373-5377 (2005).

(Continued)

*Primary Examiner*—Kamal A. Saeed
*Assistant Examiner*—Joseph R. Kosack
(74) *Attorney, Agent, or Firm*—Lahive & Cockfield, LLP; Giulio A. DeConti; Maria Laccotripe Zacharakis

(57) ABSTRACT

The present invention relates to compounds which modulate the activity of the S1P1 receptor, the use of these compounds for treating conditions associated with signaling through the S1P1 receptor, and pharmaceutical compositions comprising these compounds.

22 Claims, 1 Drawing Sheet

OTHER PUBLICATIONS

An, Songzhu, "Molecular Identification and Characterization of G Protein-Coupled Receptors for Lysophosphatidic Acid and Sphingosine 1-Phosphate," *Annals New York Academy of Sciences*, vol. 95:25-33 (2000).

Bai, Yalai et al, "L-Selectin-Dependent Lymphoid Occupancy Is Required to Induce Alloantigen-Specific Tolerance," *The Journal of Immunology*, vol. 168:1579-1589 (2002).

Bandhuvula, Padmavathi et al, "The Immune Modulator FTY720 Inhibits Sphingosine-1-phosphate Lyase Activity," *The Journal of Biological Chemistry*, vol. 280(40):33697-33700 (2005).

Baudhuin, Linnea M. et al, "Akt Activation Induced by Lysophosphatidic Acid and Sphingosine-1-phosphate Requires Both Mitogen-Activated Protein Kinase Kinase and p38 Mitogen-Activated Protein Kinase and Is Cell-Line Specific," *Molecular Pharmacology*, vol. 62(3):660-671 (2002).

Billich, Andreas et al, "Phosphorylation of the Immunomodulatory Drug FTY720 by Sphingosine Kinases," *The Journal of Biological Chemistry*, vol. 278(48):47408-47415 (2003).

Böhler, T. et al, "FTY 720Amediates reduction of lymphocyte counts in human renal allograft recipients by an apoptosis-independent mechanism," *Transpl. Int.*, vol. 13(Suppl. 1):S311-S313 (2000).

Brinkmann, Volker et al, "Pulmonary and vascular pharmacology of sphingosine 1-phosphate," *Current Opinion in Pharmacology*, vol. 6:244-250 (2006).

Brinkmann, Volker et al, "The Immune Modulator FTY720 Targets Sphingosine 1-Phosphate Receptors," *The Journal of Biological Chemistry*, vol. 277(24):21453-21457 (2002).

Brown, Michael S. et al, "A proteolytic pathway that controls the cholesterol content of membranes, cells, and blood," *Proc. Natl. Acad. Sci. USA*, vol. 96:11041-11048 (1999).

Budde, Klemens et al, "First Human Trial of FTY720, a Novel Immunomodulator, in Stable Renal Transplant Patients," *J. Am. Soc. Nephrol.*, vol. 13:1073-1083 (2002).

Budde, Klemens et al, "Pharmacodynamics of Single Doses of the Novel Immunosuppressant FTY720 in Stable Renal Transplant Patients," *American Transplantation*, vol. 3:846-854 (2003).

Chiba, K. et al, "Immunosuppressive Activity of FTY720, Sphingosine 1-Phosphate Receptor Agonist: I. Prevention of Allograft Rejection in Rats and Dogs by FTY720 and FTY720-Phosphate," *Transplantation Proceedings*, vol. 37:102-106 (2005).

Chiba, Kenji et al, "FTY720, a Novel Immunosuppressant Induces Sequestration of Circulating Mature Lymphocytes by Acceleration of Lymphocyte Homing in Rats. I. FTY720 Selectively Decreases the Number of Circulating Mature Lymphocytes by Acceleration of Lymphocyte Homing," *The Journal of Immunology*, vol. 160:5037-5044 (1998).

Chua, Chee-Wai et al, "FTY720, a fungus metabolite, inhibits in vivo growth by androgen-independent prostate cancer," *Int. J. Cancer*, vol. 117:1039-1048 (2005).

Chueh, Shih-Chieh J. et al, "Update on FTY720: review of mechanisms and clinical results," *Current Opinion in Organ Transplantation*, vol. 8:288-298 (2003).

Chun, Jerold et al, "International Union of Pharmacology. XXXIV. Lysophospholipid Receptor Nomenclature," *Pharmacological Reviews*, vol. 54(2):265-269 (2002).

Chun, Jerold et al, "Lysophospholipid Receptors as Potential Drug Targets in Tissue Transplantation and Autoimmune Diseases," *Current Pharmaceutical Design*, vol. 12:161-171 (2006).

Clemens, Jeremy J. et al, "Synthesis of *Para*-Alkyl Aryl Amide Analogues of Sphingosine-1-phosphate: Discovery of Potent S1P Receptor Agonists," *Bioorganic & Medicinal Chemistry Letters*, vol. 13:3401-3404 (2003).

De Jonghe, Steven et al, "Structure-Activity Relationship of Short-Chain Sphingoid Bases as Inhibitors of Sphingosine Kinase," *Bioorganic & Medicinal Chemistry Letters*, vol. 9:3175-3180 (1999).

*Drugs of the Future*, "FTY-720," vol. 27(5):501-506 (2002).

Dumont, Francis J., "Fingolimod Mitsubishi Pharma/Novartis," *IDrugs*, vol. 8(3):236-253 (2005).

Ettmayer, Peter et al, "NBD-labeled derivatives of the immunomodulatory drug FTY720 as tools for metabolism and mode of action studies," *Bioorganic & Medicinal Chemistry Letters*, vol. 16:84-87 (2006).

Fang, Xianjun et al, "Lysophospholipid Growth Factors in the Initiation, Progression, Metastases, and Management of Ovarian Cancer," *Annals of New York Academy of Sciences*, vol. 905:188-208 (2000).

Forrest, M. et al, "Immune Cell Regulation and Cardiovascular Effects of Sphingosine 1-Phosphate Receptor Agonists in Rodents Are Mediated via Distinct Receptor Subtypes," *The Journal of Pharmacology and Experimental Therapeutics*, vol. 309(2):758-768 (2004).

Gijsbers, Sofie et al, "1-*O*-Hexadecyl-2-desoxy-2-amino-*sn*-glycerol, a substrate for human sphingosine kinase," *Biochimica et Biophysica Acta*, vol. 1580:1-8 (2002).

Gon, Yasuhiro et al, "S1P3 Receptor-induced reorganization of epithelial tight junctions compromises lung barrier integrity and is potentiated by TNF," *PNAS*, vol. 101(26):9270-9275 (2005).

Graeler, Markus et al, "Cutting Edge: Suppression of T Cell Chemotaxis by Sphingosine 1-Phosphate," *The Journal of Immunology*, vol. 169:4084-4087 (2002).

Graeler, Markus et al, "Activation-regulated expression and chemotactic function of sphingosine 1-phosphate receptors in mouse splenic T cells," *FASEB J.*, vol. 16:1874-1878 (2002).

Graeler, Markus H. et al, "Protein Kinase C ε Dependence of the Recovery from Down-reguation of S1P$_1$ G Protein-coupled Receptors of T Lymphocytes," *The Journal of Biological Chemistry*, vol. 278(30):27737-27741 (2003).

Gräler, Markus H. et al, "The immunosuppressant FTY720 down-regulates sphingosine 1-phosphate G protein-coupled receptors," *The FASEB Journal*, vol. 18(3):551-553 (2004).

Gräler, Markus H. et al, "The Sphingosine 1-Phosphate Receptor S1P$_4$ Regulates Cell Shape and Motility via Coupling to G$_i$ and G$_{12/13}$," *Journal of Cellular Biochemistry*, vol. 89:507-519 (2003).

Hale, Jeffrey J. et al, "Synthesis, Stereochemical determination and biochemical characterization of the enantiometric phosphate esters of the novel immunosuppressive agent FTY720," *Bioorganic & Medicinal Chemistry*, vol. 12:4803-4807 (2004).

He, Jing-Hua et al, "Effect of 2-amino-2-[2-(4-octylphenyl) ethyl] propane-1,3-diol hydrochloride (FTY 720) on immune liver injury in mice," *World of Gastroenterology*, vol. 11(4):573-576 (2005).

Henning, Golo et al, "CC Chemokine Receptor 7-dependent and -independent Pathways for Lymphocyte Homing: Modulation by FTY720," *J. Exp. Med.*, vol. 194(12):1875-1881 (2001).

Hla, Timothy, "Signaling and biological actions of sphingosine 1-phosphate," *Pharmacological Research*, vol. 47:401-407 2003).

Ho, Joanna W.Y. et al, "Effects of novel immunomodulating agent, FTY720, on tumor growth and angiogenesis in hepatocellular carcinoma," *Mol. Cancer Ther.*, vol. 4(9):1430-1438 (2005).

Honig, Shaun M. et al, "FTY720 stimulates multidrug transporter- and cysteinyl leukotriene-dependent T cell chemotaxis to lymph nodes," *The Journal of Clinical Investigation*, vol. 111(5):627-637 (2003).

Igarashi, Junsuke et al, "VEGF induces S1P1 receptors in endothelial cells: Implications for cross talk between sphingolipid and growth factor receptors," *PNAS*, vol. 100(19):10664-10669 (2003).

Inoki, Isao et al, "Negative regulation of endothelial morphogenesis and angiogenesis by S1P$_2$ receptor," *Biochemical and Biophysical Research Communications*, vol. 346:293-300 (2006).

Jin, Yixin et al, "Sphingosine 1-phosphate is a novel inhibitor of T-cell proliferation," *Blood*, vol. 101(12):4909-4915 (2003).

Kaneko, Takashi et al, "Sphingosine-1-phosphate receptor agonists suppress concanavalin A-induced hepatic injury in mice," *Biochemical and Biophysical Research Communications*, vol. 345:85-92 (2006).

Kim, Yong-Mi et al, "Graft versus-host disease can be separated from graft-versus-lymphoma effects by control of lymphocyte trafficking with FTY720," *The Journal of Clinical Investigation*, vol. 111(5):659-669 (2003).

Kimura, Takuya et al, "FTY720 Reduces T-Cells Recruitment Into Murine Intestinal Allograft and Prevents Activation of Graft-Infiltrating Cells," *Transplantation*, vol. 75(9):1469-1474 (2003).
Kiuchi, Masatoshi et al, "Synthesis and Immunosuppressive Activity of 2-Substituted 2-Aminopropane-1,3-diols and 2-Aminoethanols," *J. Med. Chem.*, vol. 43:2946-2961 (2000).
Kiuchi, Masatoshi et al, "Asymmetric synthesis and biological evaluation of the enantiomeric isomers of the immunosuppressive FTY720-phosphate," *Bioorganic & Medicinal Chemistry*, vol. 13:425-432 (2005).
Kohno, Takayuki et al, "Sphingosine 1-phosphate promotes cell migration through the activation of Cdc42 in Edg-6/S1P4-expressing cells," *Genes to Cells*, vol. 8:685-697 (2003).
Kovarik, John M. et al, "Multiple-Dose FTY720: Tolerability, Pharmacokinetics, and Lymphocyte Responses in Healthy Subjects," *J. Clin. Pharmacol.*, vol. 44:532-537 (2004).
Kovarik, J. M. et al, "FTY720 Pharmacokinetics in Mild to Moderate Hepatic Impairment," *J. Clin. Pharmacol.*, vol. 45:446-452 (2005).
Kovarik, John M. et al, "Fingolimod (FTY720) in Severe Hepatic Impairment: Pharmacokinetics and Relationship to Markers of Liver Function," *J. Clin. Pharmacol.*, vol. 46:149-156 (2006).
Kovarik, John M. et al, "Overview of FTY720 Clinical Pharmacokinetics and Pharmacology," *Ther. Drug Monit.*, vol. 26(6):585-587 (2004).
LaMontagne, Kenneth et al, "Antagonism of Sphingosine-1-Phosphate Receptors by FTY720 Inhibits Angiogenesis and Tumor Vascularization," *Cancer Res.*, vol. 66(1):221-231 (2006).
Li, Hongshan et al, "Pharmacokinetics and Cell Trafficking Dynamics of 2-Amino-2-[2-(4-octylphenyl)ethyl]propane-1,3-diol Hydrochloride (FTY720) in Cynomolgus Monkeys after Single Oral and Intravenous Doses," *The Journal of Pharmacology and Experimental Therapeutics*, vol. 301(2):519-526 (2002).
Lim, Hyun-Suk et al, "Synthesis of Sphingosine-1-phosphate Stereoisomers and Analogues and Their Interaction with EDG Receptors," *Bioorganic & Medicinal Chemistry Letters*, vol. 13:237-240 (2003).
Lu, Xuequan et al, "Total Synthesis of Two Photoactivatable Analogues of the Growth-Factor-Like Mediator Sphingosine 1-Phosphate: Differential Interaction with Protein Targets," *J. Org. Chem.*, vol. 68:7046-7050 (2003).
Lynch, Kevin R. et al, "Structure activity relationships of lysophospholipid mediators," *Prostaglandins & other Lipid Mediators*, vol. 64:33-45 (2001).
MacKinnon, Alison C. et al, "Sphingosine Kinase: A Point of Convergence in the Action of Diverse Neutrophil Priming Agents," *The Journal of Immunology*, vol. 169:6394-6400 (2002).
Mandala, Suzanne et al, "Alteration of Lymphocyte Trafficking by Sphingosine-1-Phosphate Receptor Agonists," *Science*, vol. 296:346-349 (2002).
Matloubian, Mehrdad et al, "Lymphocyte egress from thymus and peripheral lymphoid organs is dependent on S1P receptor 1," *Nature*, vol. 427:355-360 (2004).
Matsuda, Satoshi et al, "Differential Activation of c-Jun $NH_2$-Terminal Kinase and p38 Pathways During FTY720-Induced Apoptosis of T Lymphocytes That Is Suppressed by the Extracellular Signal-Regulated Kinase Pathway," *The Journal of Immunology*, vol. 162:3321-3326 (1999).
Meno-Tetang, Guy M.L. et al, "On the Prediction of the Human Response: A Recycled Mechanistic Pharmacokinetic/Pharmacodynamic Approach," *Basic & Clinical Pharmacology & Toxicology*, vol. 96:182-192 (2005).
Meno-Tetang, Guy M.L. et al, "Physiologically-Based Pharmacokinetic (PBPK) Modeling of FTY720 in Rats Following Oral and Intravenous Doses," *American Society for Pharmacology and Experimental Therapeutics*, pp. 1-27 (2006).
Moolenaar, Wouter H., "Development of Our Current Understanding of Bioactive Lysophopholipids," *Annals New York Academy of Sciences*, vol. 905:1-10 (2000).
Moolenaar, Wouter H., "Bioactive Lysophospholipids and Their G Protein-Coupled Receptors," *Experimental Cell Research*, vol. 253:230-238 (1999).

Mulgaonkar, S. et al, "FTY720/Cyclosporine Regimens in De Novo Renal Transplantation: A 1-Year Dose-Finding Study," *American Journal of Transplantation*, vol. 6:1848-1857 (2006).
Müller, Gerd et al, "Role of Homeostatic Chemokine adn Sphingosine-1-Phosphate Receptors in the Organization of Lymphoid Tissue," *Ann. N.Y. Acad. Sci.*, vol. 987:107-116 (2003).
Park, S.I. et al, "Pharmacokinetic/pharmacodynamic relationships of FTY720 in kidney transplant recipients," *Brazilian Journal of Medical and Biological Research*, vol. 38:683-694 (2005).
Paugh, Steven W. et al, "Sphingosine and Its Analog, the Immunosuppressant 2-Amino-2-(2-[4-octylphenyl]ethyl)-1,3-propanediol, Interact with the $CB_1$ Cannabinoid Receptor," *Molecular Pharmacology*, vol. 70(1):41-50 (2006).
Paugh, Steven W. et al, "The immunosuppressant FTY720 in phosphorylated by sphingosine kinase type 2," *FEBS Letters*, vol. 554:189-193 (2003).
Payne, Shawn G. et al, "Sphingosine-1-phosphate: dual messenger functions," *FEBS Letters*, vol. 531:54-57 (2002).
Peng, Xinqi et al, "Protective Effects of Sphingosine 1-Phosphate in Murine Endotoxin-induced Inflammatory Lung Injury," *Am. J. Respir. Crit. Care Med.*, vol. 169:1245-1251 (2004).
Pettus, Benjamin et al, "The sphingosine kinase 1/sphingosine-1-phosphate pathway mediates COX-2 induction and $PGE_2$ production in response to TNF-α," *FASEB J.*, vol. 17:1411-1421 (2003).
Pinschewer, Daniel D. et al, "FTY720 Immunosuppression Impairs Effector T-Cell Peripheral Homing Without Affecting Induction, Expansion, and Memory," *The Journal of Immunology*, vol. 164:5761-5770 (2000).
Pyne, Susan et al, "Sphingosine 1-phosphate signaling mammalian cells," *Biochem. J.*, vol. 349:385-402 (2000).
Quesniaux, Valerie F.J. et al, "The novel immunosuppressant FTY720 induces peripheral lymphodepletion of both T- and B-cells in cynomolgus monkeys when given alone, with Cyclosphorine Neoral® or with RAD," *Transplant Immunology*, vol. 8:177-187 (2000).
Quesniaux, Valerie F.J. et al, "A novel immunosuppressant, FTY720, induces peripheral lymphodepletion of both T- and B cells and immunosuppression in baboons," *Transplant Immunology*, vol. 7:149-157 (1999).
Rosen, Hugh et al, "Sphingosine 1-phosphate pathway therapeutics: a lipid ligand-receptor paradigm," *Current Opinion in Chemical Biology*, vol. 7:461-468 (2003).
Rosen, Hugh et al, "Rapid induction of medullary thymocyte phenotypic maturation and egress inhibition by nanomolar sphingosine 1-phosphate receptor agonist," *PNAS*, vol. 100(19):10907-10912 (2003).
Sanchez, Teresa et al, "Phosphorylation and Action of the Immunomodulator FTY720 Inhibits Vascular Endothelial Cell Growth Factor-induced Vascular Permeability," *The Journal of Biological Chemistry*, vol. 278(47):47281-47290 (2003).
Sanna, M. Germana et al, "Sphingosine 1-PHosphate (S1P) Receptor Subtypes $S1P_1$ and $S1P_3$, Respectively, Regulate Lymphocyte Recirculation and Heart Rate," *The Journal of Biological Chemistry*, vol. 279(14):13839-13848 (2004).
Shiojima, Ichiro et al, "Role of Akt Signaling in Vascular Homeostasis and Angiogenesis," *Circ. Res.*, vol. 90:1243:1250 (2002).
Singer, Irwin I. et al, "Sphingosine-1-Phosphate Agonists Increase Macrophage Homing, Lymphocyte Contacts, and Endothelial Junctional Complex Formation in Murine Lymph Nodes," *The Journal of Immunology*, vol. 175:7151-7161 (2005).
Skerjanec, Andrej et al, "FTY720, a Novel Immunomodulator in de Novo Kidney Transplant Patients: Pharmacokinetics and Exposure-Response Relationship," *J. Clin. Pharmacol.*, vol. 45: 1268-1278 (2005).
Spiegel, Sarah et al, "Sphingosine 1-phosphate signaling: providing cells with a sense of direction," *TRENDS in Cell Biology*, vol. 12(5):236-242 (2002).
Spiegel, S. et al, "Sphingosine 1-phosphate as a therapeutic agent," *Leukemia*, vol. 16:1596-1602 (2002).
Spiegel, Sarah et al, "Sphingosine-1-Phosphate: an Enigmatic Signaling Lipid," *Nature*, vol. 4:397-407 (2003).

Suzuki, Chihiro et al, "Efficacy of Mycophenolic Acid Combined with KRP-203, a Novel Immunomodulator, in a Rat Heart Transplantation Model," *The Journal of Heart and Lung Transplantation*, vol. 25(3):302-309 (2006).

Suzuki, Tomomi et al, "A new immunosuppressant, FTY720, in canine kidney transplantation: effect of single-drug, induction and combination treatments," *Tranpl. Int.*, vol. 17:574-584 (2004).

Takahashi, M. et al, "A Novel Immunomodulator KRP-203 Combined With Cyclosporine Prolonged Graft Survival and Abrogated Transplant Vasculopathy in Rat Heart Allografts," *Transplantation Proceedings*, vol. 37:143-145 (2005).

Takuwa, Yoh et al, "The Edg Family G Protein-Coupled Receptors for Lysophospholipids: Their Signaling Properties and Biological Activities," *J. Biochem.*, vol. 131:767-771 (2002).

Tamama, Kenichi et al, "Sphingosine 1-phosphate signaling in atherosclerosis and vascular biology," *Curr. Opin. Lipidol.*, vol. 13:489-495 (2002).

Tedesco-Silva, Helio et al, "FTY720, A Novel Immunomodulator: Efficacy and Safety Results from the First Phase 2A Study in de novo Renal Transplantation," *Transplantation*, vol. 79(11):1553-1560 (2005).

Tölle, Markus et al, "Immunomodulator FTY720 Induces eNOS-Dependent Arterial Vasodilatation via the Lysophospholipid Receptor $S1P_3$," *Circulation Research*, vol. 96:913-920 2005).

Troncoso, Pablo et al, "Preclinical Evaluation of a New Immunosuppressive Agent, FTY720," *Clinical Biochemistry*, vol. 31(5):369-373 (1998).

Van Brocklyn, James R. et al, "Sphingosine-1-phosphate is a ligand for the G protein-coupled receptor EDG-6," *Blood*, vol. 95:2624-2629 (2000).

Wang, De-an et al, "A Single Amino Acid Determines Lysophospholipid Specificity of the $S1P_1$ (EDG1) and $LPA_1$ (EDG2) Phospholipid Growth Factor Receptors," *The Journal of Biological Chemistry*, vol. 276(52):49213-49220 (2001).

Watterson, Kenneth et al, "Pleiotropic actions of sphingosine-1-phosphate," *Progress in Lipid Research*, (2003).

Watterson, Kenneth R. et al, "Dual Regulation of EDG1/$S1P_1$ Receptor Phosphorylation and Internalization by Protein Kinase C and G-protein-coupled Receptor Kinase 2," *The Journal of Biological Chemistry*, vol. 277(8):5767-5777 (2002).

Xia, Pu et al, "Tumor necrosis factor-α induces adhesion molecule expression through the sphingosine kinase pathway," *Proc. Natl. Acad. Sci. USA*, vol. 95:14196-14201 (1998).

Xie, Jenny H. et al, "Sphingosine-1-Phosphate Receptor Agonism Impairs the Efficiency of the Local Immune Response by Altering Trafficking of Naive and Antigen-Activated CD4[+] T Cells," *The Journal of Immunology*, vol. 170:3662-3670 (2003).

Yanagawa, Yoshiki et al, "FTY720, a Novel Immunosuppressant, Induces Sequestration of Circulating Mature Lymphocytes by Acceleration of Lymphocyte Homing in Rats, II. FTY720 Prolongs Skin Allograft Survival by Decreasing T Cell Infiltration into Grafts But Not Cytokine Production In Vivo," *The Journal of Immunology*, vol. 160:5493-5499 (1998).

Yang, Zandong et al, "The immune modulator FYT720 prevents autoimmune diabetes in nonobese diabetic mice," *Clinical Immunology*, vol. 107:30-35 (2003).

Yasui, Hiroshi et al, "FTY720 Induces Apoptosis in Multiple Myeloma Cells and Overcomes Drug Resistance," *Cancer Res.*, vol. 65(16):7478-7484 (2005).

Zemann, Barbara et al, "Sphingosine kinase type 2 is essential for lymphopenia induced by the immunomodulatory drug FTY720," *Blood*, vol. 107(4):1454-1458 (2006).

McDonald, Robert et al, "Sphingosine kinase inhibitors reduce neointimal hyperplasia through inhibition of p42/p44 MAPK activation and DNA synthesis in the porcine model of arterial injury," In the Proceedings of 4th Annual Conference on Atherosclerosis, Thrombosis and Vascular Biology, Washington DC, 2003; *Atheroscler Thromb Vasc Biol* vol. 23(5):a23 (2003).

International Search Report for Application No. PCT/US2005/028914, dated Nov. 28, 2005.

Brinkmann et al. "The Immune Modulator FTY720 Targets Sphingosine 1-Phosphate Receptors" *J. Biol. Chem.* 2002, 277(24): 21453-21457.

Chi et al. "Cutting Edge: Regulation of T Cell Trafficking and Primary Immune Responses by Sphingosine 1-Phosphate Receptor 1" *J. Immunol.* 2005; 174: 2485-2488.

Chun et al. "Lysophospholipid Receptors as Potential Drug Targets in Tissue Transplantation and Autoimmune Diseases" *Current Pharmaceutical Design* 2006; 12: 161-171.

Goetzl et al. "Sphingosine 1-Phosphate and Its G Protein-Coupled Receptors Constitute a Multifunctional Immunoregulatory System" *J. Cell Biochem.* 2004; 92(6): 1104-1114.

\* cited by examiner

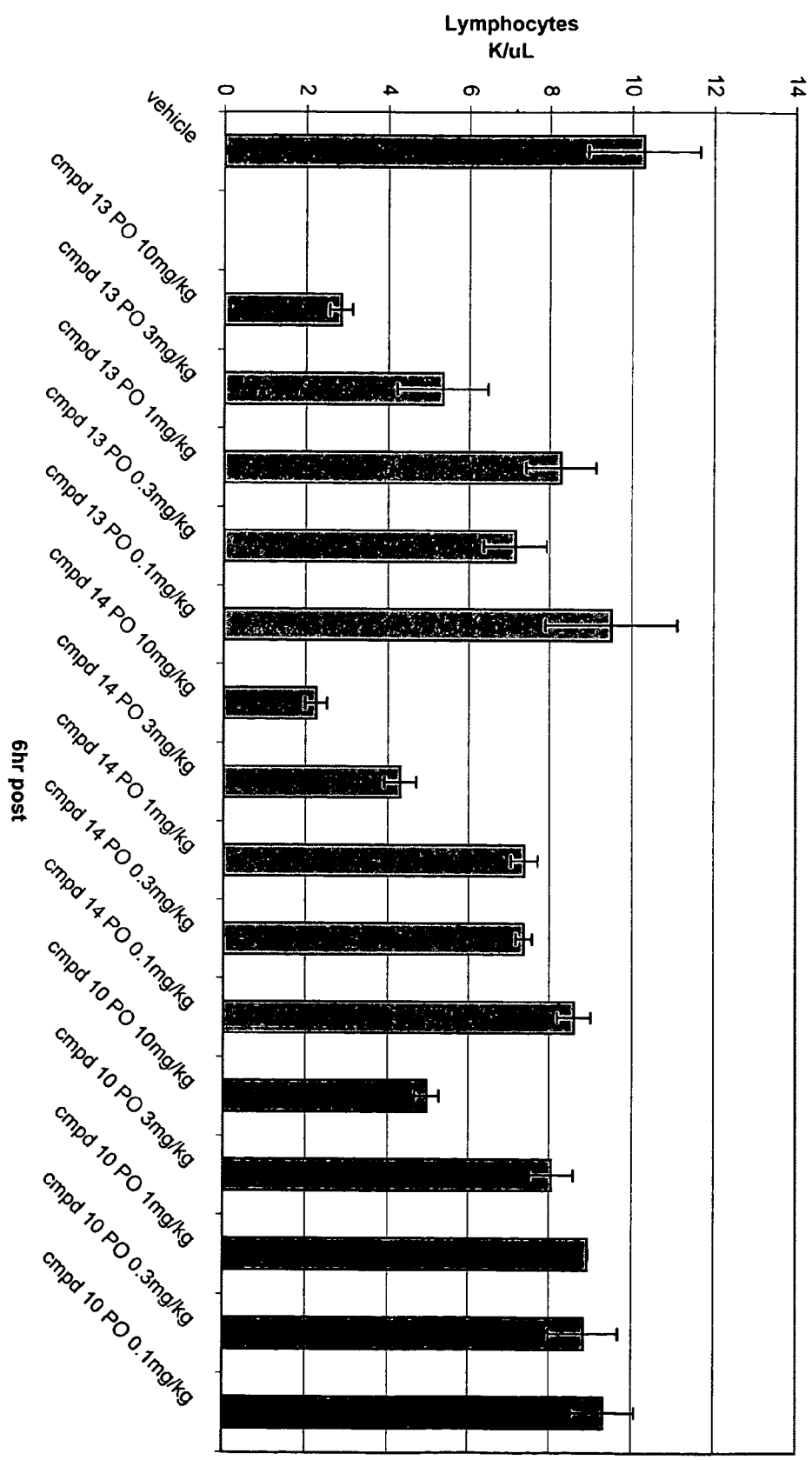

METHODS AND COMPOSITIONS FOR MODULATING SPHINGOSINE-1-PHOSPHATE (S1P) RECEPTOR ACTIVITY

RELATED APPLICATIONS

This application relates to PCT application No. PCT/US2005/028914, filed Aug. 12, 2005 and also claims the benefit of and priority to U.S. Provisional Patent Application Ser. No. 60/601,232, filed Aug. 13, 2004, and U.S. Provisional Patent Application Ser. No. 60/646,436, filed Jan. 21, 2005, the entire contents of each of which are incorporated herein by reference.

BACKGROUND OF THE INVENTION

The sphingosine-1-phosphate (S1P) receptors 1–5 constitute a family of seven transmembrane G-protein coupled receptors. These receptors, referred to as S1P1 to S1P5, are activated via binding by sphingosine-1-phosphate, which is produced by the sphingosine kinase-catalyzed phosphorylation of sphingosine. S1P receptors are cell surface receptors involved in a variety of cellular processes, including cell proliferation and differentiation, cell survival, cell invasion, lymphocyte trafficking, and cell migration. Sphingosine-1-phosphate is found in plasma and a variety of other tissues, and exerts autocrine and paracrine effects, including regulating the secretion of growth factors.

Administration of S1P to an animal results in sequestration of lymphocytes into the lymph nodes and Peyers patches without causing lymphocyte depletion. This activity, which is of potential utility in treating diseases or conditions associated with inappropriate immune response, including transplant rejection and autoimmune diseases, is believed to proceed via activation of the S1P1 receptor. Administration of S1P in vivo also has negative effects, including hypotension and bradycardia, which are believed due to signaling through one or more of the other S1P receptors, S1P2 to S1P5. Accordingly, there is a great need in the art for compounds which are potent and selective agonists of the S1P1 receptor.

SUMMARY OF THE INVENTION

The present invention relates to compounds which modulate the activity of the S1P1 receptor, the use of these compounds for treating conditions associated with signaling through the S1P1 receptor, and pharmaceutical compositions comprising these compounds.

The compounds of the present invention are characterized by a unique structure which imparts surprisingly improved properties to these compounds as compared to the prior art compounds. Specifically, the compounds of the present invention are characterized by the presence of a substituted biphenyl moiety. This biphenyl moiety, in combination with an amide linkage within the core of the structure, enhances the selectivity of the compounds described herein for the S1P1 receptor versus other receptors, such as S1P3. The compounds of the present invention are further characterized by their potent binding to the S1P1 receptor.

In one embodiment, the invention pertains, at least in part, to compounds of Formula I:

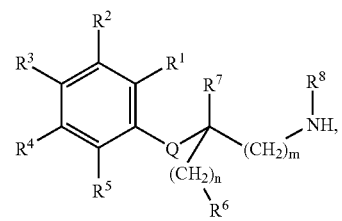

(I)

wherein:

wherein one of $R^3$ and $R^4$ is $C_4$–$C_{20}$-alkyl, $C_4$–$C_{20}$-alkoxy; an oxaalkyl, thiaalkyl or azaalkyl group having a chain length of from 4 to 20 atoms, a phenyl or substituted phenyl group, a phenoxy or substituted phenoxy group, a substituted or unsubstituted arylalkyl group, a substituted or unsubstituted arylalkoxy group, a substituted or unsubstituted heteroarylalkyl group; or a substituted or unsubstituted heteroarylalkoxy group; and the other is hydrogen, halogen, cyano, straight chain or branched $C_1$–$C_6$-alkyl, straight chain or branched $C_1$–$C_6$-alkoxy, straight chain or branched halo-$C_1$–$C_6$-alkyl (e.g., trifluoromethyl), straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-$SO_2$ or N(R)R', where R and R' are each independently hydrogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl or $C_1$–$C_6$-alkyl-$SO_2$;

$R^1$, $R^2$, and $R^5$ are each independently selected from the group consisting of hydrogen, halogen, cyano, straight chain or branched $C_1$–$C_6$-alkyl, straight chain or branched $C_1$–$C_6$-alkoxy, straight chain or branched halo-$C_1$–$C_6$-alkyl (eg., trifluoromethyl), straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-$SO_2$ or N(R)R', where R and R' are each independently hydrogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl or $C_1$–$C_6$-alkyl-$SO_2$;

Q is —$CH_2NR$—, —$CH_2NR(CO)$—, —NH(CO)—, —(CO)NH—, —(CO)—, —O—, —S—, —SO—, —$SO_2$—, —$NRSO_2$—, —$SO_2$—NR— or heteroaryl, where R is hydrogen or straight chain or branched $C_1$–$C_6$-alkyl;

$R^6$ is —OH, —$CO_2R^9$, —$CH_2$=$CH(CO)OR^9$, —$OPO_2R^{10}R^{11}$, —$OPO_3R^{10}R^{11}$, —$CH_2PO_3R^{10}R^{11}$, —$OPO^2(S)R^{10}R^{11}$ or —$C(Y)(X)PO_3R^{10}R^{11}$, where X is hydroxyl or halide and Y is H or halide; or analogues of other carboxylate, phosphate or phosphonate isosteres not limited to those shown below; $R^9$ is H, straight chain or branched $C_1$–$C_6$-alkyl, or a substituted or unsubstituted aryl group; $R^{10}$ and $R^{11}$ are each independently H, straight chain or branched $C_1$–$C_6$-alkyl, a substituted or unsubstituted aryl group or selected from, but not limited to, the prodrugs listed below:

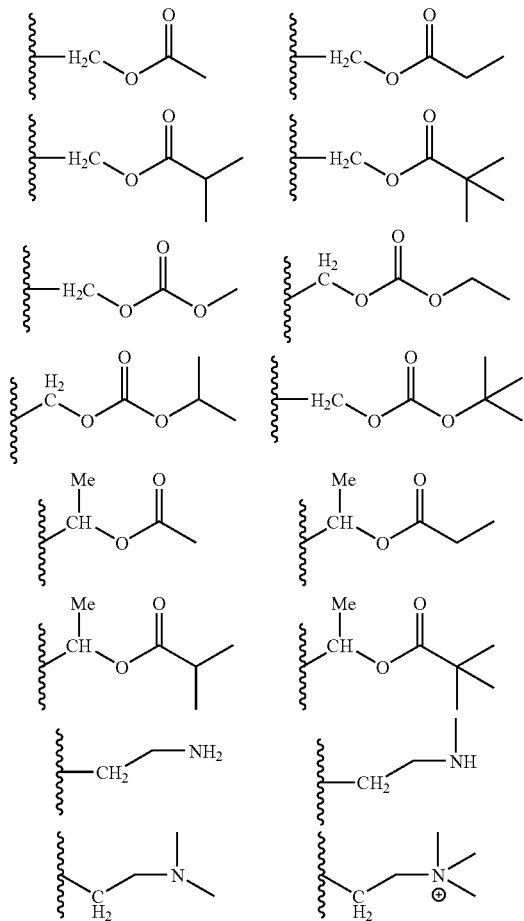

R[7] is H, C$_1$–C$_6$-alkyl, hydroxy-C$_1$–C$_6$-alkyl, aryl, or together with R8 form a C$_2$–C$_5$-alkylene or a C$_2$–C$_5$-alkenylene group;

R[8] is H or C$_1$–C$_6$-alkyl; and m and n are each, independently, an integer from 0 to 3;

provided that when R[4] is C$_4$–C$_{20}$-alkyl, at least one of R[1], R[2], R[3] and R[5] is not hydrogen; and when R[3] is C$_4$–C$_{20}$-alkyl, at least one of R[1], R[2], R[4] and R[5] is not hydrogen; and pharmaceutically acceptable salts thereof.

In another embodiment, the invention provides a compound of Formula II:

(II)

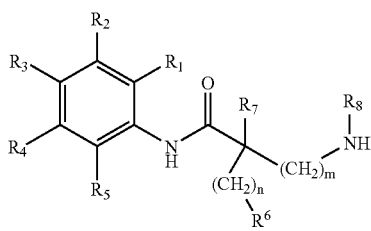

wherein one of R[3] and R[4] is C$_4$–C$_{20}$-alkyl, C$_4$–C$_{20}$-alkoxy; an oxaalkyl, thiaalkyl or azaalkyl group having a chain length of from 4 to 20 atoms, a phenyl or substituted phenyl group, a phenoxy or substituted phenoxy group, a substituted or unsubstituted arylalkyl group, a substituted or unsubstituted arylalkoxy group, a substituted or unsubstituted heteroarylalkyl group; or a substituted or unsubstituted heteroarylalkoxy group; and the other is hydrogen, halogen, cyano, straight chain or branched C$_1$–C$_6$-alkyl, straight chain or branched C$_1$–C$_6$-alkoxy, straight chain or branched halo-C$_1$–C$_6$-alkyl, straight chain or branched halo-C$_1$–C$_6$-alkoxy, C$_1$–C$_6$-alkoxy-C$_1$–C$_6$-alkyl, hydroxyl-C$_1$–C$_6$-alkyl, carboxy-C$_1$–C$_6$-alkyl, C$_1$–C$_6$-alkyl-SO$_2$ or N(R)R', where R' and R' are each independently hydrogen, straight chain or branched C$_1$–C$_6$-alkyl, straight chain or branched C$_1$–C$_6$-alkoxy, straight chain or branched halo-C$_1$–C$_6$-alkyl, straight chain or branched halo-C$_1$–C$_6$-alkoxy, C$_1$–C$_6$-alkoxy-C$_1$–C$_6$-alkyl, hydroxyl-C$_1$–C$_6$-alkyl, carboxy-C$_1$–C$_6$-alkyl or C$_1$–C$_6$-alkyl-SO$_2$;

R[1], R[2], and R[5] are each independently selected from the group consisting of hydrogen, halogen, cyano, straight chain or branched C$_1$–C$_6$-alkyl, straight chain or branched C$_1$–C$_6$-alkoxy, straight chain or branched halo-C$_1$–C$_6$-alkyl, straight chain or branched halo-C$_1$–C$_6$-alkoxy, C$_1$–C$_6$-alkoxy-C$_1$–C$_6$-alkyl, hydroxyl-C$_1$–C$_6$-alkyl, carboxy-C$_1$–C$_6$-alkyl, C$_1$–C$_6$-alkyl-SO$_2$ or N(R)R', where R and R' are each independently hydrogen, straight chain or branched C$_1$–C$_6$-alkyl, straight chain or branched C$_1$–C$_6$-alkoxy, straight chain or branched halo-C$_1$–C$_6$-alkyl, straight chain or branched halo-C$_1$–C$_6$-alkoxy, C$_1$–C$_6$-alkoxy-C$_1$–C$_6$-alkyl, hydroxyl-C$_1$–C$_6$-alkyl, carboxy-C$_1$–C$_6$-alkyl or C$_1$–C$_6$-alkyl-SO$_2$;

Q is —CH$_2$NR—, —CH$_2$NR(CO)—, —NH(CO)—, —(CO)NH—, —(CO)—, —O—, —S—, —SO—, —SO$_2$—, —NRSO$_2$—, —SO$_2$—NR— or heteroaryl, where R is hydrogen or straight chain or branched C$_1$–C$_6$-alkyl;

R[6] is —OH, —CO$_2$R[9], —CH$_2$=CH(CO)OR[9], —OPO$_2$R[10]R[11], —OPO$_3$R[10]R[11], —CH$_2$PO$_3$R[10]R[11], —OPO$^2$(S)R[10]R[11] or —C(Y)(X)PO$_3$R[10]R[11], where X is hydroxyl or halide and Y is H or halide; or analogues of other carboxylate, phosphate or phosphonate isosteres not limited to those shown below; R[9] is H, straight chain or branched C$_1$–C$_6$-alkyl, or a substituted or unsubstituted aryl group; R[10] and R[11] are each independently H, straight chain or branched C$_1$–C$_6$-alkyl, a substituted or unsubstituted aryl group or selected from, but not limited to, the prodrugs listed below:

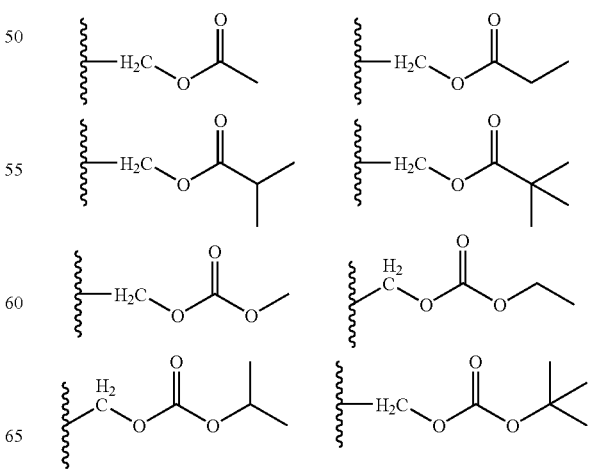

-continued

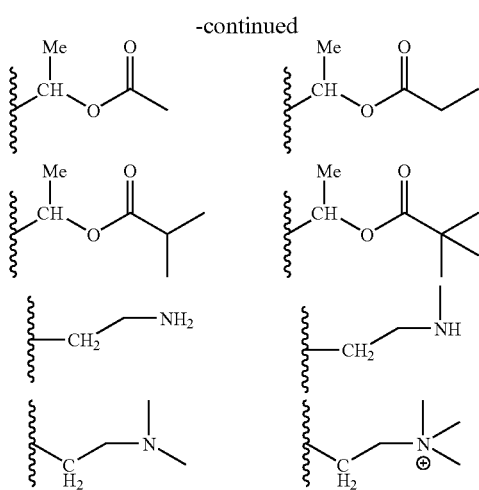

$R^7$ is H, $C_1$–$C_6$-alkyl, hydroxy-$C_1$–$C_6$-alkyl, aryl, or together with $R_8$ form a $C_2$–$C_5$-alkylene or a $C_2$–$C_5$-alkenylene group;

$R^8$ is H or $C_1$–$C_6$-alkyl; and m and n are each, independently, an integer from 0 to 3;
provided that when $R^4$ is $C_4$–$C_{20}$-alkyl, at least one of $R^1$, $R^2$, $R^3$ and $R^5$ is not hydrogen; and when $R^3$ is $C_4$–$C_{20}$-alkyl, at least one of $R^1$, $R^2$, $R^4$ and $R^5$ is not hydrogen; and pharmaceutically acceptable salts thereof.

In another embodiment, the invention provides compounds of Formula III:

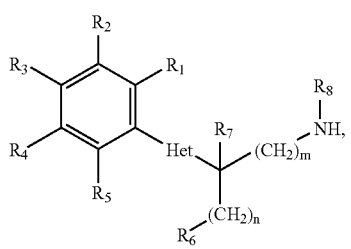

(III)

wherein:

Het is heteroaryl group;

$R_3$ and $R_4$ are each independently hydrogen, $C_4$–$C_{20}$-alkyl group, $C_4$–$C_{20}$-alkoxy group or an oxaalkyl, thiaalkyl or azaalkyl group having a chain length of from 4 to 20 atoms; a phenyl or substituted phenyl group, a phenoxy or substituted phenoxy group, a substituted or unsubstituted arylalkyl group, a substituted or unsubstituted arylalkoxy group, a substituted or unsubstituted heteroarylalkyl group; or a substituted or unsubstituted heteroarylalkoxy group;

$R_1$, $R_2$, and $R_5$ are each independently hydrogen, halogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-SO$_2$ or N(R)R', where R and R' are each independently hydrogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl or $C_1$–$C_6$-alkyl-SO$_2$;

$R^6$ is —OH, —CO$_2R^9$, —CH$_2$=CH(CO)OR$^9$, —OPO$_2R^{10}R^{11}$, —OPO$_3R^{10}R^{11}$, —CH$_2$PO$_3R^{10}R^{11}$, —OPO$^2$(S)R$^{10}R^{11}$ or —C(Y)(X)PO$_3R^{10}R^{11}$, where X is hydroxyl or halide and Y is H or halide; or analogues of other carboxylate, phosphate or phosphonate isosteres not limited to those shown below; $R^9$ is H, straight chain or branched $C_1$–$C_6$-alkyl, or a substituted or unsubstituted aryl group; $R^{10}$ and $R^{11}$ are each independently H, straight chain or branched $C_1$–$C_6$-alkyl, a substituted or unsubstituted aryl group or selected from, but not limited to, the prodrugs listed below:

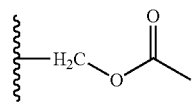 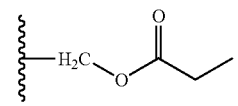

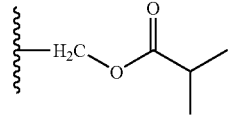 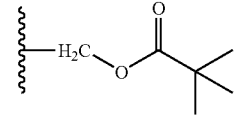

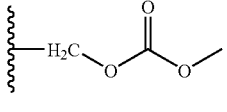 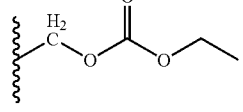

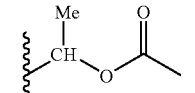 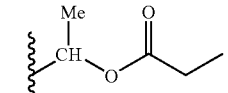

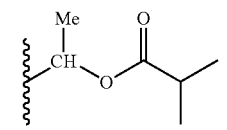 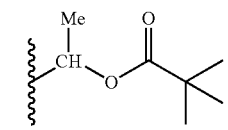

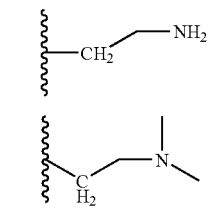 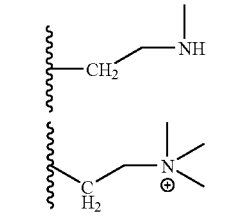

$R_7$ is H, $C_1$–$C_6$-alkyl, hydroxy-$C_1$–$C_6$-alkyl, aryl or together with $R_8$ form a $C_2$–$C_5$-alkylene or a $C_2$–$C_5$-alkenylene group;

$R_8$ is H or $C_1$–$C_6$-alkyl;

m and n are each, independently, an integer from 0 to 3.

provided that when $R^4$ is $C_4$–$C_{20}$-alkyl, at least one of $R^1$, $R^2$, $R^3$ and $R^5$ is not hydrogen; and when $R^3$ is $C_4$–$C_{20}$-alkyl, at least one of $R^1$, $R^2$, $R^4$ and $R^5$ is not hydrogen; and pharmaceutically acceptable salts thereof.

In a preferred embodiment, the invention provides compounds of Formula IV:

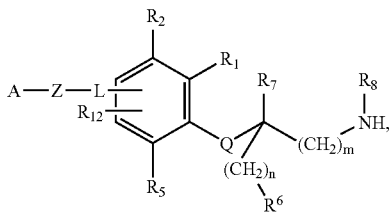

(IV)

wherein:

L is alkoxy, a covalent bond, substituted or unsubstituted alkyl, alkylcarbonyl, thioether, alkylsulfonyl, alkylcarbonylamino, alkylaminocarbonyl, alkyloxycarbonyl, alkylcarbonyloxy, or substituted or unsubstituted heteroaryl;

Z and A are each independently substituted or unsubstituted aryl, wherein Z and A may be linked by a covalent bond, substituted or unsubstituted alkyl, NH, alkyloxy, O, thioether, S, aminocarbonyl, carbonylamino, carbonyloxy, or oxycarbonyl;

$R^1$, $R^2$, $R^5$ and $R^{12}$ are each independently selected from the group consisting of hydrogen, halogen, cyano, substituted or unsubstituted aryl, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-$SO_2$ or N(R)R', wherein R and R' are each independently hydrogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl or $C_1$–$C_6$-alkyl-$SO_2$;

Q is —$CH_2$NR—, —$CH_2$NR(CO)—, —NH(CO)—, —(CO)NH—, —(CO)—, —O—, —S—, —SO—, —$SO_2$—, —NR$SO_2$—, —$SO_2$—NR— or heteroaryl, where R is hydrogen or straight chain or branched $C_1$–$C_6$-alkyl;

$R^6$ is —OH, —$CO_2R^9$, —$CH_2$=CH(CO)O$R^9$, —OPO$_2R^{10}R^{11}$, —OPO$_3R^{10}R^{11}$, —$CH_2$PO$_3R^{10}R^{11}$, —OPO$^2$(S)$R^{10}R^{11}$ or —C(Y)(X)PO$_3R^{10}R^{11}$, where X is hydroxyl or halide and Y is H or halide; or analogues of other carboxylate, phosphate or phosphonate isosteres not limited to those shown below; $R^9$ is H, straight chain or branched $C_1$–$C_6$-alkyl, or a substituted or unsubstituted aryl group; R10 and R11 are each independently H, straight chain or branched $C_1$–$C_6$-alkyl, a substituted or unsubstituted aryl group or selected from, but not limited to, the prodrugs listed below:

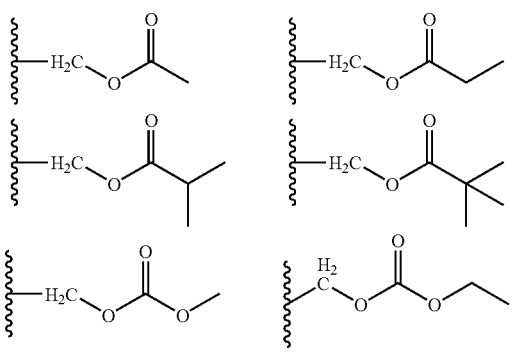
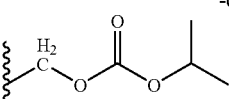
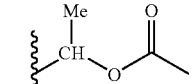
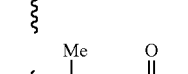
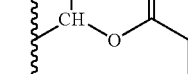
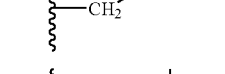
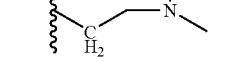
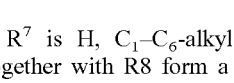

$R^7$ is H, $C_1$–$C_6$-alkyl, hydroxy-$C_1$–$C_6$-alkyl, aryl, or together with R8 form a $C_2$–$C_5$-alkylene or a $C_2$–$C_5$-alkenylene group;

$R^8$ is H or $C_1$–$C_6$-alkyl; and m and n are each, independently, an integer from 0 to 3;

provided that when $R^4$ is $C_4$–$C_{20}$-alkyl, at least one of $R^1$, $R^2$, $R^3$ and $R^5$ is not hydrogen; and when $R^3$ is $C_4$–$C_{20}$-alkyl, at least one of $R^1$, $R^2$, $R^4$ and $R^5$ is not hydrogen; and pharmaceutically acceptable salts thereof.

In yet another embodiment, the invention includes a method for treating a sphingosine 1-phosphate associated disorder in a subject. The method includes administering to the subject an effective amount of a compound of the invention, e.g., a compound of Formula I or otherwise described herein, such that the subject is treated for the sphingosine 1-phosphate associated disorder.

In a further embodiment, the invention pertains, at least in part, to a pharmaceutical composition comprising a therapeutically effective amount of a compound of the invention, e.g., a compound of Formula I or otherwise described herein, and a pharmaceutically acceptable carrier.

BRIEF DESCRIPTION OF THE DRAWING

FIG. 1 is a graph showing the results of the lymphopenia assay for certain compounds of the invention.

DETAILED DESCRIPTION OF THE INVENTION

The compounds provided by the present invention are modulators of the S1P1 receptor and are preferably agonists of the S1P1 receptor. More preferably, the compounds are selective agonists of the S1P1 receptor. In addition to the S1P1 modulator compounds, the invention also provides pharmaceutical compositions comprising these compounds and methods of using these compounds for treating a condition associated an inappropriate immune response, such as transplant rejection or an autoimmune disease.

Definitions

As used herein, "alkyl" groups include saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (isopropyl, tert-butyl, sec-butyl, isobutyl, etc.), and alkyl-substituted alkyl groups (e.g., alkyl-substituted cycloalkyl groups and cycloalkyl-substituted alkyl groups). The term "aliphatic group" includes organic moieties characterized by straight or branched-chains, typically having between 1 and 22 carbon atoms. In complex structures, the chains may be branched, bridged, or cross-linked. Aliphatic groups include alkyl groups, alkenyl groups, and alkynyl groups.

In certain embodiments, a straight-chain or branched-chain alkyl group may have 30 or fewer carbon atoms in its backbone, e.g., $C_1$–$C_{30}$ for straight-chain or $C_3$–$C_{30}$ for branched-chain. In certain embodiments, a straight-chain or branched-chain alkyl group may have 20 or fewer carbon atoms in its backbone, e.g., $C_1$–$C_{20}$ for straight-chain or $C_3$–$C_{20}$ for branched-chain, and more preferably 18 or fewer. Likewise, preferred cycloalkyl groups have from 4–10 carbon atoms in their ring structure, and more preferably have 4–7 carbon atoms in the ring structure. The term "lower alkyl" refers to alkyl groups having from 1 to 6 carbons in the chain, and to cycloalkyl groups having from 3 to 6 carbons in the ring structure.

Unless the number of carbons is otherwise specified, "lower" as in "lower aliphatic," "lower alkyl," "lower alkenyl," etc. as used herein means that the moiety has at least one and less than about 8 carbon atoms. In certain embodiments, a straight-chain or branched-chain lower alkyl group has 6 or fewer carbon atoms in its backbone (e.g., $C_1$–$C_6$ for straight-chain, $C_3$–$C_6$ for branched-chain), and more preferably 4 or fewer. Likewise, preferred cycloalkyl groups have from 3–8 carbon atoms in their ring structure, and more preferably have 5 or 6 carbons in the ring structure. The term "$C_1$–$C_6$" as in "$C_1$–$C_6$ alkyl" means alkyl groups containing 1 to 6 carbon atoms.

Moreover, unless otherwise specified the term alkyl includes both "unsubstituted alkyls" and "substituted alkyls," the latter of which refers to alkyl groups having substituents replacing one or more hydrogens on one or more carbons of the hydrocarbon backbone. Such substituents may include, for example, alkenyl, alkynyl, halogen, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclic, alkylaryl, or aromatic (including heteroaromatic) groups.

An "arylalkyl" group is an alkyl group substituted with an aryl group (e.g., phenylmethyl (i.e., benzyl)). An "alkylaryl" moiety is an aryl group substituted with an alkyl group (e.g., p-methylphenyl (i.e., p-tolyl)). The term "n-alkyl" means a straight-chain (i.e., unbranched) unsubstituted alkyl group. An "alkylene" group is a divalent analog of the corresponding alkyl group. Examples of alkylene groups include ethylene (—$CH_2CH_2$—), propylene (—$CH_2CH_2CH_2$—), butylene (—$CH_2CH_2CH_2CH_2$—) and 1-methyethylene (—CH($CH_3$)$CH_2$—). The terms "alkenyl", "alkynyl" and "alkenylene" refer to unsaturated aliphatic groups analogous to alkyls, but which contain at least one double or triple carbon-carbon bond respectively. Examples of alkenylene groups include ethenylene (—CH═CH—), propenylene (—CH═$CHCH_2$—), 2-butenylene (—$CH_2$CH═$CHCH_2$—) and 1-methyethenylene (—C($CH_3$)CH—). Suitable alkenyl and alkynyl groups include groups having 2 to about 12 carbon atoms, preferably from 2 to about 6 carbon atoms.

The term "aromatic group" or "aryl group" includes unsaturated and aromatic cyclic hydrocarbons (e.g., benzyl or phenyl) as well as unsaturated and aromatic heterocycles containing one or more rings. Aryl groups may also be fused or bridged with a bond (e.g., biphenyl), alicyclic or heterocyclic rings that are not aromatic so as to form a polycycle (e.g., tetralin). An "arylene" group is a divalent analog of an aryl group.

The term "heterocyclic group" includes closed ring structures analogous to carbocyclic groups in which one or more of the carbon atoms in the ring is an element other than carbon, for example, nitrogen, sulfur, or oxygen. Heterocyclic groups may be saturated or unsaturated. Additionally, heterocyclic groups (such as pyrrolyl, pyridyl, isoquinolyl, quinolyl, purinyl, and furyl) may have aromatic character, in which case they may be referred to as "heteroaryl" or "heteroaromatic" groups.

Unless otherwise stipulated, aryl and heterocyclic (including heteroaryl) groups may also be substituted at one or more constituent atoms. Examples of heteroaromatic and heteroalicyclic groups may have 1 to 3 separate or fused rings with 3 to about 8 members per ring and one or more N, O, or S heteroatoms. In general, the term "heteroatom" includes atoms of any element other than carbon or hydrogen, preferred examples of which include nitrogen, oxygen, sulfur, and phosphorus. Heterocyclic groups may be saturated or unsaturated or aromatic.

Examples of heterocycles include, but are not limited to, acridinyl; azocinyl; benzimidazolyl; benzofuranyl; benzothiofuranyl; benzothiophenyl; benzoxazolyl; benzthiazolyl; benztriazolyl; benztetrazolyl; benzisoxazolyl; benzisothiazolyl; benzimidazolinyl; carbazolyl; 4aH-carbazolyl; carbolinyl; chromanyl; chromenyl; cinnolinyl; decahydroquinolinyl; 2H,6H-1,5,2-dithiazinyl; dihydrofuro[2,3-b]tetrahydrofuran; furanyl; furazanyl; imidazolidinyl; imidazolinyl; imidazolyl; 1H-indazolyl; indolenyl; indolinyl; indolizinyl; indolyl; 3H-indolyl; isobenzofuranyl; isochromanyl; isoindazolyl; isoindolinyl; isoindolyl; isoquinolinyl; isothiazolyl; isoxazolyl; methylenedioxyphenyl; morpholinyl; naphthyridinyl; octahydroisoquinolinyl; oxadiazolyl; 1,2,3-oxadiazolyl; 1,2,4-oxadiazolyl; 1,2,5-oxadiazolyl; 1,3,4-oxadiazolyl; oxazolidinyl; oxazolyl; oxazolidinyl; pyrimidinyl; phenanthridinyl; phenanthrolinyl; phenazinyl; phenothiazinyl; phenoxathiinyl; phenoxazinyl; phthalazinyl; piperazinyl; piperidinyl; piperidonyl; 4-piperidonyl; piperonyl; pteridinyl; purinyl; pyranyl; pyrazinyl; pyrazolidinyl; pyrazolinyl; pyrazolyl; pyridazinyl; pyridooxazole; pyridoimidazole; pyridothiazole; pyridinyl; pyridyl; pyrimidinyl; pyrrolidinyl; pyrrolinyl; 2H-pyrrolyl; pyrrolyl; quinazolinyl; quinolinyl; 4H-quinolizinyl; quinoxalinyl; quinuclidinyl; tetrahydrofuranyl; tetrahydroisoquinolinyl; tetrahydroquinolinyl; tetrazolyl; 6H-1,2,5-thiadiazinyl; 1,2,3-thiadiazolyl; 1,2,4-thiadiazolyl; 1,2,5-thiadiazolyl; 1,3,4-thiadiazolyl; thianthrenyl; thiazolyl; thienyl; thienothiazolyl; thienooxazolyl; thienoimidazolyl; thiophenyl; triazinyl; 1,2,3-triazolyl; 1,2,4-triazolyl; 1,2,5- triazolyl; 1,3,4-triazolyl; and xanthenyl. Preferred heterocycles include, but are not limited to, pyridinyl; furanyl; thienyl; pyrrolyl; pyrazolyl; pyrrolidinyl; imidazolyl; indolyl; benzimidazolyl; 1H-indazolyl; oxazolidinyl; benzotriazolyl; benzisoxazolyl; oxindolyl; benzoxazolinyl; and isatinoyl groups. Also included are fused ring and spiro compounds containing, for example, the above heterocycles.

A common hydrocarbon aryl group is a phenyl group having one ring. Two-ring hydrocarbon aryl groups include naphthyl, indenyl, benzocyclooctenyl, benzocycloheptenyl, pentalenyl, and azulenyl groups, as well as the partially hydrogenated analogs thereof such as indanyl and tetrahydronaphthyl. Exemplary three-ring hydrocarbon aryl groups include acephthylenyl, fluorenyl, phenalenyl, phenanthrenyl, and anthracenyl groups.

Aryl groups also include heteromonocyclic aryl groups, i.e., single-ring heteroaryl groups, such as thienyl, furyl, pyranyl, pyrrolyl, imidazolyl, pyrazolyl, pyridinyl, pyrazinyl, pyrimidinyl, and pyridazinyl groups; and oxidized analogs thereof such as pyridonyl, oxazolonyl, pyrazolonyl, isoxazolonyl, and thiazolonyl groups. The corresponding hydrogenated (i.e., non-aromatic) heteromonocylic groups include pyrrolidinyl, pyrrolinyl, imidazolidinyl, imidazolinyl, pyrazolidinyl, pyrazolinyl, piperidyl and piperidino, piperazinyl, and morpholino and morpholinyl groups.

Aryl groups also include fused two-ring heteroaryls such as indolyl, isoindolyl, indolizinyl, indazolyl, quinolinyl, isoquinolinyl, phthalazinyl, quinoxalinyl, quinazolinyl, cinnolinyl, chromenyl, isochromenyl, benzothienyl, benzimidazolyl, benzothiazolyl, purinyl, quinolizinyl, isoquinolonyl, quinolonyl, naphthyridinyl, and pteridinyl groups, as well as the partially hydrogenated analogs such as chromanyl, isochromanyl, indolinyl, isoindolinyl, and tetrahydroindolyl groups. Aryl groups also include fused three-ring groups such as phenoxathiinyl, carbazolyl, phenanthridinyl, acridinyl, perimidinyl, phenanthrolinyl, phenazinyl, phenothiazinyl, phenoxazinyl, and dibenzofuranyl groups.

Some typical aryl groups include substituted or unsubstituted 5- and 6-membered single-ring groups. In another aspect, each Ar group may be selected from the group consisting of substituted or unsubstituted phenyl, pyrrolyl, furyl, thienyl, thiazolyl, isothiaozolyl, imidazolyl, triazolyl, tetrazolyl, pyrazolyl, oxazolyl, isooxazolyl, pyridinyl, pyrazinyl, pyridazinyl, and pyrimidinyl groups. Further examples include substituted or unsubstituted phenyl, 1-naphthyl, 2-naphthyl, biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl groups.

The term "amine" or "amino," as used herein, refers to an unsubstituted or substituted moiety of the formula $-NR^aR^b$, in which $R^a$ and $R^b$ are each independently hydrogen, alkyl, aryl, or heterocyclyl, or $R^a$ and $R^b$, taken together with the nitrogen atom to which they are attached, form a cyclic moiety having from 3 to 8 atoms in the ring. Thus, the term amino includes cyclic amino moieties such as piperidinyl or pyrrolidinyl groups, unless otherwise stated. Thus, the term "alkylamino" as used herein means an alkyl group having an amino group attached thereto. Suitable alkylamino groups include groups having 1 to about 12 carbon atoms, preferably from 1 to about 6 carbon atoms. The term amino includes compounds or moieties in which a nitrogen atom is covalently bonded to at least one carbon or heteroatom. The term "dialkylamino" includes groups wherein the nitrogen atom is bound to at least two alkyl groups. The term "arylamino" and "diarylamino" include groups wherein the nitrogen is bound to at least one or two aryl groups, respectively. The term "alkylarylamino" refers to an amino group which is bound to at least one alkyl group and at least one aryl group. The term "alkaminoalkyl" refers to an alkyl, alkenyl, or alkynyl group substituted with an alkylamino group. The term "amide" or "aminocarbonyl" includes compounds or moieties which contain a nitrogen atom which is bound to the carbon of a carbonyl or a thiocarbonyl group. The term "azaalkyl" refers to an alkyl group in which one or more $-CH_2-$ units have been replaced by an $-N(R)-$ group, where R is hydrogen or $C_1-C_4$-alkyl. If an azaalkyl group includes two or more N(R) groups, any two N(R) groups are separated by one or more carbon atoms.

The terms "alkylthio" or "thiaalkoxy" refers to an alkyl group, having a sulfhydryl group attached thereto. Suitable alkylthio groups include groups having 1 to about 12 carbon atoms, preferably from 1 to about 6 carbon atoms. The term "thiaalkyl" refers to an alkyl group in which one or more $-CH_2-$ units have been replaced by a sulfur atom. If a thiaalkyl group includes two or more sulfur atoms, any two sulfur atoms are separated by one or more carbon atoms.

The term "alkylcarboxyl" as used herein means an alkyl group having a carboxyl group attached thereto.

The term "alkoxy" as used herein means an alkyl group having an oxygen atom attached thereto. Representative alkoxy groups include groups having 1 to about 12 carbon atoms, preferably 1 to about 6 carbon atoms, e.g., methoxy, ethoxy, propoxy, tert-butoxy and the like. Examples of alkoxy groups include methoxy, ethoxy, isopropyloxy, propoxy, butoxy, and pentoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc., as well as perhalogenated alkyloxy groups. The term "oxaalkyl" refers to an alkyl group in which one or more $-CH_2-$ units have been replaced by an oxygen atom. If an oxaalkyl group includes two or more oxygen atoms, any two oxygen atoms are separated by one or more carbon atoms.

The term "acylamino" includes moieties wherein an amino moiety is bonded to an acyl group. For example, the acylamino group includes alkylcarbonylamino, arylcarbonylamino, carbamoyl and ureido groups.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "ether" or "ethereal" includes compounds or moieties which contain an oxygen atom bonded to two carbon atoms. For example, an ether or ethereal group includes "alkoxyalkyl" which refers to an alkyl, alkenyl, or alkynyl group substituted with an alkoxy group.

The term "nitro" means $-NO_2$; the term "halogen" or "halogen" or "halo" designates $-F$, $-Cl$, $-Br$ or $-I$; the term "thiol," "thio," or "mercapto" means SH; and the term "hydroxyl" or "hydroxy" means $-OH$.

The term "acyl" refers to a carbonyl group that is attached through its carbon atom to a hydrogen (i.e., a formyl), an aliphatic group (e.g., acetyl), an aromatic group (e.g., benzoyl), and the like. The term "substituted acyl" includes acyl groups where one or more of the hydrogen atoms on one or more carbon atoms are replaced by, for example, an alkyl group, alkynyl group, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless otherwise specified, the chemical moieties of the compounds of the invention, including those groups discussed above, may be "substituted or unsubstituted." In some embodiments, the term "substituted" means that the moiety has substituents placed on the moiety other than hydrogen (i.e., in most cases, replacing a hydrogen), which allow the molecule to perform its intended function. Examples of substituents include moieties selected from straight or branched alkyl (preferably $C_1-C_5$), cycloalkyl (preferably $C_3-C_8$), alkoxy (preferably $C_1-C_6$), thioalkyl (preferably $C_1-C_6$), alkenyl (preferably $C_2-C_6$), alkynyl (preferably $C_2-C_6$), heterocyclic, carbocyclic, aryl (e.g., phenyl), aryloxy (e.g., phenoxy), arylkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, and heteroaryl groups, as well as $(CR'R'')_{0-3}NR'R''$ (e.g., $-NH_2$), $(CR'R'')_{0-3}CN$ (e.g., $-CN$), $-NO_2$, halogen (e.g., $-F$, $-Cl$, $-Br$, or $-I$), $(CR'R'')_{0-3}C(halogen)_3$ (e.g., $-CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}(CR'R'')_{0-3}H$, $(CR'R'')_{0-3}S(O)_{0-3}R'$ (e.g., $-SO_3H$), $(CR'R'')_{0-3}(CR'R'')_{0-3}H$ (e.g., $-CH_2OCH_3$ and $-OCH_3$), $(CR'R'')_{0-3}S(CR'R'')_{0-3}H$ (e.g., $-SH$ and $-SCH_3$), $(CR'R'')_{0-3}OH$ (e.g., $-OH$), $(CR'R'')_{0-3}COR'$, $(CR'R'')_{0-3}$(substituted or unsubstituted phenyl), $(CR'R'')_{0-3}(C_3-C_8$ cycloalkyl), $(CR'R'')_{0-3}CO_2R'$ (e.g., $-CO_2H$), and $(CR'R'')_{0-3}OR'$ groups, wherein R' and R" are each independently hydrogen, a $C_1-C_5$ alkyl, $C_2-C_5$ alkenyl, $C_2-C_5$ alkynyl, or aryl group; or the side chain of any naturally occurring amino acid.

In another embodiment, a substituent may be selected from straight or branched alkyl (preferably $C_1-C_5$), cycloalkyl (preferably $C_3-C_8$), alkoxy (preferably $C_1-C_6$), thioalkyl (preferably $C_1-C_6$), alkenyl (preferably $C_2-C_6$), alkynyl (preferably $C_2-C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-10}NR'R''$ (e.g., $-NH_2$), $(CR'R'')_{0-10}CN$ (e.g., $-CN$), $NO_2$, halogen (e.g., F, Cl, Br, or I), $(CR'R'')_{0-10}C(halogen)_3$ (e.g., $-CF_3$), $(CR'R'')_{0-10}CH(halogen)_2$, $(CR'R'')_{0-10}CH_2(halogen)$, $(CR'R'')_{0-10}CONR'R''$, $(CR'R'')_{0-10}(CNH)NR'R''$, $(CR'R'')_{0-10}S(O)_{1-2}NR'R''$, $(CR'R'')_{0-10}CHO$, $(CR'R'')_{0-10}(CR'R'')_{0-10}H$, $(CR'R'')_{0-10}S(O)_{0-3}R'$ (e.g., $-SO_3H$), $(CR'R'')_{0-10}(CR'R'')_{0-10}H$ (e.g., $-CH_2OCH_3$ and $-OCH_3$), $(CR'R'')_{0-10}S(CR'R'')_{0-3}H$ (e.g., $-SH$ and $-SCH_3$), $(CR'R'')_{0-10}OH$ (e.g., $-OH$), $(CR'R'')_{0-10}COR'$, $(CR'R'')_{0-10}$ (substituted or unsubstituted phenyl), $(CR'R'')_{0-10}(C_3-C_8$ cycloalkyl), $(CR'R'')_{0-10}CO_2R'$ (e.g., $-CO_2H$), or $(CR'R'')_{0-10}OR'$ group, or the side chain of any naturally occurring amino acid; wherein R' and R" are each independently hydrogen, a $C_1-C_5$ alkyl, $C_2-C_5$ alkenyl, $C_2-C_5$ alkynyl, or aryl group, or R' and R" taken together are a benzylidene group or a $-(CH_2)_2O(CH_2)_2-$ group.

It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is meant to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more.

In some embodiments, a "substituent" may be selected from the group consisting of, for example, halogen, trifluoromethyl, nitro, cyano, $C_1-C_6$ alkyl, $C_2-C_6$ alkenyl, $C_2-C_6$ alkynyl, $C_1-C_6$ alkylcarbonyloxy, arylcarbonyloxy, $C_1-C_6$ alkoxycarbonyloxy, aryloxycarbonyloxy, $C_1-C_6$ alkylcarbonyl, $C_1-C_6$ alkoxycarbonyl, $C_1-C_6$ alkoxy, $C_1-C_6$ alkylthio, arylthio, heterocyclyl, aralkyl, and aryl (including heteroaryl) groups.

Compounds of the Invention

In one embodiment, the invention pertains, at least in part, to compounds of Formula (I):

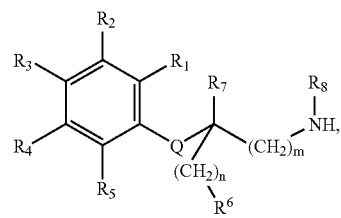

wherein:

one of $R_3$ and $R_4$ is $C_4-C_{20}$-alkyl, $C_4-C_{20}$-alkoxy; an oxaalkyl, thiaalkyl or azaalkyl group having a chain length of from 4 to 20 atoms, a phenyl or substituted phenyl group, a phenoxy or substituted phenoxy group, a substituted or unsubstituted arylalkyl group, a substituted or unsubstituted arylalkoxy group, a substituted or unsubstituted heteroarylalkyl group; or a substituted or unsubstituted heteroarylalkoxy group; and the other is hydrogen, halogen, cyano, straight chain or branched $C_1-C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-$SO_2$ or N(R)R', where R and R' are each independently hydrogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl or $C_1$–$C_6$-alkyl-$SO_2$;

$R^1$, $R^2$, and $R^5$ are each independently selected from the group consisting of hydrogen, halogen, cyano, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-$SO_2$ or N(R)R', where R and R' are each independently hydrogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl or $C_1$–$C_6$-alkyl-$SO_2$;

Q is —$CH_2NR$—, —$CH_2NR(CO)$—, —NH(CO)—, —(CO)NH—, —(CO)— —O—, —S—, —SO—, —$SO_2$—, —$NRSO_2$—, —$SO_2$—NR— or heteroaryl, where R is hydrogen or straight chain or branched $C_1$–$C_6$-alkyl;

$R^6$ is —OH, —$CO_2R^9$, —$CH_2$=CH(CO)$OR^9$, —$OPO_2R^{10}R^{11}$, —$OPO_3R^{10}R^{11}$, —$CH_2PO_3R^{10}R^{11}$, —$OPO^2(S)R^{10}R^{11}$ or —C(Y)(X)$PO_3R^{10}R^{11}$, where X is hydroxyl or halide and Y is H or halide; or analogues of other carboxylate, phosphate or phosphonate isosteres not limited to those shown below; $R^9$ is H, straight chain or branched $C_1$–$C_6$-alkyl, or a substituted or unsubstituted aryl group; $R^{10}$ and $R^{11}$ are each independently H, straight chain or branched $C_1$–$C_6$-alkyl, a substituted or unsubstituted aryl group or selected from, but not limited to, the prodrugs listed below:

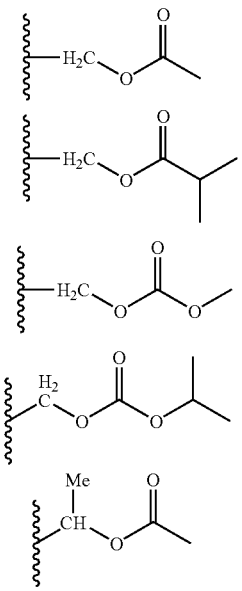

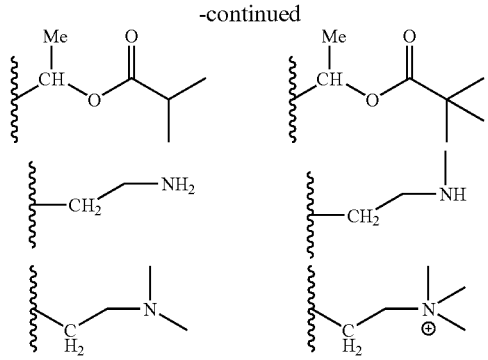

-continued $R^7$ is H, $C_1$–$C_6$-alkyl, hydroxy-$C_1$–$C_6$-alkyl, aryl, or together with R8 form a $C_2$–$C_5$-alkylene or a $C_2$–$C_5$-alkenylene group;

$R^8$ is H or $C_1$–$C_6$-alkyl; and m and n are each, independently, an integer from 0 to 3;

provided that when $R^4$ is $C_4$–$C_{20}$-alkyl, at least one of $R^1$, $R^2$, $R^3$ and $R^5$ is not hydrogen; and when $R^3$ is $C_4$–$C_{20}$-alkyl, at least one of $R^1$, $R^2$, $R^4$ and $R^5$ is not hydrogen; and pharmaceutically acceptable salts thereof;

provided that when Q is NH(C=O), O, or heteroaryl; $R^6$ is OH; n is 1–4; one of $R^1$, $R^2$, $R^3$, $R^4$, and $R^5$ is $C_1$–$C_{18}$ alkyl, $C_2$–$C_{18}$ alkenyl, $C_2$–$C_{18}$ alkynyl, $C_5$–$C_{18}$-alkoxy, $(CH_2)_{1-10}(CH_2)_{1-10}$, $C_5$–$C_{10}$(aryl), $C_5$–$C_{10}$(aryl)($C_1$–$C_{10}$alkyl), $C_5$–$C_{10}$(heteroaryl), $C_5$–$C_{10}$(heteroaryl)($C_1$–$C_{10}$alkyl), $C_5$–$C_{10}$ cycloalkyl, $C_5$–$C_{10}$(cycloalkyl)-($C_1$–$C_5$ alkyl), $C_5$–$C_{10}$alkoxy(aryl), $C_5$–$C_{10}$alkoxy(aryl)($C_1$–$C_{10}$ alkyl), $C_5$–$C_{10}$alkoxy(heteroaryl), $C_5$–$C_{10}$alkoxy(heteroaryl)($C_1$–$C_{10}$ alkyl), $C_5$–$C_{10}$alkoxy(cycloalkyl), or $C_5$–$C_{10}$alkoxy(cycloalkyl)($C_1$–$C_{10}$ alkyl); and one of $R^1$, $R^2$, $R^3$, $R^4$, and $R^5$ is H, halogen, $NH_2$, $C_1$–$C_6$ alkyl, $C_1$–$C_6$ alkoxy, $C_1$–$C_6$ alkylamino, $C_1$–$C_6$ alkylcyano, or $C_1$–$C_6$ alkylthio, then $R^8$ is not hydrogen;

provided that when Q is heteroaryl; one of $R^1$, $R^2$, $R^3$, $R^4$, and $R^5$ is alkyl, alkenyl, alkynyl, optionally substituted aryl, optionally substituted heteroaryl, alkyl (optionally substituted aryl), arylalkyl, or arylalkyl (optionally substituted (aryl); $R^8$ is hydrogen; n is 1; then $R^6$ is not OH;

and provided that when Q is NH(C=O); $R^6$ is OH; $R^1$, $R^2$, $R^3$, $R^4$, and $R^5$ are each independently halogen, hydrogen, amino, or alkyl; then $R^8$ is not hydrogen.

In a further embodiment, $R^1$ is hydrogen. In another further embodiment, $R^2$ is hydrogen, alkyl, or halogen (e.g., fluoro, bromo, chloro or iodo).

In another further embodiment, $R^3$ is substituted or unsubstituted alkyl or cycloalkyl group. The alkyl $R^3$ group may be substituted with any substituent which allows the compound of Formula I to perform its intended function, e.g., modulate sphingosine 1-phosphate receptor. Examples of such substituents include halogens and hydroxyl groups. Other examples of possible substituents for alkyl $R^3$ groups include substituted or unsubstituted arylthioether, alkylthioether, alkylsulfoxide, arylsulfoxide, arylsulfonyl and alkylsulfonyl groups.

In a further embodiment, $R^3$ is a substituted or unsubstituted alkoxy or cycloalkoxy group (e.g., a $C_1$–$C_{20}$ alkoxy group). In a further embodiment, the substituted $R^3$ alkoxy group is substituted with one or more substituted or unsubstituted aryl groups. These aryl groups may further be substituted with any substituent which allows the compounds of the invention to perform their intended function, e.g., modulate sphingosine 1-phosphate 1 receptors. Examples of such substituents include alkoxy groups, such as methoxy, ethoxy, and propoxy. These alkoxy groups may further be substituted with any substituents such as halogens, hydroxyl groups, cyano groups, and other substituents described herein.

In another embodiment, $R^3$ is a substituted or unsubstituted aryloxy group, e.g., a substituted or unsubstituted phenoxy group. Furthermore, the phenoxy group may further be substituted with one or more substituents which allow the compound of the invention to perform its intended function. Examples of such substituents include substituted or unsubstituted alkyl or substituted or unsubstituted aryl groups. Examples of aryl groups which may be used to substitute the phenoxy $R^3$ groups include substituted or unsubstituted phenyl groups. Examples of substituents for these phenyl groups include halogens, cyano, alkoxy, alkyl groups, or any of the other possible substituents described herein.

In another embodiment, $R^3$ is a substituted or unsubstituted aryl or heteroaryl group. The substituted aryl or heteroaryl $R^3$ group may further be substituted with one or more halogens, such as fluorine, chlorine, bromine, or iodine. It also may be substituted with any of the other substituents described herein.

In yet another embodiment, $R^3$ is a substituted or unsubstituted alkyl amino carbonyl or a substituted or unsubstituted aryl amino carbonyl. In yet another embodiment, $R^3$ is a substituted or unsubstituted aryl carbonyl, a substituted or unsubstituted alkyl carbonyl, substituted or unsubstituted aryl alkyl carbonyl.

In another embodiment, $R^4$ is hydrogen, a cyano group, a substituted or unsubstituted alkyl group, or a substituted or unsubstituted alkoxy group. In a further embodiment, $R^5$ is hydrogen, a substituted or unsubstituted alkyl group or a halogen. $R^4$ and $R^5$ may be substituted with any of the substituents described herein, such that the compound of formula (I) is capable of performing its intended function, e.g., modulate the sphingosine 1-phosphate receptor.

In yet another further embodiment, Q is —NH—CO— or —CO—NH—. In yet another further embodiment, Q is a substituted or unsubstituted aryl group, e.g., phenyl or heteroaryl. Examples of heteroaryl Q groups include pyridyl, indolyl, imidazolyl, furanyl, and other N, S, and O containing heteroaryls.

In another embodiment, Q is a carbonyl or thiocarbonyl group.

In another embodiment, Q is $CH_2NR$—, —$CH_2NR(CO)$, —$NRSO_2$— or —$SO_2$—NR.

In another embodiment, $R^6$ is hydrogen, an alkoxy group, or an alkyl ether group. In another further embodiment, $R^6$ is a hydroxyl, substituted or unsubstituted alkyl group. $R^6$ may be substituted with any substituent which allows the resulting compound of formula (I) to perform its intended function. In another embodiment, $R^6$ is a substituted or unsubstituted aryloxy group. Examples of substituted or unsubstituted $R^6$ aryloxy group include substituted or unsubstituted phenoxy group. These phenoxy groups may further be substituted with, for example, one or more substituted or unsubstituted alkyl groups.

In yet another embodiment, $R^6$ is a phosphate, alkyl phosphate, cycloalkyl phosphate, phosphonate, thiophosphate, alkylthiophosphate, cycloalkylthiophosphate, or thiophosphonate. Other examples of $R^6$ include carboxylic acids and substituted and unsubstituted alkyl esters and aryl esters.

In yet another further embodiment, $R^7$ is hydrogen, or a substituted or unsubstituted alkyl group. Examples of substituents for alkyl $R^7$ groups include hydroxy groups.

In yet another further embodiment, $R^8$ is hydrogen, hydroxyl, or substituted or unsubstituted alkyl.

In one embodiment, the invention provides compounds of Formula II:

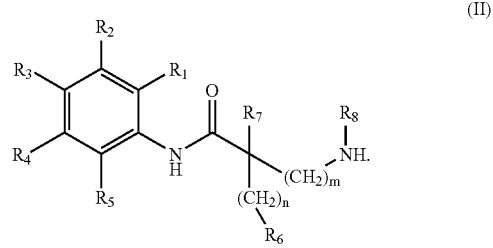

In a first set of compounds of Formula II, $R_4$ is $C_4$–$C_{20}$-alkoxy or an oxaalkyl, thiaalkyl or azaalkyl group having a chain length of from 4 to 20 atoms; a phenyl or substituted phenyl group, a phenoxy or substituted phenoxy group, a substituted or unsubstituted arylalkyl group, a substituted or unsubstituted arylalkoxy group, a substituted or unsubstituted heteroarylalkyl group; or a substituted or unsubstituted heteroarylalkoxy group. $R_1$, $R_2$, $R_3$ and $R_5$ are each independently selected from the group consisting of hydrogen, halogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-$SO_2$ and N(R)R', wherein R and R' are each independently hydrogen, halogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl or $C_1$–$C_6$-alkyl-$SO_2$. $R^6$ is —OH, —$CO_2R^9$, —$CH_2$=$CH(CO)OR^9$, —$OPO_2R^{10}R^{11}$, —$OPO_3R^{10}R^{11}$, —$CH_2PO_3R^{10}R^{11}$, —$OPO_2(S)R^{10}R^{11}$ or —$C(Y)(X)PO_3R^{10}R^{11}$, where X is hydroxyl or halide and Y is H or halide; or analogues of other carboxylate, phosphate or phosphonate isosteres not limited to those shown below; $R^9$ is H, straight chain or branched $C_1$–$C_6$-alkyl, or a substituted or unsubstituted aryl group; $R^{10}$ and $R^{11}$ are each independently H, straight chain or branched $C_1$–$C_6$-alkyl, a substituted or unsubstituted aryl group or selected from, but not limited to, the prodrugs listed below:

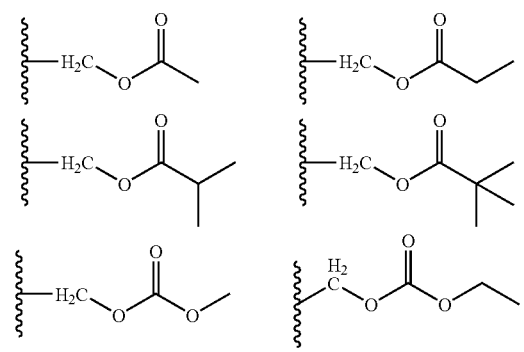

-continued

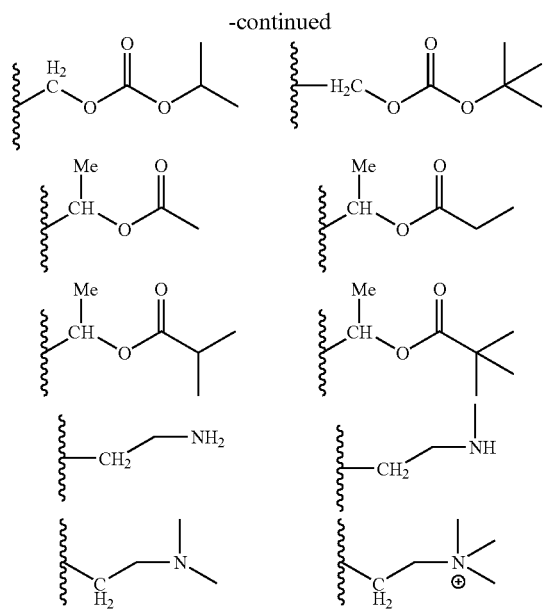

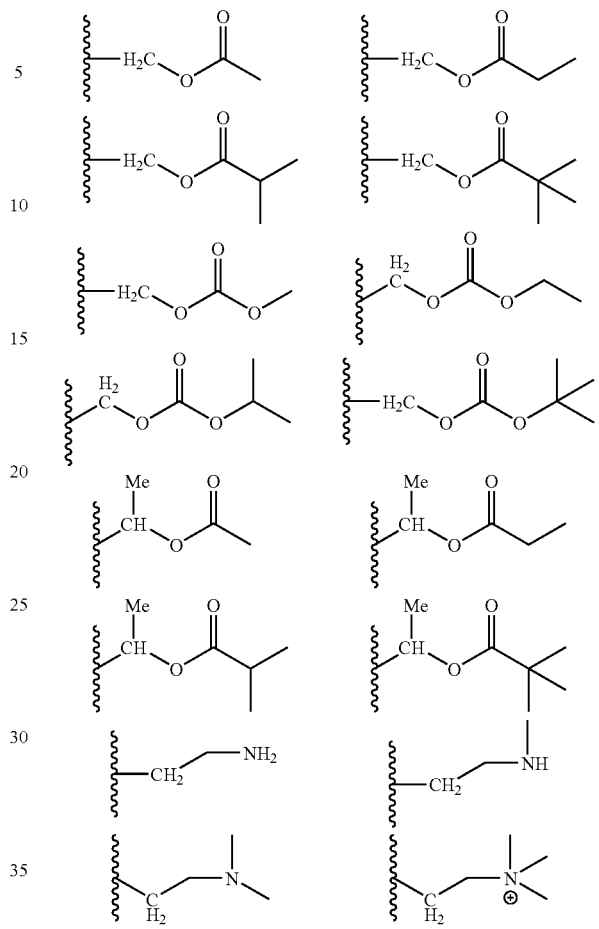

$R_7$ is H, $C_1$–$C_6$-alkyl, hydroxy-$C_1$–$C_6$-alkyl or aryl. $R_8$ is H or $C_1$–$C_6$-alkyl. $R_7$ and $R_8$ can also together form a $C_2$–$C_5$-alkylene or a $C_2$–$C_5$-alkenylene group; m and n are each, independently, an integer from 0 to 3; provided that when $R^4$ is $C_4$–$C_{20}$-alkyl, at least one of $R^1$, $R^2$, $R^3$ and $R^5$ is not hydrogen; and when $R^3$ is $C_4$–$C_{20}$-alkyl, at least one of $R^1$, $R^2$, $R^4$ and $R^5$ is not hydrogen; and pharmaceutically acceptable salts thereof.

In a second set of compounds of Formula II, $R_3$ is $C_4$–$C_{20}$-alkoxy or an oxaalkyl, thiaalkyl or azaalkyl group having a chain length of from 4 to 20 atoms; a phenyl or substituted phenyl group, a phenoxy or substituted phenoxy group, a substituted or unsubstituted arylalkyl group, a substituted or unsubstituted arylalkoxy group, a substituted or unsubstituted heteroarylalkyl group; or a substituted or unsubstituted heteroarylalkoxy group. $R_1$, $R_2$, $R_4$ and $R_5$ are each independently selected from the group consisting of hydrogen, halogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-SO$_2$ or N(R)R', wherein R and R' are each independently hydrogen, halogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl or $C_1$–$C_6$-alkyl-SO$_2$. $R^6$ is —OH, —CO$_2$R$^9$, —CH$_2$=CH(CO)OR$^9$, —OPO$_2$R$^{10}$R$^{11}$, —OPO$_3$R$^{10}$R$^{11}$, —CH$_2$PO$_3$R$^{10}$R$^{11}$, —OPO$_2$(S)R$^{10}$R$^{11}$ or —C(Y)(X)PO$_3$R$^{10}$R$^{11}$, where X is hydroxyl or halide and Y is H or halide; or analogues of other carboxylate, phosphate or phosphonate isosteres not limited to those shown below; $R^9$ is H, straight chain or branched $C_1$–$C_6$-alkyl, or a substituted or unsubstituted aryl group; $R^{10}$ and $R^{11}$ are each independently H, straight chain or branched $C_1$–$C_6$-alkyl, a substituted or unsubstituted aryl group or selected from, but not limited to, the prodrugs listed below:

$R_7$ is H, $C_1$–$C_6$-alkyl, hydroxy-$C_1$–$C_6$-alkyl or aryl. $R_8$ is H or $C_1$–$C_6$-alkyl. $R_7$ and $R_8$ can also together form a $C_2$–$C_5$-alkylene or a $C_2$–$C_5$-alkenylene group; m and n are each, independently, an integer from 0 to 3, provided that when $R^4$ is $C_4$–$C_{20}$-alkyl, at least one of $R^1$, $R^2$, $R^3$ and $R^5$ is not hydrogen; and when $R^3$ is $C_4$–$C_{20}$-alkyl, at least one of $R^1$, $R^2$, $R^4$ and $R^5$ is not hydrogen; and pharmaceutically acceptable salts thereof.

In a third set of compounds of Formula II, $R_3$ is $C_4$–$C_{20}$-alkyl and $R_1$, $R_2$, $R_4$ and $R_5$ are each independently selected from the group consisting of hydrogen, halogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-SO$_2$ or N(R)R', wherein R and R' are each independently hydrogen, halogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl or $C_1$–$C_6$-alkyl-SO$_2$, provided that at least one of $R_1$, $R_2$, $R_4$ and $R_5$ is not hydrogen. $R^6$ is —OH, —CO$_2$R$^9$, —CH$_2$=CH(CO)OR$^9$, —OPO$_2$R$^{10}$R$^{11}$, —OPO$_3$R$^{10}$R$^{11}$, —CH$_2$PO$_3$R$^{10}$R$^{11}$, —OPO$_2$(S)R$^{10}$R$^{11}$ or —C(Y)(X) PO$_3$R$^{10}$R$^{11}$, where X is hydroxyl or halide and Y is H or halide; or analogues of other carboxylate, phosphate or phosphonate isosteres not limited to those shown below; $R^9$ is H, straight chain or branched $C_1$–$C_6$-alkyl, or a substituted or unsubstituted aryl group; $R^{10}$ and $R^{11}$ are each independently H, straight chain or branched $C_1$–$C_6$-alkyl, a substituted or unsubstituted aryl group or selected from, but not limited to, the prodrugs listed below:

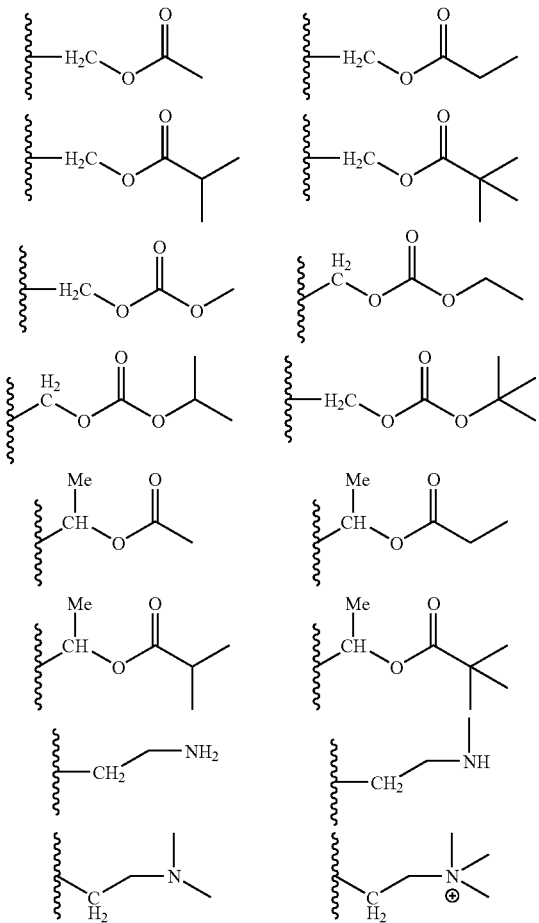

$R_7$ is H, $C_1$–$C_6$-alkyl, hydroxy-$C_1$–$C_6$-alkyl or aryl. $R_8$ is H or $C_1$–$C_6$-alkyl. $R_7$ and $R_8$ can also together form a $C_2$–$C_5$-alkylene or a $C_2$–$C_5$-alkenylene group; m and n are each, independently, an integer from 0 to 3; provided that when $R^4$ is $C_4$–$C_{20}$-alkyl, at least one of $R^1$, $R^2$, $R^3$ and $R^5$ is not hydrogen; and when $R^3$ is $C_4$–$C_{20}$-alkyl, at least one of $R^1$, $R^2$, $R^4$ and $R^5$ is not hydrogen; and pharmaceutically acceptable salts thereof.

In a fourth set of compounds of Formula II, $R_4$ is $C_4$–$C_{20}$-alkyl; $R_1$, $R_2$, $R_3$ and $R_5$ are each independently selected from the group consisting of hydrogen, halogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-$SO_2$ or N(R)R', wherein R and R' are each independently hydrogen, straight chain or branched $C_1$–$C_6$-alkyl, straight chain or branched $C_1$–$C_6$-alkoxy, straight chain or branched halo-$C_1$–$C_6$-alkoxy, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl or $C_1$–$C_6$-alkyl-$SO_2$, provided that at least one of $R_1$, $R_2$, $R_3$ and $R_5$ is not hydrogen. $R^6$ is —OH, —$CO_2R^9$, —$CH_2$=CH(CO)$OR^9$, —$OPO_2R^{10}R^{11}$, —$OPO_3R^{10}R^{11}$, —$CH_2PO_3R^{10}R^{11}$, —$OPO_2(S)R^{10}R^{11}$ or —C(Y)(X)$PO_3R^{10}R^{11}$, where X is hydroxyl or halide and Y is H or halide; or analogues of other carboxylate, phosphate or phosphonate isosteres not limited to those shown below; $R^9$ is H, straight chain or branched $C_1$–$C_6$-alkyl, or a substituted or unsubstituted aryl group $R^{10}$ and $R^{11}$ are each independently H, straight chain or branched $C_1$–$C_6$-alkyl, a substituted or unsubstituted aryl group or selected from, but not limited to, the prodrugs listed below:

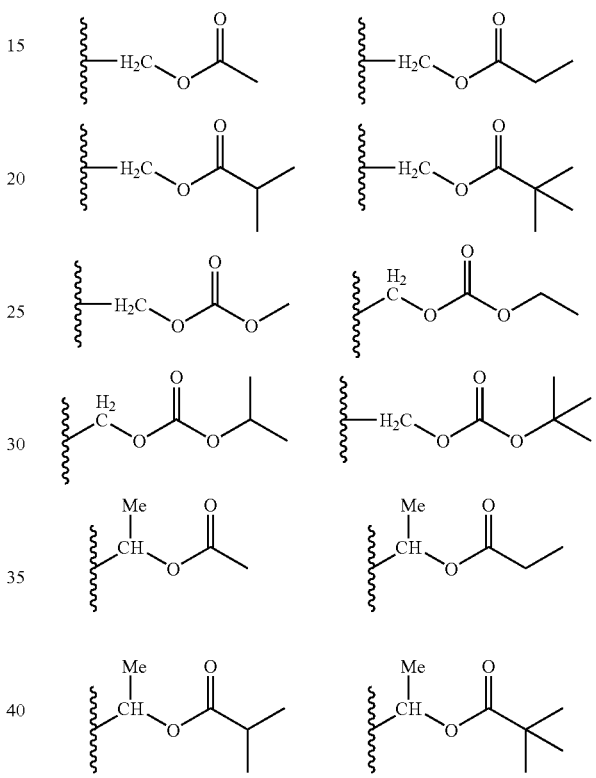

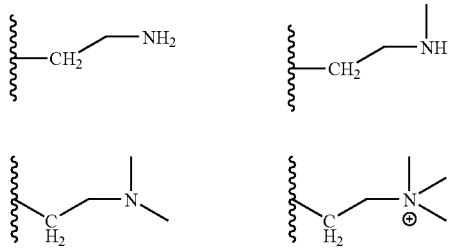

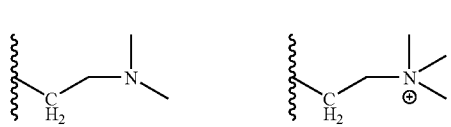

$R_7$ is H, $C_1$–$C_6$-alkyl, hydroxy-$C_1$–$C_6$-alkyl or aryl. $R_8$ is H or $C_1$–$C_6$-alkyl. $R_7$ and $R_8$ can also together form a $C_2$–$C_5$-alkylene or a $C_2$–$C_5$-alkenylene group; m and n are each, independently, an integer from 0 to 3; provided that when $R^4$ is $C_4$–$C_{20}$-alkyl, at least one of $R^1$, $R^2$, $R^3$ and $R^5$ is not hydrogen; and when $R^3$ is $C_4$–$C_{20}$-alkyl, at least one of $R^1$, $R^2$, $R^4$ and $R^5$ is not hydrogen; and pharmaceutically acceptable salts thereof;

A preferred subset of compounds of the invention are the compounds of Formula IV:

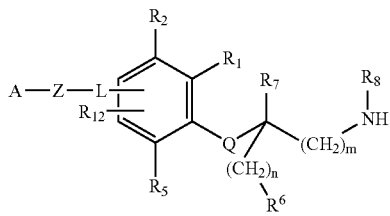

wherein:

L is alkoxy, a covalent bond, substituted or unsubstituted alkyl, alkylcarbonyl, thioether, alkylsulfonyl, alkylcarbonylamino, alkylaminocarbonyl, alkyloxycarbonyl, alkylcarbonyloxy, or substituted or unsubstituted heteroaryl;

Z and A are each independently substituted or unsubstituted aryl, wherein Z and A may be linked by a covalent bond, substituted or unsubstituted alkyl, NH, alkyloxy, O, thioether, S, aminocarbonyl, carbonylamino, carbonyloxy, or oxycarbonyl;

$R^1$, $R^2$, $R^5$ and $R^{12}$ are each independently selected from the group consisting of hydrogen, halogen, cyano, substituted or unsubstituted aryl, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-SO$_2$ or N(R)R', wherein R and R' are each independently hydrogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl or $C_1$–$C_6$-alkyl-SO$_2$;

Q is —CH$_2$NR—, —CH$_2$NR(CO)—, —NH(CO)—, —(CO)NH—, —(CO)—, —O—, —S—, —SO—, —SO$_2$—, —NRSO$_2$—, —SO$_2$—NR— or heteroaryl, where R is hydrogen or straight chain or branched $C_1$–$C_6$-alkyl;

$R^6$ is —OH, —CO$_2$R$^9$, —CH$_2$=CH(CO)OR$^9$, —OPO$_2$R$^{10}$R$^{11}$, —OPO$_3$R$^{10}$R$^{11}$, —CH$_2$PO$_3$R$^{10}$R$^{11}$, —OPO$^2$(S)R$^{10}$R$^{11}$ or —C(Y)(X)PO$_3$R$^{10}$R$^{11}$, where X is hydroxyl or halide and Y is H or halide; or analogues of other carboxylate, phosphate or phosphonate isosteres not limited to those shown below; R$^9$ is H, straight chain or branched $C_1$–$C_6$-alkyl, or a substituted or unsubstituted aryl group; R$^{10}$ and R$^{11}$ are each independently H, straight chain or branched $C_1$–$C_6$-alkyl, a substituted or unsubstituted aryl group or selected from, but not limited to, the prodrugs listed below:

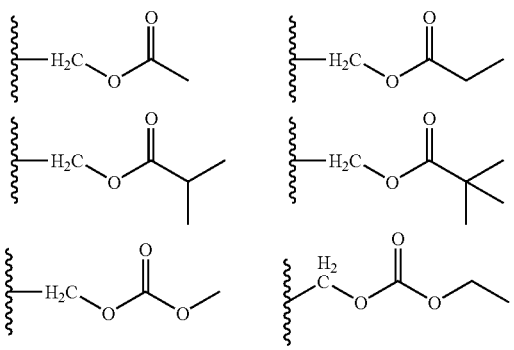

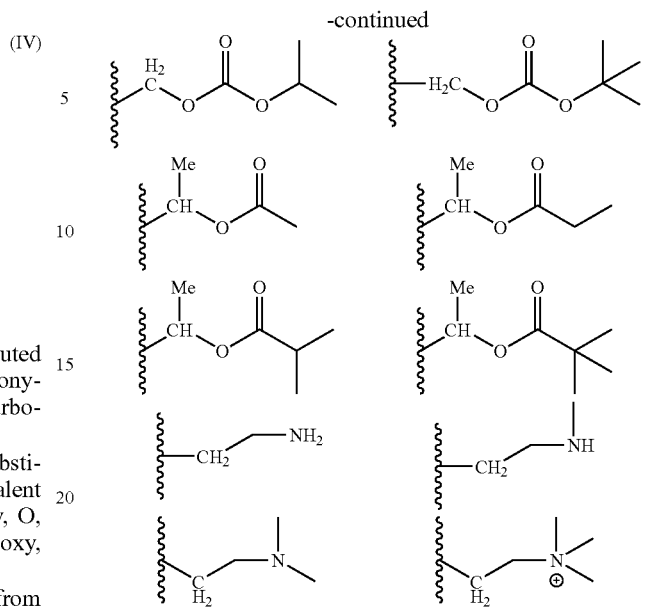

R$^7$ is H, $C_1$–$C_6$-alkyl, hydroxy-$C_1$–$C_6$-alkyl, aryl, or together with R8 form a $C_2$–$C_5$-alkylene or a $C_2$–$C_5$-alkenylene group;

R$^8$ is H or $C_1$–$C_6$-alkyl; and m and n are each, independently, an integer from 0 to 3;

provided that when R$^4$ is $C_4$–$C_{20}$-alkyl, at least one of R$^1$, R$^2$, R$^3$ and R$^5$ is not hydrogen; and when R$^3$ is $C_4$–$C_{20}$-alkyl, at least one of R$^1$, R$^2$, R$^4$ and R$^5$ is not hydrogen; and pharmaceutically acceptable salts thereof.

In yet another embodiment, the present invention provides compounds of Formula V:

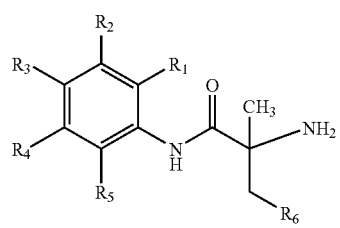

In a first set of compounds of Formula V, R$_3$ is $C_6$–$C_{12}$-alkoxy or an oxaalkyl, thiaalkyl or azaalkyl group having a chain length of from 6 to 12 atoms; a phenyl or C1–C6-aalkylphenyl group, a phenoxy or C1–C6-alkylphenoxy group, a substituted or unsubstituted arylalkyl group, a substituted or unsubstituted arylalkoxy group, a substituted or unsubstituted heteroarylalkyl group; or a substituted or unsubstituted heteroarylalkoxy group. R$_1$, R$_2$, R$_4$ and R$_5$ are each independently selected from the group consisting of hydrogen, halogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-SO$_2$ and N(R)R', wherein R and R' are each independently hydrogen, straight chain or branched $C_1$–$C_6$-alkyl, straight chain or branched $C_1$–$C_6$-alkoxy, straight chain or branched halo- $C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl or $C_1$–$C_6$-alkyl-$SO_2$. $R^6$ is —OH, —$CO_2R^9$, —$CH_2$=$CH(CO)OR^9$, —$OPO_2R^{10}R^{11}$, —$OPO_3R^{10}R^{11}$, —$CH_2PO_3R^{10}R^{11}$, —$OPO_2(S)R^{10}R^{11}$ or —$C(Y)(X)PO_3R^{10}R^{11}$, where X is hydroxyl or halide and Y is H or halide; or analogues of other carboxylate, phosphate or phosphonate isosteres not limited to those shown below; $R^9$ is H, straight chain or branched $C_1$–$C_6$-alkyl, or a substituted or unsubstituted aryl group; $R^{10}$ and $R^{11}$ are each independently H, straight chain or branched $C_1$–$C_6$-alkyl, a substituted or unsubstituted aryl group or selected from, but not limited to, the prodrugs listed below:

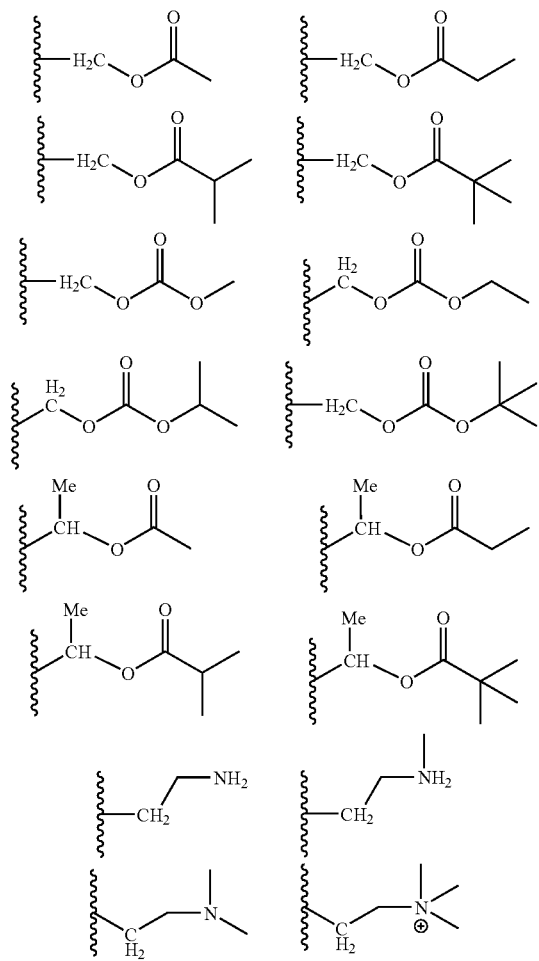

In a second set of compounds of Formula V, $R_4$ is $C_6$–$C_{12}$-alkoxy or an oxaalkyl, thiaalkyl or azaalkyl group having a chain length of from 6 to 12 atoms; a phenyl or C1–C6-aalkylphenyl group, a phenoxy or C1–C6-alkylphenoxy group, a substituted or unsubstituted arylalkyl group, a substituted or unsubstituted arylalkoxy group, a substituted or unsubstituted heteroarylalkyl group; or a substituted or unsubstituted heteroarylalkoxy group. $R_1$, $R_2$, $R_3$ and $R_5$ are each independently selected from the group consisting of hydrogen, halogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-$SO_2$ or N(R)R', wherein R and R' are each independently hydrogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl or $C_1$–$C_6$-alkyl-$SO_2$. $R^6$ is —OH, —$CO_2R^9$, —$CH_2$=$CH(CO)OR^9$, —$OPO_2R^{10}R^{11}$, —$OPO_3R^{10}R^{11}$, —$CH_2PO_3R^{10}R^{11}$, —$OPO_2(S)R^{10}R^{11}$ or —$C(Y)(X)PO_3R^{10}R^{11}$, where X is hydroxyl or halide and Y is H or halide; or analogues of other carboxylate, phosphate or phosphonate isosteres not limited to those shown below; $R^9$ is H, straight chain or branched $C_1$–$C_6$-alkyl, or a substituted or unsubstituted aryl group; $R^{10}$ and $R^{11}$ are each independently H, straight chain or branched $C_1$–$C_6$-alkyl, a substituted or unsubstituted aryl group or selected from, but not limited to, the prodrugs listed below:

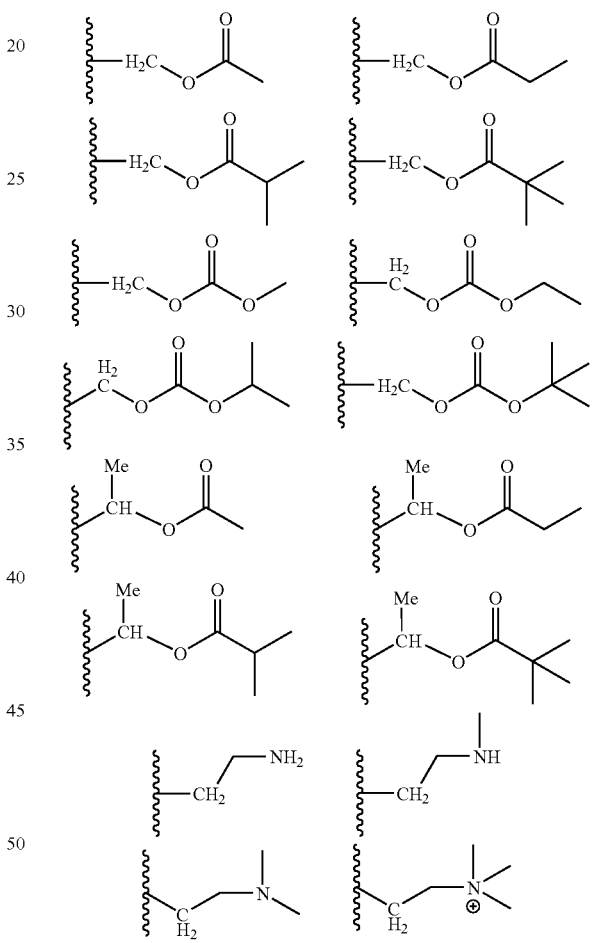

In a third set of compounds of Formula V, $R_3$ is $C_6$–$C_{12}$-alkyl; $R_1$, $R_2$, $R_4$ and $R_5$ are each independently selected from the group consisting of hydrogen, halogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-$SO_2$ or N(R)R', wherein R and R' are each independently hydrogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$- alkyl, hydroxyl-$C_1$–$C_6$-alkyl, carboxy-$C_1$–$C_6$-alkyl or $C_1$–$C_6$-alkyl-$SO_2$, and at least one of $R_1$, $R_2$, $R_4$ and $R_5$ is not hydrogen. $R^6$ is —OH, —$CO_2R^9$, —$CH_2$=CH(CO)$OR^9$, —$OPO_2R^{10}R^{11}$, —$OPO_3R^{10}R^{11}$, —$CH_2PO_3R^{10}R^{11}$, —$OPO_2(S)R^{10}R^{11}$ or —$C(Y)(X)PO_3R^{10}R^{11}$, where X is hydroxyl or halide and Y is H or halide; or analogues of other carboxylate, phosphate or phosphonate isosteres not limited to those shown below; $R^9$ is H, straight chain or branched $C_1$–$C_6$-alkyl, or a substituted or unsubstituted aryl group; $R^{10}$ and $R^{11}$ are each independently H, straight chain or branched $C_1$–$C_6$-alkyl, a substituted or unsubstituted aryl group or selected from, but not limited to, the prodrugs listed below:

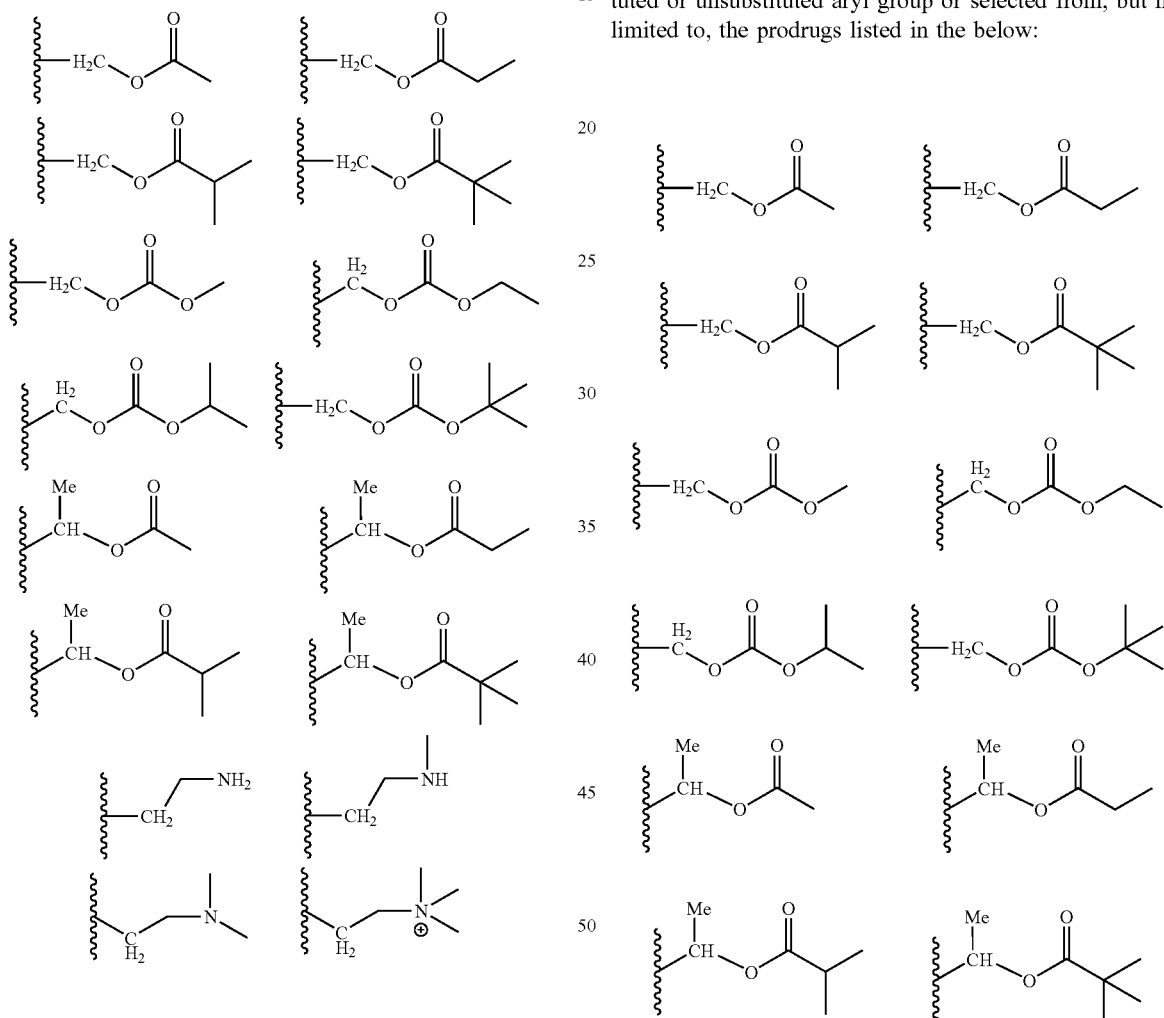

provided that when $R^4$ is $C_4$–$C_{20}$-alkyl, at least one of $R^1$, $R^2$, $R^3$ and $R^5$ is not hydrogen; and when $R^3$ is $C_4$–$C_{20}$-alkyl, at least one of $R^1$, $R^2$, $R^4$ and $R^5$ is not hydrogen; and pharmaceutically acceptable salts thereof.

In a fourth set of compounds of Formula V, $R_4$ is $C_6$–$C_{12}$-alkyl; $R_1$, $R_2$, $R_3$ and $R_5$ are each independently selected from the group consisting of hydrogen, halogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-$SO_2$ and N(R)R', wherein R and R' are each independently hydrogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl or $C_1$–$C_6$-alkyl-$SO_2$, and at least one of $R_1$, $R_2$, $R_3$ and $R_5$ is not hydrogen. $R^6$ is —OH, —$CO_2R^9$, —$CH_2$=CH(CO)$OR^9$, —$OPO_2R^{10}R^{11}$, —$OPO_3R^{10}R^{11}$, —$CH_2PO_3R^{10}R^{11}$, —$OPO_2(S)R^{10}R^{11}$ or —$C(Y)(X)PO_3R^{10}R^{11}$, where X is hydroxyl or halide and Y is H or halide; or analogues of other carboxylate, phosphate or phosphonate isosteres not limited to those shown below; $R^9$ is H, straight chain or branched $C_1$–$C_6$-alkyl, or a substituted or unsubstituted aryl group; $R^{10}$ and $R^{11}$ are each independently H, straight chain or branched $C_1$–$C_6$-alkyl, a substituted or unsubstituted aryl group or selected from, but not limited to, the prodrugs listed in the below:

The compounds of Formula I can have the stereochemistry shown below as Formula V or Formula VI, wherein $R_1$–$R_8$ have the meanings given above for Formula I:

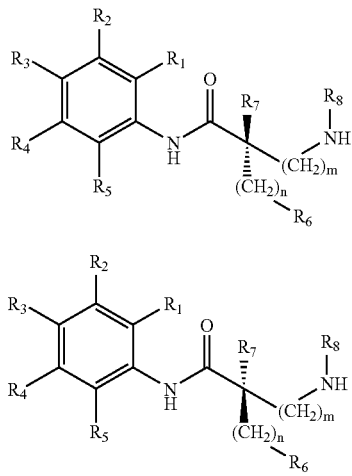

In a first subset of compounds of Formula VI, $R_4$ is $CH_3(CH_2)_7$—O— or $CH_3(CH_2)_6$—O—; and $R_1$, $R_2$, $R_3$ and $R_5$ are independently selected from the group consisting of hydrogen, methyl, chloro, fluoro, and methoxy. In a preferred embodiment, at least one of $R_1$, $R_2$, $R_3$ and $R_5$ is not hydrogen.

In a second subset of compounds of Formula VI, $R_3$ is $CH_3(CH_2)_7$—O— or $CH_3(CH_2)_6$—O—; and $R_1$, $R_2$, $R_4$ and $R_5$ are independently selected from the group consisting of hydrogen, methyl, chloro, fluoro, trifluoromethyl and methoxy. In a preferred embodiment, at least one of $R_1$, $R_2$, $R_4$ and $R_5$ is not hydrogen.

In a third subset of compounds of Formula VI, $R_4$ is $CH_3(CH_2)_8$— or $CH_3(CH_2)_7$—; and $R_1$, $R_2$, $R_3$ and $R_5$ are independently selected from the group consisting of hydrogen, methyl, chloro, fluoro, trifluoromethyl, and methoxy, provided that at least one of $R_1$, $R_2$, $R_3$ and $R_5$ is not hydrogen.

In a fourth subset of compounds of Formula VI, $R_3$ is $CH_3(CH_2)_8$— or $CH_3(CH_2)_7$—; and $R_1$, $R_2$, $R_4$ and $R_5$ are independently selected from the group consisting of hydrogen, methyl, chloro, fluoro, trifluoromethyl and methoxy, provided that at least one of $R_1$, $R_2$, $R_4$ and $R_5$ is not hydrogen.

In a first subset of compounds of Formula VII, $R_4$ is $CH_3(CH_2)_7$—O— or $CH_3(CH_2)_6$—O—; and $R_1$, $R_2$, $R_3$ and $R_5$ are independently selected from the group consisting of hydrogen, methyl, chloro, fluoro, and methoxy. In a preferred embodiment, at least one of $R_1$, $R_2$, $R_3$ and $R_5$ is not hydrogen.

In a second subset of compounds of Formula VII, $R_3$ is $CH_3(CH_2)_7$—O— or $CH_3(CH_2)_6$—O—; and $R_1$, $R_2$, $R_4$ and $R_5$ are independently selected from the group consisting of hydrogen, methyl, chloro, fluoro, trifluoromethyl and methoxy. In a preferred embodiment, at least one of $R_1$, $R_2$, $R_4$ and $R_5$ is not hydrogen.

In a third subset of compounds of Formula VIII, $R_4$ is $CH_3(CH_2)_8$— or $CH_3(CH_2)_7$—; and $R_1$, $R_2$, $R_3$ and $R_5$ are independently selected from the group consisting of hydrogen, methyl, chloro, fluoro, trifluoromethyl, and methoxy, provided that at least one of $R_1$, $R_2$, $R_3$ and $R_5$ is not hydrogen.

In a fourth subset of compounds of Formula VIII, $R_3$ is $CH_3(CH_2)_8$— or $CH_3(CH_2)_7$—; and $R_1$, $R_2$, $R_4$ and $R_5$ are independently selected from the group consisting of hydrogen, methyl, chloro, fluoro, trifluoromethyl and methoxy, provided that at least one of $R_1$, $R_2$, $R_4$ and $R_5$ is not hydrogen.

A preferred subset of compounds of Formula III includes compounds of Formula IX:

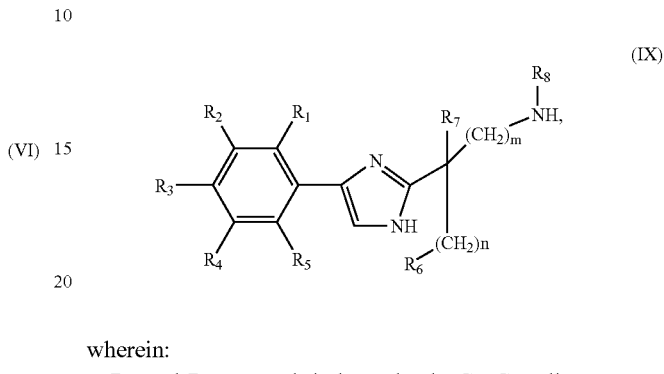

wherein:

$R_3$ and $R_4$ are each independently $C_6$–$C_{12}$-alkoxy or an oxaalkyl, thiaalkyl or azaalkyl group having a chain length of from 6 to 12 atoms; a phenyl or $C_1$–$C_6$-alkylphenyl group, a phenoxy or $C_1$–$C_6$-alkylphenoxy group, a substituted or unsubstituted arylalkyl group, a substituted or unsubstituted arylalkoxy group, a substituted or unsubstituted heteroarylalkyl group; or a substituted or unsubstituted heteroarylalkoxy group;

$R_1$, $R_2$, and $R_5$ are each independently selected from the group consisting of hydrogen, halogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-$SO_2$ and N(R)R', wherein R and R' are each independently hydrogen, straight chain or branched $C_1$–$C_6$-alkyl, straight chain or branched $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl or $C_1$–$C_6$-alkyl-$SO_2$;

$R^6$ is —OH, —$CO_2R^9$, —$CH_2$=CH(CO)$OR^9$, —$OPO_2R^{10}R^{11}$, —$OPO_3R^{10}R^{11}$, —$CH_2PO_3R^{10}R^{11}$, —$OPO^2(S)R^{10}R^{11}$ or —C(Y)(X)$PO_3R^{10}R^{11}$, where X is hydroxyl or halide and Y is H or halide; or analogues of other carboxylate, phosphate or phosphonate isosteres not limited to those shown below; $R^9$ is H, straight chain or branched $C_1$–$C_6$-alkyl, or a substituted or unsubstituted aryl group; $R^{10}$ and $R^{11}$ are each independently H, straight chain or branched $C_1$–$C_6$-alkyl, a substituted or unsubstituted aryl group or selected from, but not limited to, the prodrugs listed below:

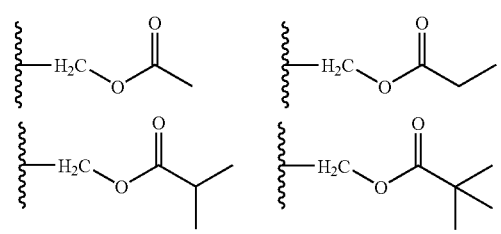

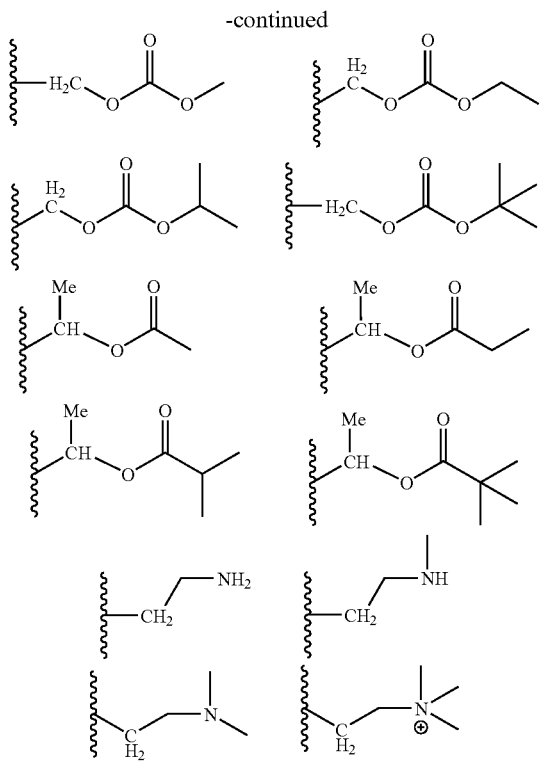

provided that when $R^4$ is $C_4$–$C_{20}$-alkyl, at least one of $R^1$, $R^2$, $R^3$ and $R^5$ is not hydrogen; and when $R^3$ is $C_4$–$C_{20}$-alkyl, at least one of $R^1$, $R^2$, $R^4$ and $R^5$ is not hydrogen; and pharmaceutically acceptable salts thereof;

The invention also provides compounds of Formula X or Formula XI:

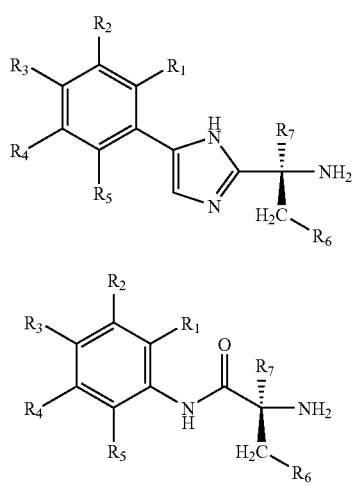

wherein:

$R_3$ and $R_4$ are selected from the group consisting of optionally substituted $C_6$–$C_{10}$-alkoxy, optionally substituted aryl-$C_1$–$C_6$-alkoxy, optionally substituted heteroaryl-$C_1$–$C_6$-alkoxy, optionally substituted cycloalkyl-$C_1$–$C_6$-alkoxy, optionally substituted aryl-$C_1$–$C_6$-alkyl, optionally substituted heteroaryl-$C_1$–$C_6$-alkyl, optionally substituted cycloalkyl-$C_1$–$C_6$-alkyl, optionally substituted aryl, optionally substituted heteroaryl, optionally substituted aryloxy and optionally substituted heteroaryloxy;

$R_1$, $R_2$, and $R_5$ are each independently selected from the group consisting of halogen, trifluoromethyl, $C_1$–$C_6$-alkyl, and $C_1$–$C_6$-alkoxy;

$R_7$ is a $C_1$–$C_6$-alkyl group, preferably methyl; and $R^6$ is —OH, —$CO_2R^9$, —$CH_2$=CH(CO)$OR^9$, —$OPO_2R^{10}R^{11}$, —$OPO_3R^{10}R^{11}$, —$CH_2PO_3R^{10}R^{11}$, —$OPO_2(S)R^{10}R^{11}$ or —C(Y)(X)$PO_3R^{10}R^{11}$, where X is hydroxyl or halide and Y is H or halide; or analogues of other carboxylate, phosphate or phosphonate isosteres not limited to those shown below; $R^9$ is H, straight chain or branched $C_1$–$C_6$-alkyl, or a substituted or unsubstituted aryl group; $R^{10}$ and $R^{11}$ are each independently H, straight chain or branched $C_1$–$C_6$-alkyl, a substituted or unsubstituted aryl group or selected from, but not limited to, the prodrugs listed below:

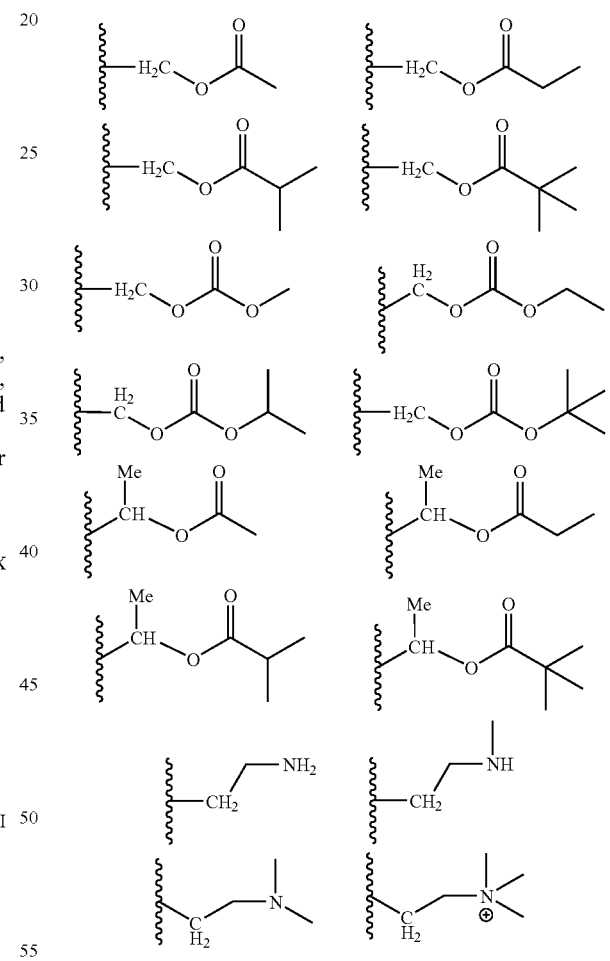

and pharmaceutically acceptable salts, esters and prodrugs thereof.

$R_3$ and $R_4$ are preferably biphenyl-$C_1$–$C_4$-alkoxy, where the biphenyl group optionally includes one or more substituents selected from $C_1$–$C_4$-alkyl, $C_1$–$C_4$-alkenyl, $C_1$–$C_4$-alkoxy, cyano, halogen and trifluoromethyl; phenyl-$C_1$–$C_4$-alkoxy, wherein the phenyl group optionally includes one or more substituents selected from $C_1$–$C_4$-alkyl, $C_1$–$C_4$-alkenyl, $C_1$–$C_4$-alkoxy, cyano, halogen, methylenedioxy, and trifluoromethyl; naphthyl-$C_1$–$C_4$-alkoxy, wherein the naphthyl group optionally includes one or more substituents selected from $C_1$–$C_4$-alkyl, $C_1$–$C_4$-alkenyl, $C_1$–$C_4$-alkoxy, cyano, halogen and trifluoromethyl; $C_5$–$C_8$-cycloalkyl-$C_1$–$C_4$-alkoxy; heteroaryl-$C_1$–$C_4$-alkoxy, wherein the heteroaryl group is imidazolyl; 2-, 3- or 4-pyridyl; or thiophene, optionally substituted by one or more $C_1$–$C_4$-alkyl, $C_1$–$C_4$-alkenyl, $C_1$–$C_4$-alkoxy, cyano, halogen, benzyl, benzyloxy or trifluoromethyl groups; phenyl, optionally substituted by one or more $C_1$–$C_4$-alkyl, $C_1$–$C_4$-alkenyl, $C_1$–$C_4$-alkoxy, cyano, halogen, methylenedioxy, benzyl, benzyloxy or trifluoromethyl groups; naphthyl, optionally substituted by one or more $C_1$–$C_4$-alkyl, $C_1$–$C_4$-alkenyl, $C_1$–$C_4$-alkoxy, cyano, halogen, methylenedioxy, benzyl, benzyloxy or trifluoromethyl groups; or heteroaryl, such as imidazolyl; 2-, 3- or 4-pyridyl or thiophene; optionally substituted by one or more $C_1$–$C_4$-alkyl, $C_1$–$C_4$-alkenyl, $C_1$–$C_4$-alkoxy, cyano, halogen, benzyl, benzyloxy or trifluoromethyl groups.

In one set of compounds of Formulas X and XI, $R_3$ or $R_4$ is a group selected from, but not limited to, those shown below:

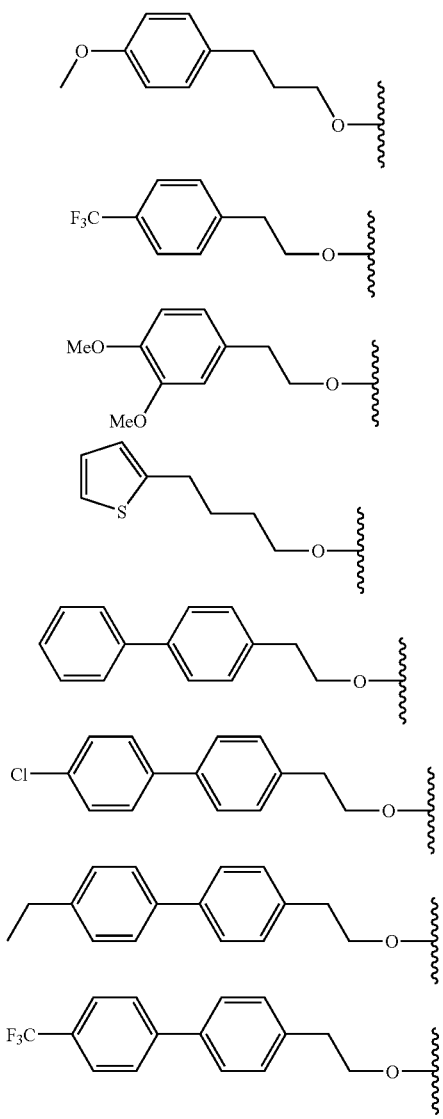

-continued

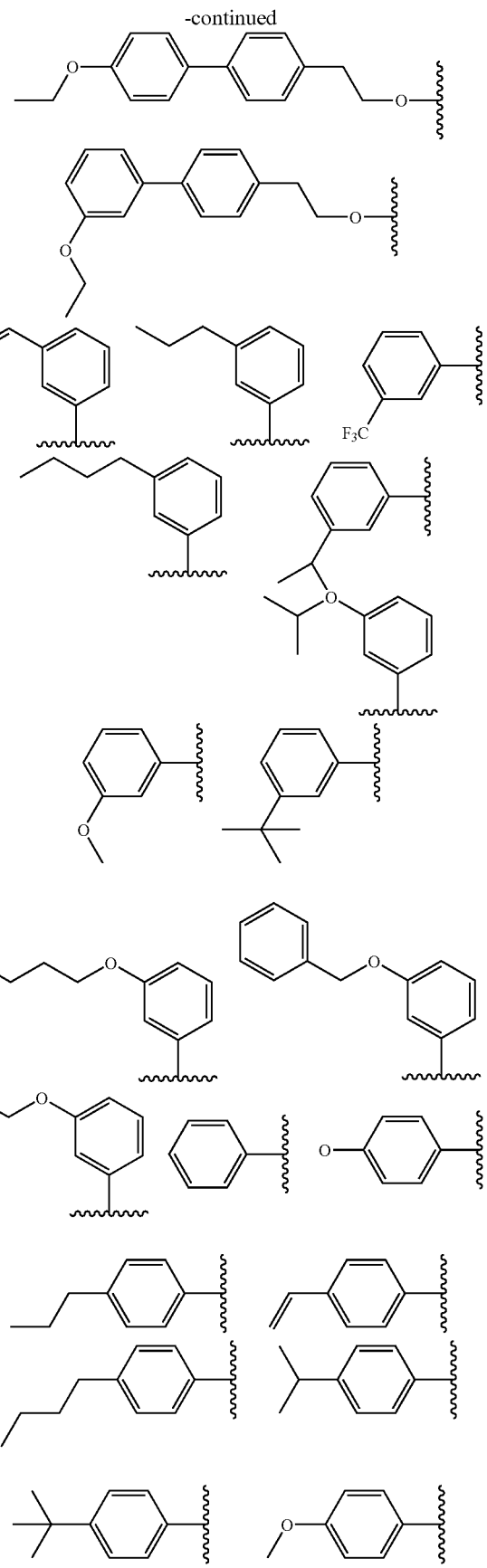

-continued

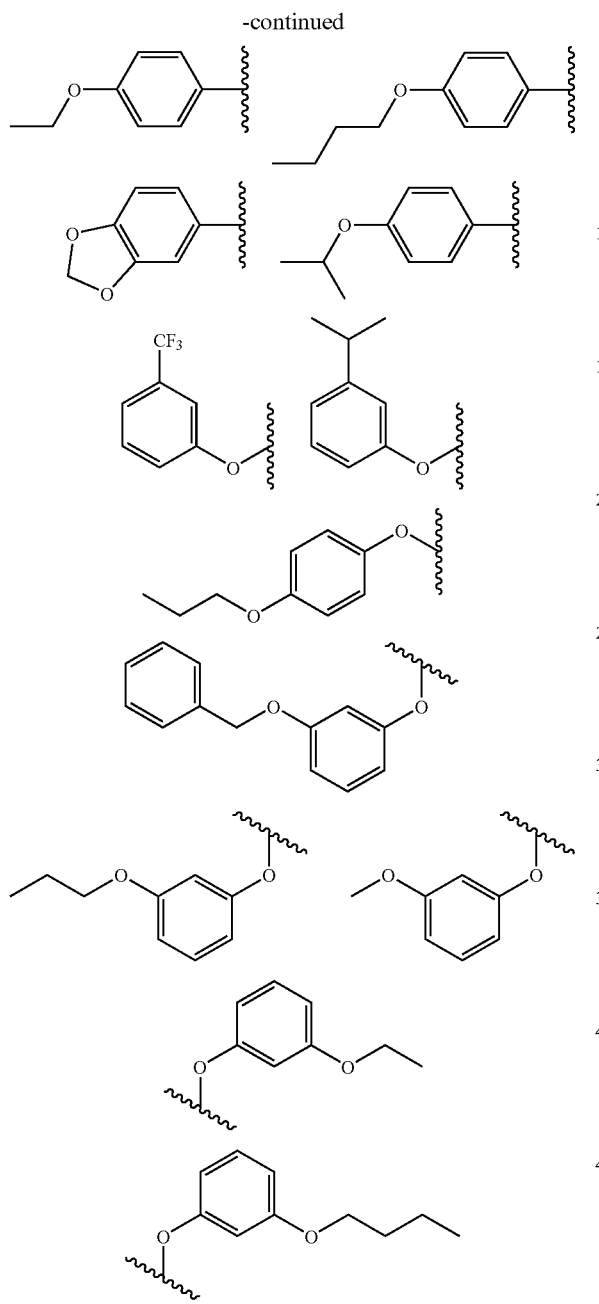

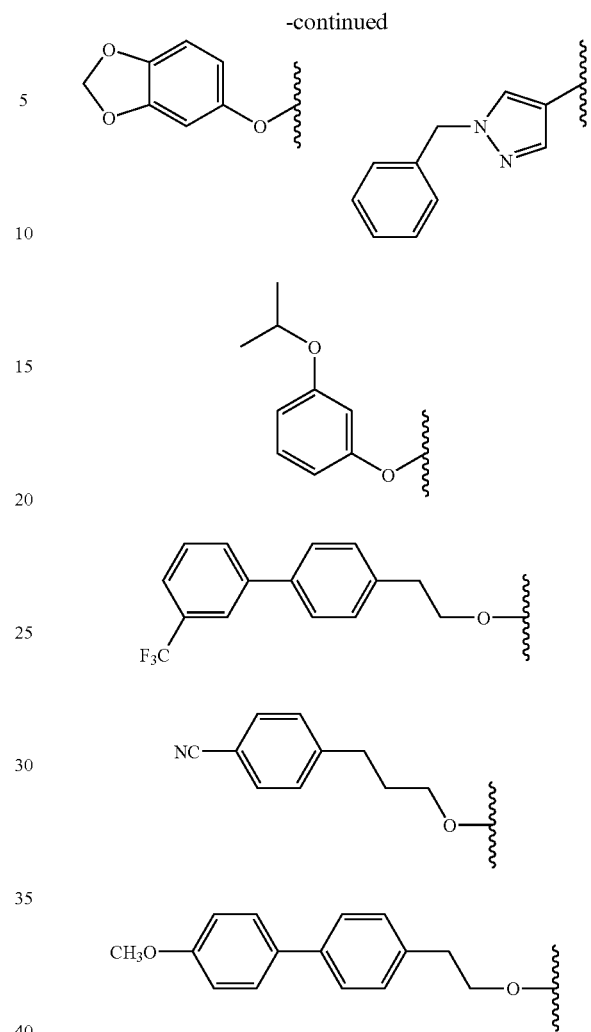

Specific compounds of the invention include, but are not limited to, those set forth below and their salts. While the compounds below are represented as alcohols ($R_6$ is hydroxy) or phosphates ($R_6$ is $-OPO_3H_2$), specific compounds of the invention further include derivatives of these compounds where $R_6$ is carboxylate, methylenephosphonate, thiophosphate hydroxymethylenephosphonate, fluoromethylenephosphonate.

34

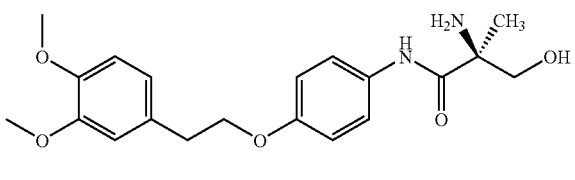

38

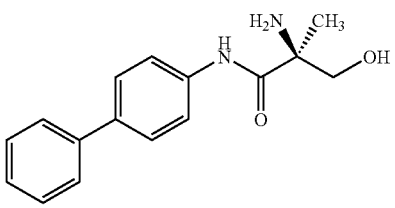

-continued
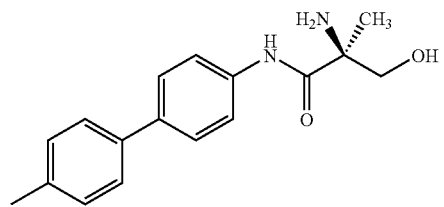
39
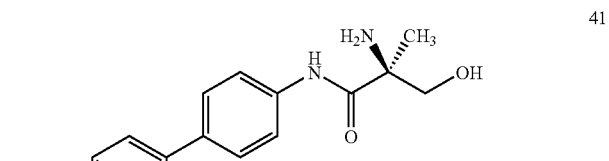
41
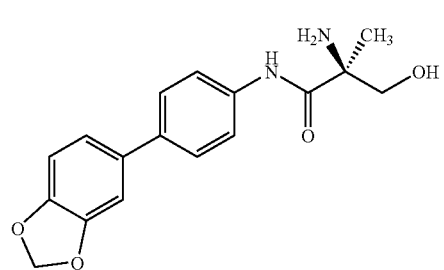
42
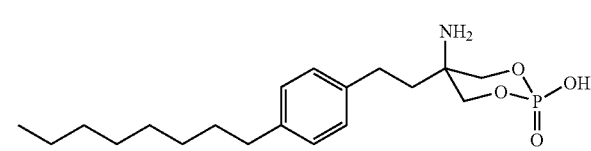
40
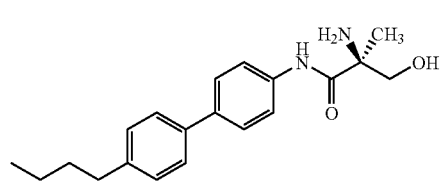
44
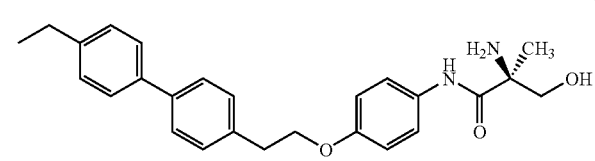
45
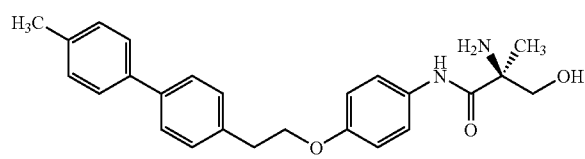
43
47
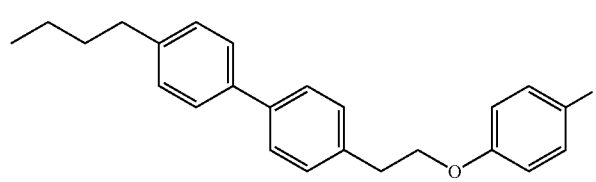
48
46
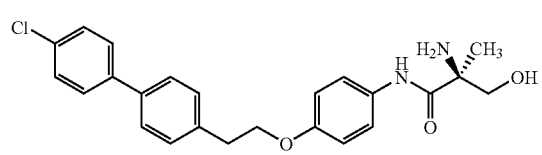
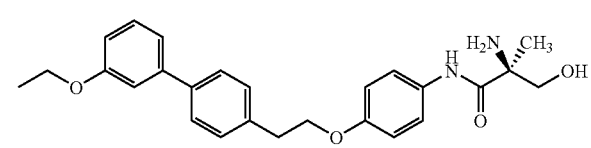
50
51
49
53

-continued
54
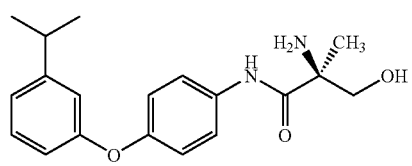
52
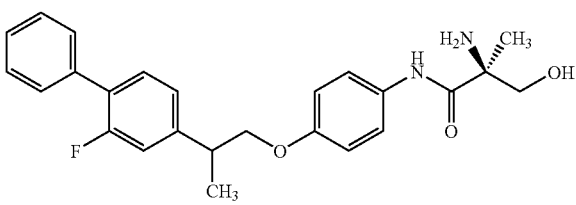
56
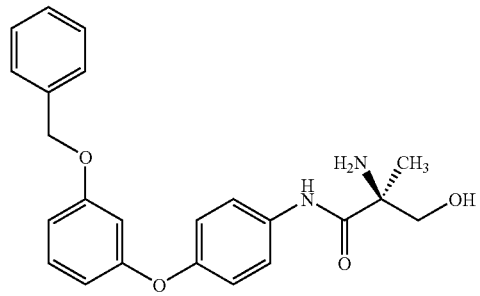
57
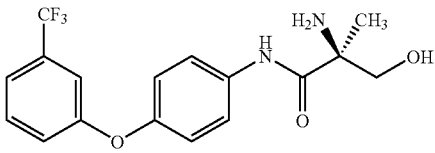
55
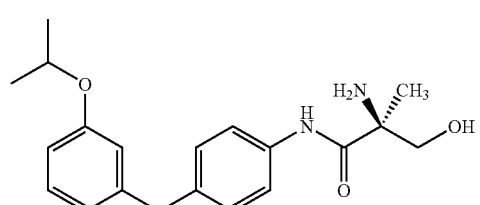
59
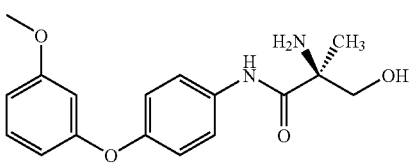
60
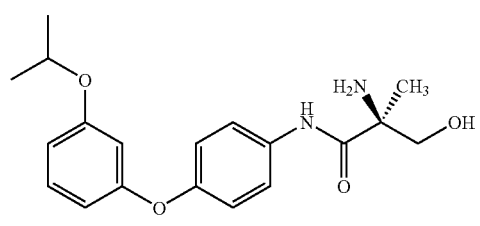
58
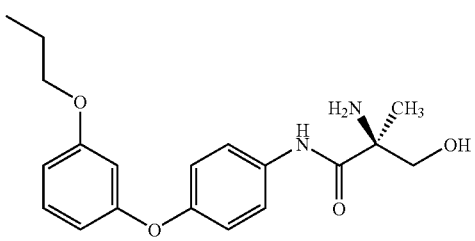
62
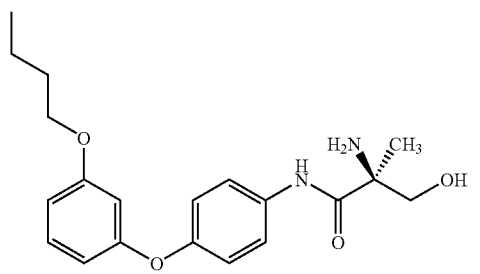
63
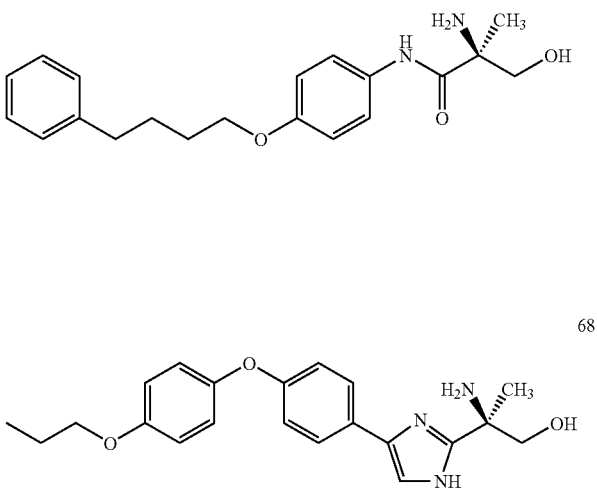
61
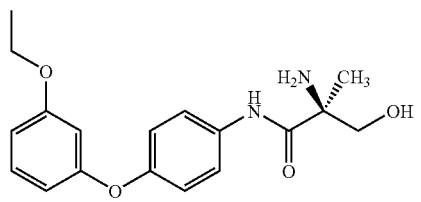

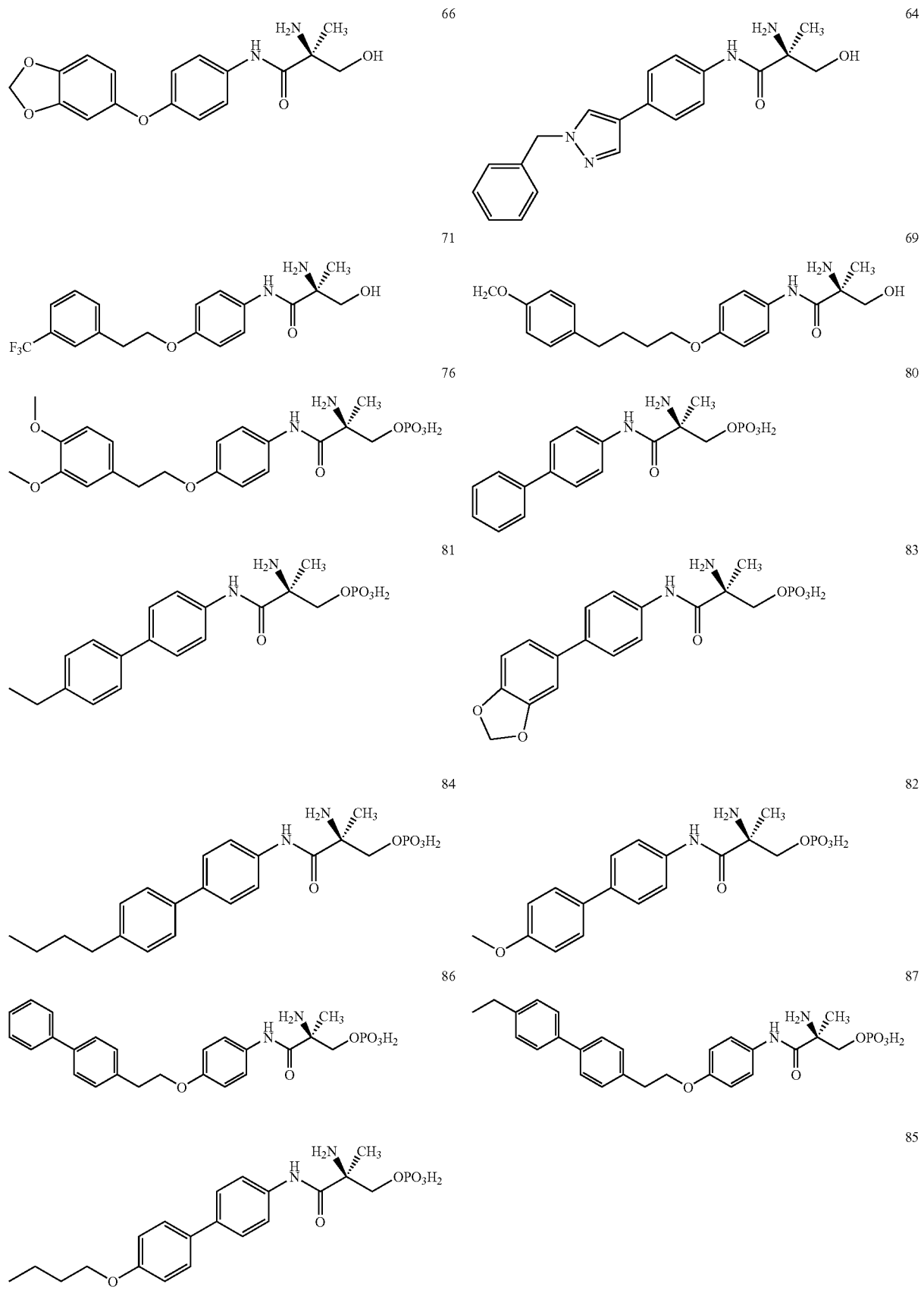

-continued
89
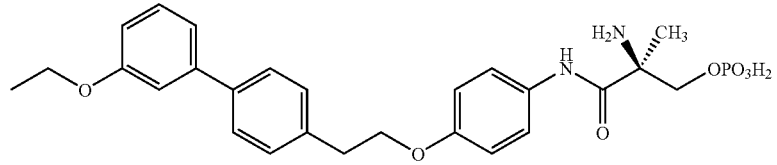
90
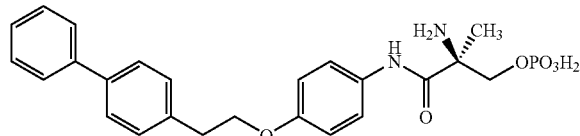
88
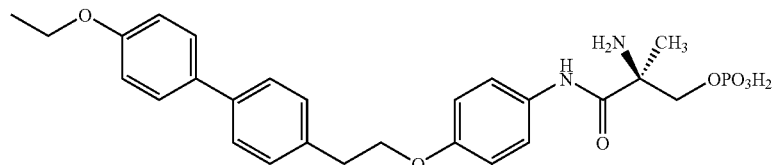
92
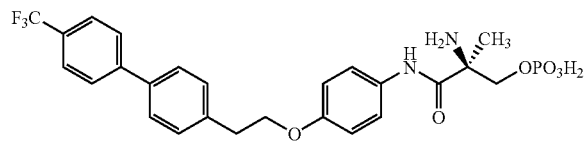
93
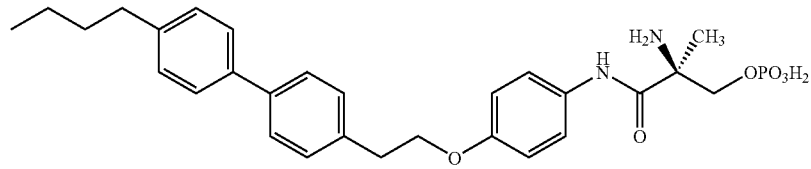
91
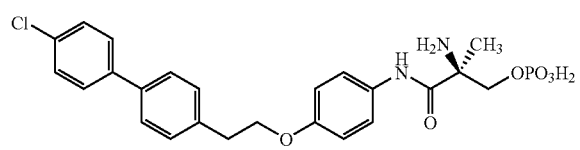
95
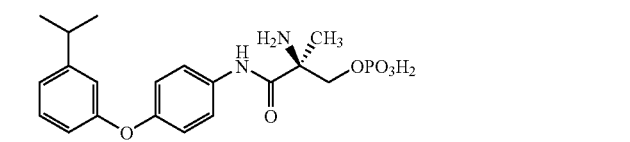
96
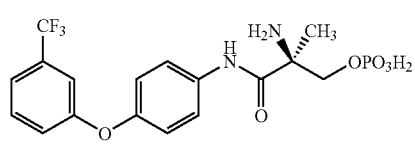
94
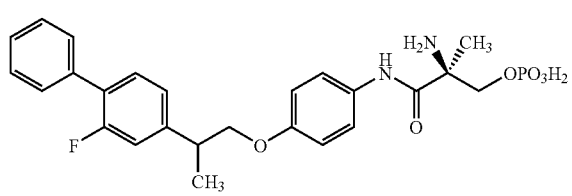
98
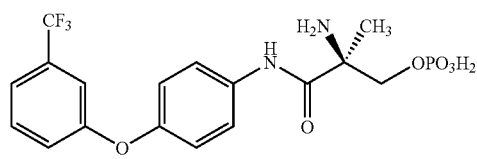
99
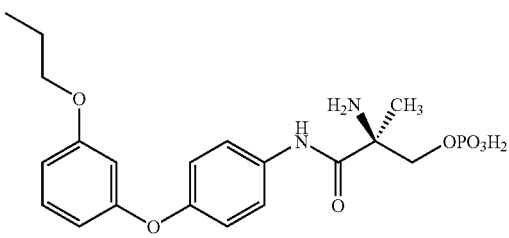

-continued
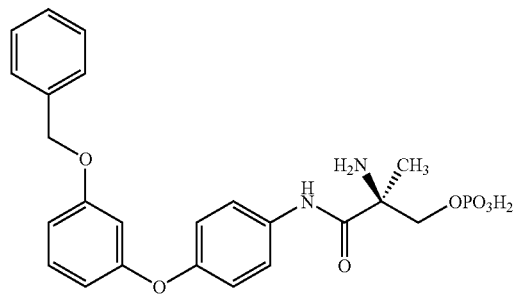
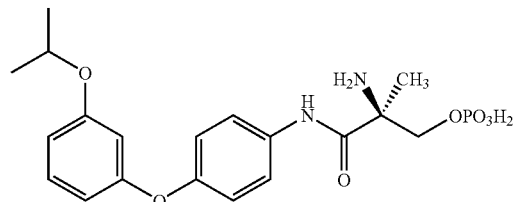
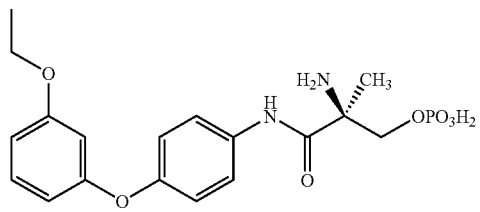
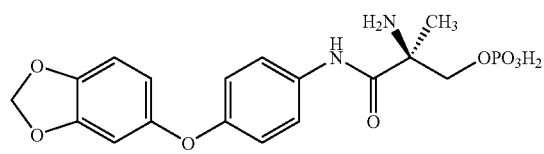
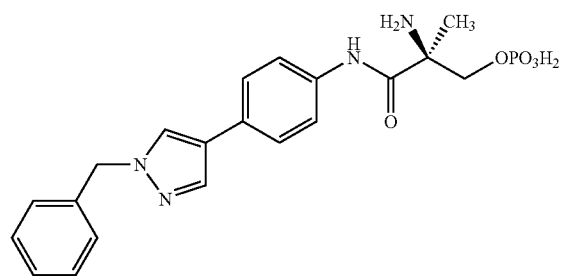
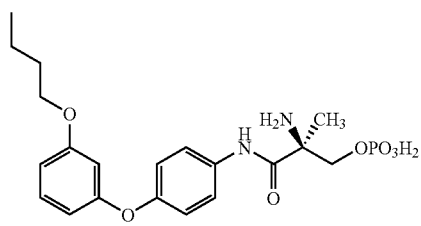
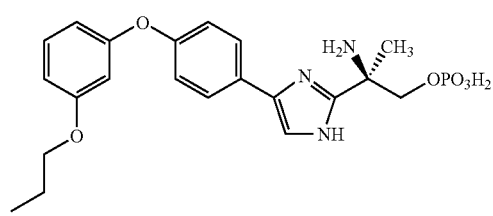
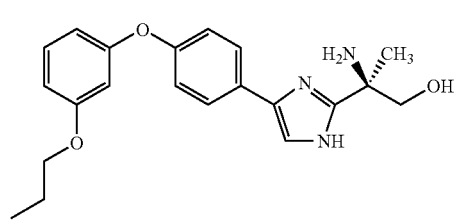
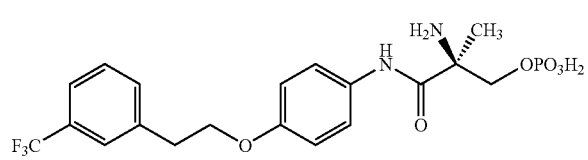

-continued
126 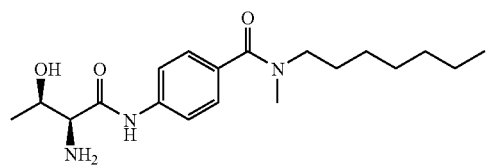
121 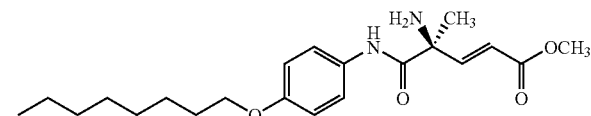
125 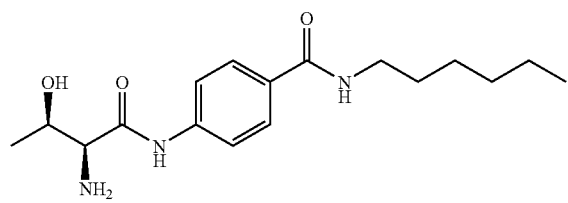
129 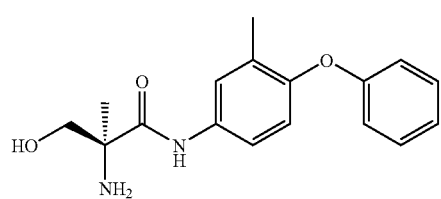
124 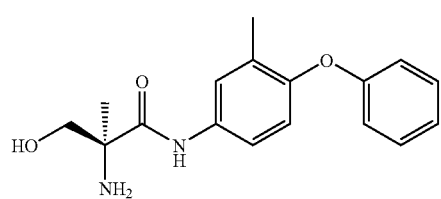
128 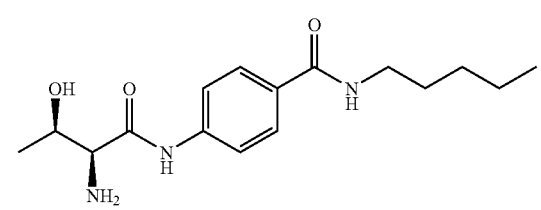
132 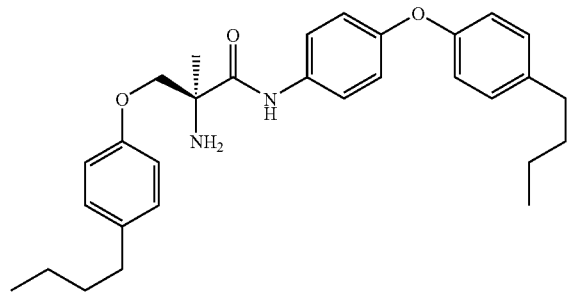
127 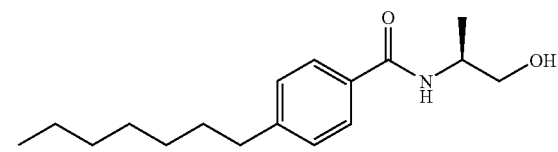
131 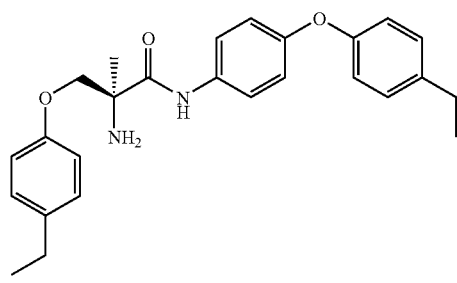
135 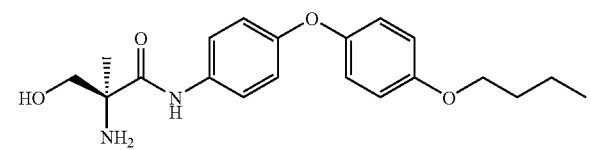
130 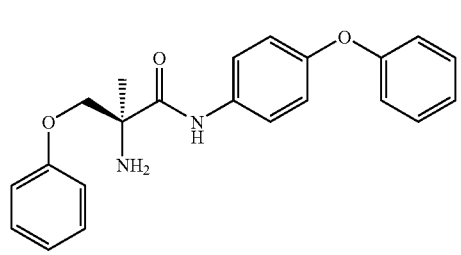
134 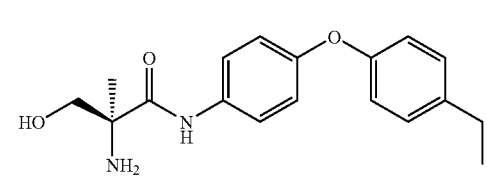

-continued
138
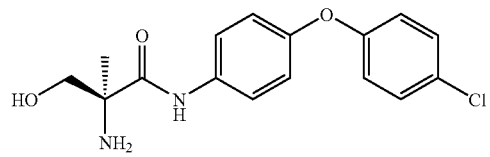
133
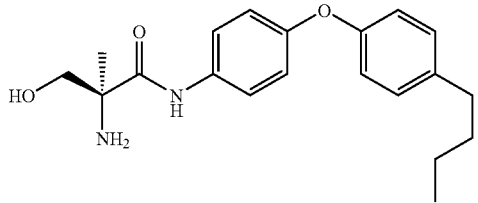
137
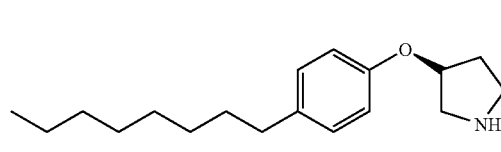
141
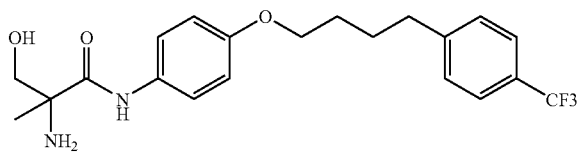
136
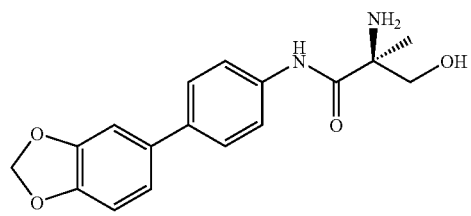
144
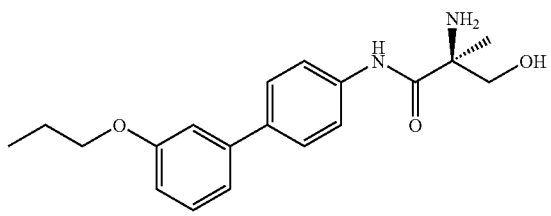
139
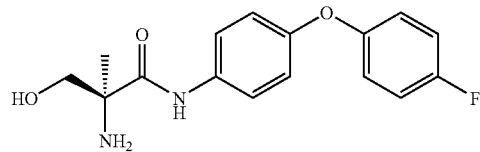
143
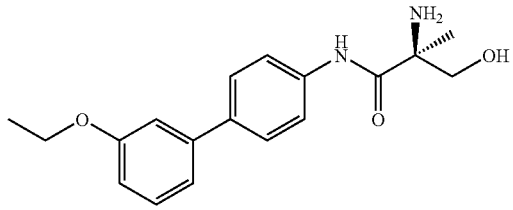
147
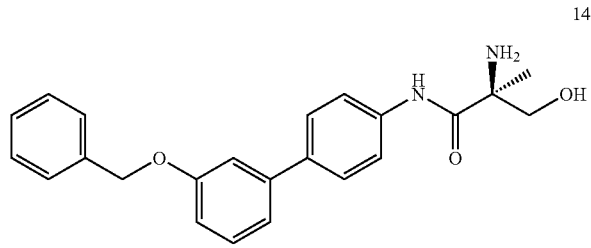
142
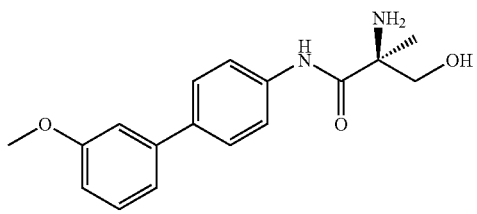
146
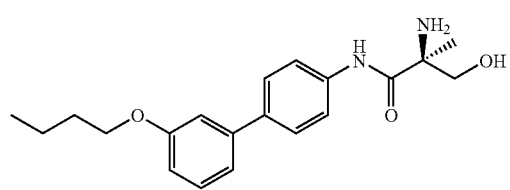
150
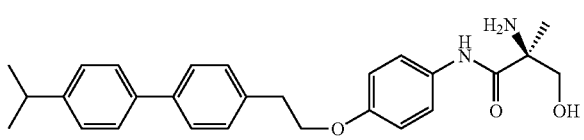
145
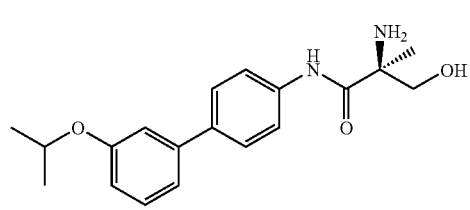
149
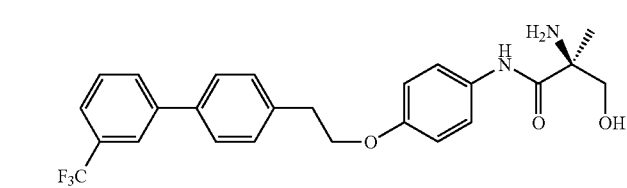

-continued
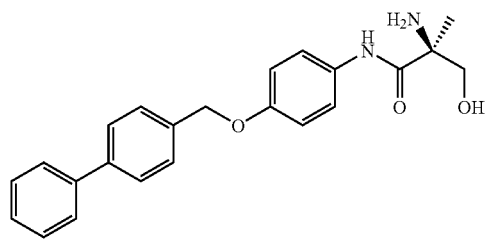
153
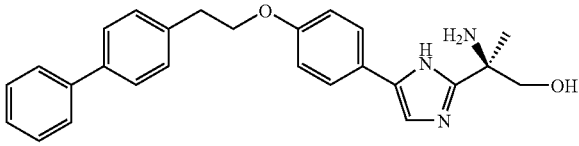
148
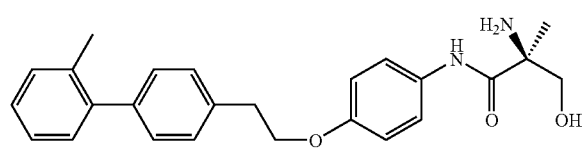
152
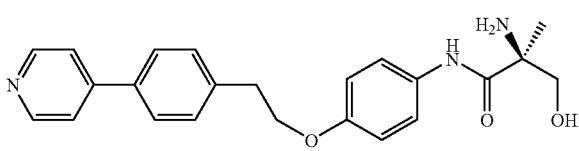
156
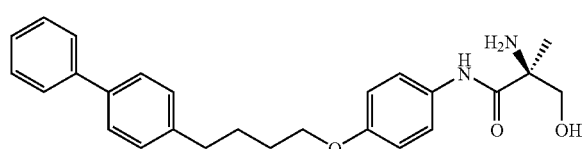
151
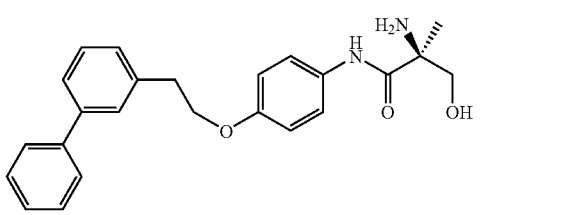
155
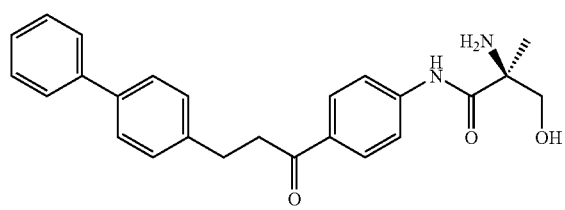
159
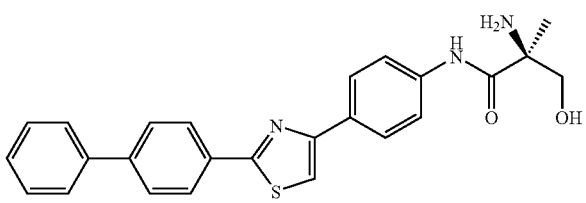
154
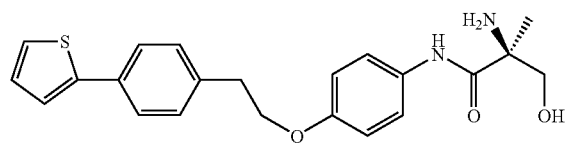
158
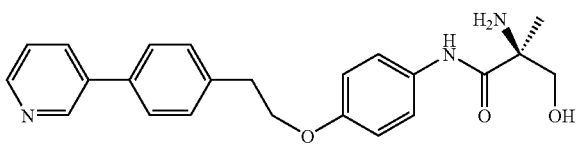
162
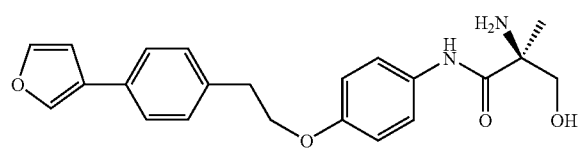
157
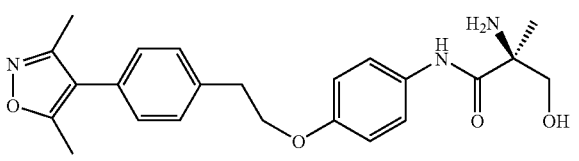
161
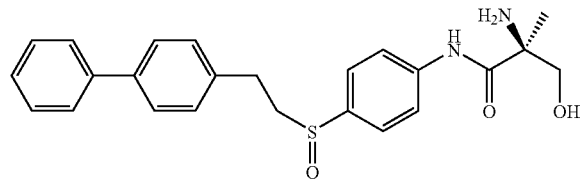
165

-continued
164
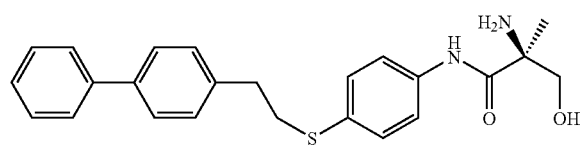
168
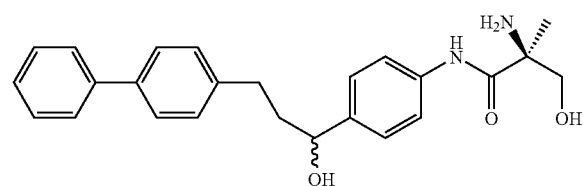
163
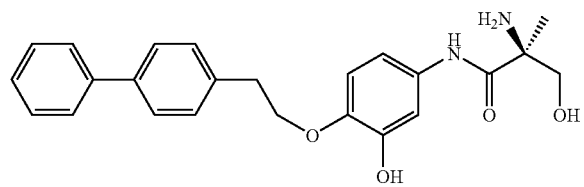
167
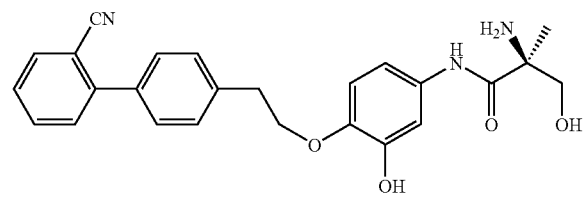
171
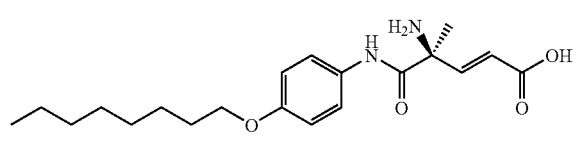
166
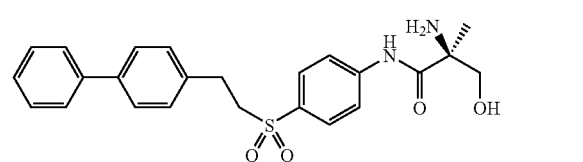
170
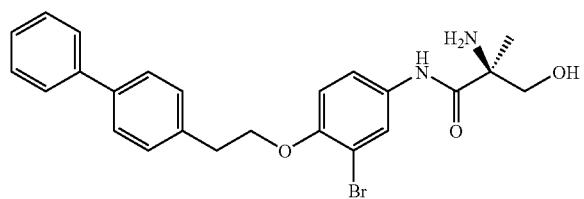
174
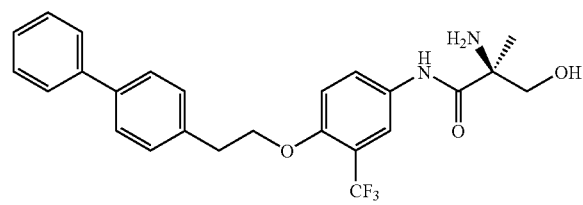
169
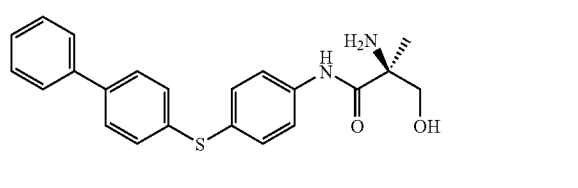
173
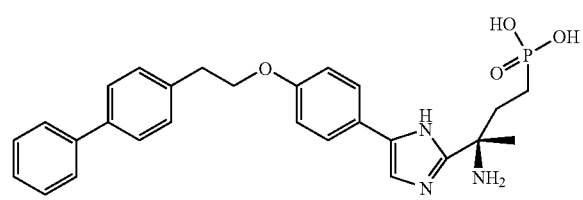
177
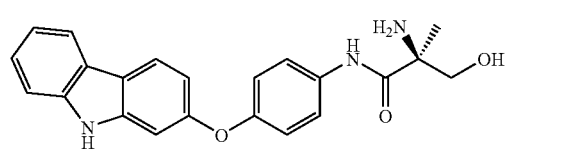
172
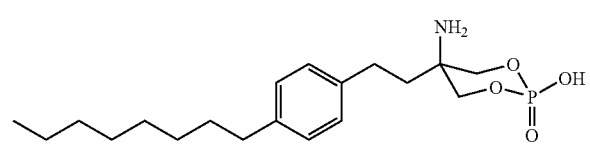
176
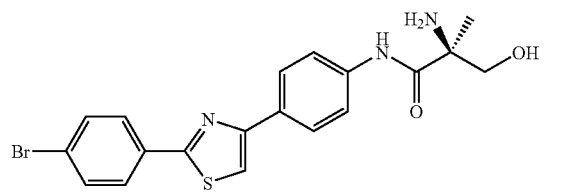
180
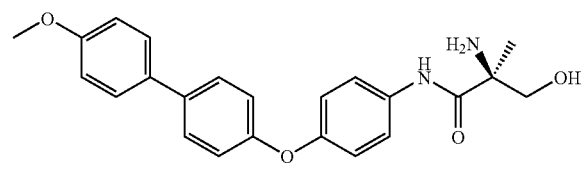

-continued
175
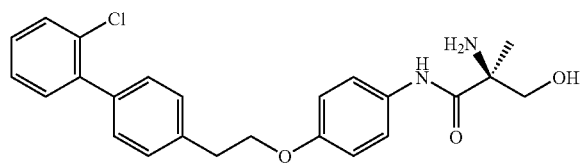
179
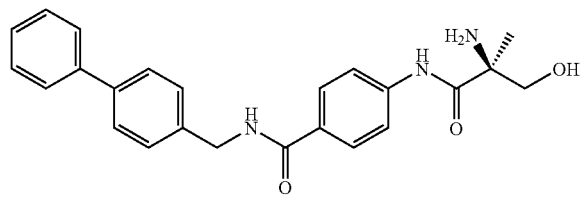
183
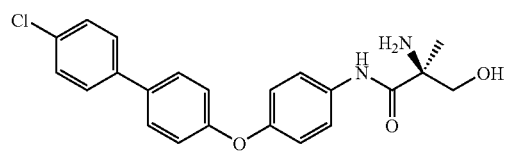
178
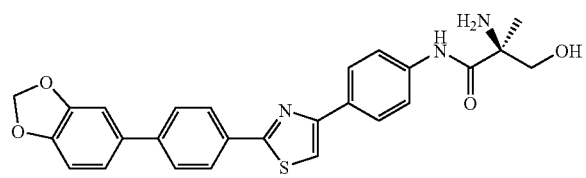
182
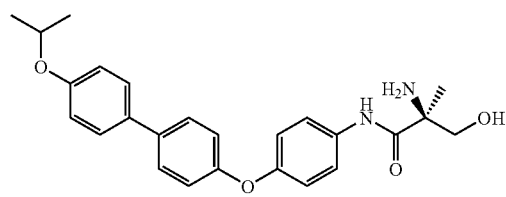
186
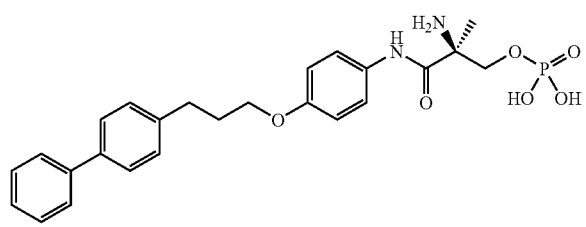
181
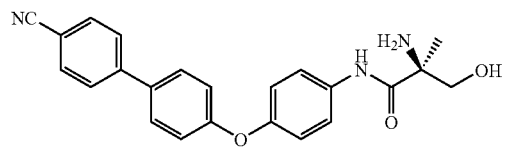
185
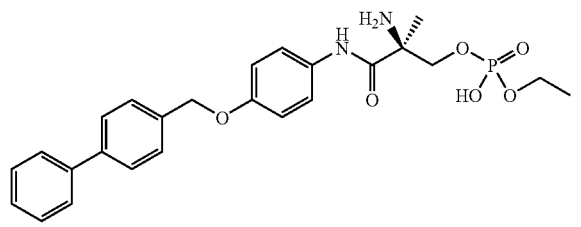
189
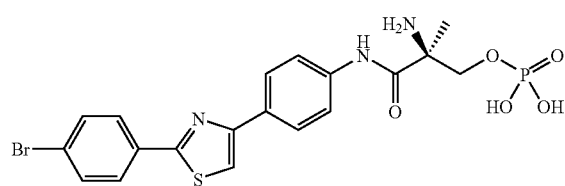
184
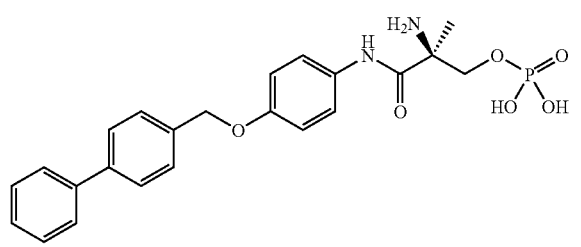
188
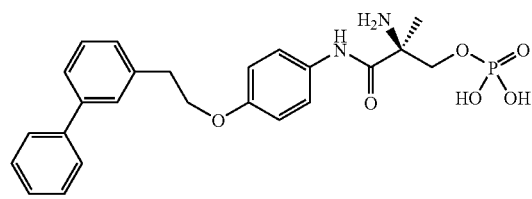
192
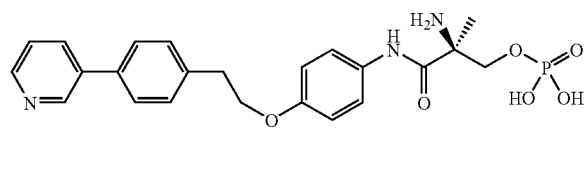
187
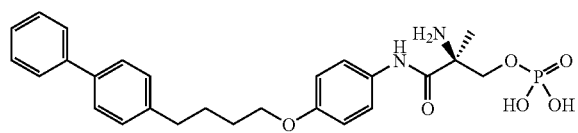
191
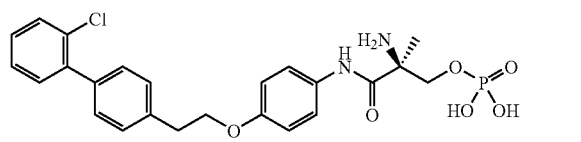

-continued
195
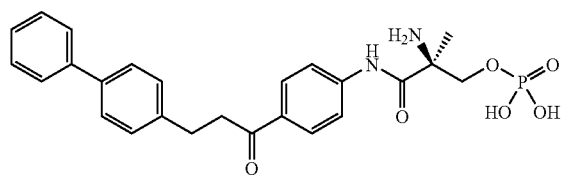
190
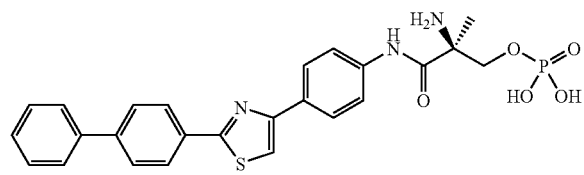
194
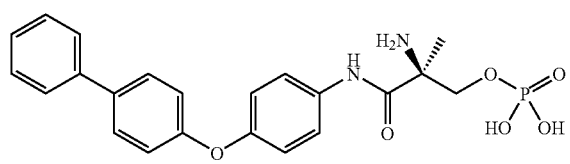
198
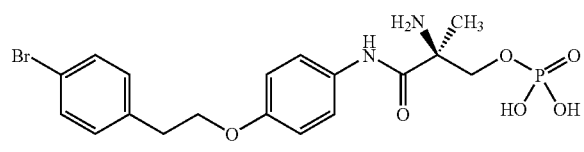
193
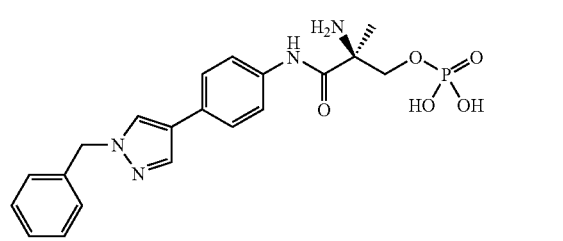
197
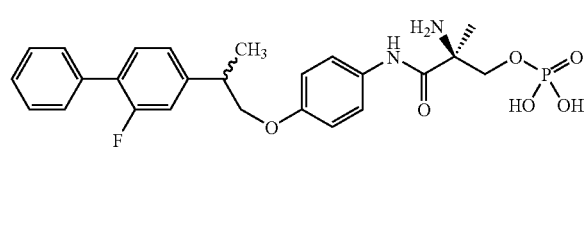
201
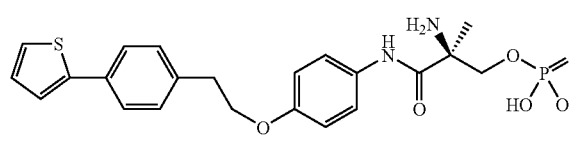
196
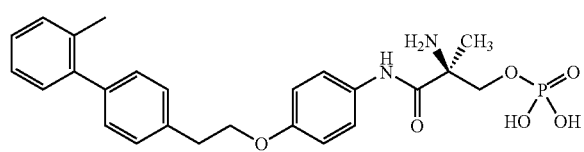
200
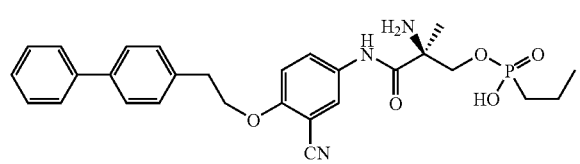
204
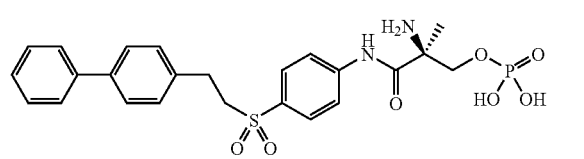
199
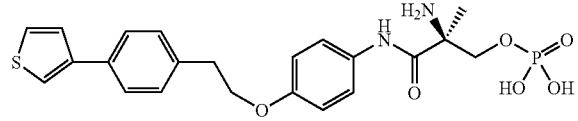
203
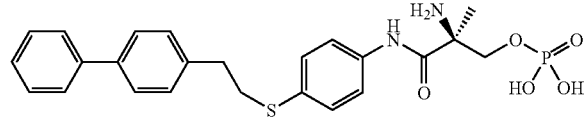
207
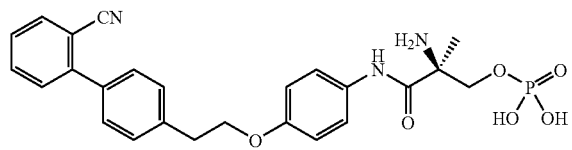
202
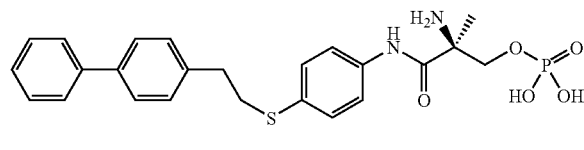
206
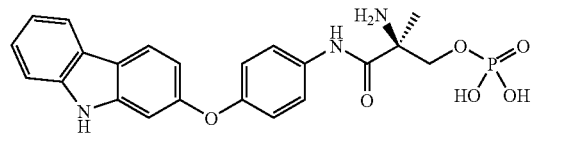
210
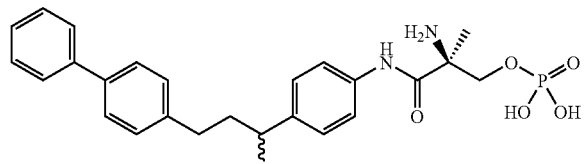

-continued
205
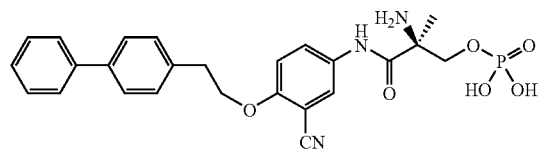
209
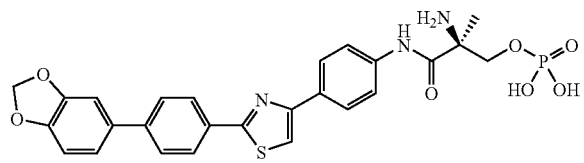
213
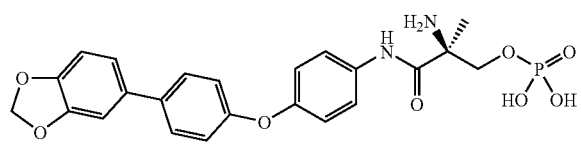
208
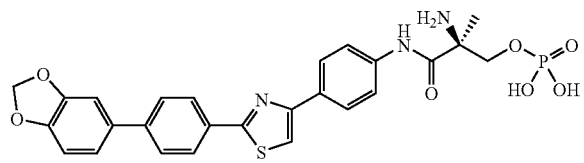
205
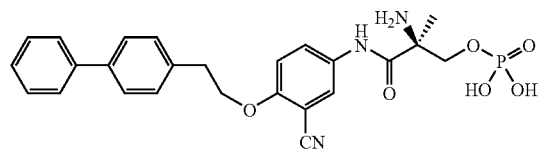
209
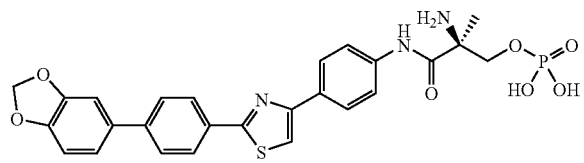
213
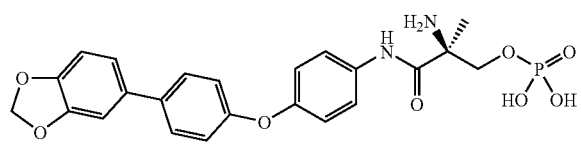
208
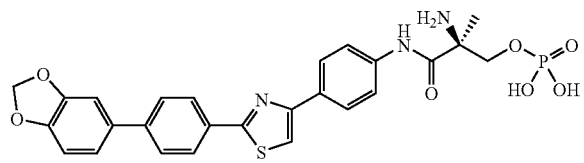
212
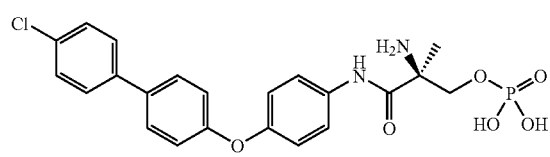
216
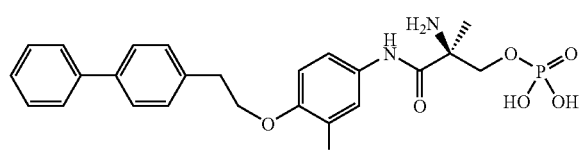
211
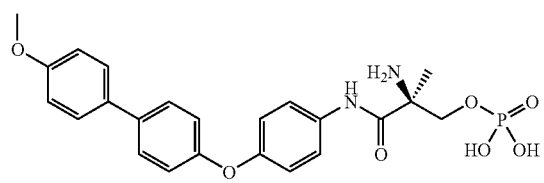
215
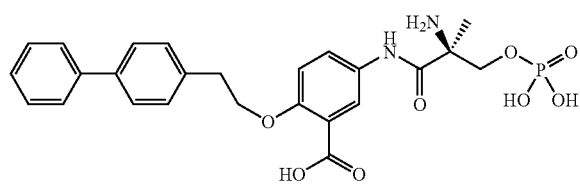
219
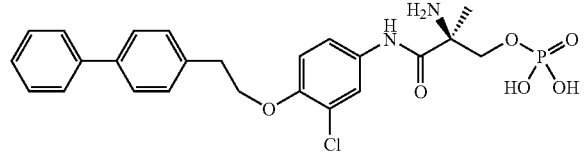
214
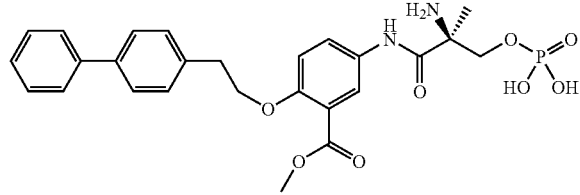
218
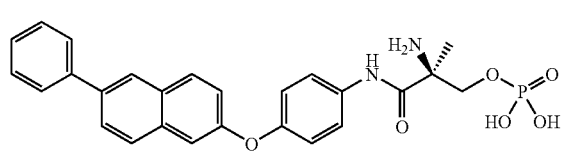
222
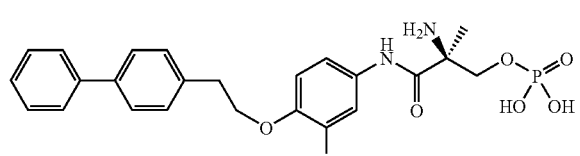
217
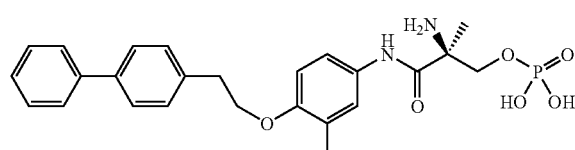
221
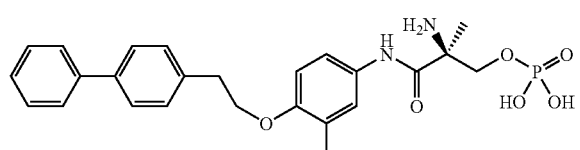

-continued
225
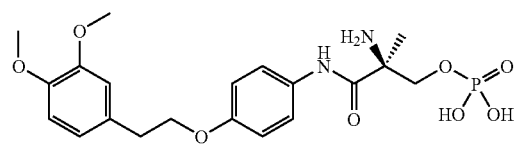
220
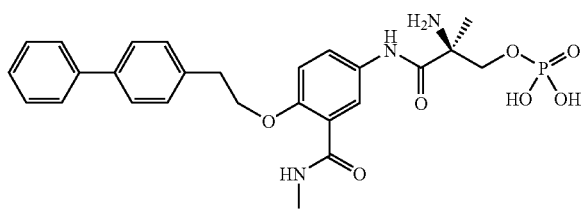
224
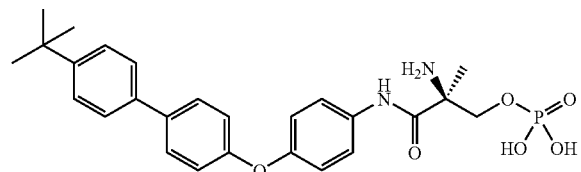
228
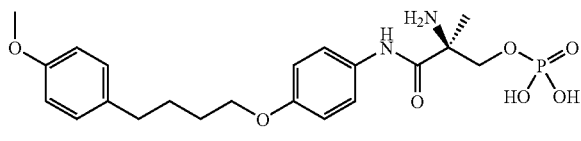
223
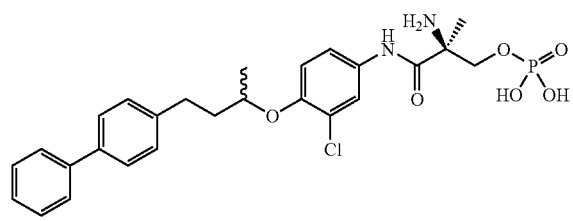
227
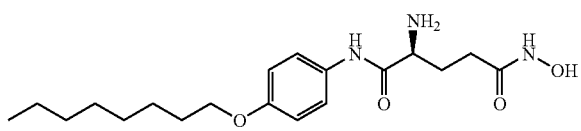
226
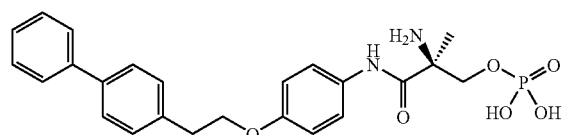
230
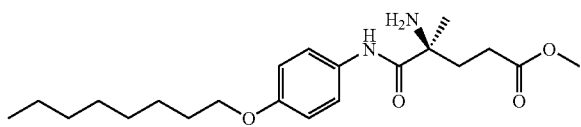
234
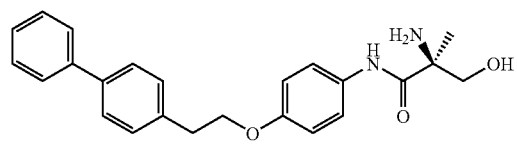
229
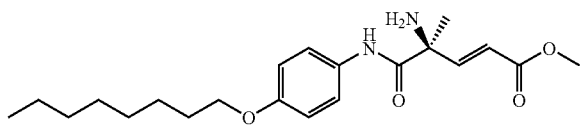
233
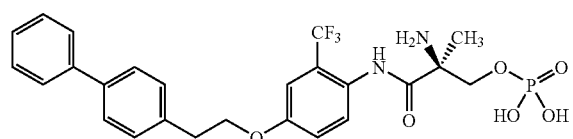
235
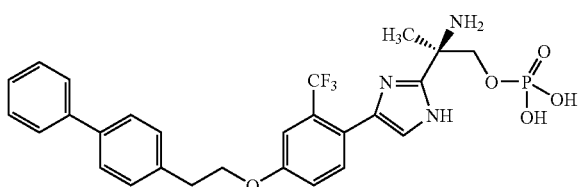
232
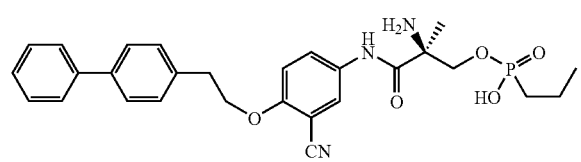
236
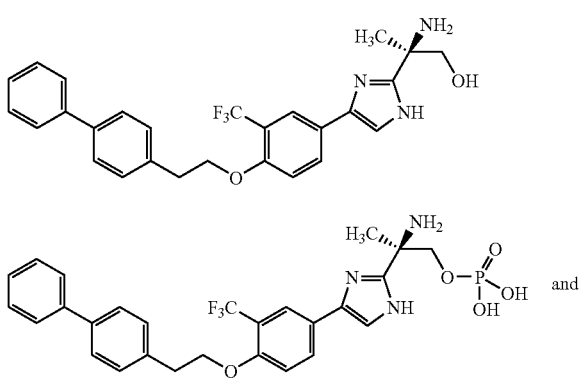
and -continued

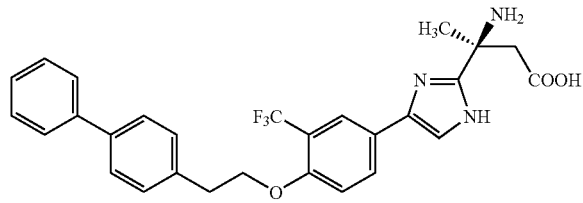

The invention also relates to salts of the compounds of the invention and, in particular, to pharmaceutically acceptable salts. A "pharmaceutically acceptable salt" includes a salt that retains the desired biological activity of the parent compound and does not impart any undesired toxicological effects. The salts can be, for example, salts with a suitable acid, such as hydrochloric acid, hydrobromic acid, sulfuric acid, phosphoric acid, nitric acid, and the like; acetic acid, oxalic acid, tartaric acid, succinic acid, malic acid, benzoic acid, pamoic acid, alginic acid, methanesulfonic acid, naphthalenesulfonic acid, and the like. Also included are salts of cations such as ammonium, sodium, potassium, lithium, zinc, copper, barium, bismuth, calcium, and the like; or organic cations such as tetralkylammonium and trialkylammonium cations. Combinations of the above salts are also useful. Salts of other acids and/or cations are also included, such as salts with trifluoroacetic acid, chloroacetic acid, and trichloroacetic acid.

The invention also includes different crystal forms, hydrates and solvates of the compounds of the invention, as well as stereoisomers of the compounds of the invention. Included are substantially pure single stereoisomers and mixtures of stereoisomers.

In a further embodiment, the compound of Formula I is an agonist of a sphingosine 1-phosphate 1 receptor.

Preferred compounds of Formulas I, II IV and IX include compounds which are agonists of the S1P receptor. Particularly preferred are compounds which are selective for the S1P1 receptor compared to one or more of the other S1P receptors. For example, one set of preferred compounds includes compounds which are selective for the S1P1 receptor relative to the S1P3 receptor. Compounds selective for the S1P1 receptor can be agonists of the S1P1 receptor, significantly weaker agonists of one or more other receptors and/or antagonists of one or more other receptors. A compound is "selective" for the S1P1 receptor relative to a second receptor, if the $IC_{50}$ of the compound for the second receptor is at least two-fold, preferably at least 10-fold, and more preferably at least 100-fold greater than the $IC_{50}$ for the S1P1 receptor. The $IC_{50}$ of a compound is determined using the $^{35}$S-GTPγS binding assay, as described in WO 03/061567, the contents of which are incorporated herein by reference.

The terms "agonist" or "S1P1 receptor agonist" as used herein include the compounds described herein which bind to and/or agonize the S1P1 receptor. In one embodiment, the S1P receptor agonists have an $IC_{50}$ for the S1P1 receptor of about 100 nM–0.25 nM, about 50 nM–0.25 nM, about 25 nM–0.5 nM, about 100 nM or less, about 75 nM or less, about 50 nM or less, about 40 nM or less, about 30 nM or less, about 20 nM or less, about 10 nM or less, about 5 nM or less, about 1 nM or less, about 0.5 nM or less, or about 0.25 nM or less. The compounds' $IC_{50}$ for the S1P1 receptor can be measured using the binding assays described in Example 11 or those described in WO 03/061567.

Ranges intermediate to the above recited values are also intended to be part of this invention. For example, ranges using a combination of any of the above recited values as upper and/or lower limits are intended to be included.

In a further embodiment, the S1P receptor agonist has an $IC_{50}$ value for the S1P3 receptor of about 10 nM–10,000 nM, about 100 nM–5000 nM, about 100 nM–3000 nM, about 10 nM or greater, about 20 nM or greater, about 40 nM or greater, about 50 nM or greater, about 75 nM or greater, or about 100 nM or greater. In another embodiment, the S1P compound of the invention binds the S1P3 receptor with an $IC_{50}$ of 1000 nM or greater, 2000 nM or greater, 3000 nM or greater, 5000 nM or greater, 10,000 nM or greater. The $IC_{50}$ for of S1P3 receptor can be measured using the binding assays described in Example 11 or those described in WO 03/061567.

Ranges intermediate to the above recited values are also intended to be part of this invention. For example, ranges using a combination of any of the above recited values as upper and/or lower limits are intended to be included.

In yet another embodiment, the S1P receptor agonists described herein have an $IC_{50}$ value for the S1P1 receptor that is about 5-fold lower, about 10-fold lower, about 20-fold lower, about 50-fold lower, about 100-fold lower, about 200-fold lower, about 500-fold lower or about 1000-fold lower than their $IC_{50}$ value for the S1P3 receptor.

Ranges intermediate to the above recited values are also intended to be part of this invention. For example, ranges using a combination of any of the above recited values as upper and/or lower limits are intended to be included.

In a further embodiment, when Q is NH(C=O), O, or heteroaryl; $R^6$ is OH; n is 1–4; one of $R^1$, $R^2$, $R^3$, $R^4$, and $R^5$ is $C_1$–$C_{18}$ alkyl, $C_2$–$C_{18}$ alkenyl, $C_2$–$C_{18}$ alkynyl, $C_5$–$C_{18}$-alkoxy, $(CH_2)_{1-10}O(CH_2)_{1-10}$, $C_5$–$C_{10}$(aryl), $C_5$–$C_{10}$(aryl)($C_1$–$C_{10}$alkyl), $C_5$–$C_{10}$(heteroaryl), $C_5$–$C_{10}$(heteroaryl)($C_1$–$C_{10}$alkyl), $C_5$–$C_{10}$ cycloalkyl, $C_5$–$C_{10}$(cycloalkyl)-($C_1$–$C_5$ alkyl), $C_5$–$C_{10}$alkoxy(aryl), $C_5$–$C_{10}$alkoxy(aryl)($C_1$–$C_{10}$ alkyl), $C_5$–$C_{10}$alkoxy(heteroaryl), $C_5$–$C_{10}$alkoxy(heteroaryl)($C_1$–$C_{10}$ alkyl), $C_5$–$C_{10}$alkoxy(cycloalkyl), or $C_5$–$C_{10}$alkoxy(cycloalkyl)($C_1$–$C_{10}$ alkyl); and one of $R^1$, $R^2$, $R^3$, $R^4$, and $R^5$ is H, halogen, $NH_2$, $C_1$–$C_6$ alkyl, $C_1$–$C_6$ alkoxy, $C_1$–$C_6$ alkylamino, $C_1$–$C_6$ alkylcyano, or $C_1$–$C_6$ alkylthio, $R^8$ is not hydrogen.

In another further embodiment, when Q is heteroaryl; one of $R^1$, $R^2$, $R^3$, $R^4$, and $R^5$ is alkyl, alkenyl, alkynyl, optionally substituted aryl, optionally substituted heteroaryl, alkyl (optionally substituted aryl), arylalkyl, or arylalkyl (optionally substituted (aryl); $R^8$ is hydrogen; n is 1; $R^6$ is not OH.

In another further embodiment, when Q is NH(C=O); $R^6$ is OH; $R^1$, $R^2$, $R^3$, $R^4$, and $R^5$ are each independently halogen, hydrogen, amino, or alkyl; $R^8$ is not hydrogen.

In one embodiment, the compounds of the invention do not include the compounds described in WO 05/041899A2, WO 04/010949A2, WO 04/024673 A1 and WO 02/064616; the entire contents of each of which are hereby incorporated herein by reference.

Methods of Using the Compounds of the Invention

In a further embodiment, the invention pertains, at least in part to a method for treating a sphingosine 1-phosphate associated disorder in a subject. The method includes administering to a subject an S1P compound described herein in an amount effective for treating an S1P associated disorder.

The term "sphingosine 1-phosphate associated disorder" includes disorders, diseases or conditions which are associated with or caused by a misregulation in S1P receptor function and/or signalling or S1P receptor ligand funtion. The term also includes diseases, disorders or conditions which can be treated by administering to a subject an effective amount of a sphingosine 1-phosphate receptor agonist. Such disorders include disorders that are associated with an inappropriate immune response and conditions associated with an overactive immune response.

In another embodiment, the present invention provides a method of treating a condition associated with an overactive immune response. An "overactive immune response" is an undesirable or inappropriate immune response and in conditions associated with an overactive immune response, the immune response is deleterious to the subject. Included are conditions such as autoimmune disorders, organ and tissue transplants, including transplant rejection and graft versus host disease, and chronic inflammatory disorders. The method includes administering to the subject a therapeutically effective amount of a compound of the present invention, thereby treating the condition associated with an overactive immune response in the subject.

The compounds of the invention can be used to treat subjects undergoing, or who have undergone, an organ, tissue or cell transplant from a donor. In one embodiment, the transplanted tissue, organ or cell is bone marrow, stem cells, pancreatic cells, such as islet cells, or cornea. In another embodiment, the transplanted organ is a solid organ, such as a liver, a kidney, a heart or a lung.

Autoimmune disorders which can be treated with the compounds of the invention include systemic lupus erythematosus, rheumatoid arthritis, multiple sclerosis, myasthenia gravis, type 1 diabetes, ankylosing spondylitis, psoriatic arthritis, scleroderma, Kawasaki syndrome and other rheumatic diseases as set forth in Primer on the Rheumatic Diseases, 11th Edition (John H. Klippel M D, editor; Arthritis Foundation: Atlanta Ga. (1997)).

Other autoimmune diseases that can be treated with the present compounds include active chronic hepatitis, Addison's Disease, anti-phospholipid syndrome, atopic allergy, autoimmune atrophic gastritis, achlorhydra autoimmune, Celiac Disease, Crohn's Disease, Cushing's Syndrome, dermatomyositis, Goodpasture's Syndrome, Grave's Disease, Hashimoto's thyroiditis, idiopathic adrenal atrophy, idiopathic thrombocytopenia, Lambert-Eaton Syndrome, lupoid hepatitis, mixed connective tissue disease, pemphigoid, pemphigus vulgaris, pernicious anemia, phacogenic uveitis, polyarteritis nodosa, primary biliary cirrhosis, primary sclerosing cholangitis, psoriasis, Raynauds, Reiter's Syndrome, relapsing polychondritis, Schmidt's Syndrome, Sjogren's Syndrome, sympathetic ophthalmia, Takayasu's Arteritis, temporal arteritis, thyrotoxicosis, Type B Insulin Resistance, ulcerative colitis, and Wegener's granulomatosis.

As used herein, the term "subject" includes warm-blooded animals, preferably mammals, including humans, cats, dogs, horses, bears, lions, tigers, ferrets, rabbits, mice, cows, sheep, pigs, etc. In a preferred embodiment, the subject is a primate. In an even more preferred embodiment, the primate is a human.

As used herein, the term "administering" to a subject includes dispensing, delivering or applying a compound of the invention in a pharmaceutical formulation (as described herein), to a subject by any suitable route for delivery of the compound to the desired location in the subject, including delivery by either the parenteral or oral route, intramuscular injection, subcutaneous/intradermal injection, intravenous injection, buccal administration, topical delivery, transdermal delivery and administration by the rectal, colonic, vaginal, intranasal or respiratory tract route.

As used herein, the term "effective amount" includes an amount effective, at dosages and for periods of time necessary, to achieve the desired result, e.g., sufficient to treat the condition in a subject. An effective amount of a compound of the invention, as defined herein, may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the compound are outweighed by the therapeutically beneficial effects.

A therapeutically effective amount of a compound of the invention (i.e., an effective dosage) may range from about 0.001 to 30 mg/kg body weight, preferably about 0.01 to 25 mg/kg body weight, more preferably about 0.1 to 20 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, preferably, can include a series of treatments. It will also be appreciated that the effective dosage of the compound used for treatment may increase or decrease over the course of a particular treatment.

The methods of the invention further include administering to a subject a therapeutically effective amount of a compound of the invention in combination with another pharmaceutically active compound known to treat the disease or condition, e.g., an immunomodulatory agent or an anti-inflammatory agent. Pharmaceutically active compounds that may be used depend upon the condition to be treated, but include as examples cyclosporin, rapamycin, FK506, methotrexate, etanercept, infliximab, adalimumab, non-steroidal anti-inflammatory agents, cyclooxygenase-2-inhibitors, such as celecoxib and rofecoxib, and corticosteroids. Other suitable compounds can be found in Harrison's Principles of Internal Medicine, Thirteenth Edition, Eds. T. R. Harrison et al. McGraw-Hill N.Y., N.Y.; and the Physicians Desk Reference 50th Edition 1997, Oradell N.J., Medical Economics Co., the complete contents of which are expressly incorporated herein by reference. The compound of the invention and the additional pharmaceutically active compound may be administered to the subject in the same pharmaceutical composition or in different pharmaceutical compositions (at the same time or at different times).

Pharmaceutical Compositions of the Compounds of the Invention

The present invention also provides pharmaceutically acceptable formulations and compositions comprising one or more compounds of the invention, e.g., compounds of Formula I or compounds otherwise described herein. Preferably, the compound of the invention is present in the formulation in a therapeutically effective amount, e.g., an amount effective to treat a sphingosine 1-phosphate associated disorder.

Such pharmaceutically acceptable formulations typically include one or more compounds of the invention as well as one or more pharmaceutically acceptable carriers and/or excipients. As used herein, "pharmaceutically acceptable carrier" includes any and all solvents, dispersion media, coatings, antibacterial and antifungal agents, isotonic and absorption delaying agents, and the like that are physiologically compatible. The use of such media and agents for pharmaceutically active substances is well known in the art. Except insofar as any conventional media or agent is incompatible with the compounds of the invention, use thereof in the pharmaceutical compositions is contemplated.

Supplementary pharmaceutically active compounds known to treat transplant or autoimmune disease, i.e., immunomodulatory agents and anti-inflammatory agents, as described above, can also be incorporated into the compositions of the invention. Suitable pharmaceutically active compounds that may be used can be found in Harrison's Principles of Internal Medicine (supra).

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injection include sterile aqueous solutions (where water soluble) or dispersions, or sterile powders for the extemporaneous preparation of sterile injectable solutions or dispersions. For intravenous administration, suitable carriers include physiological saline, bacteriostatic water, Cremophor EI™ (BASF, Parsippany, N.J.) or phosphate buffered saline (PBS). In all cases, the pharmaceutical composition must be sterile and should be fluid to the extent that easy syringability exists. It must also be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the compound of the invention in the required amount in an appropriate solvent with one or a combination of the ingredients enumerated above, as required, followed by filtered sterilization. Generally, dispersions are prepared by incorporating the compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the compound plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the compound of the invention can be incorporated with excipients and used in the form of tablets, troches, or capsules. Oral compositions can also include an enteric coating. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds of the invention are delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds of the invention are formulated into ointments, salves, gels, or creams as generally known in the art.

The present pharmaceutical compositions can also be prepared in the form of suppositories (e.g., with conventional suppository bases such as cocoa butter and other glycerides) or retention enemas for rectal delivery.

In one embodiment, the compounds are prepared with carriers that will protect the compound against rapid elimination from the body, such as a controlled release formulation, including implants and microencapsulated delivery systems. Biodegradable, biocompatible polymers can be:used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811, U.S. Pat. No. 5,455,044 and U.S. Pat. No. 5,576,018, and U.S. Pat. No. 4,883,666, the contents of all of which are incorporated herein by reference.

The compounds of the invention can also be incorporated into pharmaceutical compositions which allow for the sustained delivery of the compounds to a subject for a period of at least several weeks to a month or more. Such formulations are described in published PCT application no. WO 02/74247, incorporated herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of a compound of the invention calculated to produce the desired therapeutic effect in association with the required pharmaceutical carrier. The specification for the unit dosage forms of the invention are dictated by and directly dependent on the unique characteristics of the compound and the particular therapeutic effect to be achieved, and the limitations inherent in the art of compounding such compounds for the treatment of individuals.

This invention is further illustrated by the following examples, which should not be construed as limiting. The contents of all references, patents, patent applications cited throughout this application are incorporated herein by reference.

EXAMPLES

Example 1

Synthesis of Phenylamide Compounds with Alkoxy Tail Group

Certain of the target compounds were synthesized using either the method illustrated in Scheme 1 or the method illustrated in Scheme 2. In Scheme 1, alkylation of the hydroxyl group of a substituted aminophenol is achieved using alkyl bromide and a catalytic amount of NaI in the presence of either $Cs_2CO_3$ in DMF (60° C.) or KO$^t$Bu in acetone (50° C.). The amino group of the desired intermediate is then acylated with Boc-protected amino acid using either N-ethylcarbodiimide (EDC), 1-hydroxybenzotriazole (HOBt), and N,N-diisopropylethylamine (DIPEA) in $CH_2Cl_2$ or O-(7-azabenzotriazol-1-yl)-1,1,3,3-tetramethyluronium hexafluorophosphate (HATU) and DIPEA in DMF. The final compound was obtained in good yields from Boc deprotection of the later intermediate with 30% trifluoroacetic acid (TFA) in $CH_2Cl_2$. Scheme 2 provides an alternative approach to synthesis of the desired final compound in which the amino group of the aminophenol is acylated first, followed by alkylation of the hydroxyl residue.

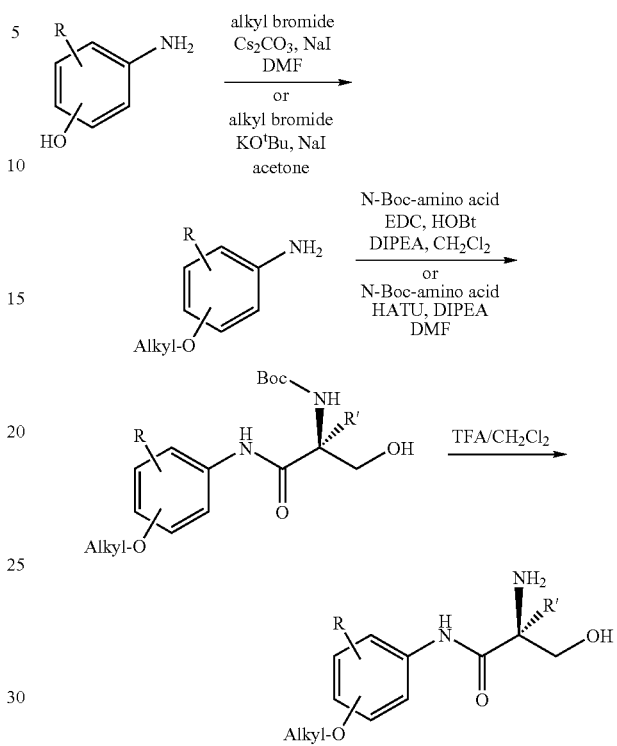

Scheme 1

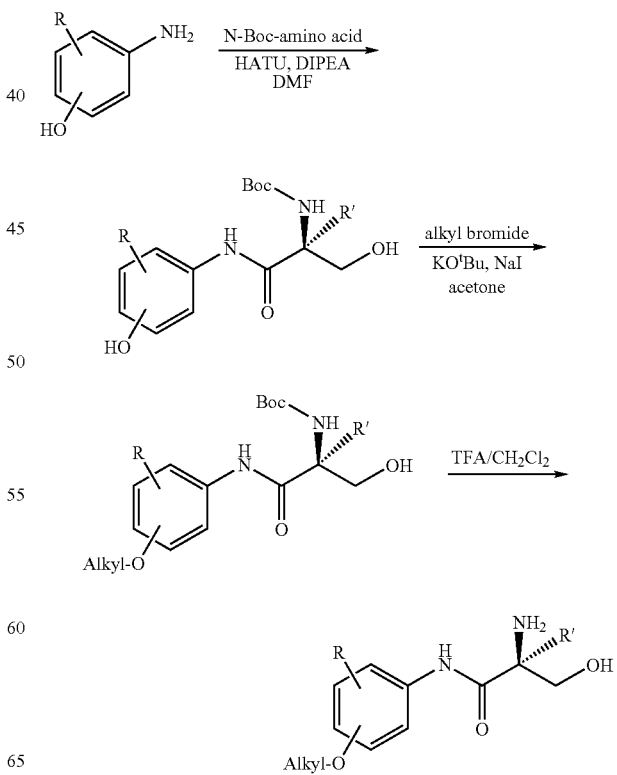

Scheme 2

Alkylation of Hydroxyl Group

To a solution of desired substituted aminophenol (0.50 g, 1.0 equiv) and NaI (0.1 equiv) in acetone (10 mL) was added a 1.0 M solution of KO$^t$Bu in tetrahydrofuran (THF) (1.1 equiv, 2.1 equiv was used if aminophenol was a hydrochloride salt). To the reaction mixture was added the desired alkyl bromide (1.1 equiv). The reaction was stirred and heated under an atmosphere of nitrogen at 50° C. for 12–24 hours. The reaction was then diluted with EtOAc (25 mL) and washed with H$_2$O (2×25 mL) and saturated NaCl (1×25 mL). The organic layer was dried over anhydrous MgSO$_4$ then the solvent removed in vacuo. The crude produce was purified using silica gel column chromatography (3:1 Hex:EtOAc).

4-(Heptyloxy)benzenamine

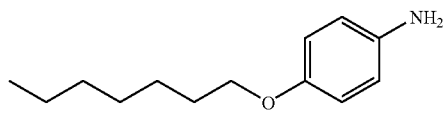

The product was obtained as a yellowish-brown solid in 71% (0.47 g) yield. TLC (3:1 Hex:EtOAc), R$_f$=0.4; $^1$H NMR (400 MHz, CDCl$_3$) δ 6.69–6.74 (m, 2H), 6.59–6.63 (m, 2H), 3.86 (t, 2H, J=6.8 Hz), 3.40 (br s, 2H), 1.68–1.78 (m, 2H), 1.21–1.48 (m, 8H), 0.88 (t, 3H, J=6.8 Hz).

4-(Octyloxy)benzenamine

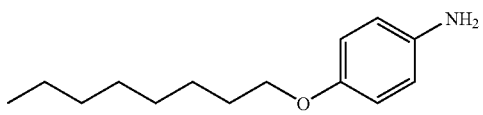

The product was obtained as brownish thick oil in 59% (0.45 g) yield. TLC (3:1 Hex:EtOAc), R$_f$=0.4; $^1$H NMR (400 MHz, CDCl$_3$) δ 6.69–6.74 (m, 2H), 6.59–6.63 (m, 2H), 3.86 (t, 2H, J=6.9 Hz), 3.41 (br s, 2H), 1.69–1.79 (m, 2H), 1.22–1.47 (m, 10H), 0.88 (t, 3H, J=7.1 Hz).

3-Chloro-4-(heptyloxy)benzenamine

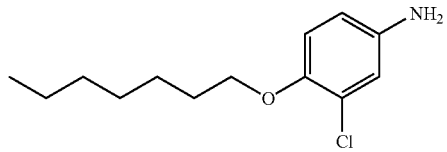

The product was obtained as a white solid in 51% (0.43 g) yield. TLC (3:1 Hex:EtOAc), R$_f$=0.5; $^1$H NMR (400 MHz, CDCl$_3$) δ 6.74 (d, 1H, J=8.5 Hz), 6.72 (d, 1H, J=2.8 Hz), 6.50 (dd, 1H, J=8.5 Hz, J=2.8 Hz), 3.91 (t, 2H, J=6.8 Hz), 3.44 (br s, 2H), 1.73–1.82 (m, 2H), 1.24–1.52 (m, 8H), 0.89 (t, 3H, J=6.8 Hz).

3-Chloro-4-(octyloxy)benzenamine

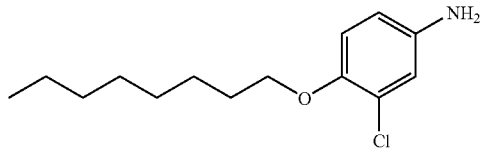

The product was obtained as a white solid in 65% (0.58 g) yield. TLC (3:1 Hex:EtOAc), R$_f$=0.5; $^1$H NMR (400 MHz, CDCl$_3$) δ 6.74 (d, 1H, J=8.4 Hz), 6.72 (d, 1H, J=2.8 Hz), 6.51 (dd, 1H, J=8.4 Hz, J=2.8 Hz), 3.91 (t, 2H, J=6.4 Hz), 3.44 (br s, 2H), 1.73–1.81 (m, 2H), 1.23–1.51 (m, 10H), 0.88 (t, 3H, J=7.1 Hz).

3-Methyl-4-(octyloxy)benzenamine

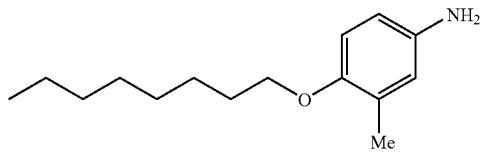

The product was obtained as a yellowish oil in 85% (0.81 g) yield. TLC (3:1 Hex:EtOAc), R$_f$=0.3; $^1$H NMR (400 MHz, CDCl$_3$) δ 6.62 (d, 1H, J=8.4 Hz), 6.51 (d, 1H, J=2.4 Hz), 6.45 (dd, 1H, J=8.4 Hz, J=2.4 Hz), 3.85 (t, 2H, J=6.8 Hz), 3.40 (br s, 2H), 2.15 (s, 3H), 1.73–1.80 (m, 2H), 1.23–1.50 (m, 10H), 0.90 (t, 3H, J=6.8 Hz).

Acylation of Substituted Alkoxy-Benzenamines:

To a solution of the desired substituted alkoxy-benzenamines (0.20 g, 1.0 equiv) and N-protected amino acid (1.0 equiv) in DMF (10 mL) was added DIPEA (3.0 equiv) and HATU (1.2 equiv). The reaction mixture was stirred at room temperature under an atmosphere of nitrogen 12–24 hours. The reaction was then diluted with EtOAc (25 mL) and washed with 10% NH$_4$Cl (2×25 mL), 5% NaHCO$_3$ (2×25 mL), and saturated NaCl (1×25 mL). The organic layer was dried over anhydrous MgSO$_4$ then the solvent removed in vacuo. The crude produce was purified using silica gel column chromatography.

tert-Butyl (S)-2-(4-(heptyloxy)phenylcarbamoyl)-1-hydroxypropan-2-ylcarbamate

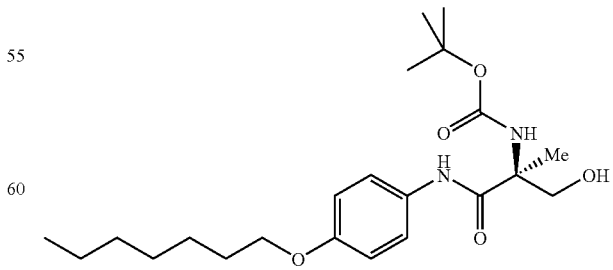

The product was obtained as a brownish solid in 78% (0.29 g) yield. TLC (1:1 EtOAc:Hex), R$_f$=0.3; $^1$H NMR (400 MHz, CDCl$_3$) δ 9.40 (br s, 1H), 7.37 (d, 2H, J=8.8 Hz), 6.83

(d, 2H, J=8.8), 5.57 (br s, 1H), 4.02–4.12 (m, 1H), 3.91 (t, 2H, J=6.4 Hz), 3.55 (br t, 1H), 3.27 (br t, 1H), 1.71–1.80 (m, 2H), 1.55 (s, 3H), 1.46 (s, 9H), 1.23–1.50 (m, 8H), 0.89 (t, 3H, J=7.2 Hz).

tert-Butyl (S)-2-(4-(octyloxy)phenylcarbamoyl)-1-hydroxypropan-2-ylcarbamate

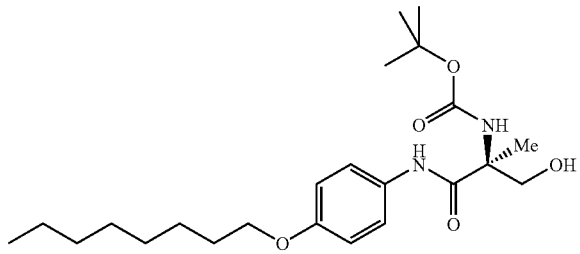

The product was obtained as a brownish solid in 49% (0.185 g) yield. TLC (1:1 EtOAc:Hex), R$_f$=0.4; $^1$H NMR (400 MHz, CDCl$_3$) δ 9.42 (br s, 1H), 7.36 (d, 2H, J=9.0 Hz), 6.83 (d, 2H, J=9.0), 5.59 (br s, 1H), 4.03–4.13 (m, 1H), 3.91 (t, 2H, J=6.4 Hz), 3.55 (br t, 1H), 3.26 (br t, 1H), 1.71–1.80 (m, 2H), 1.56 (s, 3H), 1.46 (s, 9H), 1.23–1.50 (m, 10H), 0.88 (t, 3H, J=6.8 Hz).

tert-Butyl (S)-2-(3-chloro-4-(heptyloxy)phenylcarbamoyl)-1-hydroxypropan-2-ylcarbamate

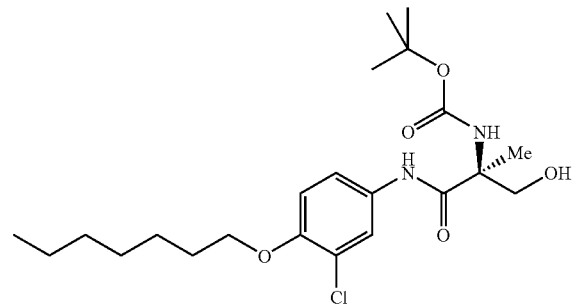

The product was obtained as an off white solid in 47% (0.169 g) yield. TLC (1:1 EtOAc:Hex), R$_f$=0.4; $^1$H NMR (400 MHz, CDCl$_3$) δ 9.52 (br s, 1H), 7.53 (d, 1H, J=2.4 Hz), 7.28 (dd, 1H, J=8.8 Hz, J=2.4 Hz), 6.84 (d, 1H, J=8.8), 5.75 (br s, 1H), 4.02–4.10 (m, 1H), 3.98 (t, 2H, J=6.4 Hz), 3.54 (br t, 1H), 3.21 (br t, 1H), 1.76–1.85 (m, 2H), 1.55 (s, 3H), 1.46 (s, 9H), 1.24–1.51 (m, 8H), 0.89 (t, 3H, J=7.2 Hz).

tert-Butyl (S)-2-(3-chloro-4-(octyloxy)phenylcarbamoyl)-1-hydroxypropan-2-ylcarbamate

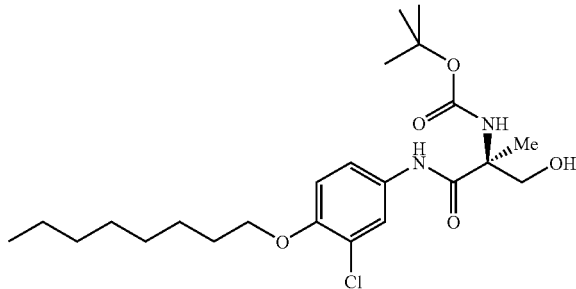

The product was obtained as a brownish solid in 40% (0.158 g) yield. TLC (1:1 EtOAc:Hex), R$_f$=0.4; $^1$H NMR (400 MHz, CDCl$_3$) δ 9.50 (br s, 1H), 7.57 (d, 1H, J=2.4 Hz), 7.28 (dd, 1H, J=8.8 Hz, J=2.4 Hz), 6.84 (d, 1H, J=8.8), 5.58 (br s, 1H), 4.02–4.11 (m, 1H), 3.98 (t, 2H, J=6.4 Hz), 3.54 (br t, 1H), 3.21 (br t, 1H), 1.76–1.85 (m, 2H), 1.53 (s, 3H), 1.47 (s, 9H), 1.23–1.53 (m, 10H), 0.88 (t, 3H, J=6.8 Hz).

tert-Butyl (S)-2-(3-methyl-4-(octyloxy)phenylcarbamoyl)-1-hydroxypropan-2-ylcarbamate

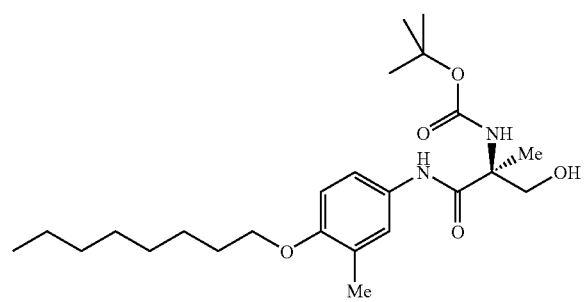

The product was obtained as an off white solid in 93% (0.133 g) yield. TLC (1:3 EtOAc:Hex), R$_f$=0.4; $^1$H NMR (400 MHz, CDCl$_3$) δ 7.18–7.26 (m, 2H), 6.70 (d, 1H, J=8.0 Hz), 5.74 (br s, 1H), 3.94–4.08 (m, 1H), 3.89 (t, 2H, J=6.4 Hz), 3.71–3.79 (br t, 1H), 3.55–3.67 (br t, 1H), 2.19 (s, 3H), 1.72–1.82 (m, 2H), 1.55 (s, 3H), 1.45 (s, 9H), 1.22–1.52 (m, 10H), 0.89 (t, 3H, J=6.8 Hz).

Removal of Boc Protecting Group:

To a solution of the desired starting material (65 mg) in dry CH$_2$Cl$_2$ (2 mL) was added trifluoroacetic acid (TFA, 1 mL). The reaction mixture was stirred at room temperature 3–4 hours then evaporated to dryness under reduced pressure. The obtained residue was then azeotroped with CH$_2$Cl$_2$ (2×2 mL) to remove any excess TFA. The final product was either used as is or purified by reverse phase prep HPLC.

(S)-2-Amino-N-(4-(heptyloxy)phenyl)-3-hydroxy-2-methylpropanamide

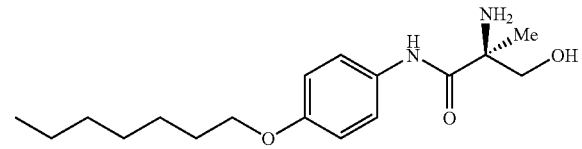

The product was obtained as a white solid in 73% (30 mg) yield. MS (ESI, M+H$^+$)=309.47

(S)-2-Amino-3-hydroxy-2-methyl-N-(4-(octyloxy)phenyl)propanamide

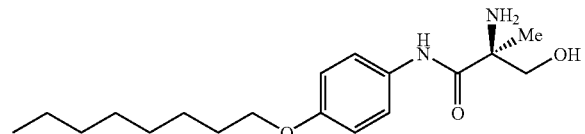

The product was obtained as a white solid in 78% (40 mg) yield. MS (ESI, M+H$^+$)=323.65

(S)-2-Amino-N-(3-chloro-4-(heptyloxy)phenyl)-3-hydroxy-2-methylpropanamide

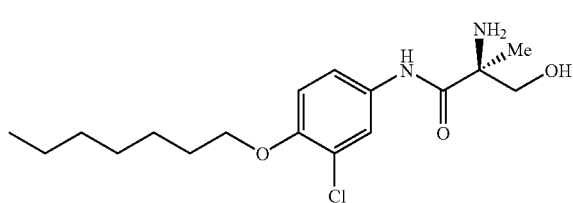

The product was obtained as a white solid in 24% (40 mg) yield. MS (ESI, M+H$^+$)=343.39

(S)-2-Amino-N-(3-chloro-4-(octyloxy)phenyl)-3-hydroxy-2-methylpropanamide

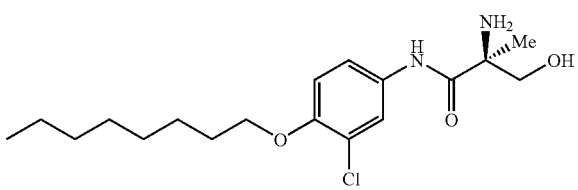

The product was obtained as a white solid in 81% (25 mg) yield. MS (ESI, M+H$^+$)=357.98

(S)-2-Amino-3-hydroxy-2-methyl-N-(3-methyl-4-(octyloxy)phenyl)propanamide

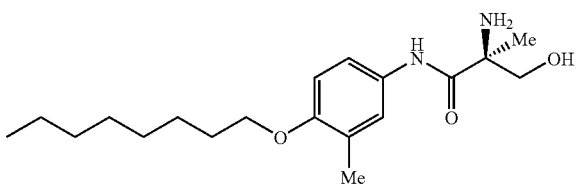

The product was obtained as a white solid in 32% (40 mg) yield. MS (ESI, M+H$^+$)=337.56.

(S)-2-(4-(Octyloxy)phenylcarbamoyl)-2-aminopropyl dihydrogen phosphate

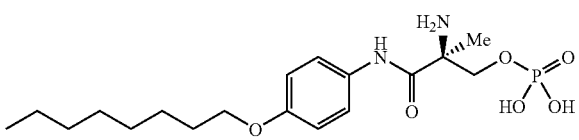

The product was obtained as white solid in 63% (24.9 mg) yield. MS (ESI, M+H$^+$)=403.71; $^1$H NMR (400 MHz, DMSO-d$_6$) δ 10.04 (s, 1H), 7.50 (d, 2H, J=8.8 Hz), 6.87 (d, 2H, J=8.8 Hz), 4.25 (dd, 1H, J=12.4 Hz, J=6.8 Hz), 4.10 (dd, 1H, J=12.8 Hz, J=6.8 Hz), 3.90 (t, 2H, J=6.4 Hz), 1.62–1.72 (m, 2H), 1.47 (s, 3H), 1.20–1.44 (m, 10H), 0.85 (t, 3H, J=7.2 Hz).

(S)-2-(3-Fluoro-4-(octyloxy)phenylcarbamoyl)-2-aminopropyl dihydrogen phosphate

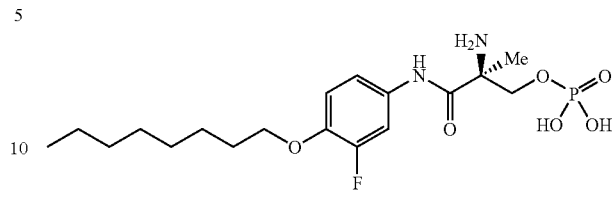

The product was obtained as white solid in 42% (2.5 mg) yield. MS (ESI, M+H$^+$)=421.17; $^1$H NMR (400 MHz, DMSO-d$_6$) δ 10.19 (s, 1H), 7.52 (dd, 1H, J=14.0 Hz, J=2.4 Hz), 7.27 (dd, 1H, J=10.0 Hz, J=1.2 Hz), 7.05 (t, 1H, J=9.6 Hz), 4.20 (dd, 1H, J=11.6 Hz, J=6.4 Hz), 4.03 (dd, 1H, J=11.6 Hz, J=6.8 Hz), 3.93 (t, 2H, J=6.4 Hz), 1.59–1.68 (m, 2H), 1.41 (s, 3H), 1.14–1.38 (m, 10H), 0.80 (t, 3H, J=7.2 Hz).

Example 2

Synthesis of Phenylimidazole Compounds with Alkoxy Tail Group

The desired compounds were synthesized as described in Scheme 3. Substituted phenols were alkylated with the appropriate alkyl bromide using KO$^t$Bu in acetone and a catalytic amount of NaI at 50° C., or in a microwave at 80° C. using KO$^t$Bu in THF. Friedel-Crafts acylation of the corresponding phenyl ether provides the desired bromoacetophenone precursor. Reaction of the bromoacetophenone with an amino acid gave the amino acid ester as an intermediate which, upon intramolecular cyclization in the presence of excess ammonium acetate, provided the desired phenylimidazole. The phenylimidazole was either deprotected to remove the Boc group using 30% TFA in CH$_2$Cl$_2$, or was phosphorylated as illustrated in Scheme 4.

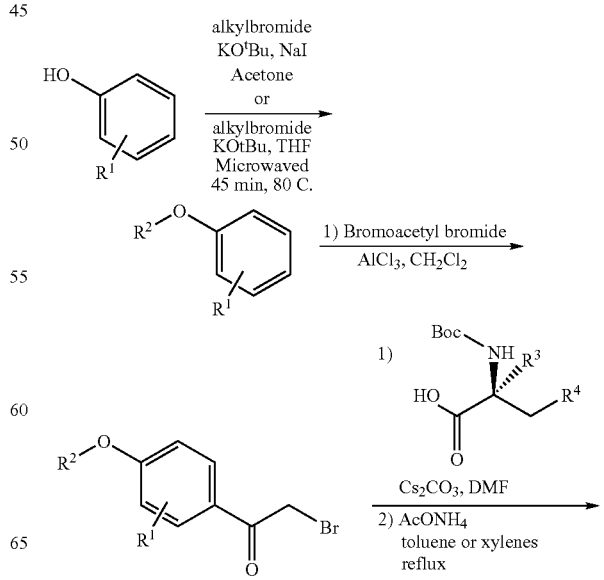

Scheme 3

-continued

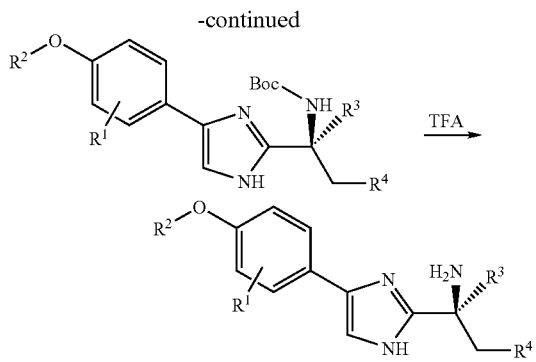

General Method for Phosphate Synthesis

This method is illustrated in Scheme 4 below. To a solution of the Boc-protected aminoalcohol (1.0 equiv) in dry $CH_2Cl_2$ at room temperature was added excess diethyl chlorophosphate (10–20 equiv) and triethylamine (2.5 equiv) and the reaction stirred for 12–18 hours. The crude was then loaded onto a silica gel column chromatography, as is, to purify the desired phospho-diester. The phopho-diester intermediate was reacted with excess bromotrimethylsilane (20 equiv) in dry $CH_2Cl_2$ at room temperature, under an atmosphere of nitrogen, over a period of 6–10 hours afforded the final phosphate which was purified by reverse-phase preparative HPLC.

Scheme 4

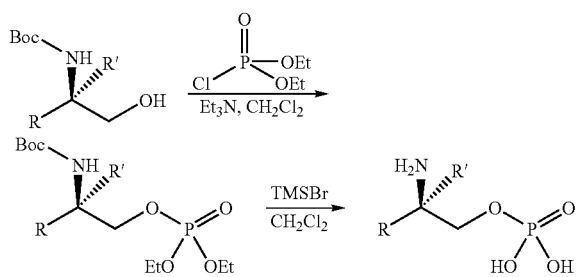

General Methods for Alkylation of Substituted Phenols

Procedure A: To a solution of desired substituted phenol (0.50 g, 1.0 equiv) and NaI (0.1 equiv) in acetone (10 mL) was added a 1.0 M solution of KO$^t$Bu in THF (1.1 equiv). To the reaction mixture is then added the desired alkyl bromide (1.1 equiv). The reaction was stirred and heated under an atmosphere of nitrogen at 50° C. for 12–24 hours. The reaction was then diluted with EtOAc (25 mL) and washed with $H_2O$ (2×25 mL) and saturated NaCl (1×25 mL). The organic layer was dried over anhydrous $MgSO_4$ then the solvent removed in vacuo. The crude product was purified using silica gel column chromatography (9:1 Hex:EtOAc).

Procedure B: To a microwave tube containing the substituted phenol (0.50 g, 1.0 equiv) was added a 1.0 M solution of KO$^t$Bu in THF (1.1 equiv). To the reaction mixture was added the desired alkyl bromide (1.1 equiv). The reaction mixture was then microwaved at 80° C. for 45 minutes. The reaction was then diluted with EtOAc (25 mL) and washed with $H_2O$ (2×25 mL) and saturated NaCl (1×25 mL). The organic layer was dried over anhydrous $MgSO_4$ then the solvent removed in vacuo. The crude product was purified using silica gel column chromatography (9:1 Hex:EtOAc).

1-(Octyloxy)benzene

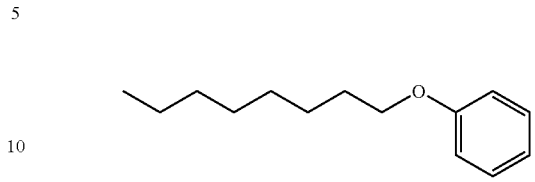

The product was obtained as an off white solid in 79% (1.0 g) yield. TLC (1:3 EtOAc:Hex), $R_f$=0.85; $^1$H NMR (400 MHz, CDCl$_3$) δ 7.24 (m, 2H), 6.89 (m, 3H), 3.93 (t, 2H, J=6.4 Hz), 1.76–1.81 (m, 2H), 1.42–1.48 (m, 2H), 1.20–1.38 (m, 8H), 0.89 (t, 3H, J=6.8 Hz).

1-(Heptyloxy)benzene

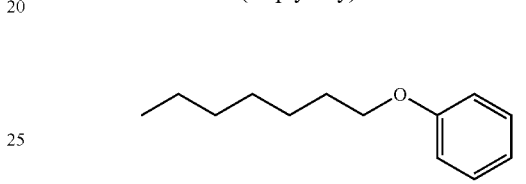

The product was obtained as brownish thick oil in 59% (0.45 g) yield. TLC (1:3 EtOAc:Hex), $R_f$=0.4; $^1$H NMR (400 MHz, CDCl$_3$) δ 6.69–6.74 (m, 2H), 6.59–6.63 (m, 2H), 3.86 (t, 2H, J=6.9 Hz), 3.41 (br s, 2H), 1.69–1.79 (m, 2H), 1.22–1.47 (m, 10H), 0.88 (t, 3H, J=7.1 Hz).

1-Fluoro-3-(octyloxy)benzene

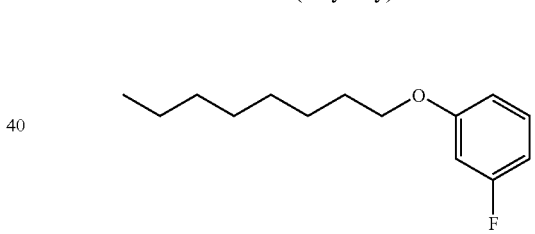

The product was obtained as a colorless oil in 84% (2.10 g) yield. TLC (1:9 EtOAc:Hex), $R_f$=0.8; $^1$H NMR (400 MHz, CDCl$_3$) δ 7.16–7.23 (m, 1H), 6.57–6.69 (m, 3H), 3.93 (t, 2H, J=6.4 Hz), 1.73–1.82 (m, 2H), 1.23–1.50 (m, 10H), 0.89 (t, 3H, J=7.2 Hz).

1-Fluoro-2-(octyloxy)benzene

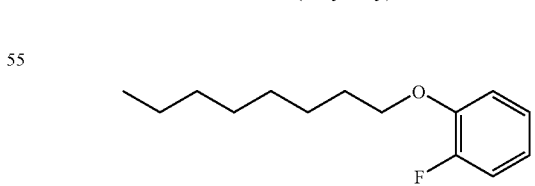

The product was obtained as a yellowish solid in 71% (0.92 g) yield. TLC (1:3 EtOAc:Hex), $R_f$=0.83; $^1$H NMR (400 MHz, CDCl$_3$) δ 7.08–7.10 (m, 2H), 6.94 (dd, 1H), 6.80–6.88 (m, 1H), 4.02 (t, 2H, J=6.8 Hz), 1.76–1.82 (m, 2H), 1.42–1.48 (m, 2H), 1.20–1.38 (m, 8H), 0.88 (t, 3H, J=6.8 Hz).

General Method for Friedel-Crafts Acylation

To a solution of the desired phenyl ether (8.92 mmol, 1.0 equiv) in dry $CH_2Cl_2$ (20 mL) at −20° C. (water/salt bath) is added $AlCl_3$ (1.1 equiv) in portions. Bromoacetyl bromide (1.2 equiv) is then added dropwise to the reaction mixture over a period of 10–15 min. The reaction was then allowed to warm up to 0° C. or room temperature and monitored by TLC (reaction time generally 4–12 hours). The mixture was diluted with $CH_2Cl_2$ (50 mL), washed with $H_2O$ (2×50 mL), and saturated NaCl (1×50 mL). The organic layer was dried over anhydrous $MgSO_4$ then the solvent was removed in vacuo. The crude product was purified using silica gel column chromatography (9:1 Hex:EtOAc).

2-Bromo-1-(4-(octyloxy)phenyl)ethanone

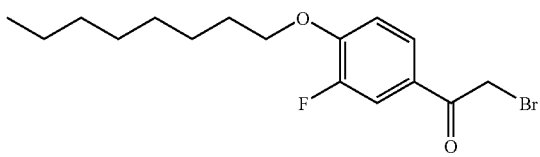

The product was obtained as an off white solid in 59% (0.461 g) yield. TLC (1:3 EtOAc:Hex), $R_f$=0.85; $^1$H NMR (400 MHz, $CDCl_3$) δ 8.23 (d, 2H, J=6.0 Hz), 7.22 (d, 2H, J=8.0 Hz), 4.68 (s, 2H), 4.31 (t, 2H, J=6.8 Hz), 2.09 (m, 2H), 1.75 (m, 2H), 1.58 (m, 10H), 1.17 (t, 3H, J=6.8 Hz).

2-Bromo-1-(4-(heptyloxy)phenyl)ethanone

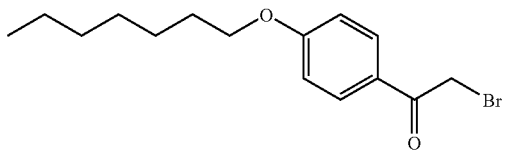

The product was obtained as an off white solid in 30% (0.93 g) yield. TLC (1:3 EtOAc:Hex), $R_f$=0.68; $^1$H NMR (400 MHz, $CDCl_3$) δ 7.95 (d, 2H, J=7.2 Hz), 6.94 (d, 2H, J=8.8 Hz), 4.39 (s, 2H), 4.03 (t, 2H, J=6.8 Hz), 1.82 (m, 2H), 1.45 (m, 2H), 1.31 (m, 6H), 0.90 (t, 3H, J=7.2 Hz).

2-Bromo-1-(3-fluoro-4-(octyloxy)phenyl)ethanone

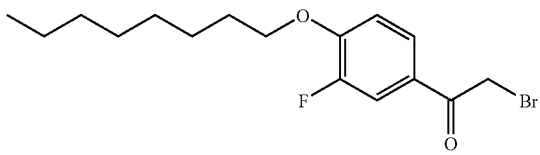

The product was obtained as a whitish solid in 39% (0.1 g). TLC (1:3 EtOAc:Hex), $R_f$=0.6; $^1$H NMR (400 MHz, $CDCl_3$) δ 7.70–7.76 (m, 2H), 7.00 (t, 1H, J=8.0 Hz), 4.37 (s, 2H), 4.11 (t, 2H, J=6.4 Hz), 1.82–1.88 (m, 2H), 1.44–1.53 (m, 2H), 1.28–1.34 (m, 8H), 0.88 (t, 3H, J=6.8 Hz).

General Method for Imidazole Synthesis

A mixture of desired amino acid (1.0 equiv) and $Cs_2CO_3$ (0.5 equiv) was stirred in DMF (4 mL) for 5 minutes then to the solution was added the desired bromo-ketone (0.77 mmol, 1.0 equiv) then the mixture was stirred at room temperature for 1 hour. The reaction mixture was diluted with EtOAc (25 mL) and washed with $H_2O$ (2×25 mL), and saturated NaCl (1×25 mL) to remove access DMF and CsBr salt. The organic layer was dried over anhydrous $MgSO_4$ and the solvent removed in vacuo (the DMF could also be removed either under reduced pressure without the necessity for the work-up).

To the obtained ester was then added excess (~20 eq) ammonium acetate, and the mixture was suspended in either toluene or xylenes and refluxed for 4–6 hours under Dean-Stark conditions. The mixture was diluted with EtOAc (25 mL) and washed with $H_2O$ (2×25 mL), and saturated NaCl (1×25 mL). The organic layer was dried over anhydrous $MgSO_4$ and the solvent removed in vacuo. The crude product was purified using silica gel column chromatography.

tert-Butyl-(R)-1-hydroxy-2-(4-(4-(octyloxy)phenyl)-1H-imidazol-2-yl)propan-2-ylcarbamate

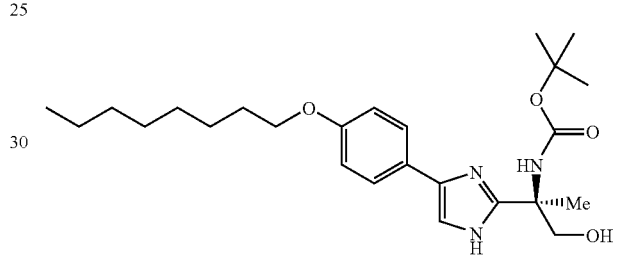

The product was obtained as a colorless foam in 35% (72 mg) yield. TLC (1:1 EtOAc:Hex), $R_f$=0.3; $^1$H NMR (400 MHz, $CDCl_3$) δ 10.40 (br s, 1H), 7.63 (d, 2H, J=8.4 Hz), 7.10 (br s, 1H), 6.90 (d, 2H, J=8.4), 5.66 (br s, 1H), 4.85 (br s, 1H), 4.31 (d, 1H, J=11.2), 3.96 (t, 2H, J=6.8 Hz), 3.62 (d, 1H, J=11.2 Hz), 1.73–1.82 (m, 2H), 1.66 (s, 3H), 1.44 (s, 9H), 1.24–1.52 (m, 10H), 0.89 (t, 3H, J=7.2 Hz).

tert-Butyl-(R)-2-(4-(4-(heptyloxy)phenyl)-1H-imidazol-2-yl)-1-hydroxypropan-2-ylcarbamate

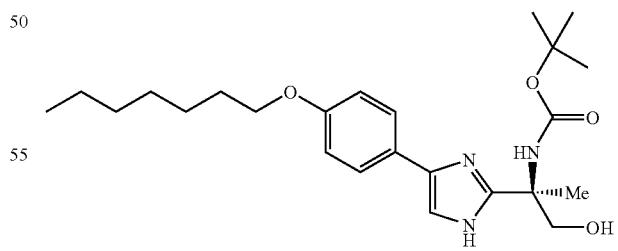

The product was obtained as a brownish solid in 17% (56 mg) yield. TLC (2:1 EtOAc:Hex), $R_f$=0.3; $^1$H NMR (400 MHz, $CDCl_3$) δ 7.56 (d, 2H, J=8.4 Hz), 7.09 (br s, 1H), 6.90 (d, 2H, J=8.4), 5.70 (br s, 1H), 4.30 (d, 1H, J=11.2), 3.97 (t, 2H, J=6.8 Hz), 3.63 (d, 1H, J=11.2 Hz), 1.74–1.83 (m, 2H), 1.66 (s, 3H), 1.43 (s, 9H), 1.24–1.50 (m, 8H), 0.90 (t, 3H, J=7.2 Hz).

tert-Butyl-(R)-2-(4-(2-fluoro-4-(octyloxy)phenyl)-1H-imidazol-2-yl)-1-hydroxypropan-2-ylcarbamate

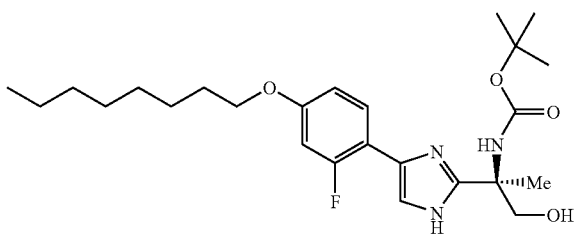

The product was obtained as a yellowish-brown solid in 20% (320 mg) yield. TLC (1:2 EtOAc:Hex), $R_f$=0.4; $^1$H NMR (400 MHz, CDCl$_3$) δ 7.84 (br s, 1H), 7.25 (br s, 1H), 6.73 (dd, 1H, J=12.9 Hz, J=2.4 Hz), 6.66 (dd, 1H, J=12.9 Hz, J=2.4 Hz), 5.68 (br s, 1H), 4.31 (d, 1H, J=11.2), 3.95 (t, 2H, J=6.4 Hz), 3.63 (d, 1H, J=11.2 Hz), 1.74–1.83 (m, 2H), 1.67 (s, 3H), 1.44 (s, 9H), 1.22–1.52 (m, 10H), 0.89 (t, 3H, J=7.0 Hz).

tert-Butyl (R)-2-(4-(3-fluoro-4-(octyloxy)phenyl)-1H-imidazol-2-yl)-1-hydroxy propan-2-ylcarbamate

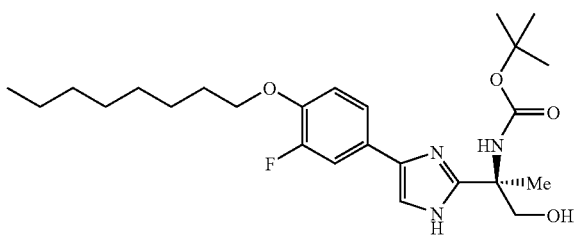

The final product was obtained as a white solid in 31% (30 mg). TLC (1:3 EtOAc:Hex), $R_f$=0.16; $^1$H NMR (400 MHz, CDCl$_3$) δ 7.34–7.4 (m, 2H), δ 7.101 (s, 1H), 6.944 (t, 1H, J=8.4 Hz), 4.3 (d, 1H, J=11.6), 4.033 (t, 2H, J=6.8), 3.62 (d, 1H, J=11.6 Hz), 1.81–1.86 (m, 2H), 1.66 (s, 3H), 1.44–1.52 (m, 10H), 0.88 (t, 3H, J=6.8 Hz). MS (ESI, M+H$^+$)=364.5 tert-Butyl (S)-2-((benzyloxy)carbonyl)-1-(4-(4-(octyloxy)phenyl)-1H-imidazol-2-yl)ethylcarbamate

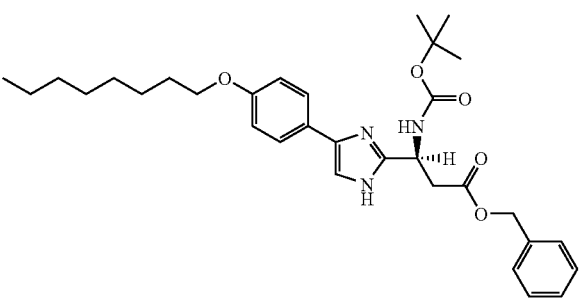

The product was obtained as a colorless oil in 64% (160 mg) yield. TLC (2:1 EtOAc:Hex), $R_f$=0.2; $^1$H NMR (400 MHz, CDCl$_3$) δ 7.62 (br s, 1H), 7.28–7.35 (m, 7H), 7.08 (s, 1H), 6.89 (d, 2H, J=9.2 Hz), 5.90 (br s, 1H), 5.08–5.21 (m, 3H), 3.97 (t, 2H, J=6.0 Hz), 3.26 (br m, 1H), 3.00 (dd, 1H, J=16.4 Hz, J=7.2 Hz), 1.74–1.84 (m, 2H), 1.46 (s, 9H), 1.23–1.54 (m, 10H), 0.89 (t, 3H, J=7.2 Hz).

General Method for Removal of Boc Protecting Group

To a solution of the desired starting material (100 mg) in CH$_2$Cl$_2$ (2 mL) was added TFA (1 mL). The reaction mixture was stirred at room temperature 2 hours then evaporated to dryness under reduced pressure. The final product was purified by reverse phase preparative HPLC.

(R)-2-Amino-2-(4-(4-(octyloxy)phenyl)-1H-imidazol-2-yl)propan-1-ol

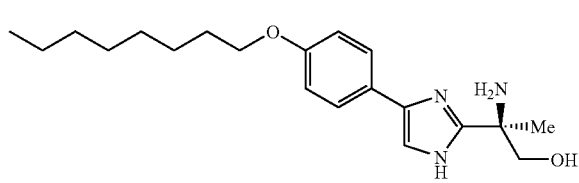

The product was obtained as a white solid in 81% (29 mg) yield. MS (ESI, M+H$^+$)=346.30; $^1$H NMR (400 MHz, DMSO-d$_6$) δ 8.38 (br s, 2H), 7.67 (d, 2H, J=8.4 Hz), 7.50 (br s, 1H), 6.92 (d, 2H, J=8.4), 5.82 (br s, 1H), 3.94 (t, 2H, J=6.4 Hz), 3.75 (d, 1H, J=11.6 Hz), 3.64 (d, 1H, J=11.6 Hz), 1.65–1.74 (m, 2H), 1.55 (s, 3H), 1.22–1.45 (m, 10H), 0.85 (t, 3H, J=7.2 Hz).

(R)-2-Amino-2-(4-(4-(heptyloxy)phenyl)-1H-imidazol-2-yl)propan-1-ol

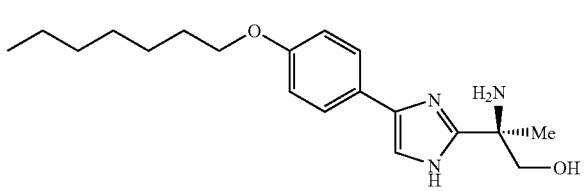

The product was obtained as a white solid in 99% (58 mg) yield. MS (ESI, M+H$^+$)=332.60; $^1$H NMR (400 MHz, DMSO-d$_6$) δ 8.34 (br s, 2H), 7.67 (d, 2H, J=8.4 Hz), 7.40 (br s, 1H), 6.92 (d, 2H, J=8.4), 5.66 (br s, 1H), 3.94 (t, 2H, J=6.8 Hz), 3.74 (d, 1H, J=11.6 Hz), 3.64 (d, 1H, J=11.6 Hz), 1.64–1.76 (m, 2H), 1.55 (s, 3H), 1.22–1.44 (m, 8H), 0.86 (t, 3H, J=7.0 Hz).

(R)-2-Amino-2-(4-(2-fluoro-4-(octyloxy)phenyl)-1H-imidazol-2-yl)propan-1-ol

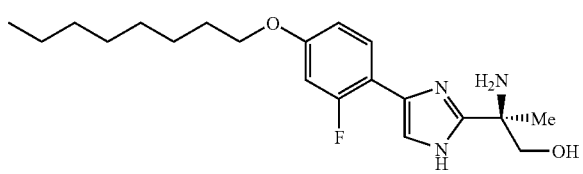

The product was obtained as a white solid in 75% (77 mg) yield. MS (ESI, M+H⁺)=364.60; ¹H NMR (400 MHz, DMSO-d₆) δ 8.40 (br s, 2H), 7.93 (br t, 1H), 7.38 (d, 2H, J=3.6 Hz), 6.81–6.70 (m, 2H), 5.67 (br s, 1H), 3.97 (t, 2H, J=6.2 Hz), 3.74 (d, 1H, J=11.6 Hz), 3.66 (d, 1H, J=11.6 Hz), 1.64–1.75 (m, 2H), 1.55 (s, 3H), 1.21–1.44 (m, 10H), 0.85 (t, 3H, J=7.2 Hz).

(R)-2-Amino-2-(4-(3-fluoro-4-(octyloxy)phenyl)-1H-imidazol-2-yl)propan-1-ol

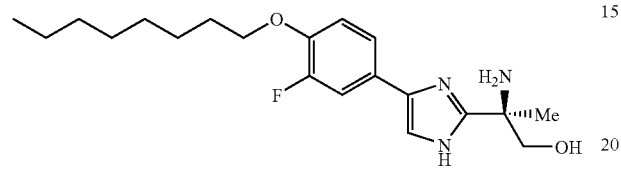

The final product was obtained as a white solid in 31% (30 mg). ¹H NMR (400 MHz, CDCl₃) δ 7.34–7.4 (m, 2H), δ 7.101 (s, 1H), 6.944 (t, 1H, J=8.4 Hz), 4.3 (d, 1H, J=11.6), 4.033 (t, 2H, J=6.8), 3.62 (d, 1H, J=11.6 Hz), 1.81–1.86 (m, 2H), 1.66 (s, 3H), 1.52–1.44 (m, 10H), 0.88 (t, 3H, J=6.8 Hz). MS (ESI, M+H⁺)=364.5

(R)-2-Amino-2-(4-(4-(octyloxy)phenyl)-1H-imidazol-2-yl)propyl dihydrogen phosphate

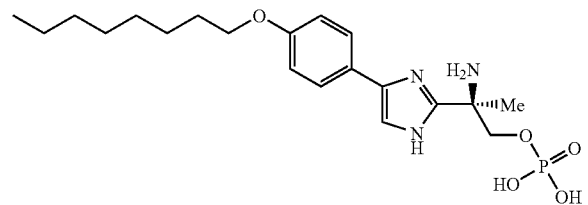

The product was obtained as white solid in 69% (22.8 mg) yield. MS (ESI, M+H⁺)=426.65; ¹H NMR (400 MHz, DMSO-d₆) δ 7.67 (d, 2H, J=8.6 Hz), 7.48 (s, 1H), 6.91 (d, 2H, J=8.6 Hz), 4.16 (dd, 1H, J=10.8 Hz, J=6.8 Hz), 4.05 (dd, 1H, J=10.8 Hz, J=6.8 Hz), 3.94 (t, 2H, J=6.8 Hz), 1.64–1.73 (m, 2H), 1.59 (s, 3H), 1.21–1.45 (m, 10H), 0.85 (t, 3H, J=7.2 Hz).

Example 3

Synthesis of Phenylamide Compounds with Aryl Tail Groups

Several biphenyls were synthesized using the process described in Scheme 5. Microwave assisted Suzuki cross-coupling of substituted arylboronic acids with substituted anilines afforded good to excellent yields of the biaryl amine intermediates. Furthermore, the acylation of the substituted biaryl amines with desired headpiece followed by deprotection of the Boc group afforded the final compounds.

Scheme 5

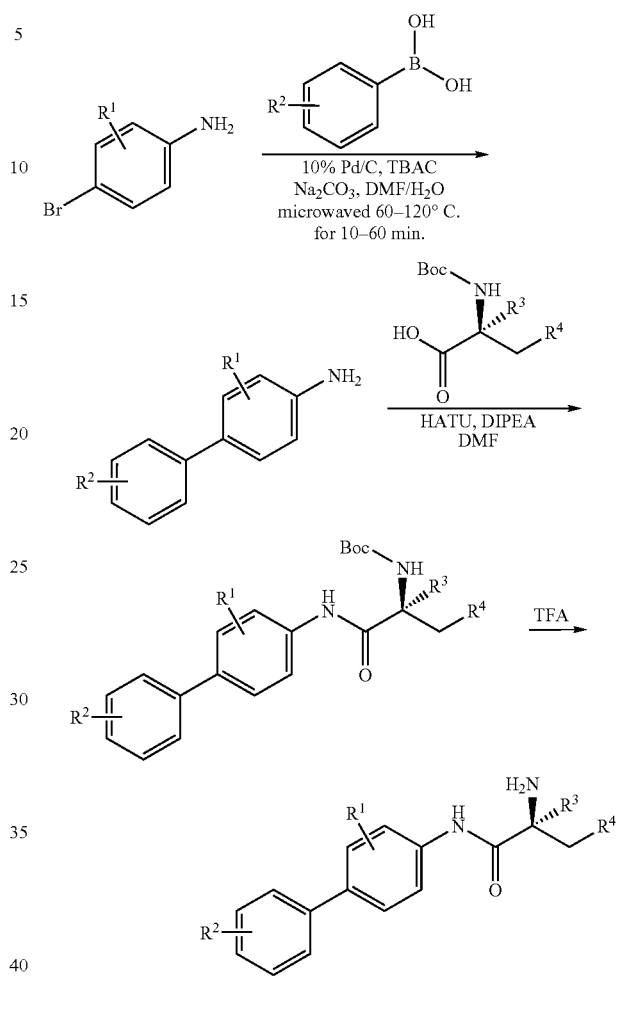

General Method for Suzuki Cross-Coupling

To a mixture of a substituted bromoaniline (1.0 equiv), substituted aryl boronic acid (1.2 equiv), 10% Pd on carbon (0.1 equiv), tetrabutylammonium chloride (0.1 equiv), and sodium carbonate (1.0 to 2.0 equiv), in a microwave tube was added a 1:1 mixture of DMF:H₂O. The mixture was then heated to 60–120° C. for 10–60 minutes using a microwave. The reaction is then diluted with EtOAc (25 mL) and washed with H₂O (2×25 mL) and saturated NaCl (1×25 mL). The organic layer was dried over anhydrous MgSO₄ and the solvent removed in vacuo. The crude product was purified using silica gel column chromatography (Hex:EtOAc) as required.

4-(4-tolyl)benzenamine

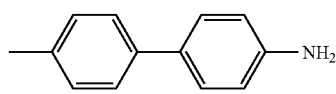

85

The product was obtained as a white solid in 66% (140 mg) yield. TLC (2:1 Hex:EtOAc), $R_f$=0.3; $^1$H NMR (400 MHz, CDCl$_3$) δ 7.29–7.38 (m, 4H), 7.12 (d, 2H, J=8.4 Hz), 6.67 (d, 2H, J=8.4 Hz), 3.60 (br s, 2H), 2.31 (s, 3H).

4-(4-ethylbenzyl)benzenamine

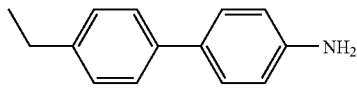

The product was obtained as a white solid in 87% (200 mg) yield. TLC (2:1 Hex:EtOAc), $R_f$=0.5; $^1$H NMR (400 MHz, CDCl$_3$) δ 7.38–7.48 (m, 4H), 7.24 (d, 2H, J=8.0 Hz), 6.75 (d, 2H, J=8.0 Hz), 3.40 (br s, 2H), 2.68 (q, 2H, J=7.2 Hz), 1.27 (t, 3H, J=7.2 Hz).

4-(benzo[d][1,3]dioxol-6-yl)benzenamine

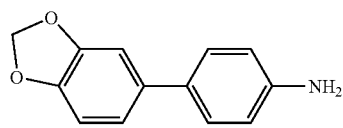

The product was obtained as a white solid in 75% (186 mg) yield. TLC (2:1 Hex:EtOAc), $R_f$=0.4; $^1$H NMR (400 MHz, CDCl$_3$) δ 7.53–7.58 (m, 2H), 7.44–7.49 (m, 2H), 7.01–7.06 (m, 2H), 6.86 (dd, 1H, J=7.6 Hz, J=1.4 Hz), 6.00 (s, 2H), 3.40 (br s, 2H).

tert-butyl (S)-2-(4-(4-tolyl)phenylcarbamoyl)-1-hydroxypropan-2-ylcarbamate

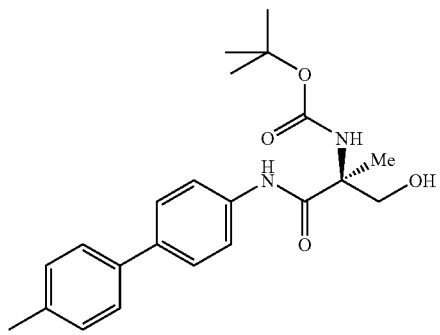

The product was obtained as a white solid in 35% (104 mg) yield. TLC (1:1 Hex:EtOAc), $R_f$=0.3; $^1$H NMR (400 MHz, CDCl$_3$) δ 9.63 (s, 1H), 7.43–7.53 (m, 4H), 7.36–7.42 (m, 2H), 7.15–7.25 (m, 2H), 5.56 (br s, 1H), 4.05 (br s, 1H), 3.49 (br s, 1H), 3.13 (br s, 1H), 2.32 (s, 3H), 1.54 (s, 3H), 1.44 (m, 9H).

86 tert-butyl (S)-2-(4-(4-ethylbenzyl)phenylcarbamoyl)-1-hydroxypropan-2-yl carbamate

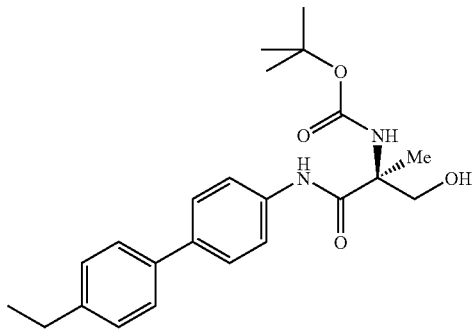

The product was obtained as a white solid in 31% (125 mg) yield. TLC (1:1 Hex:EtOAc), $R_f$=0.4; $^1$H NMR (400 MHz, CDCl$_3$) δ 9.70 (br s, 1H), 7.42–7.64 (m, 6H), 7.24–7.32 (m, 2H), 5.62 (br s, 1H), 4.10 (br s, 1H), 3.60 (br s, 1H), 3.20 (br s, 1H), 2.70 (q, 2H, J=7.0 Hz), 1.55 (s, 3H), 1.45 (m, 9H), 1.30 (t, 3H, J=7.0 Hz).

tert-Butyl (S)-2-(4-(benzo[d][1,3]dioxol-6-yl)phenylcarbamoyl)-1-hydroxypropan-2-ylcarbamate

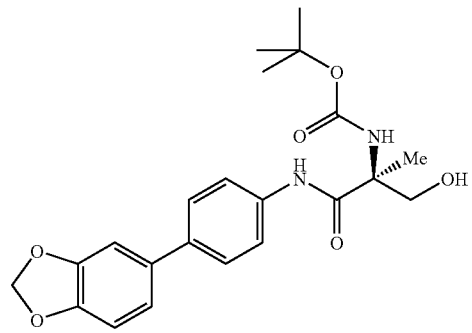

The product was obtained as a white solid in 20% (89 mg) yield. TLC (1:1 Hex:EtOAc), $R_f$=0.3; $^1$H NMR (400 MHz, CDCl$_3$) δ 9.70 (s, 1H), 7.53–7.58 (m, 2H), 7.45–7.50 (m, 2H), 7.01–7.05 (m, 2H), 6.86 (dd, 1H, J=7.6 Hz, J=1.2 Hz), 6.00 (s, 2H), 5.62 (br s, 1H), 4.13 (br s, 1H), 3.57 (br s, 1H), 3.20 (br s, 1H), 1.55 (s, 3H), 1.48 (m, 9H).

(S)-2-Amino-N-(4-(4-tolyl)phenyl)-3-hydroxy-2-methylpropanamide

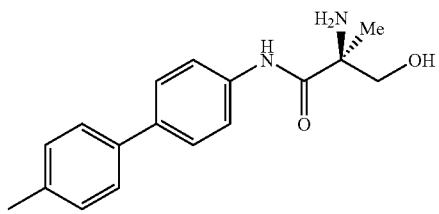

The product was obtained as a white solid in 98% (36 mg) yield. MS (ESI, M+H⁺)=285.40; ¹H NMR (400 MHz, DMSO-d₆) δ 9.94 (br s, 1H), 8.16 (br s, 2H), 7.61–7.72 (m, 4H), 7.54 (d, 2H, J=7.6 Hz), 7.24 (d, 2H, J=7.6 Hz), 5.78 (t, 1H, J=4.8 Hz), 4.00 (dd, 1H, J=11.6 Hz, J=4.8 Hz), 3.65 (dd, 1H, J=11.6 Hz, J=5.2 Hz), 2.32 (s, 3H), 1.50 (s, 3H).

(S)-2-Amino-N-(4-(4-ethylbenzyl)phenyl)-3-hydroxy-2-methylpropanamide

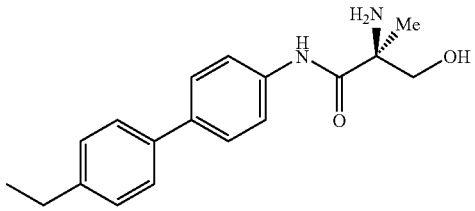

The product was obtained as a white solid in 64% (28 mg) yield. MS (ESI, M+H⁺)=299.30; ¹H NMR (400 MHz, DMSO-d₆) δ 9.95 (br s, 1H), 8.18 (br s, 2H), 7.61–7.72 (m, 4H), 7.55 (d, 2H, J=8.2 Hz), 7.26 (d, 2H, J=8.2 Hz), 5.80 (br s, 1H), 4.00 (d, 1H, J=11.6 Hz), 3.65 (d, 1H, J=11.6 Hz), 2.61 (q, 2H, J=7.6 Hz), 1.50 (s, 3H), 1.19 (t, 3H, J=7.6 Hz).

(S)-2-amino-N-(4-(benzo[d][1,3]dioxol-6-yl)phenyl)-3-hydroxy-2-methylpropanamide

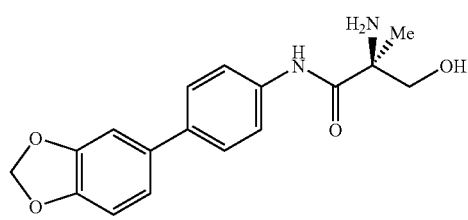

The product was obtained as a white solid in 47% (32 mg) yield. MS (ESI, M+H⁺)=315.40; ¹H NMR (400 MHz, DMSO-d₆) δ 9.93 (br s, 1H), 8.17 (br s, 2H), 7.66 (d, 2H, J=8.4 Hz), 7.59 (d, 2H, J=8.4 Hz), 7.22 (d, 1H, J=1.6 Hz), 7.12 (dd, 1H, J=6.8 Hz, J=2.0 Hz), 6.97 (d, 1H, J=8.4 Hz), 6.04 (s, 2H), 5.79 (br s, 1H), 4.00 (d, 1H, J=11.2 Hz), 3.65 (d, 1H, J=11.2 Hz), 1.50 (s, 3H).

Example 4

Synthesis of Substituted Biaryl Ether Compounds

General Method for the Synthesis of Substituted Biaryl Ethers

The biaryl ethers were synthesized using the general method shown in Scheme 6. To a flame dried round bottom flask is added the acylated 4-aminophenol (1 equiv. 0.15 gm), cupric acetate [Cu(OAc)₂, 1.1. equiv], desired substituted boronic acid (2.5 equiv.), and excess of 4A molecular sieves (0.6–0.9 gm). Dry dichloromethane (DCM) is then added to the reaction flask followed by the addition of anhydrous pyridine (5.0 equiv.). Oxygen is then bubbled through the reaction mixture for approximately 2 min and the reaction is stirred over night at room temperature under an atmosphere of oxygen. The following day the reaction mixture was filtered using a plug of celite to remove the molecular sieves, and the filtrate was concentrated to give a greenish solid. The crude product was purified using silica gel chromatography, EtOAc-Hexane gradient, (25%–100% EtOAc over 30 min.). The fractions corresponding to the product are pooled and the solvent removed under vacuo to give product as a white solid.

Scheme 6

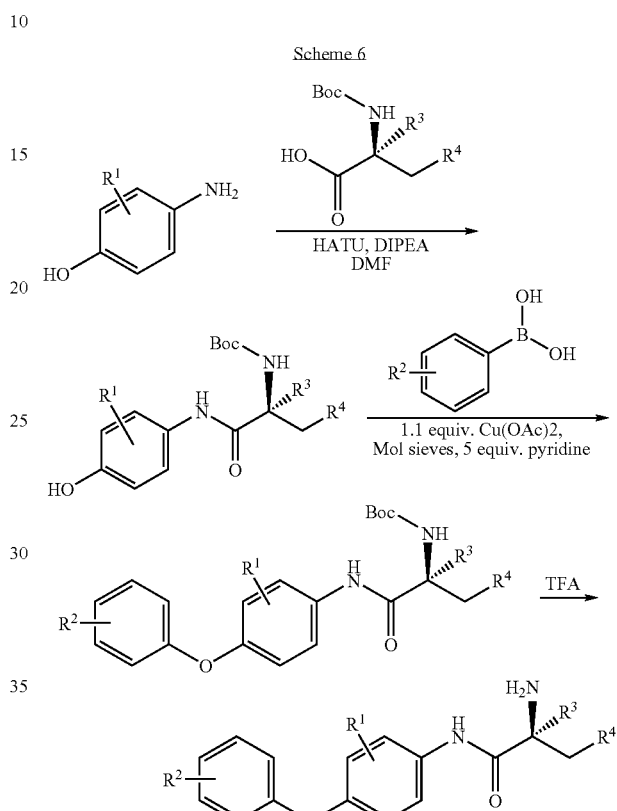

tert-Butyl (S)-2-(4-hydroxyphenylcarbamoyl)-1-hydroxypropan-2-ylcarbamate

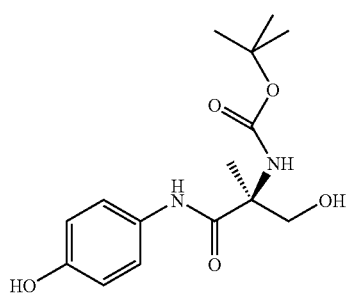

The final product was obtained as a white solid after silica gel purification using an EtOAc-Hexane gradient (15% EtOAc to 80% EtOAc over 25 min.), in 61% yield. TLC (2:1 EtOAc:Hex), R_f(product)=0.3; ¹H NMR (400 MHz, CDCl₃) δ 8.01 (s, 1H), δ 7.34 (d, 2H, J=8.8 Hz), 6.79 (d, 2H, J=8.8 Hz), 5.60 (br. s, 1H), 4.06 (m, 1H), 3.58 (d, 1H, J=12), 1.58 (s, 3H), 1.46 (s, 9H).

89

(S)-[2-Hydroxy-1-methyl-1-(4-phenoxy-phenylcarbamoyl)-ethyl]-carbamic acid tert-butyl ester

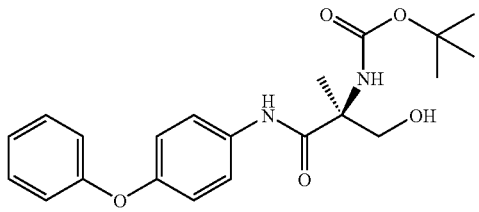

The final product was obtained as white solid following silica gel purification, in 58% yield, (0.08 g). TLC (1:1 EtOAc:Hex), $R_f$=0.2; MS (ESI, M+H$^+$)=387.45; $^1$H NMR (400 MHz, CDCl$_3$) δ 9.46 (s, 1H), δ 7.48 (d, 2H, J=8.8 Hz), 7.30 (m, 2H), 7.07 (m, 1H), 6.97 (m, 4H), 4.16 (s, 1H), 3.65 (s, 1H), 1.58 (s, 3H) 1.46 (s, 9H).

(S)-{1-[4-(4-Ethyl-phenoxy)-phenylcarbamoyl]-2-hydroxy-1-methyl-ethyl}-carbamic acid tert-butyl ester

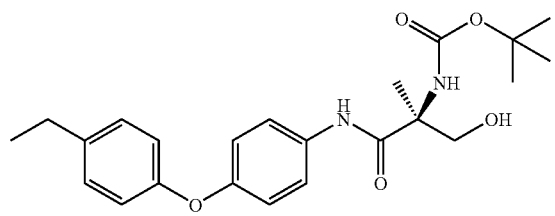

The final product was obtained as white solid following silica gel purification, in 65% yield, (0.05 g). TLC (1:1 EtOAc:Hex), $R_f$=0.3; $^1$H NMR (400 MHz, CDCl$_3$) δ 8.6 (s, 1H), δ 7.47 (d, 2H, J=8.0 Hz), 7.13 (d, 2H, J=8.4 Hz), 6.92 (d, 2H, J=10 Hz), 6.88 (m, 2H), 4.05 (m, 1H), 3.64 (d, 1H, J=10.8), 2.62 (q, 2H, J=16 Hz, J=8 Hz), 1.58 (s, 3H) 1.46 (s, 9H), 1.23 (t, 3H, J=7.6 Hz).

(S)-{1-[4-(4-Butyl-phenoxy)-phenylcarbamoyl]-2-hydroxy-1-methyl-ethyl}-carbamic acid tert-butyl ester

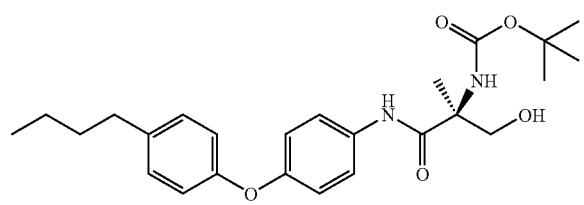

The final product was obtained as white solid following silica gel purification, in 45% yield, (0.092 g). TLC (1:2 EtOAc:Hex), $R_f$=0.2; $^1$H NMR (400 MHz, CDCl$_3$) δ 9.56 (s, 1H), 7.45 (d, 2H, J=9.2 Hz), 7.12 (d, 2H, J=8.8 Hz), 6.96 (d, 2H, J=8.8 Hz), 6.89 (d, 2H, J=8.4 Hz), 4.07 (m, 1H), 3.59 (m, 1H), 2.58 (t, 2H, J=7.6 Hz), 1.51–1.62 (m, 5H), 1.46 (s, 9H), 1.35 (m, 2H), 0.93 (t, 3H, J=7.6 Hz).

90

(S)-{1-[4-(4-Butoxy-phenoxy)-phenylcarbamoyl]-2-hydroxy-1-methyl-ethyl}-carbamic acid tert-butyl ester

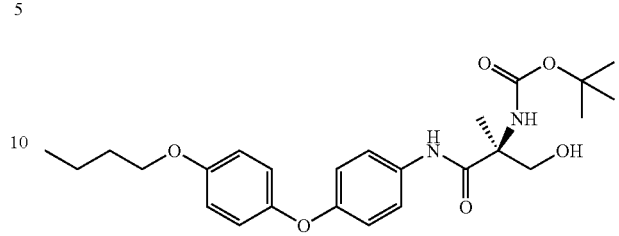

The final product was obtained as white solid following silica gel purification, in 25% yield, (0.023 g). TLC (1:1 EtOAc:Hex), $R_f$=0.4; $^1$H NMR (400 MHz, CDCl$_3$) δ 9.56 (s, 1H), 7.43 (d, 2H, J=9.2 Hz), 6.90–6.94 (m, 4H), 6.85 (d, 2H, J=9.2 Hz), 4.07 (m, 1H), 3.93 (t, 2H, J=7.6 Hz) 3.58 (m, 1H), 1.74–1.78 (m, 2H), 1.58 (s, 3H), 1.50 (m, 2H), 1.46 (s, 9H), 0.98 (t, 2H, J=7.2 Hz).

(S)-{1-[4-(4-chloro-phenoxy)-phenylcarbamoyl]-2-hydroxy-1-methyl-ethyl}-carbamic acid tert-butyl ester

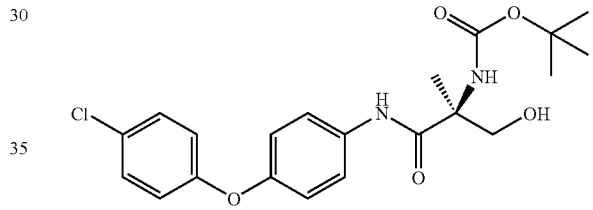

The final product was obtained as white solid following silica gel purification, in 53% yield, (0.107 g). TLC (1:3 EtOAc:Hex), $R_f$=0.2; $^1$H NMR (400 MHz, CDCl$_3$) δ7.49 (d, 2H, J=9.2 Hz), 7.26 (d, 2H, J=8.8 Hz), 6.97 (d, 2H, J=8.8 Hz), 6.90 (d, 2H, J=8.8 Hz), 4.08 (m, 1H), 3.60 (d, 1H, J=11.2 Hz), 1.59 (s, 3H), 1.47 (s, 9H).

(S)-{1-[4-(4-fluoro-phenoxy)-phenylcarbamoyl]-2-hydroxy-1-methyl-ethyl}-carbamic acid tert-butyl ester

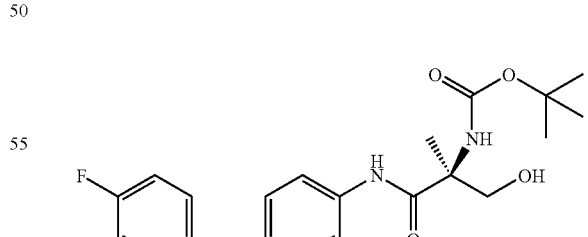

The final product was obtained as a hygroscopic solid following silica gel purification, in 33% yield, (0.063 g). TLC (1:2 EtOAc:Hex), $R_f$=0.4; $^1$H NMR (400 MHz, CDCl$_3$) δ 7.47 (d, 2H, J=9.2 Hz), 6.99 (d, 2H, J=8.0 Hz), 6.92–6.95 (m, 4H), 4.06 (m, 1H), 3.64 (d, 1H, J=10.4 Hz), 1.58 (s, 3H), 1.46 (s, 9H).

(S)-2-Amino-3-hydroxy-2-methyl-N-(3-methyl-4-phenoxy-phenyl)-propionamide

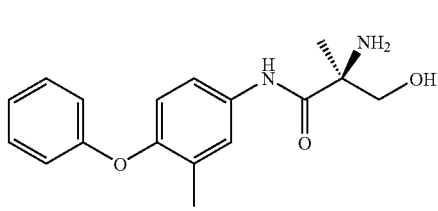

The final product was obtained as a white solid after HPLC, in 35% yield, (0.01 g). MS (ESI, M+H$^+$)=301.19; $^1$H NMR (400 MHz, CDCl$_3$) δ 9.16 (s, 1H), δ 7.25 (m, 1H), δ 7.2 (m, 3H,), 6.95 (t, 1H, J=7.6 Hz), 6.75 (d, 2H, J=8 Hz), 6.69 (d, 1H, J=7.6), 4.13 (s, 1H), 3.92 (s, 1H), 2.05 (s, 3H), 1.52 (s, 3H).

(S)-2-Amino-3-hydroxy-N-[4-(3-methoxy-phenoxy)-phenyl]-2-methylpropionamide

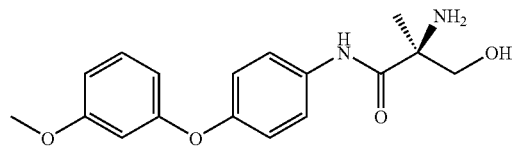

The final product was obtained as an off white solid following HPLC purification. $^1$H NMR (400 MHz, DMSO-d$_6$) δ 9.95 (s, 1H), 8.18 (s, 2H), 7.63 (d, 2H, J=8.8 Hz), 7.24 (t, 1H, J=8.4 Hz), 7.02 (d, 2H, J=9.2 Hz), 6.68 (m, 1H), 6.52 (t, 1H, J=2.4 Hz), 6.48 (m, 1H), 3.98 (d, 1H, J=11.6 Hz), 3.71 (s, 3H), 3.64 (d, 1H, J=12.0 Hz), 1.48 (s, 3H).

(S)-2-Amino-3-hydroxy-N-[4-(3-propoxy-phenoxy)-phenyl]-2-methylpropionamide

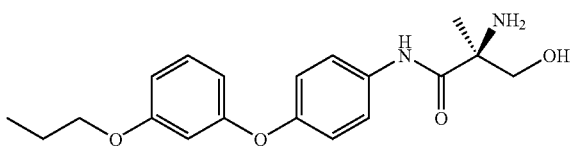

The final product was obtained as an off white solid following HPLC. $^1$H NMR (400 MHz, DMSO-d$_6$) δ 9.93 (s, 1H), 8.14 (s, 2H), 7.63 (d, 2H, J=9.2 Hz), 7.23 (t, 1H, J=8.4 Hz), 7.02 (d, 2H, J=8.8 Hz), 6.67 (m, 1H), 6.48 (m, 2H), 5.79 (t, 1H, J=4.8 Hz), 3.98 (dd, 1H, J=4.8 and 11.6 Hz), 3.86 (t, 2H, J=6.8 Hz), 3.63 (dd, 1H, J=4.8 and 11.6 Hz), 1.68 (m, 2H), 1.48 (s, 3H) 0.93 (t, 3H, J=7.2 Hz).

(S)-2-Amino-3-hydroxy-N-[4-(3-isopropyl-phenoxy)-phenyl]-2-methylpropionamide

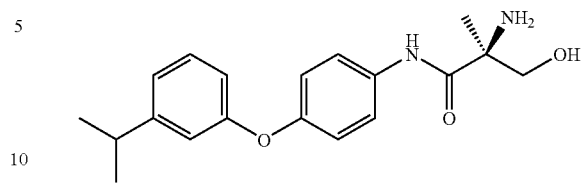

$^1$H NMR (400 MHz, DMSO-d$_6$) δ 9.93 (s, 1H), 7.63 (d, 2H, J=8.8 Hz), 7.28 (t, 1H, J=8 Hz), 7.03 (m, 1H), 7.01 (m, 2H), 6.87 (t, 1H, J=2.0 Hz), 6.74 (m, 1H), 3.98 (dd, 1H, J=4.4 and 11.2 Hz), 3.62 (dd, 1H, J=4.4 and 11.6 Hz), 3.09 (q, 1H, J=7.6 and 14.8 Hz), 2.87 (m, 1H), 1.47 (s, 3H) 1.18 (d, 6H, J=6.0 Hz).

(S)-2-Amino-3-hydroxy-N-[4-(3-trifluoromethyl-phenoxy)-phenyl]-2-methylpropionamide

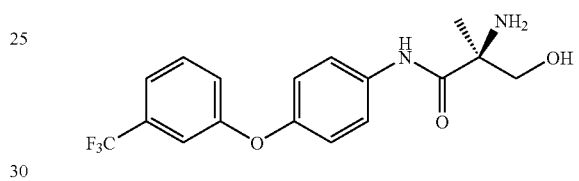

$^1$H NMR (400 MHz, DMSO-d$_6$) δ 9.98 (s, 1H), 7.70 (d, 2H, J=9.2 Hz), 7.47 (m, 1H), 7.26 (m, 2H), 7.14 (d, 2H, J=9.2 Hz), 4.01 (dd, 1H, J=4.0 and 11.2 Hz), 3.66 (dd, 1H, J=4.0 and 11.6 Hz), 1.51 (s, 3H).

(S)-2-Amino-N-[4-(3-benzyloxy-phenoxy)-phenyl]-3-hydroxy-2-methylpropionamide

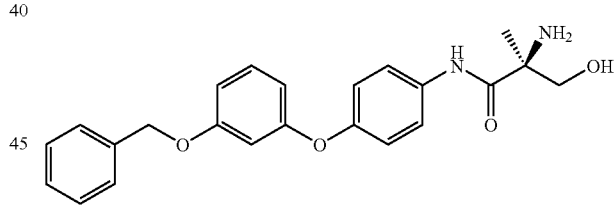

$^1$H NMR (400 MHz, DMSO-d$_6$) δ 9.93 (s, 1H), 8.17 (s, 2H), 7.64 (d, 2H, J=9.2 Hz), 7.41 (m, 2H), 7.38 (m, 1H), 7.35 (m, 1H), 7.27 (t, 1H, J=8.0 Hz), 7.04 (d, 2H, J=9.2 Hz), 6.78 (m, 1H), 6.61 (t, 1H, J=2.4 Hz), 6.52 (m, 1H), 5.80 (t, 1H, J=4.8 Hz), 5.08 (s, 2H), 4.00 (dd, 1H, J=4.4 and 11.2 Hz), 3.65 (dd, 1H, J=4.8 and 11.2 Hz), 1.49 (s, 3H).

(S)-2-Amino-3-hydroxy-N-[4-(3-isopropoxy-phenoxy)-phenyl]-2-methylpropionamide

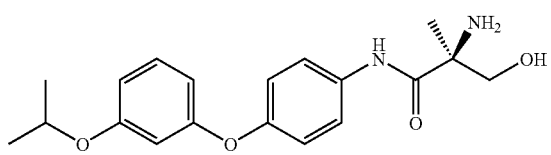

¹H NMR (400 MHz, DMSO-d₆) δ 8.15 (s, 2H), 7.62 (d, 2H, J=9.2 Hz), 7.22 (t, 1H, J=8.8 Hz), 7.03 (d, 2H, J=8.8 Hz), 6.65 (m, 1H), 6.47 (m, 2H), 5.76 (t, 1H, J=4.4 Hz), 4.55 (m, 1H), 3.98 (dd, 1H, J=5.2 and 12.0 Hz), 3.62 (dd, 1H, J=4.8 and 12.0 Hz), 1.47 (s, 3H), 1.23 (s, 3H), 1.21 (s, 3H).

(S)-2-Amino-N-[4-(3-butoxy-phenoxy)-phenyl]-3-hydroxy-2-methylpropionamide

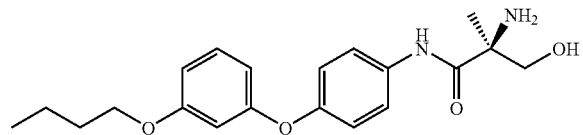

¹H NMR (400 MHz, DMSO-d₆) δ 7.62 (d, 2H, J=9.2 Hz), 7.23 (t, 1H, J=8.4 Hz), 7.03 (d, 2H, J=9.2 Hz), 6.66 (m, 1H), 6.48 (m, 2H), 5.75 (t, 1H, J=4.4 Hz), 3.97 (dd, 1H, J=5.2 and 11.2 Hz), 3.93 (t, 2H, J=9.2 Hz), 3.62 (dd, 1H, J=5.2 and 11.6 Hz), 1.65 (m, 2H), 1.47 (s, 3H), 1.39 (m, 2H), 0.90 (t, 3H, J=7.2 Hz).

(S)-2-Amino-N-[4-(3-ethoxy-phenoxy)-phenyl]-3-hydroxy-2-methylpropionamide

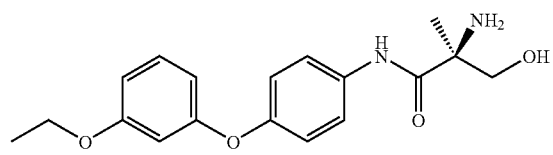

¹H NMR (400 MHz, DMSO-d₆) δ 7.62 (d, 2H, J=8.8 Hz), 7.24 (t, 1H, J=8.8 Hz), 7.03 (d, 2H, J=9.2 Hz), 6.66 (m, 1H), 6.49 (m, 2H), 5.77 (t, 1H, J=4.4 Hz), 3.96 (m, 3H), 3.63 (dd, 1H, J=5.2 and 12.0 Hz), 1.467 (s, 3H), 1.28 (t, 3H, J=7.2 Hz).

Example 5

Synthesis of Phenylamide Compounds with Arylalkoxy and Cycloalkylalkoxy Tail Groups (A) (S)-2-amino-3-hydroxy-2-methyl-N-(4-(biphenethyloxy)phenyl)propanamide trifluoroacetic acid salt

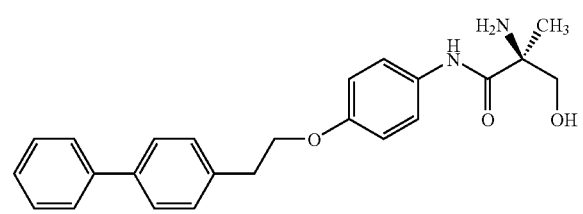

1-(2-(4-nitrophenoxy)ethyl)biphenyl 2-biphenyl ethanol (1 g, 5 mmol), 4-nitrophenol (834 mg, 6 mmol), and triphenylphosphine (1.59 g, 6 mmol) was dissolved in 20 mL dichloromethane. The solution was chilled in an ice-water bath prior to the addition of diethylazodicarboxylate (949 µl, 6 mmol). The reaction was then stirred overnight, and the ice-water bath slowly warmed to room temperature. Crude product was purified by flash chromatography to yield 640 mg crystalline solid. ¹H NMR (400 MHz, DMSO-d₆) δ 8.1 (d), 7.6 (m), 7.47–7.41 (m), 7.34 (m), 7.17 (m), 4.39 (t, 2H), 3.13 (t, 2H).

tert-butyl (S)-2-(4-(phenethyloxy)biphenylcarbamoyl)-1-hydroxypropan-2-ylcarbamate 1-(2-(4-nitrophenoxy)ethyl)biphenyl (300 mg, 0.94 mmol) was dissolved in a mixture of absolute ethanol and ethyl acetate. The mixture was purged with nitrogen gas prior to the addition of 150 mg 10% Pd on carbon. The reaction was capped with a septum and stirred under 1 atm H₂ (g) overnight. Reaction was judged complete by TLC (R_f product ~0.5 in 1:1 EtOAc:hexanes). The solution was filtered through celite and the solvent evaporated under vacuum. Without further purification, the crude product was combined with N-(Boc)-α-methylserine (210 mg), HATU (364 mg), DIPEA (416 µl), and 10 mL DMF. The solution was stirred at room temperature for 3 hours. Solvent was removed by rotary evaporator and crude product purified by flash chromatography to yield 240 mg yellow liquid, 52% yield.

2-amino-3-hydroxy-2-methyl-N-(4-(phenethyloxy)biphenyl)propanamide trifluoroacetic acid salt tert-butyl(S)-2-(4-(phenethyloxy)biphenylcarbamoyl)-1-hydroxypropan-2-ylcarbamate (80 mg) was dissolved in a 1:1 mixture of 2 mL DCM:TFA for 3 hours. The title compound was purified by reverse phase chromatography and 29.6 mg white solid isolated as the TFA salt (in some cases reverse phase purification was not necessary). MS (ESI, M+H⁺)=391.2; ¹H NMR (400 MHz, DMSO-d₆) δ 7.65 (m), 7.60 (m), 7.52–7.40 (m), 6.93 (m), 4.197 (t, 2H), 3.8 (bm, 1H), 3.5 (bm, 1H), 3.06 (t, 2H), 1.38 (s, 3H).

(B) (S)-2-(4-(biphenethyloxy)phenylcarbamoyl)-2-aminopropyl dihydrogen phosphate

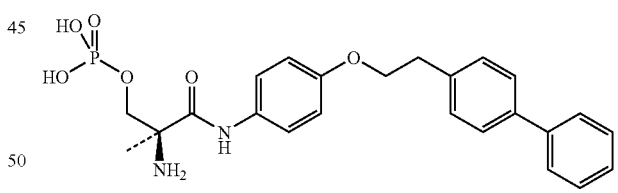

tert-butyl (S)-2-(4-(phenethyloxy)phenylcarbamoyl)-1-diethylphosphatidylpropan-2-ylcarbamate 2-amino-3-hydroxy-2-methyl-N-(4-(phenethyloxy)biphenyl)propanamide trifluoroacetic acid salt (116 mg), diethylchloridophosphite (171 µl, 5 eq), and DIPEA (8 eq) were combined in 2 ml anhydrous DCM under N₂ atmosphere. After 8 hours conversion to product remained low, ~20%, as judged by TLC (R_f~0.2 in 80% EtOAc:hexanes). More diethylchloridophosphite (171 µl, 5 eq) and DIPEA (8 eq) were added to the reaction mixture and the solution stirred overnight. The next morning TLC showed ~100% conversion to product. Flash chromatography yielded 10 mg of pure product (20% yield). MS (ESI, M+Na⁺)=649.

(S)-2-(4-(biphenethyloxy)phenylcarbamoyl)-2-aminopropyl dihydrogen phosphate (S)-2-(4-(phenethyloxy)phenylcarbamoyl)-2-aminopropyl diethyl phosphate (10 mg) was dissolved in 3 ml DCM, immersed in an ice bath, and excess trimethylsilylbromide added (20 eq). The reaction was monitored by liquid chromatography/mass spectrometry (LCMS). Complete disappearance of the starting material occurred overnight while stirring at room temperature. Solvent was evaporated and the crude product purified by reverse phase chromatography to yield 1.5 mg of the title compound (16% yield). MS (ESI, M+H$^+$)=471.1; $^1$H NMR (400 MHz, DMSO-d$_6$) δ 7.66–7.63 (m), 7.60–7.40 (m), 7.36 (m), 4.3 (m, 1H), 4.20 (t, 2H), 4.05 (bm, 1H), 3.051 (t, 2H), 1.48 (s).

(C) (S)-N-(4-(4-(thiophen-2-yl)butoxy)phenyl)-2-amino-3-hydroxy-2-methylpropanamide trifluoroacetic acid salt

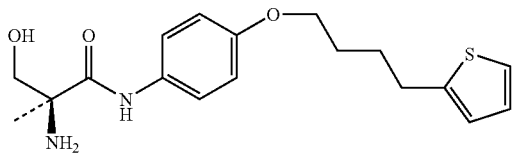

tert-butyl (S)-2-(4-(4-(thiophen-2-yl)butoxy)phenylcarbamoyl)-1-hydroxypropan-2-ylcarbamate This compound was synthesized from 2-(4-(4-nitrophenoxy)butyl)thiophene (280 mg), N-(Boc)-α-methylserine (205 mg), HATU (442 mg), and DIPEA (506 μl) following the procedure described in Example 5(A) to yield 280 mg product (62% yield). $^1$H NMR (400 MHz, DMSO-d$_6$) δ 9.24 (s, 1H), 7.44 (m, 2H), 7.29 (m, 1H), 6.9 (m, 1H), 6.84–6.81 (m, 3H), 5.00 (t, 1H), 3.93 (t, 2H), 3.61 (m, 2H), 2.84 (t, 2H), 1.73 (m, 4H), 1.48 (overlapping singlets, 9H).

(S)-N-(4-(4-(thiophen-2-yl)butoxy)phenyl)-2-amino-3-hydroxy-2-methylpropanamide trifluoroacetic acid salt This compound was synthesized from tert-butyl (S)-2-(4-(4-(thiophen-2-yl)butoxy)phenylcarbamoyl)-1-hydroxypropan-2-ylcarbamate (140 mg) according to the procedure provided in Example 5(A) to yield 31 mg white solid title compound. MS (ESI, M+H$^+$)=349.5; $^1$H NMR (400 MHz, DMSO-d$_6$) δ 9.79 (bs, 1H), 7.48 (m, 2H), 7.29 (m, 1H), 6.9–6.8 (m, 5H), 5.6 (bs, 1H), 3.95+3.8 (overlapping signals, 3H), 3.55 (m, 1H), 2.84 (m, 2H), 1.73 (m, 4H), 1.41 (s, 3H).

(D) (S)-2-(4-(4-(thiophen-2-yl)butoxy)phenylcarbamoyl)-2-aminopropyl dihydrogen phosphate

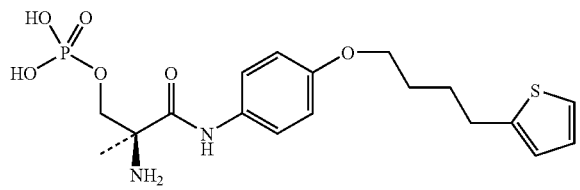

(S)-N-(4-(4-(thiophen-2-yl)butoxy)phenyl)-2-amino-3-hydroxy-2-methylpropanamide trifluoroacetic acid salt (116 mg), di(tert-butyl) diisopropylamidophosphite (143 mg, 163 μl), and 1H-tetrazole (108 mg) were combined in 3 ml anhydrous THF under N$_2$ (g) and stirred overnight. LCMS showed leftover starting material and more di(tert-butyl) diisopropylamidophosphite (143 mg, 163 μl), and 1H-tetrazole (108 mg) were added to the reaction mixture. The reaction was complete after several days stirring at room temperature. 264 ul of 30% aq H$_2$O$_2$ was then added to the solution and the reaction stirred for an additional 2.5 hours prior to quenching with 1 mL saturated sodium thiosulfite soln. The resulting mixture was diluted with EtOAc and the organic layer collected, concentrated, and purified by flash chromatography yielding 45 mg tert-butyl (S)-2-(4-(4-(thiophen-2-yl)butoxy)phenylcarbamoyl)-1-di-tert-butyl phosphatidylpropan-2-ylcarbamate. The purified sample was then dissolved in 2 mL 25% TFA:DCM and stirred for 1 hour. The solution was concentrated to yield 24 mg of the title compound. MS (ESI, M+H$^+$)=429.2; $^1$H NMR (400 MHz, DMSO-d$_6$) δ 9.8 (bs, 1H), 7.48 (m, 2H), 7.29 (m, 1H), 6.9–6.8 (m, 5H), 4.25 (m, 1H), 4.05 (m, 1H), 3.95 (bt, 3H), 3.55 (m, 1H), 2.84 (m, 2H), 1.73 (m, 4H), 1.41 (s, 3H).

(E) (S)-N-(4-(4-(4-methoxyphenyl)butoxy)phenyl)-2-amino-3-hydroxy-2-methylpropanamide trifluoroacetic acid salt

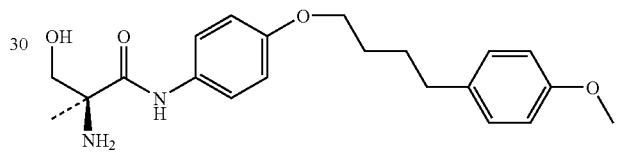

1-(4-(4-nitrophenoxy)butyl)-4-methoxybenzene (470 mg) was converted to 305 mg tert-butyl (S)-2-(4-(4-(4-methoxyphenyl)butoxy)phenylcarbamoyl)-1-hydroxypropan-2-ylcarbamate following the general procedure provided in Example 5(A) employing N-(Boc)-α-methylserine (210 mg), HATU (360 mg), and DIPEA (860 ul). MS (ESI, M+Na$^+$)=495.7. The carbamate (130 mg) was deprotected following the procedure in Example 5(A) yielding 108 mg of the title compound. MS (ESI, M+H$^+$)=373.9.

(F) (S)-2-(4-(4-(4-methoxyphenyl)butoxy)phenylcarbamoyl)-2-aminopropyl dihydrogen phosphate

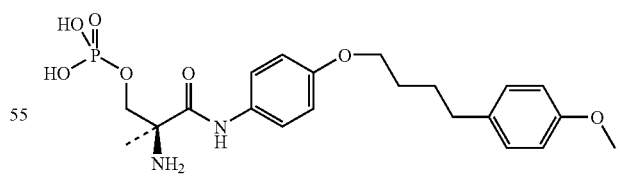

This compound was synthesized from (S)-N-(4-(4-(4-methoxyphenyl)butoxy)phenyl)-2-amino-3-hydroxy-2-methylpropanamide trifluoroacetic acid salt (115 mg) as described in Example 5(D) to yield 23 mg solid product. $^1$H NMR (400 MHz, DMSO-d$_6$) δ 9.9 (bs, 1H), 7.5 (d, 2H), 7.16 (d, 2H), 6.87 (d, 2H), 6.82 (d, 2H), 4.21 (m, 1H), 4.11 (m, 1H), 3.92 (m, 3H), 3.75 (s, 3H), 2.55 (m, 2H), 1.65 (m, 4H), 1.42 (s, 3H).

(G) (S)-N-(4-(3-(trifluoromethyl)phenethyloxy)phenyl)-2-amino-3-hydroxy-2-methylpropanamide trifluoroacetic acid salt

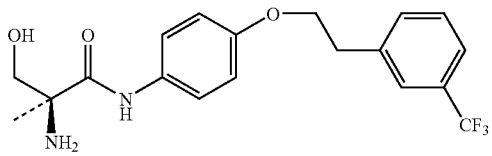

1-(3-(trifluoromethyl)phenethyloxy)-4-nitrobenzene (470 mg) was converted to 290 mg tert-butyl (S)-2-(4-(3-(trifluoromethyl)phenethyloxy)phenylcarbamoyl)-1-hydroxypropan-2-ylcarbamate following the general procedure provided in Example 5(A) employing N-(Boc)-α-methylserine (210 mg), HATU (360 mg), and DIPEA (900 μl). MS (ESI, M+H$^+$)=483.4. The carbamate (145 mg) was deprotected following the procedure in Example 5(A) yielding 143 mg of the title compound. MS (ESI, M+H$^+$)=383.1. $^1$H NMR (400 MHz, DMSO-d$_6$) δ 9.8 (bs, 1H), 7.67–7.40 (m, 6H), 6.88 (m, 2H), 5.67 (bs, 1H), 4.18 (t, 3H), 3.91 (m, 1H), 3.58 (m, 1H), 3.11 (t, 3H), 1.41 (s, 3H).

(H) (S)-2-(4-(3-(trifluoromethyl)phenethyloxy)phenylcarbamoyl)-2-aminopropyl dihydrogen phosphate

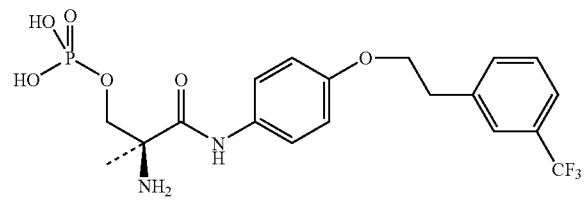

This compound was synthesized from (S)-N-(4-(3-(trifluoromethyl)phenethyloxy)phenyl)-2-amino-3-hydroxy-2-methylpropanamide trifluoroacetic acid salt (124 mg) as described for Example 5(D) to yield 50 mg solid product. MS (ESI, M+H$^+$)=463.1; $^1$H NMR (400 MHz, DMSO-d$_6$) δ 9.95 (bs, 1H), 7.68–7.49 (m, 6H), 6.90 (m, 2H), 4.18 (t, 3H), 4.05 (m, 2H), 3.11 (t, 3H), 1.41 (s, 3H).

(I) (S)-N-(4-(4-phenylbutoxy)phenyl)-2-amino-3-hydroxy-2-methylpropanamide trifluoroacetic acid salt

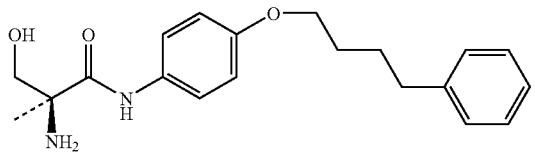

1-(4-phenylbutoxy)-4-nitrobenzene (730 mg) was converted to 305 mg tert-butyl (S)-2-(4-(4-phenylbutoxy)phenylcarbamoyl)-1-hydroxypropan-2-ylcarbamate following the general procedure provided in Example 5(A) employing N-(Boc)-α-methylserine (210 mg), HATU (360 mg), and DIPEA (860 μl). MS (ESI, M+Na$^+$)=465.5. The carbamate (152 mg) was deprotected following the procedure in AS1-C yielding 111 mg of the title compound. MS (ESI, M+H$^+$)=343.9.

(J) (S)-2-(4-(4-phenylbutoxy)phenylcarbamoyl)-2-aminopropyl dihydrogen phosphate

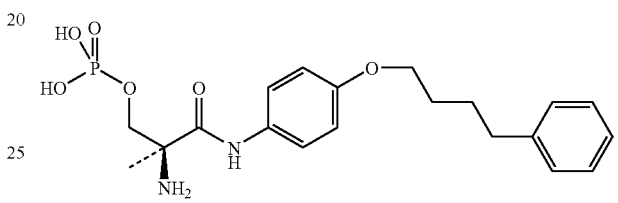

This compound was synthesized from (S)-N-(4-(4-phenylbutoxy)phenyl)-2-amino-3-hydroxy-2-methylpropanamide trifluoroacetic acid salt (120 mg) in a manner similar to that provided in Example 5(D) to yield 40 mg solid product. MS (ESI, M+H$^+$)=423.7; $^1$H NMR (400 MHz, DMSO-d$_6$) δ 9.95 (s, 1H), 7.47 (d, 6H), 7.27–7.13 (m, 5H), 6.88 (m, 2H), 4.21 (t, 1H), 4.06 (m, 1H), 3.94 (t, 2H), 2.64 (m, 2H), 1.7 (m, 4H), 1.44 (s, 3H).

(K) (S)-N-(4-(5-phenylpentyloxy)phenyl)-2-amino-3-hydroxy-2-methylpropanamide trifluoroacetic acid salt

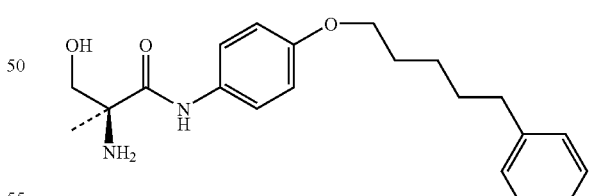

1-(5-phenylpentyloxy)-4-nitrobenzene (560 mg) was converted to 260 mg tert-butyl (S)-2-(4-(5-phenylpentyloxy)phenylcarbamoyl)-1-hydroxypropan-2-ylcarbamate following the general procedure outlined in Example 5(A) employing N-(Boc)-α-methylserine (210 mg), HATU (360 mg), and DIPEA (860 μl). MS (ESI, M+Na$^+$)=357.8. The carbamate (150 mg) was deprotected following the procedure in Example 5(A) yielding 147 mg of the title compound. MS (ESI, M+H$^+$)=357.8.

(L) (S)-2-(4-(5-phenylpentyloxy)phenylcarbamoyl)-2-aminopropyl dihydrogen phosphate

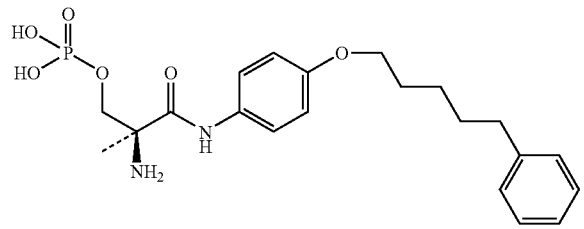

This compound was synthesized from (S)-N-(4-(5-phenylpentyloxy)phenyl)-2-amino-3-hydroxy-2-methylpropanamide (117 mg) as described in Example 5(D) to yield 66 mg solid product. MS (ESI, M+H$^+$)=437.5; $^1$H NMR (400 MHz, DMSO-d$_6$) δ 9.95 (s, 1H), 7.48 (m, 2H), 7.23 (m, 2H), 7.16 (m, 2H), 6.88 (m, 2H), 4.27 (t, 1H), 4.07 (m, 1H), 3.92 (t, 2H), 2.57 (t, 2H), 1.7 (m, 2H), 1.65 (m, 2H), 1.5 (s, 3H), 1.42 (m, 2H).

(M) (S)-N-(4-(4-cyclohexylbutoxy)phenyl)-2-amino-3-hydroxy-2-methylpropanamide trifluoroacetic acid salt

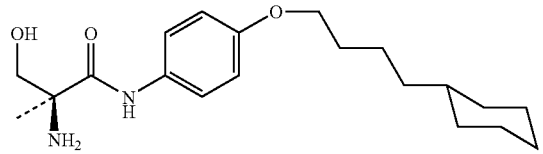

1-(4-cyclohexylbutoxy)-4-nitrobenzene (1 g) was converted to 260 mg tert-butyl (S)-2-(4-(4-cyclohexylbutoxy)phenylcarbamoyl)-1-hydroxypropan-2-ylcarbamate following the general procedure outlined in Example 5(A) employing N-(Boc)-α-methylserine (210 mg), HATU (360 mg), and DIPEA (860 μl). MS (ESI, M+Na$^+$)=449. The carbamate (87 mg) was deprotected following the procedure in Example 5(A) yielding 81 mg of the title compound. MS (ESI, M+H$^+$)=349.5. $^1$H NMR (400 MHz, DMSO-d$_6$) δ 9.73 (s, 1H), 7.47 (m, 2H), 6.88 (m, 2H), 5.65 (m, 1H), 4.27 (overlapping signals, 3H), 3.6 (m, 1H), 1.6 (m, 6H), 1.4 (m, 5H), 1.15 (m, 6H), 0.85 (m, 3H).

(N) (S)-2-(4-(4-cyclohexylbutoxy)phenylcarbamoyl)-2-aminopropyl dihydrogen phosphate

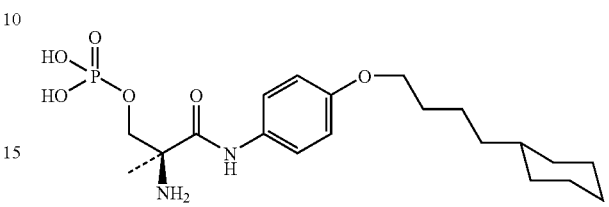

This compound was synthesized from (S)-N-(4-(4-cyclohexylbutoxy)phenyl)-2-amino-3-hydroxy-2-methylpropanamide trifluoroacetic acid salt (173 mg) as described in Example 5(D) to yield 27 mg solid product. MS (ESI, M+H$^+$)=429; $^1$H NMR (400 MHz, DMSO-d$_6$) δ 9.8 (bs, 1H), 7.47 (m, 2H), 6.88 (m, 2H), 4.15 (m, 1H), 4.02 (m, 1H), 3.90 (t, 2H), 1.68 (m, 6H), 1.4 (m, 5H), 1.15 (m, 6H), 0.85 (m, 3H).

Example 6

Synthesis of Carboxylic Acid Compounds

General Method for Acylation of Substituted 4-aminophenol

To a solution of N-(Boc)-α-methylserine (1.0 equiv) in DMF (10 mL) was added DIPEA (3.0 equiv) and HATU (1.2 equiv), followed by the addition of 4-aminophenol (1.0 equiv.). The reaction mixture was stirred at room temperature under an atmosphere of nitrogen for 12–24 hours. The reaction was then diluted with EtOAc (25 mL) and washed with 10% NH$_4$Cl (2×25 mL), 5% NaHCO$_3$ (2×25 mL), and saturated NaCl (1×25 mL). The organic layer was dried over anhydrous MgSO$_4$ then the solvent removed in vacuo. The crude product was purified using silica gel column chromatography.

tert-Butyl (S)-2-((benzyloxy)carbonyl)-1-(4 (octyloxy)phenylcarbamoyl)ethylcarbamate

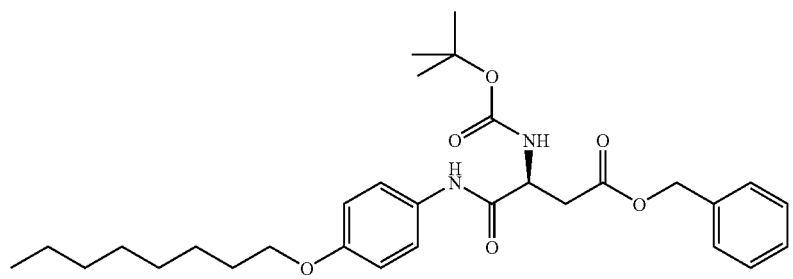

The product was obtained as a yellow solid in 94% (2.34 g) yield. TLC (1:2 EtOAc:Hex), $R_f$=0.6; $^1$H NMR (400 MHz, CDCl$_3$) δ 8.31 (br s, 1H), 7.30–7.38 (m, 7H), 6.83 (d, 2H, J=9.0 Hz), 5.80 (br s, 1H), 5.18 (d, 1H, J=12.5 Hz), 5.13 (d, 1H, J=12.5 Hz), 4.62 (br s, 1H), 3.92 (t, 2H, J=6.6 Hz), 3.05–3.13 (m, 1H), 2.75–2.83 (m, 1H), 1.72–1.81 (m, 2H), 1.23–1.50 (m, 10H), 1.47 (s, 9H), 0.89 (t, 3H, J=7.0 Hz).

tert-Butyl (S)-3-((benzyloxy)carbonyl)-1-(4-(octyloxy)phenylcarbamoyl)propylcarbamate

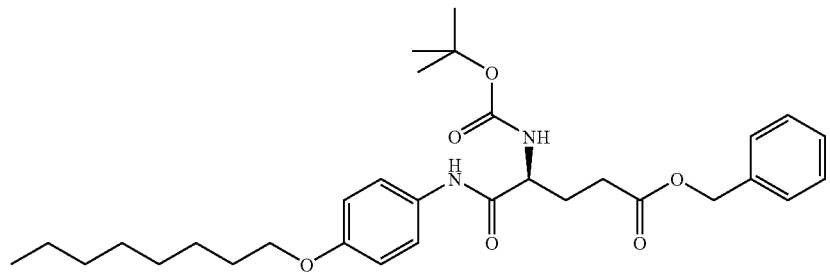

The product was obtained as a yellow solid in 94% (2.28 g) yield. TLC (1:2 EtOAc:Hex), $R_f$=0.6; $^1$H NMR (400 MHz, CDCl$_3$) δ 8.43 (br s, 1H), 7.31–7.40 (m, 7H), 6.84 (d, 2H, J=8.9 Hz), 5.30 (br s, 1H), 5.10–5.19 (m, 2H), 4.25 (br s, 1H), 3.92 (t, 2H, J=6.7 Hz), 2.60–2.70 (m, 1H), 2.45–2.56 (m, 1H), 2.13–2.28 (m, 1H), 1.95–2.06 (m, 1H), 1.72–1.80 (m, 2H), 1.23–1.48 (m, 10H), 1.45 (s, 9H), 0.89 (t, 3H, J=6.9 Hz).

General Method for Deprotection of Cbz-Amino Acids

To a solution of Boc-protected amino acid ester (1.0 equiv) in MeOH at room temperature was added 10% Pd on carbon (0.1 equiv by mass) and stirred under H$_2$ atmosphere for 6–18 hours. The solution was then filtered through Celite to remove Pd and Carbon. The filtrated was evaporated to dryness. The residue was then dissolved in CH$_2$Cl$_2$ and TFA (2:1) and stirred at room temperature 2 hours to remove the Boc protecting group. The solvent was then evaporated to dryness under reduced pressure. The final product was purified by prep HPLC as necessary.

(S)-3-amino-3-(4-(4-(octyloxy)phenyl)-1H-imidazol-2-yl)propanoic acid

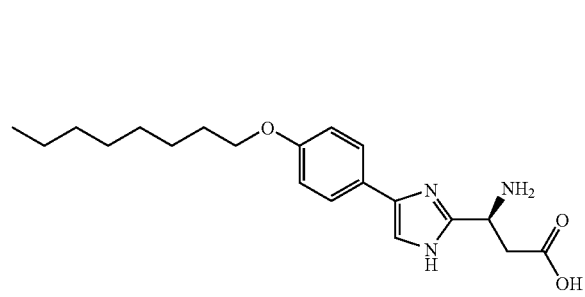

The product was obtained as a white solid in 95% (65 mg) yield. MS (ESI, M+H$^+$)=360.17; $^1$H NMR (400 MHz, DMSO-d$_6$) δ 8.42 (br s, 3H), 7.64 (d, 2H, J=8.8 Hz), 7.48 (s, 1H), 6.93 (d, 2H, J=8.8), 4.64 (br t, 1H, J=6.4 Hz), 3.94 (t, 2H, J=6.8 Hz), 3.12 (dd, 1H, J=17.2 Hz, J=6.8 Hz), 2.94 (dd, 1H, J=17.2 Hz, J=6.8 Hz), 1.64–1.75 (m, 2H), 1.20–1.45 (m, 10H), 0.85 (t, 3H, J=7.2 Hz).

(S)-3-(4-(octyloxy)phenylcarbamoyl)-3-aminopropanoic acid

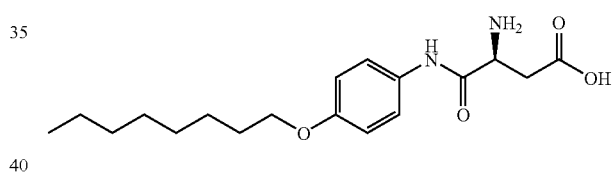

The product was obtained as a white solid in 99% (175 mg) yield. MS (ESI, M+H$^+$)=337.36; $^1$H NMR (400 MHz, DMSO-d$_6$) δ 10.30 (br s, 1H), 8.26 (br s, 3H), 7.45 (d, 2H, J=9.0 Hz), 6.88 (d, 2H, J=9.0 Hz), 4.18–4.24 (br s, 1H), 3.90 (t, 2H, J=6.3 Hz), 2.74–2.98 (m, 2H), 1.60–1.76 (m, 2H), 1.16–1.45 (m, 10H), 0.85 (t, 3H, J=7.0 Hz).

(S)-4-(4-(octyloxy)phenylcarbamoyl)-4-aminobutanoic acid

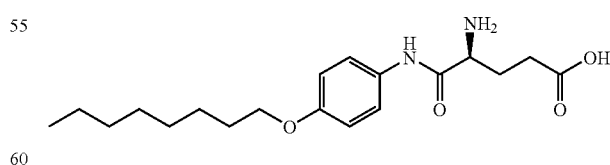

The product was obtained as a white solid in 99% (150 mg) yield. MS (ESI, M+H$^+$)=351.40; $^1$H NMR (400 MHz, DMSO-d$_6$) δ 10.30 (br s, 1H), 7.45 (d, 2H, J=9.2 Hz), 6.89 (d, 2H, J=9.2 Hz), 3.85–3.95 (m, 3H), 2.35 (t, 2H, J=7.0 Hz), 1.96–2.06 (m, 2H), 1.62–1.72 (m, 2H), 1.18–1.43 (m, 10H), 0.84 (t, 3H, J=7.0 Hz).

(S)-2-amino-N⁵-hydroxy-N¹-(4-(octyloxy)phenyl) pentanediamide

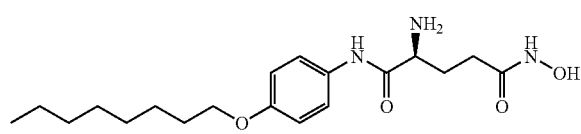

The Boc-protected carboxylate intermediate from previous step was coupled with hydroxylamine hydrochloride using general HATU coupling conditions. After TFA deprotection of Boc group the final compound was purified by prep HPLC as a white solid in 20% (12 mg) yield. MS (ESI, M+H⁺)=366.48; ¹H NMR (400 MHz, DMSO-d₆) δ 10.53 (br s, 0.5H), 10.31 (br s, 0.5H), 9.86 (br s, 0.5H), 8.80 (br s, 0.5H), 8.22 (br s, 2H), 7.85 (br s, 1H), 7.40–7.53 (m, 2H), 6.83–6.93 (m, 2H), 4.10–4.16 (m, 1H), 3.86–3.94 (m, 2H), 1.80–2.25 (m, 4H), 1.54–1.74 (m, 2H), 1.18–1.45 (m, 10H), 0.86 (t, 3H, J=6.6 Hz).

Example 7

General Procedure for Synthesis of Aryl-Alkoxy Ethers Under Mitsunobu Conditions Phenol (1.2 equiv) and triphenyl phosphine (1.2 equiv) were added to an ice cold solution of the substituted phenyl alcohols (1.0 equiv) in DCM. To this mixture on ice was added DEAD or DIAD drop-wise while maintaining the temperature of the reaction mixture under 5° C. The reaction mixture was then allowed to gradually warm to room temperature and stirred overnight. The organic layer was extracted with water, 10% NH₄Cl and then brine. The combined organic layer was dried with MgSO₄ and the solvent evaporated under reduced pressure to give yellow oil which was purified by silica-gel chromatography, EtOAc-Hexane gradient. The fractions corresponding to the product were pooled and the solvent removed in vacuo to give the desired product.

1-Phenoxy-4-phenyl butane

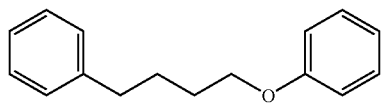

The final product was obtained as yellow oil after column chromatography, in 67% yield. ¹H NMR (400 MHz, CDCl₃) δ 7.28 (m, 4H), 7.18 (m, 3H), 6.91 (m, 3H), 3.96 (t, 2H, J=6.0 Hz), 2.68 (t, 2H, J=6.8 Hz), 1.82 (m, 4H).

1-Phenoxy-5-phenyl pentane

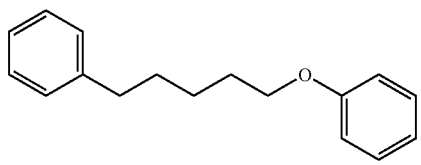

The final product was obtained as oil after column chromatography, in 37% yield. ¹H NMR (400 MHz, CDCl₃) δ 7.27 (m, 4H), 7.18 (d, 3H, J=7.2 Hz), 6.93 (dd, 1H, J=1.0 and 6.8 Hz), 6.88 (m, 2H), 3.94 (t, 2H, J=6.4 Hz), 2.64 (t, 2H, J=8.0 Hz), 1.81 (m, 2H), 1.69 (m, 2H), 1.52 (m, 2H).

2-Bromo-1-[4-(phenyl-butoxy)phenyl]-ethanone

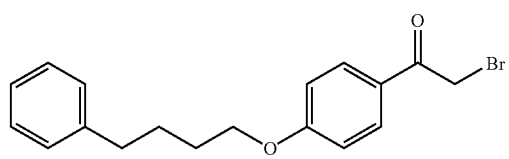

The final product was obtained as a white solid after column chromatography, in 25% yield. ¹H NMR (400 MHz, CDCl₃) δ 7.91 (d, 2H, J=8.4 Hz), 7.33–7.25 (m, 4H), 6.87–6.95 (m, 3H), 4.43 (s, 2H), 3.97 (t, 2H, J=5.6 Hz), 2.76 (t, 2H, J=7.6 Hz), 1.82 (m, 4H).

2-Bromo-1-[4-(5-phenyl-pentyloxy)phenyl]-ethanone

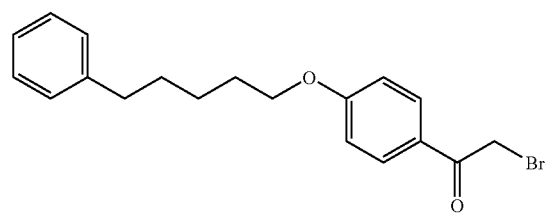

The final product was obtained as a white solid after column chromatography, in 61% yield. ¹H NMR (400 MHz, CDCl₃) δ 7.90 (d, 2H, J=8.4 Hz), 7.24–7.30 (m, 4H), 7.18 (d, 2H, J=6.4 Hz), 6.86–6.89 (m, 2H), 4.43 (s, 2H), 3.94 (t, 2H, J=6.4 Hz), 2.71 (t, 1H, J=7.6 Hz), 2.64 (t, 1H, J=7.6 Hz), 1.81 (m, 2H), 1.69 (m, 2H), 1.51 (m, 2H).

(R)-(2-Hydroxy-1-methyl-1-{5-[4-(4-phenyl-butoxy)-phenyl]-1H-imiazol-2-yl}ethyl)-carbamic acid tert-butyl ester

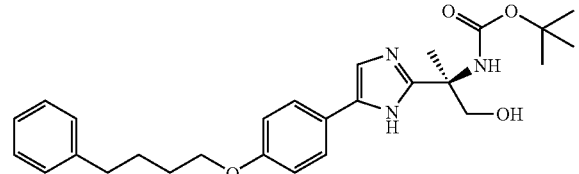

The final product was obtained as yellow oil after column chromatography, in 63% yield. ¹H NMR (400 MHz, CDCl₃) δ 7.22–7.26 (m, 4H), 7.21 (m, 2H), 7.17 (s, 1H), 6.87–6.94 (m, 2H), 4.33 (d, 1H, J=11.6 Hz), 3.97 (t, 2H, J=5.6 Hz), 3.35 (d, 1H, J=12.0 Hz), 2.69 (t, 2H, J=7.2 Hz), 2.53 (s, 2H), 1.82 (m, 4H), 1.67 (s, 3H), 1.44 (s, 9H).

105

(R)-(2-Hydroxy-1-methyl-1-{5-[4-(5-phenyl-pentyloxy)-phenyl]-1H-imiazol-2-yl}ethyl)-carbamic acid tert-butyl ester

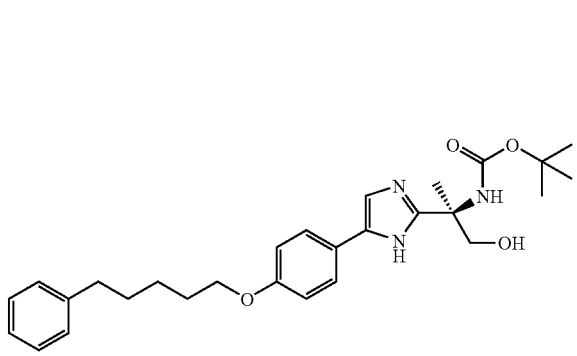

The final product was obtained as yellow oil after column chromatography, in 63% yield. $^1$H NMR (400 MHz, CDCl$_3$) δ 7.56 (d, 2H, J=7.2 Hz), 7.24–7.28 (m, 2H), 7.17 (d, 2H, J=8.0 Hz), 7.13 (s, 1H), 6.86–6.89 (m, 2H), 5.77 (s, 1H), 4.27 (d, 1H, J=11.2 Hz), 3.94 (t, 2H, J=6.4 Hz), 3.64 (d, 1H, J=11.6 Hz), 2.63 (t, 2H, J=7.6 Hz), 1.81 (m, 2H), 1.69 (m, 2H), 1.66 (s, 3H), 1.42 (s, 9H), 1.26 (m, 2H).

(R)-2-Amino-2-{5-[4-(4-phenyl-butoxy)-phenyl]-1H-imiazol-2-yl}-propan-1-ol

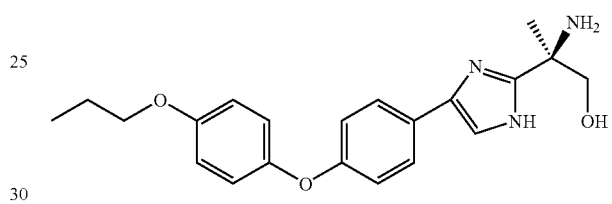

The compound was obtained as a white solid after HPLC purification. Yield: 50%, (60 mg). MS (ESI, M+H$^+$)=366.3

(R)-2-Amino-2-{5-[4-(5-phenyl-pentyloxy)-phenyl]-1H-imiazol-2-yl}-propan-1-ol

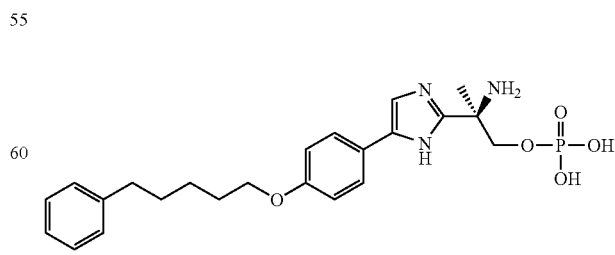

The compound was obtained as a white solid after HPLC purification. Yield: 49%, (60 mg). MS (ESI, M+H$^+$)=380.3

106

(R)-2-Amino-2-(5-(4-(biphenylethyloxy)phenyl)-1H-imidazol-2-yl)propan-1-ol

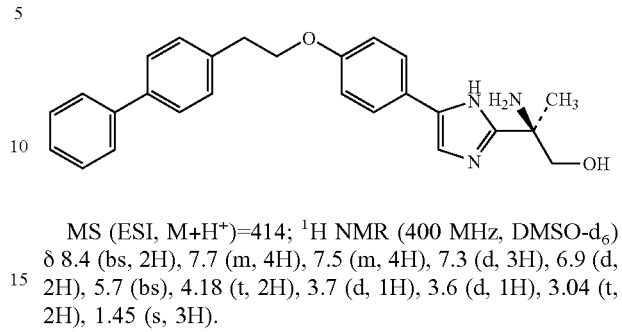

MS (ESI, M+H$^+$)=414; $^1$H NMR (400 MHz, DMSO-d$_6$) δ 8.4 (bs, 2H), 7.7 (m, 4H), 7.5 (m, 4H), 7.3 (d, 3H), 6.9 (d, 2H), 5.7 (bs), 4.18 (t, 2H), 3.7 (d, 1H), 3.6 (d, 1H), 3.04 (t, 2H), 1.45 (s, 3H).

(R)-2-Amino-2-{4-[4-(4-propoxy-phenoxy)-phenyl]-1H-imidazol-2-yl}-propan-1-ol

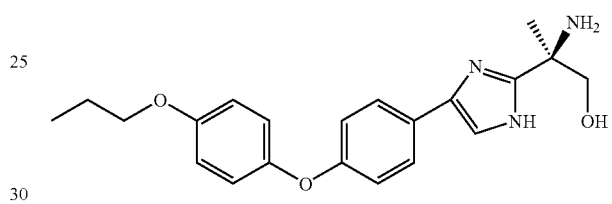

The compound was obtained as a white solid after HPLC purification. Yield: 60%, (10 mg). MS (ESI, M+H$^+$)=367.5

(R)-Phosphoric acid mono-(2-amino-2-{5-[4-(4-phenyl-butoxy)-phenyl]-1H-imidazol-2-yl}-propyl) ester

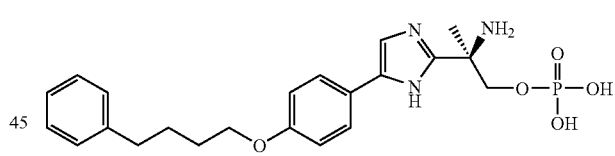

The compound was obtained as a white solid after HPLC purification. Yield: 32%, (25 mg). MS (ESI, M+H$^+$)=446.4

(R)-Phosphoric acid mono-(2-amino-2-{5-[4-(4-phenyl-pentyloxy)-phenyl]-1H-imidazol-2-yl}-propyl)ester

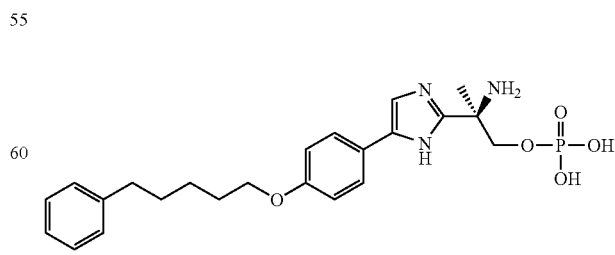

The compound was obtained as a white solid after HPLC purification. Yield: 39%, (41 mg). MS (ESI, M+H$^+$)=459.2

(R)-2-Amino-2-(5-(4-(biphylenethyloxy)phenyl)-1H-imidazol-2-yl)propyl dihydrogen phosphate

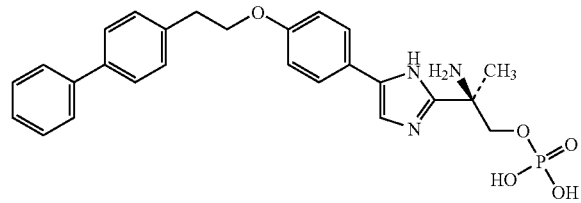

This compound was synthesized from tert-butyl (R)-1-hydroxy-2-(5-(4-(biphenylethyloxy)phenyl)-1H-imidazol-2-yl)propan-2-ylcarbamate (46 mg) to yield 9.2 mg solid product. MS (ESI, M+H⁺)=494; $^1$H NMR (400 MHz, DMSO-$d_6$) δ 9.4 (s), 8.2 (s, 1H), 7.7 (m, 6H), 7.5 (m, 5H), 7.3 (m, 1H), 6.9 (d, 2H), 5.7 (br s), 4.25 (t, 2H), 4.15 (t, 2H), 4.05 (m, 1H), 3.9 (q, 1H), 3.1 (t, 2H), 1.45 (s, 3H).

Example 8

Synthesis in Biphenyl Amide Series

Several biphenyls were synthesized using the process described in Scheme 7. Microwave assisted Suzuki cross-coupling of substituted aryl boronic acids with substituted anilines afforded good to excellent yields of the biaryl amine intermediates. Furthermore, the acylation of the substituted biaryl amines with the desired headpiece followed by deprotection of the Boc group afforded the final compounds.

Scheme 7.

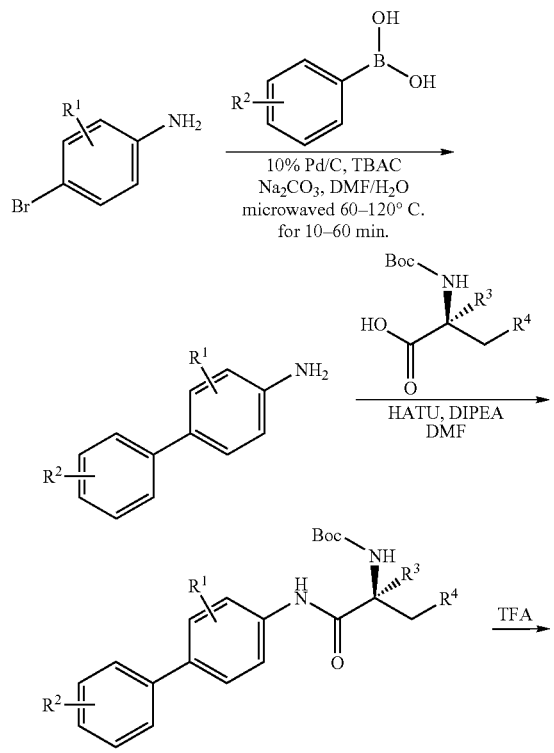

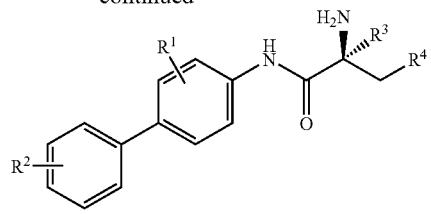

General Procedure for Suzuki Cross-Coupling:

To a mixture of a substituted bromoaniline (1.0 equiv), substituted aryl boronic acid (1.2 equiv), 10% Pd on carbon (0.1 equiv), tetrabutylammonium chloride (0.1 equiv), and sodium carbonate (1.0 equiv), in a microwave tube was added a 1:1 mixture of DMF:$H_2O$. The mixture was then heated to 70° C. for 20–60 minutes using a microwave. The reaction was then diluted with EtOAc (25 mL) and washed with $H_2O$ (2×25 mL) then the solvent removed in vacuo. The crude product was purified by silica gel column chromatography using Combi-Flash system (Hex:EtOAc) as required.

(S)-2-Amino-N-(4-(3-isopropylphenyl)phenyl)-3-hydroxy-2-methylpropanamide

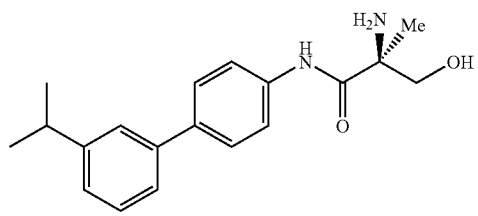

MS (ESI, M+H⁺)=313.6; $^1$H NMR (400 MHz, DMSO-$d_6$) δ 10.96 (br s, 1H), 8.18 (br s, 2H), 7.63–7.74 (m, 4H), 7.41–7.51 (m, 2H), 7.35 (t, 1H, J=7.6 Hz), 7.21 (d, 1H, J=7.6 Hz), 5.79 (t, 1H, J=4.8 Hz), 4.00 (dd, 1H, J=11.6 Hz, J=4.8 Hz), 3.65 (dd, 1H, J=11.6 Hz, J=5.2 Hz), 2.86–3.02 (m, 1H), 1.50 (s, 3H), 1.24 (d, 6H, J=7.6 Hz).

(S)-2-Amino-N-(4-(3-methoxyphenyl)phenyl)-3-hydroxy-2-methylpropanamide

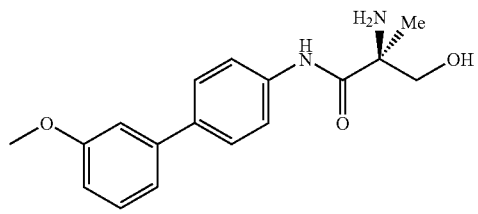

MS (ESI, M+H⁺)=301.7; $^1$H NMR (400 MHz, DMSO-$d_6$) δ 10.98 (br s, 1H), 8.19 (br s, 2H), 7.55–7.64 (m, 4H), 7.34 (t, 1H, J=7.6 Hz), 7.16–7.24 (m, 2H), 6.88–6.94 (m, 1H), 5.80 (br s, 1H), 4.00 (dd, 1H, J=11.6 Hz, J=4.8 Hz), 3.80 (s, 3H), 3.64 (dd, 1H, J=11.6 Hz, J=5.2 Hz), 1.50 (s, 3H).

(S)-2-Amino-N-(4-(3-ethoxyphenyl)phenyl)-3-hydroxy-2-methylpropanamide

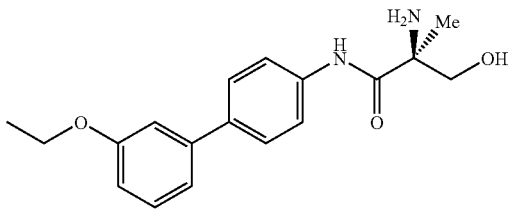

MS (ESI, M+H$^+$)=315.6; $^1$H NMR (400 MHz, DMSO-d$_6$) δ 9.97 (br s, 1H), 8.18 (br s, 2H), 7.64–7.73 (m, 4H), 7.33 (t, 1H, J=7.6 Hz), 7.14–7.23 (m, 2H), 6.86–6.91 (m, 1H), 5.80 (br s, 1H), 4.08 (q, 2H, J=7.2 Hz), 4.00 (dd, 1H, J=11.6 Hz, J=4.8 Hz), 3.64 (dd, 1H, J=11.6 Hz, J=5.2 Hz), 1.50 (s, 3H), 1.33 (t, 3H, J=7.2 Hz).

(S)-2-Amino-N-(4-(3-propoxyphenyl)phenyl)-3-hydroxy-2-methylpropanamide

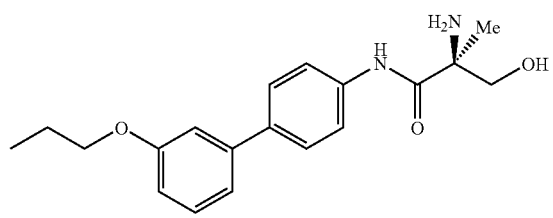

MS (ESI, M+H$^+$)=329.7; $^1$H NMR (400 MHz, DMSO-d$_6$) δ 9.96 (br s, 1H), 8.18 (br s, 2H), 7.64–7.74 (m, 4H), 7.33 (t, 1H, J=7.6 Hz), 7.13–7.22 (m, 2H), 6.86–6.92 (m, 1H), 5.80 (br t, 1H, J=4.5 Hz), 4.00 (dd, 1H, J=11.6 Hz, J=4.8 Hz), 3.98 (t, 2H, J=7.2 Hz), 3.65 (dd, 1H, J=11.6 Hz, J=5.2 Hz), 1.68–1.80 (m, 2H), 1.50 (s, 3H), 1.00 (t, 3H, J=7.2 Hz).

(S)-2-Amino-N-(4-(3-isopropoxyphenyl)phenyl)-3-hydroxy-2-methylpropanamide

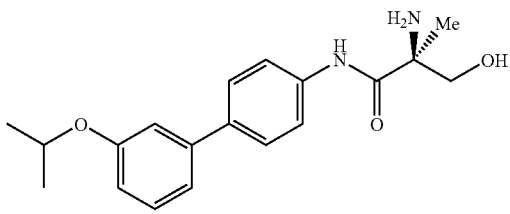

MS (ESI, M+H$^+$)=329.8; $^1$H NMR (400 MHz, DMSO-d$_6$) δ 9.96 (br s, 1H), 8.18 (br s, 2H), 7.62–7.73 (m, 4H), 7.32 (t, 1H, J=7.6 Hz), 7.11–7.20 (m, 2H), 6.86–6.92 (m, 1H), 5.80 (br t, 1H, J=4.5 Hz), 4.55–4.80 (m, 1H), 4.00 (dd, 1H, J=11.6 Hz, J=4.8 Hz), 3.65 (dd, 1H, J=11.6 Hz, J=5.2 Hz), 1.50 (s, 3H), 1.28 (d, 6H, J=7.2 Hz).

(S)-2-Amino-N-(4-(3-n-butoxyphenyl)phenyl)-3-hydroxy-2-methylpropanamide

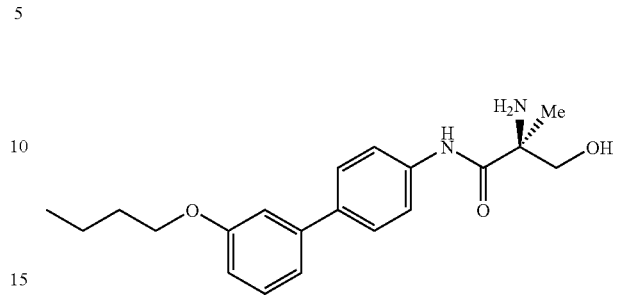

MS (ESI, M+H$^+$)=343.5; $^1$H NMR (400 MHz, DMSO-d$_6$) δ 9.97 (br s, 1H), 8.18 (br s, 2H), 7.64–7.74 (m, 4H), 7.33 (t, 1H, J=7.6 Hz), 7.13–7.22 (m, 2H), 6.86–6.92 (m, 1H), 5.79 (br t, 1H, J=4.5 Hz), 4.03 (t, 2H, J=7.2 Hz), 4.00 (dd, 1H, J=11.6 Hz, J=4.8 Hz), 3.64 (dd, 1H, J=11.6 Hz, J=5.2 Hz), 1.65–1.75 (m, 2H), 1.50 (s, 3H), 1.49–1.52 (m, 2H), 0.92 (t, 3H, J=7.2 Hz).

(S)-2-Amino-N-(4-(3-benzyloxyphenyl)phenyl)-3-hydroxy-2-methylpropanamide

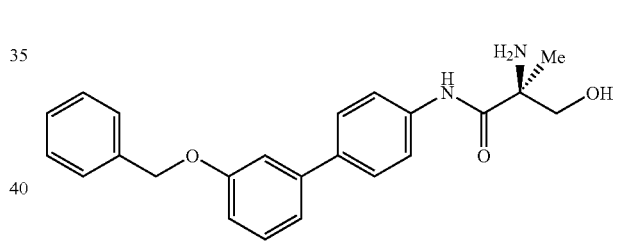

MS (ESI, M+H$^+$)=377.5; $^1$H NMR (400 MHz, DMSO-d$_6$) δ 9.96 (br s, 1H), 8.18 (br s, 2H), 7.64–7.74 (m, 4H), 7.44–7.82 (m, 2H), 7.29–7.42 (m, 6H), 6.96–7.00 (m, 1H), 5.79 (br t, 1H, J=4.5 Hz), 5.17 (s, 2H), 4.00 (dd, 1H, J=11.6 Hz, J=4.8 Hz), 3.64 (dd, 1H, J=11.6 Hz, J=5.2 Hz), 1.50 (s, 3H).

Example 9

General Procedure for Synthesis of Substituted Biaryl Ether/Thioether Analogs The 4-iodophenyl-4-nitrophenoxy ethers were synthesized by reacting 4-iodophenol with 4-fluoro-nitrobenzene in the presence of a base K$^t$OBu in THF at 50° C. (Scheme 2). The nitro group was reduced using SnCl$_2$ in EtOH at 70° C., followed Suzuki cross-coupling then acylation of the amine with L-(Boc)-α-Me-Ser-OH using HATU. The Boc-group can then be removed using TFA in DCM or the protected material is used to synthesize the phosphate before deprotection.

Scheme 8.

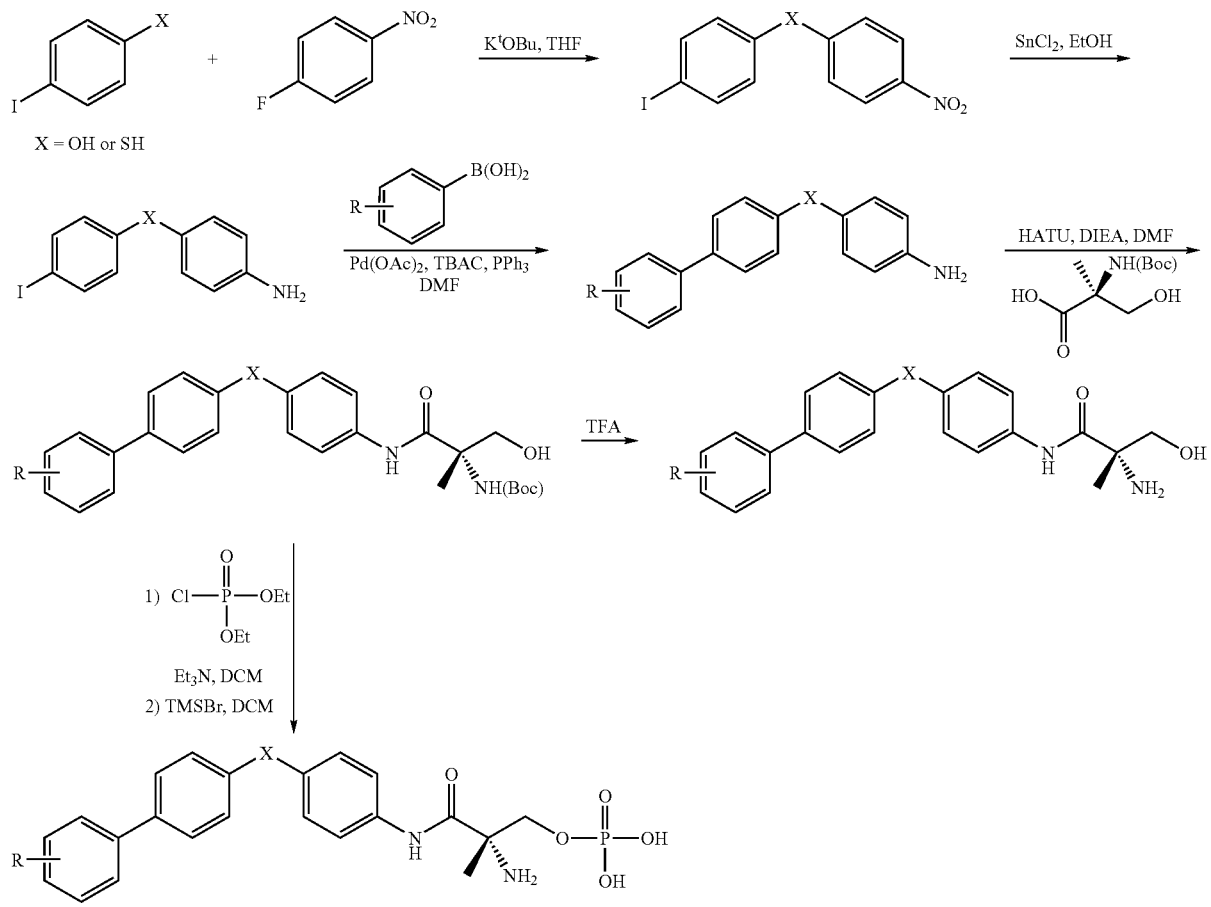

General Procedure for the Synthesis of 4-(4-iodophenoxy)-nitrobenzene:

To a THF solution of 4-iodophenol (1.0 g, 1.0 equiv) is added K'OBu (1.0M in THF, 1.0 equiv). The solution is stirred at room temperature for approximately 5 minutes and then a solution of 4-fluoro-nitrobenzene (1.1 equiv) is added dropwise. The reaction mixture is then heated to 50° C. using an oil bath and the reaction progress monitored by TLC (EtOAc:Hexane, 0.5:9.5). The reaction is complete when no more 4-iodophenol is detected by TLC. The reaction is then cooled to room temperature and put in an ice bath. Water is added slowly to quench the unreacted base, followed by extraction of the product into EtOAc. The organic layer is then washed with 10% NH4Cl and brine, dried over MgSO4, and then solvent removed under reduced pressure. The crude product is purified using Combi-Flash silica gel column chromatography, using a Hexane/EtOAc gradient. The fractions corresponding to the product are pooled and the solvent removed in vacuo to give a yellow solid (Scheme 2).

General Procedure for Synthesis of Substituted 4-biayloxy aniline:

To a DMF solution of the 4-(haloaryloxy)-aniline (1.0 equiv) and substituted aryl boronic acid in a microwave tube, was added Pd(OAc)$_2$ (0.1 equiv), triphenyl phosphine (0.2 equiv), cesium carbonate (1.0–2.0 equiv) and TBAC (0.1 equiv). The reaction was then sealed and heated at 70° C. for 3–18 hours using an oil bath. The reaction mixture was filtered through a bed of Celite and then diluted with EtOAc (25 mL), washed with water (2×10 mL) and then brine (1×10 mL). The organic layer was then dried over MgSO$_4$, and then was solvent removed under reduced pressure. The crude product was purified using Combi-Flash silica gel column chromatography, using a Hexane/EtOAc gradient.

4-(4-Iodophenoxy)-nitrobenzene

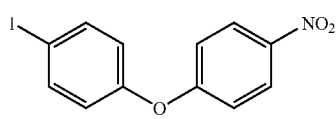

The final product was obtained as a yellow solid after purification in 73% yield. $^1$H NMR (400 MHz, CDCl$_3$) δ 8.21(d, 2H, J=8.6 Hz), 7.73(d, 2H, J=8.8 Hz), 7.02 (d, 2H, J=9.2 Hz), 6.86 (d, 2H, J=8.8 Hz).

4-(4-Iodophenoxy)-phenylamine

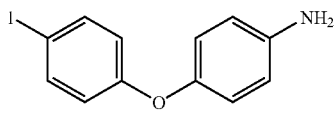

The final product was obtained as a brown solid after purification in 45% yield. ¹H NMR (400 MHz, CDCl₃) δ 7.54 (d, 2H, J=8.8 Hz), 6.84 (d, 2H, J=8.4 Hz), 6.66–6.70 (m, 4H).

4-(4'-Methoxy-biphenyl-4-yloxy)-phenylamine

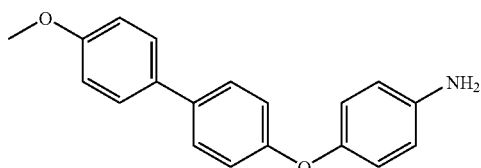

The final product was obtained as an off white solid after purification in 95% yield. ¹H NMR (400 MHz, CDCl₃) δ 7.44–7.48 (m, 4H), 6.94–6.98 (m, 4H), 6.90 (d, 2H, J=8.4 Hz), 6.69 (d, 2H, J=8.8 Hz), 3.84 (s, 3H).

4-(4'-Chloro-biphenyl-4-yloxy)-phenylamine

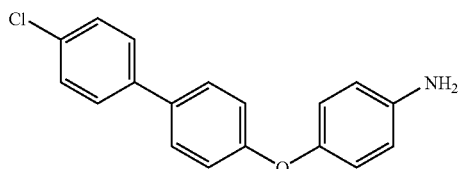

The final product was obtained as an off white solid after purification in 90% yield. ¹H NMR (400 MHz, CDCl₃) δ 7.44–7.47 (m, 4H), 7.37 (d, 2H, J=6.4 Hz), 6.97 (d, 2H, J=8.8 Hz), 6.90 (d, 2H, J=8.8 Hz), 6.70 (d, 2H, J=8.8 Hz).

4-(4'-tert-Butyl-biphenyl-4-yloxy)-phenylamine

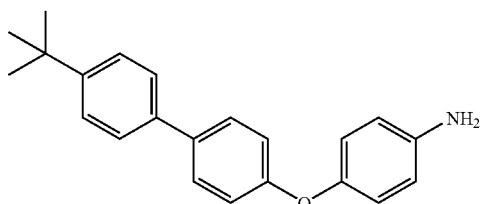

The final product was obtained as an off white solid after purification in 60% yield. ¹H NMR (400 MHz, CDCl₃) δ 7.43–7.50 (m, 6H), 6.98 (d, 2H, J=8.8 Hz), 6.91 (d, 2H, J=8.0 Hz), 6.70 (d, 2H, J=8.0 Hz), 1.37 (s, 9H).

4-([1,1',4',1'']Terphenyl-4-yloxy)-phenylamine

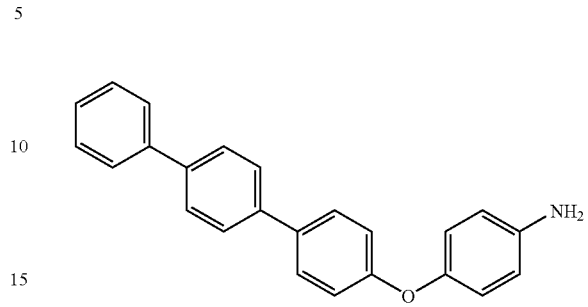

The final product was obtained as an off white solid after purification in 40% yield. ¹H NMR (400 MHz, CDCl₃) δ 7.81 (d, 1H, J=7.2 Hz), 7.77 (d, 2H, J=8.0 Hz), 7.70 (d, 2H, J=7.2 Hz), 7.63–7.64 (m, 4H), 7.55 (d, 2H, J=8.4 Hz), 7.01 (d, 2H, J=8.8 Hz), 6.92 (d, 2H, J=8.8 Hz), 6.71 (d, 2H, J=8.8 Hz).

(S)-{2-Hydroxy-1-[4-(4'-methoxy-biphenyl-4-yloxy)-phenylcarbamoyl]-1-methyl-ethyl}carbamic acid tert-butyl ester

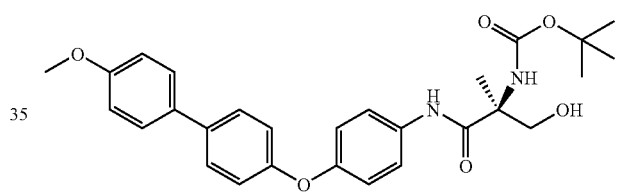

The final product was obtained as a white solid after HPLC, in 94% yield. ¹H NMR (400 MHz, CDCl₃) δ 7.47–7.50 (m, 6H,), 7.01–7.04 (m, 4H), 6.96 (d, 2H, J=8.8 Hz), 4.03 (br. s, 1H), 3.85 (s, 3H) 3.57 (d, 1H, J=11.2 Hz), 1.59 (s, 3H), 1.47 (s, 9H).

(S)-{1-[4-(4'-Chloro-biphenyl-4-yloxy)-phenylcarbamoyl]-2-hydroxy-1-methyl-ethyl}carbamic acid tert-butyl ester

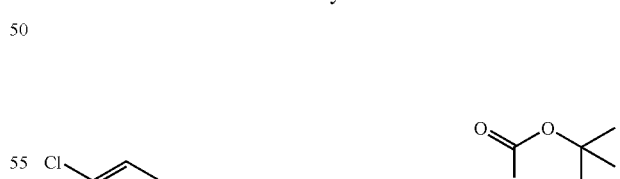

The final product was obtained as an off white solid after purification in 40% yield. ¹H NMR (400 MHz, CDCl₃) δ 7.43–7.52 (m, 6H), 6.97 (d, 2H, J=8.8 Hz), 6.90 (d, 2H, J=8.8 Hz), 6.70 (d, 2H, J=8.8 Hz) 4.03 (br. s, 1H), 3.57 (br.s, 1H,), 1.56 (s, 3H), 1.44 (s, 9H).

(S)-{1-[4-(4'-tert-Butyl-biphenyl-4-yloxy)-phenyl-carbamoyl]-2-hydroxy-1-methyl-ethyl}carbamic acid tert-butyl ester

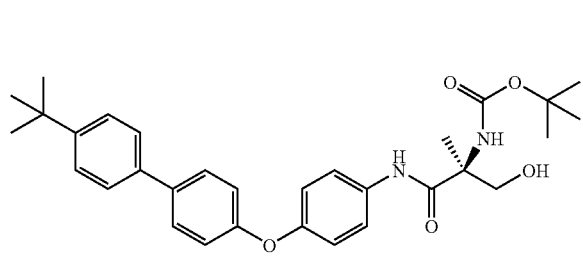

The final product was obtained as an off white solid after purification in 65% yield. $^1$H NMR (400 MHz, CDCl$_3$) δ 7.49–7.53 (m, 6H), 7.44–7.46 (m, 2H), 7.026 (dd, 4H, J=2.4 and 8.8 Hz) 4.08 (br.s, 1H), 3.62 (br.s, 1H,), 1.59 (s, 3H), 1.47 (s, 9H), 1.36 (s, 9H).

(S)-{2-Hydroxy-1-methyl-1-[4-(1,1',4',1"]terphenyl-4-yloxy)-phenylcarbamoyl]-ethyl}carbamic acid tert-butyl ester

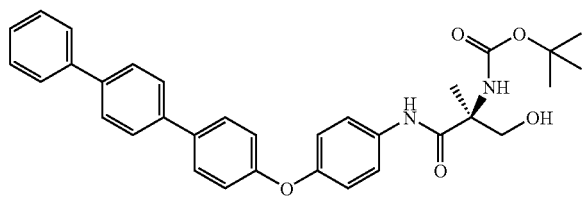

The final product was obtained as an off white solid after purification in 25% yield. $^1$H NMR (400 MHz, CDCl$_3$) δ 7.63–7.68 (m, 6H), 7.59 (d, 2H, J=8.8 Hz), 7.52 (d, 2H, J=8.8 Hz), 7.45 (t, 2H, J=7.6 Hz), 7.36 (m, 1H), 7.05 (dd, 4H, J=2.4 and 8.8 Hz), 3.62 (br. s, 1H), 3.40 (br.s, 1H,), 1.60 (s, 3H), 1.47 (s, 9H), 1.47 (s, 9H).

(S)-2-Amino-N-[4-(benzo[1,3]dioxol-5-yloxy)-phenyl}-3-hydroxy-2-methylpropionamide

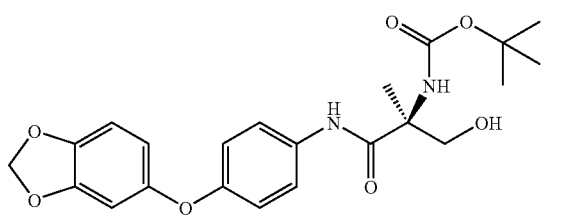

The final product was obtained as a white solid after HPLC, in 35% yield. $^1$H NMR (400 MHz, CDCl$_3$) δ 7.37 (d, 2H, J=8.8 Hz), 6.86 (d, 2H, J=8.8 Hz), 6.66 (d, 1H, J=8.4 Hz), 6.48 (d, 1H, J=2.4 Hz), 6.38 (dd, 1H, J=2.4 and 8.4 Hz), 5.89 (s, 2H), 4.13 (s, 1H), 3.51 (s, 1H), 1.519 (s, 3H) 1.398 (s, 9H). MS (ESI, M+H$^+$)=331.1

(S)-2-Amino-N-[4-(biphenyl-4-yloxy)-phenyl] 3-hydroxy-2-methylpropionamide

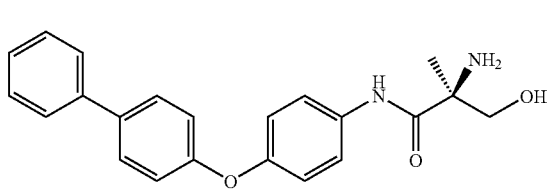

The compound was obtained as a white solid after HPLC purification. Yield: 30%, (33 mg). MS (ESI, M+H$^+$)=362.2

(S)-2-Amino-3-hydroxy-N-[4-(4'-methoxy-biphenyl-4-yloxy)-phenyl]-2-methylpropionamide

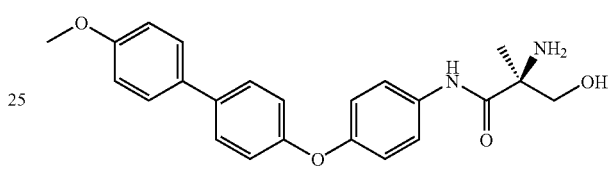

The compound was obtained as a white solid after HPLC purification. Yield: 90%, (25 mg). MS (ESI, M+H$^+$)=393.7

(S)-2-Amino-3-hydroxy-N-[4-(4'-chloro-biphenyl-4-yloxy)-phenyl]-2-methylpropionamide

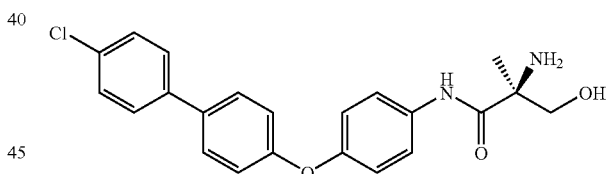

The compound was obtained as a white solid after HPLC purification. Yield: 80%, (23 mg). MS (ESI, M+H$^+$)=396.1

(S)-2-Amino-N-[4-(benzo[1,3]dioxol-5-yloxy)phenyl]-3-hydroxy-2-methylpropionamide

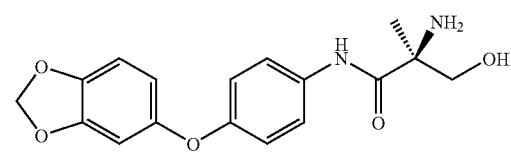

The compound was obtained as a white solid after HPLC purification. Yield: 10%, (10 mg). MS (ESI, M+H$^+$)=331.7

(S)-N-(4-(9H-Carbazol-2-yloxy)phenyl)-2-amino-3-hydroxy-2-methylpropanamide

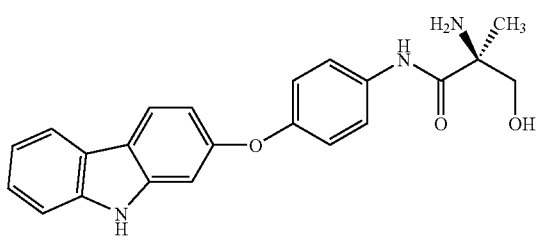

The title compound was synthesized from 2-(4-nitrophenoxy)-9H-carbazole. MS (ESI, M+H$^+$)=376; $^1$H NMR (400 MHz, DMSO-d$_6$) δ 9.92 (s, 1H), 8.17 (br s, 1H), 8.07 (br s, 1H), 7.64 (br s, 2H), 7.44 (s, 1H), 7.34 (s, 1H), 7.2–7.1 (m, 2H), 7.0 (s, 1H), 6.9 (s, 1H), 5.79 (s, 1H), 3.99 (m, 1H), 3.64 (m, 1H), 1.50 (s, 3H).

(S)-N-(4-(4-Carbonitrilephenylphenoxy)phenyl)-2-amino-3-hydroxy-2-methylpropanamide

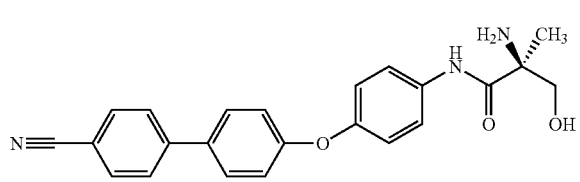

The title compound was synthesized from 4-(4-hydroxyphenyl)phenylcarbonitrile. MS (ESI, M+H$^+$)=388; $^1$H NMR (400 MHz, DMSO-d$_6$) δ 9.95 (s, 1H), 8.18 (br s, 2H), 7.92 (d, 2H), 7.86 (d, 2H), 7.75 (d, 2H), 7.67 (d, 2H), 7.12 (m, 4H), 5.79 (s, 1H), 3.99 (d, 1H), 3.64 (d, 1H), 1.50 (s, 3H).

(S)-Phosphoric acid mono-{2-amino-2-[4-(biphenyl-4-yloxy)-phenylcarbamoyl]-propyl}ester

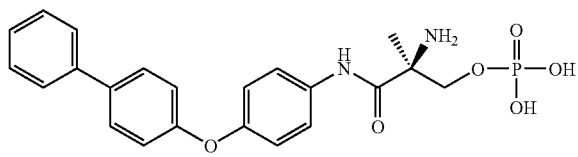

The compound was obtained as a white solid after HPLC purification. Yield: 15%, (2.5 mg). MS (ESI, M+H$^+$)=443.4

(S)-Phosphoric acid mono-{2-amino-2-[4-(4'-methoxy-biphenyl-4-yloxy)-phenylcarbamoyl]-propyl}ester

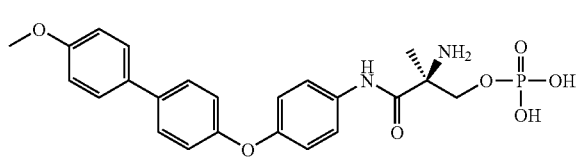

The compound was obtained as a white solid after HPLC purification. Yield: 30%, (10.0 mg). MS (ESI, M+H$^+$)=443.4

(S)-Phosphoric acid mono-{2-amino-2-[4-(4'-chloro-biphenyl-4-yloxy)-phenylcarbamoyl]-propyl}ester

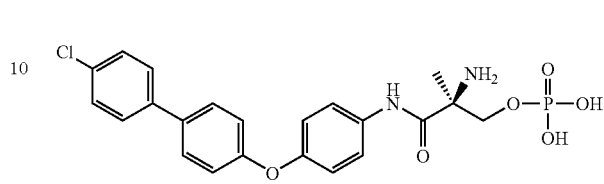

The compound was obtained as a white solid after HPLC purification. Yield: 50%, (60.0 mg). MS (ESI, M+H$^+$)=477.4

(S)-Phosphoric acid mono-{2-amino-2-[4-(4'-tert-butyl-biphenyl-4-yloxy)-phenylcarbamoyl]-propyl}ester

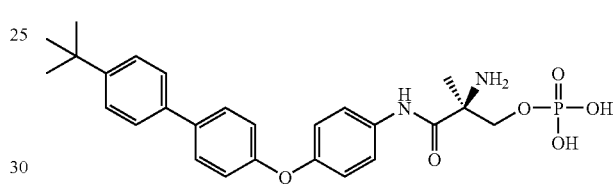

The compound was obtained as a white solid after HPLC purification. Yield: 40%, (38 mg). MS (ESI, M+H$^+$)=477.4

(S)-Phosphoric acid mono-{2-amino-2-[4-(1,1',4']-terphenyl-4-yloxy)-phenylcarbamoyl]-propyl}ester

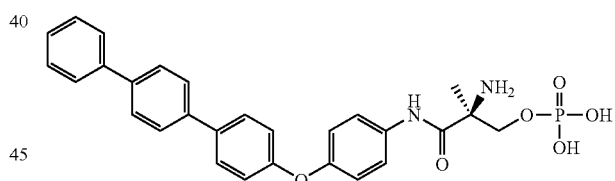

The compound was obtained as a white solid after HPLC purification. Yield: 35%, (7 mg). MS (ESI, M+H$^+$)=519.2

(S)-2-(4-(2-Phenylnaphthalen-6-yloxy)phenylcarbamoyl)-2-aminopropyl dihydrogen phosphate

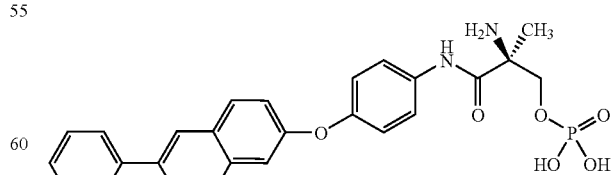

$^1$H NMR (400 MHz, DMSO-d$_6$) δ 10.15 (s, 1H), 9.4 (bs, 2H), 8.2 (d, 1H), 8.0 (d, 1H), 7.92 (m, 2H), 7.8 (m, 2H), 7.7 (m, 2H), 7.5 (m, 2H), 7.35 (m, 2H), 7.15 (m, 2H), 4.3 (t, 1H), 4.0 (t, 1H), 1.50 (s, 3H).

4-(4-Bromo-phenylsulfanyl)-nitrobenzene

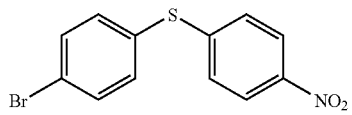

The final product was obtained as pale yellow oil after column chromatography, in 80% yield. $^1$H NMR (400 MHz, CDCl$_3$) δ 8.08 (d, 2H, J=9.2 Hz), 7.58 (d, 2H, J=8.8 Hz), 7.39 (d, 2H, J=8.8 Hz), 7.2 (d, 2H, J=9.2 Hz).

4-(4-Bromo-phenylsulfanyl)-phenylamine

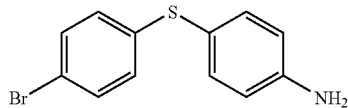

The final product was obtained as a pale yellow solid after column chromatography, in 90% yield. $^1$H NMR (400 MHz, CDCl$_3$) δ 7.28–7.32 (m, 4H), 6.96 (d, 2H, J=8.8 Hz), 6.68 (d, 2H, J=8.4 Hz).

4-(Biphenyl-4-ylsulfanyl)-phenylamine

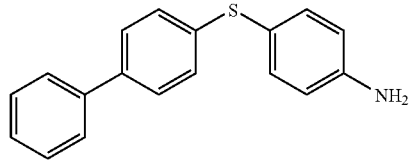

The final product was obtained as a pale yellow solid after column chromatography, in 73% yield. $^1$H NMR (400 MHz, CDCl$_3$) δ 7.53 (d, 2H, J=8.4 Hz), 7.45 (d, 2H, J=8.4 Hz), 7.40 (d, 2H, J=7.6 Hz), 7.35 (d, 2H, J=8.8 Hz), 7.31 (m, 1H), 7.19 (d, 2H, J=8.4 Hz), 6.73 (d, 2H, J=7.2 Hz).

(S)-(1-{4-[2-(Biphenyl-4-ylsulfanyl)-phenylcarbamoyl]-2-hydroxy-1-methyl-ethyl}-carbamic acid tert-butyl ester

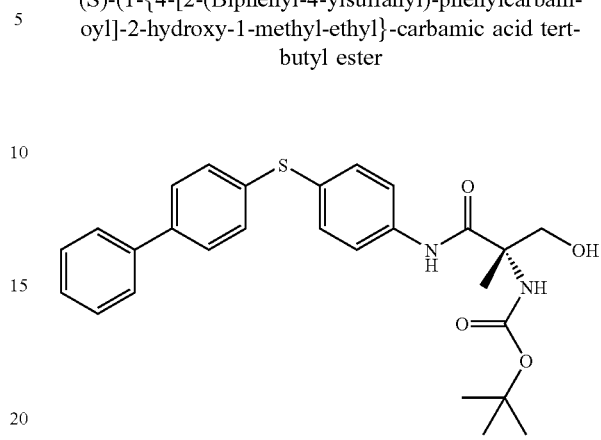

The final product was obtained as a pale yellow solid after column chromatography, in 73% yield. $^1$H NMR (400 MHz, CDCl$_3$) δ 7.51 (d, 2H, J=8.4 Hz), 7.44 (m, 4H), 7.39 (d, 2H, J=7.6 Hz), 7.35 (d, 2H, J=8.8 Hz), 7.31 (m, 1H), 7.19 (d, 2H, J=8.4 Hz), 4.08 (br.s, 1H), 3.67 (br. s, 1H), 1.58 (s, 3H), 1.46 (s, 9H).

Example 10

Synthesis of α-Methyl-Glutamate Analogs

A number of α-methyl-glutamate analogs were synthesized as potential phosphate mimics using the process described in Scheme 9. Oxidation of the alcohol in α-methyl-serine protected precursor followed by a Wittig olefination provided conjugated methyl ester as the desired intermediate. The methyl ester intermediate was then either deprotected or hydrolyzed to provide the desired product or was taken through a hydrogenation before conversion to the desired product.

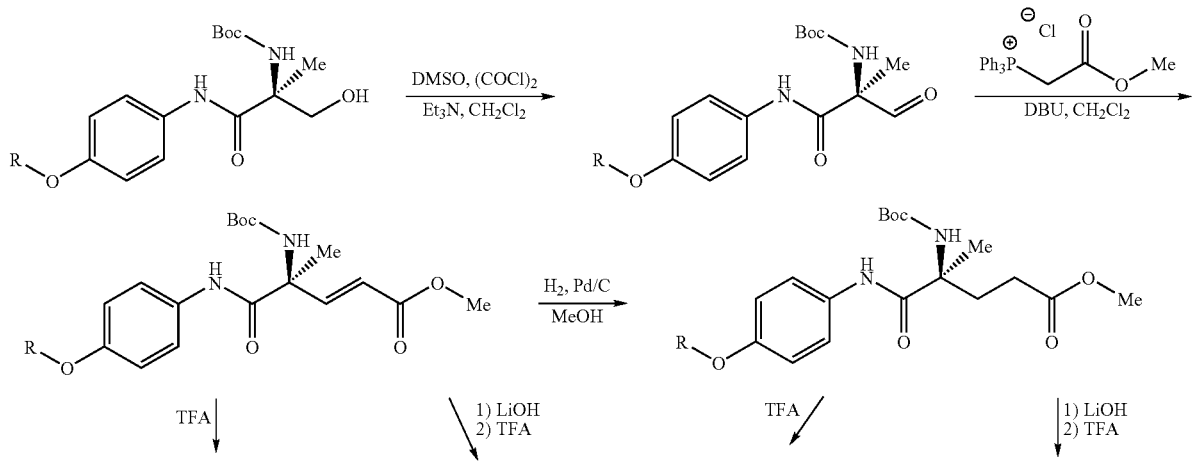

Scheme 9.

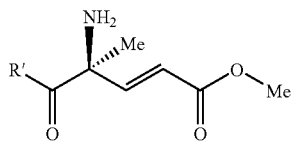
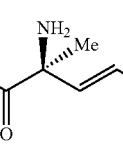
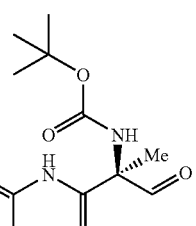
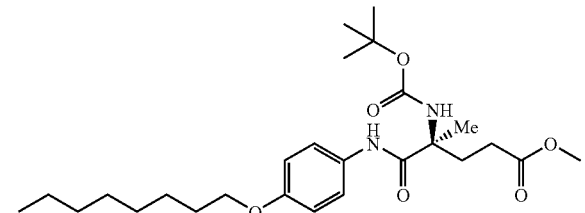

tert-Butyl (S)-1-(4-(octyloxy)phenylcarbamoyl)-1-formylethylcarbamate

To a solution of DMSO (0.28 mL, 3.3 equiv) in dry CH$_2$Cl$_2$ (10 mL) at −78° C. was added oxalyl chloride (0.95 mL, 1.6 equiv) drop wise then stirred for 10 minutes before addition of the desired alcohol (0.50 g, 1.0 equiv) in CH$_2$Cl$_2$ (5 mL). The mixture was stirred at −78° C. for 4 hours, then triethylamine (0.83 mL, 5 equiv) was added. The reaction was allowed to warm up to room temperature and loaded directly on a silica gel column for purification using Combi-Flash system (Hex:EtOAc). The product was obtained as a yellow solid in 60% (360 mg) yield. $^1$H NMR (400 MHz, CDCl$_3$) δ 9.67 (s, 1H), 8.50 (br s, 1H), 7.37 (d, 2H, J=7.6 Hz), 6.85 (d, 2H, J=7.6 Hz), 5.89 (br s, 1H), 3.94 (t, 2H, J=6.8 Hz), 1.71–1.80 (m, 2H), 1.67 (s, 3H), 1.46 (s, 9H), 1.22–1.48 (m, 10H), 0.88 (t, 3H, J=6.8 Hz).

tert-Butyl (S,E)-2-(4-(octyloxy)phenylcarbamoyl)-4-(methoxycarbonyl)but-3-en-2-ylcarbamate

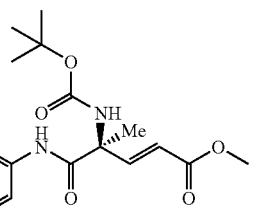

To a solution of (carbomethoxymethyl)triphenylphosphonium chloride (160 mg, 1.0 equiv) in dry CH$_2$Cl$_2$ (3 mL) at room temperature was added DBU (64 µL, 1.2 equiv) then stirred for 15 minutes before addition of the desired aldehyde (150 mg, 1.2 equiv) in CH$_2$Cl$_2$ (2 mL). The mixture was stirred at room temperature for 2 hours then directly loaded on a silica gel column for purification using Combi-Flash system (Hex:EtOAc). The product was obtained as colorless oil in 74% (125 mg) yield. $^1$H NMR (400 MHz, CDCl$_3$) δ 8.38 (br s, 1H), 7.37 (d, 2H, J=8.6 Hz), 6.85 (d, 2H, J=8.6 Hz), 6.04 (d, 1H, J=16.0 Hz), 5.30 (br s, 1H), 3.92 (t, 2H, J=6.8 Hz), 3.78 (s, 3H), 1.70–1.82 (m, 2H), 1.64 (s, 3H), 1.43 (s, 9H), 1.23–1.48 (m, 10H), 0.89 (t, 3H, J=6.8 Hz).

tert-Butyl (S)-2-(4-(octyloxy)phenylcarbamoyl)-4-(methoxycarbonyl)butan-2-ylcarbamate To a solution of the olefin (90 mg, 1.0 equiv) in MeOH (4 mL) was added activated Pd on carbon (9 mg in EtOAc (1 mL). The reaction was stirred under H$_2$ (gas) atmosphere overnight. The reaction was filtered through a layer of Celite to remove the Pd and carbon. The product was obtained as a white solid in 93% (84 mg) yield. $^1$H NMR (400 MHz, CDCl$_3$) δ 8.86 (br s, 1H), 7.39 (d, 2H, J=8.8 Hz), 6.85 (d, 2H, J=8.8 Hz), 5.42 (br s, 1H), 5.30 (s, 1H), 3.92 (t, 2H, J=6.8 Hz), 3.67 (s, 3H), 2.38–2.52 (m, 2H), 2.20–2.38 (m, 2H), 1.71–1.81 (m, 2H), 1.57 (s, 3H), 1.45 (s, 9H), 1.22–1.54 (m, 10H), 0.89 (t, 3H, J=6.8 Hz).

(S,E)-Methyl 4-(4-(octyloxy)phenylcarbamoyl)-4-aminopent-2-enoate

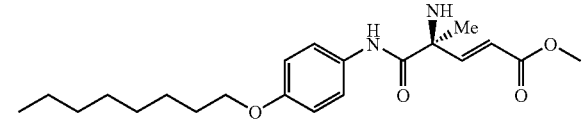

The product was obtained as colorless thick oil in 97% (14 mg) yield. MS (ESI, M+H$^+$)=377.7; $^1$H NMR (400 MHz, DMSO-d$_6$) δ 9.93 (br s, 1H), 8.70 (br s, 2H), 7.44 (d, 2H, J=8.8 Hz), 7.13 (d, 1H, J=16.0 Hz), 6.90 (d, 2H, J=8.8 Hz), 6.22 (d, 1H, J=16.0 Hz), 3.91 (t, 2H, J=6.8 Hz), 3.71 (s, 3H), 1.62–1.72 (m, 2H), 1.47 (s, 3H), 1.22–1.42 (m, 10H), 0.84 (t, 3H, J=6.8 Hz).

(S,E)-4-(4-(Octyloxy)phenylcarbamoyl)-4-amino-pent-2-enoic acid

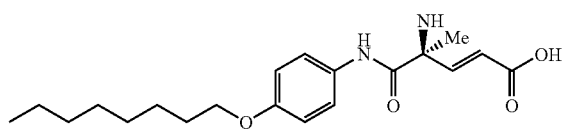

The product was obtained as a white solid in 99% (20 mg) yield. MS (ESI, M+H$^+$)=363.7; $^1$H NMR (400 MHz, DMSO-d$_6$) δ 9.95 (br s, 1H), 7.54 (d, 2H, J=8.8 Hz), 7.14 (d, 1H, J=16.0 Hz), 6.97 (d, 2H, J=8.8 Hz), 6.15 (d, 1H, J=16.0 Hz), 3.98 (t, 2H, J=6.8 Hz), 1.74 (s, 3H), 1.65–1.78 (m, 2H), 1.22–1.50 (m, 10H), 0.94 (t, 3H, J=6.8 Hz).

(S)-Methyl 4-(4-(octyloxy)phenylcarbamoyl)-4-aminopentanoate

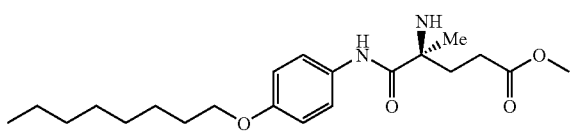

The product was obtained as colorless thick oil in 93% (13 mg) yield. MS (ESI, M+H$^+$)=379.6; $^1$H NMR (400 MHz, DMSO-d$_6$) δ 9.83 (br s, 1H), 8.26 (br s, 2H), 7.44 (d, 2H, J=8.8 Hz), 6.90 (d, 2H, J=8.8 Hz), 3.91 (t, 2H, J=6.8 Hz), 3.56 (s, 3H), 2.10–2.40 (m, 4H), 1.62–1.72 (m, 2H), 1.41 (s, 3H), 1.20–1.42 (m, 10H), 0.84 (t, 3H, J=6.8 Hz).

(S)-4-(4-(Octyloxy)phenylcarbamoyl)-4-aminopentanoic acid

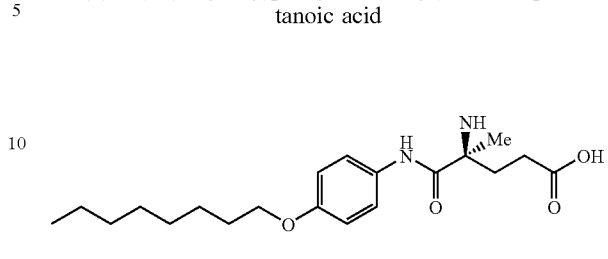

The product was obtained as a white solid in 95% (19 mg) yield. MS (ESI, M+H$^+$)=365.8; $^1$H NMR (400 MHz, DMSO-d$_6$) δ 9.88 (br s, 1H), 7.39 (d, 2H, J=8.8 Hz), 6.84 ((d, 2H, J=8.8 Hz), 3.86 (t, 2H, J=6.8 Hz), 1.92–2.30 (m, 4H), 1.57–1.67 (m, 2H), 1.49 (s, 3H), 1.15–1.38 (m, 10H), 0.81 (t, 3H, J=6.8 Hz).

Linker Modification:

A number of biphenyl-tail analogs with different linker lengths were synthesized using the process described in Scheme 10. Under Sonogashira conditions various alkynols were reacted with 4-bromobiphenyls followed by hydrogenation to afford biphenylalkyl alcohol intermediates. Reaction of the alcohol with substituted 4-fluoro-nitrobenzene under Williamson ether synthesis conditions followed by hydrogenation and coupling with amino acid provided the desired protected alcohol which was phosphorylated or deprotected to obtain the final product.

Scheme 10

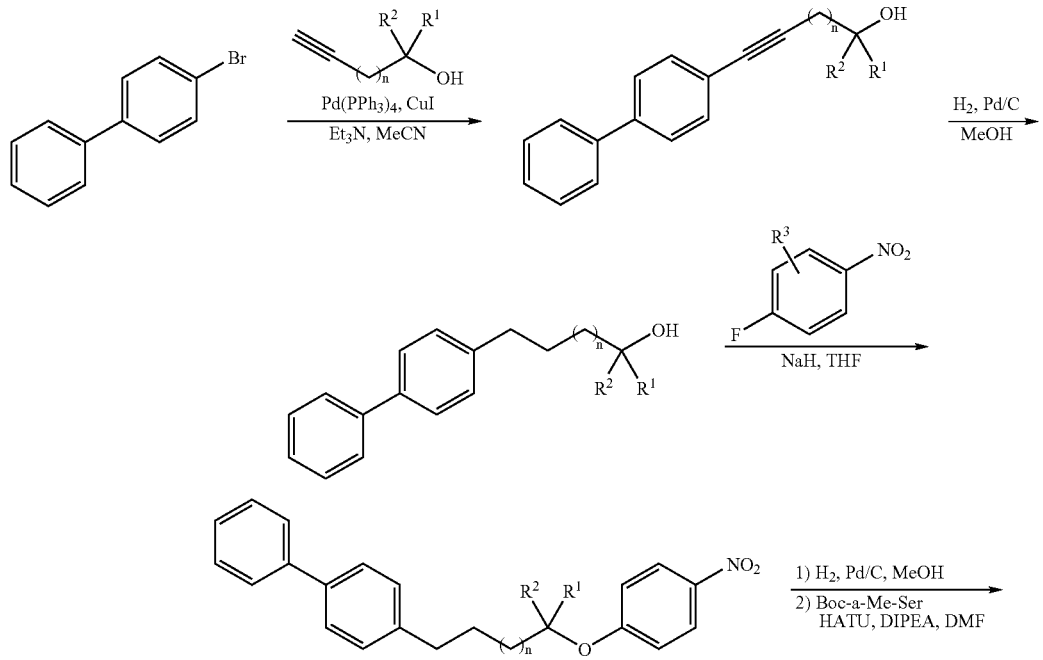

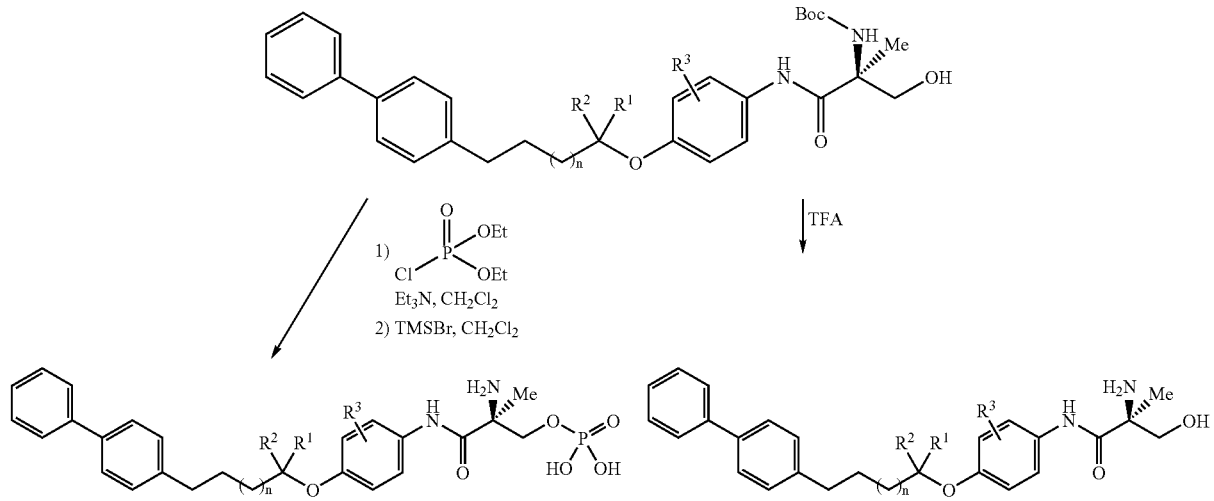

General Procedure for Sonogashira Cross-Coupling:

To a mixture of a 4-bromobiphenyl (1.0 equiv), Pd(PPh$_3$)$_4$ (0.02 equiv) and CuI (0.04 equiv) in MeCN was added the alkynol (1.5 equiv) and Et$_3$N (1.5 equiv). The reaction mixture was stirred for 2–16 hours at reflux, then the solvent removed in vacuo. The crude product was purified by silica gel column chromatography using the Combi-Flash system (Hex:EtOAc) as required.

General Procedure for Williamson Ether Synthesis:

To a solution of biphenylalkyl alcohol (1.0 equiv) in dry THF under nitrogen atmosphere was added NaH (2.5 equiv) in portions. The reaction mixture was heat at 60° C. for 15 minutes, then 4-flouro-nitrobenzene (1.0 equiv) was added and the solution stirred for 1–6 hours. The reaction was allowed to cool to room temperature then quenched with water. The mixture was then diluted with EtOAc and washed with H$_2$O (2×), 10% KHSO4 (1×), and saturated NaCl (1×). The product was either carried forward as is or it was purified by silica gel column chromatography using the Combi-Flash system (Hex:EtOAc).

3-(4-Phenylphenyl)propan-1-ol

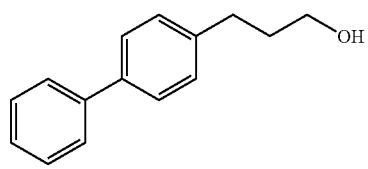

The product was obtained as a yellow solid in 57% (0.56 g) yield. $^1$H NMR (400 MHz, CDCl$_3$) δ 7.55–7.60 (m, 2H), 7.49–7.54 (m, 2H), 7.39–7.45 (m, 2H), 7.30–7.35 (m, 1H), 7.25–7.30 (m, 2H), 3.71 (t, 2H, J=6.8 Hz), 2.76 (t, 2H, J=6.8 Hz), 1.88–1.98 (m, 2H), 1.32 (br s, 1H).

4-(4-Phenylphenyl)butan-1-ol

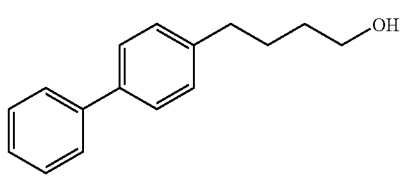

The product was obtained as a white solid in 62% (0.62 g) yield. $^1$H NMR (400 MHz, CDCl$_3$) δ 7.55–7.60 (m, 2H), 7.48–7.54 (m, 2H), 7.39–7.45 (m, 2H), 7.29–7.35 (m, 1H), 7.23–7.28 (m, 2H), 3.70 (t, 2H, J=6.8 Hz), 2.71 (t, 2H, J=6.8 Hz), 1.60–1.80 (m, 4H), 1.22 (br s, 1H).

tert-Butyl (S)-2-(4-(4-(4-phenylphenyl)butan-2-yloxy)phenylcarbamoyl)-1-hydroxypropan-2-ylcarbamate

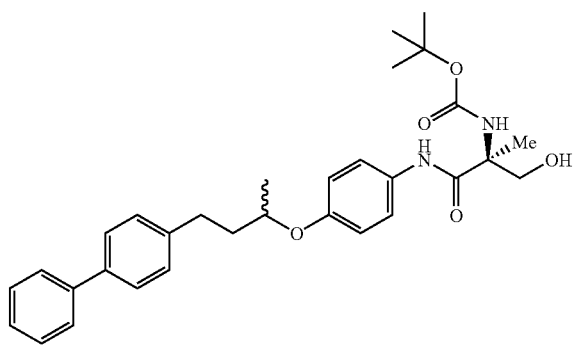

¹H NMR (400 MHz, CDCl₃) δ 9.48 (br s, 1H), 8.11 (br s, 2H), 7.60–7.64 (m, 2H), 7.58 (d, 2H, J=8.8 Hz), 7.51 (d, 2H, J=8.6 Hz), 7.37–7.48 (m, 4H), 7.32 (t, 1H, J=8.6 Hz), 6.84 (d, 2H, J=8.8 Hz), 5.61 (br s, 1H), 4.30–4.38 (m, 1H), 4.10 (br s, 1H), 3.56 (br s, 1H), 3.28 (br s, 1H), 2.70–2.90 (m, 2H), 2.01–2.14 (m, 1H), 1.84–1.96 (m, 1H), 1.58 (s, 3H), 1.46 (s, 9H), 1.31 (d, 3H, J=7.0 Hz).

(S)-N-(4-(3-(4-Phenylphenyl)propoxy)phenyl)-2-amino-3-hydroxy-2-methylpropanamide

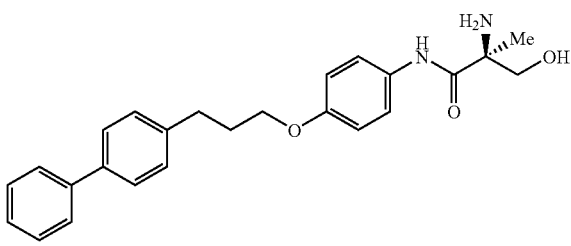

MS (ESI, M+H⁺)=405.5; ¹H NMR (400 MHz, DMSO-d₆) δ 9.74 (br s, 1H), 8.11 (br s, 2H), 7.60–7.64 (m, 2H), 7.57 (d, 2H, J=8.8 Hz), 7.47 (d, 2H, J=8.8 Hz), 7.43 (t, 2H, J=8.6 Hz), 7.28–7.35 (m, 2H), 6.92 (d, 2H, J=8.8 Hz), 3.95 (t, 2H, J=6.8 Hz), 3.93 (dd, 1H, J=12.0 Hz, J=4.8 Hz), 3.61 (dd, 1H, J=12.0 Hz, J=5.0 Hz), 2.76 (t, 2H, J=6.8 Hz), 1.98–2.08 (m, 2H), 1.47 (br s, 1H).

(S)-N-(4-(4-(4-Phenylphenyl)butoxy)phenyl)-2-amino-3-hydroxy-2-methylpropanamide

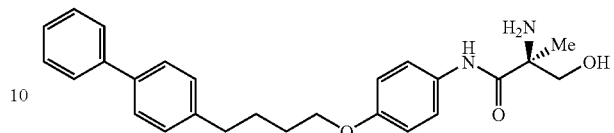

MS (ESI, M+H⁺)=419.5; ¹H NMR (400 MHz, DMSO-d₆) δ 9.73 (br s, 1H), 8.11 (br s, 2H), 7.60–7.64 (m, 2H), 7.56 (d, 2H, J=8.8 Hz), 7.40–7.49 (m, 4H), 7.27–7.35 (m, 3H), 6.91 (d, 2H, J=8.8 Hz), 3.95 (t, 2H, J=6.8 Hz), 3.94 (dd, 1H, J=12.0 Hz, J=4.8 Hz), 3.60 (dd, 1H, J=12.0 Hz, J=5.2 Hz), 2.62–2.70 (m, 2H), 1.68–1.77 (m, 4H), 1.46 (br s, 1H).

(S)-2-(4-(3-(4-Phenylphenyl)propoxy)phenylcarbamoyl)-2-aminopropyl dihydrogen phosphate

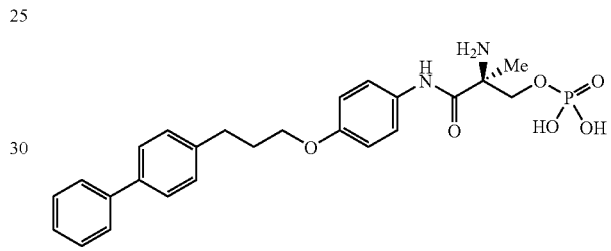

The product was obtained as a white solid in 25% (7.0 mg) yield over two steps. MS (ESI, M+H⁺)=485.6.

(S)-2-(4-(4-(4-Phenylphenyl)butoxy)phenylcarbamoyl)-2-aminopropyl dihydrogen phosphate

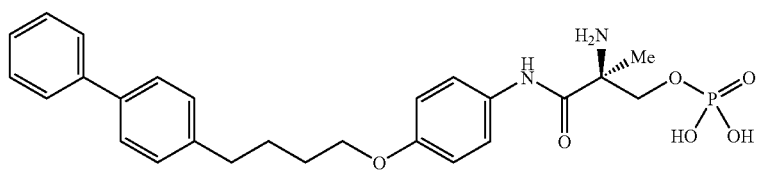

The product was obtained as a white solid in 43% (12.0 mg) yield over two steps. MS (ESI, M+H⁺)=499.6.

(S)-2-(4-(4-(4-Phenylphenyl)butan-2-yloxy)phenyl-carbamoyl)-2-aminopropyl dihydrogen phosphate

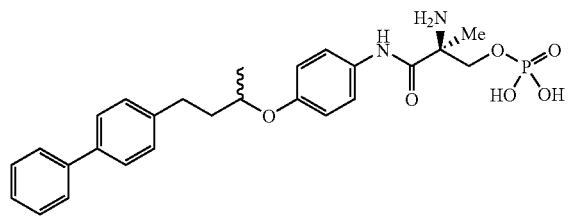

The product was obtained as a white solid in 30% (9.0 mg) yield over two steps. MS (ESI, M+H⁺)=499.6.

One Carbon Length Linker:

One carbon-ether length biphenyl-tail analogs were synthesized using the process described in Scheme 11. After N-acylation of 4-aminophenol, benzyl ether synthesis was achieved under mild alkylation condition. The biphenyl tail was synthesized using mild Suzuki cross-coupling using phenylboronic acid. The obtained protected alcohol was then further modified to phosphorylate or deprotected to produce the desired final product.

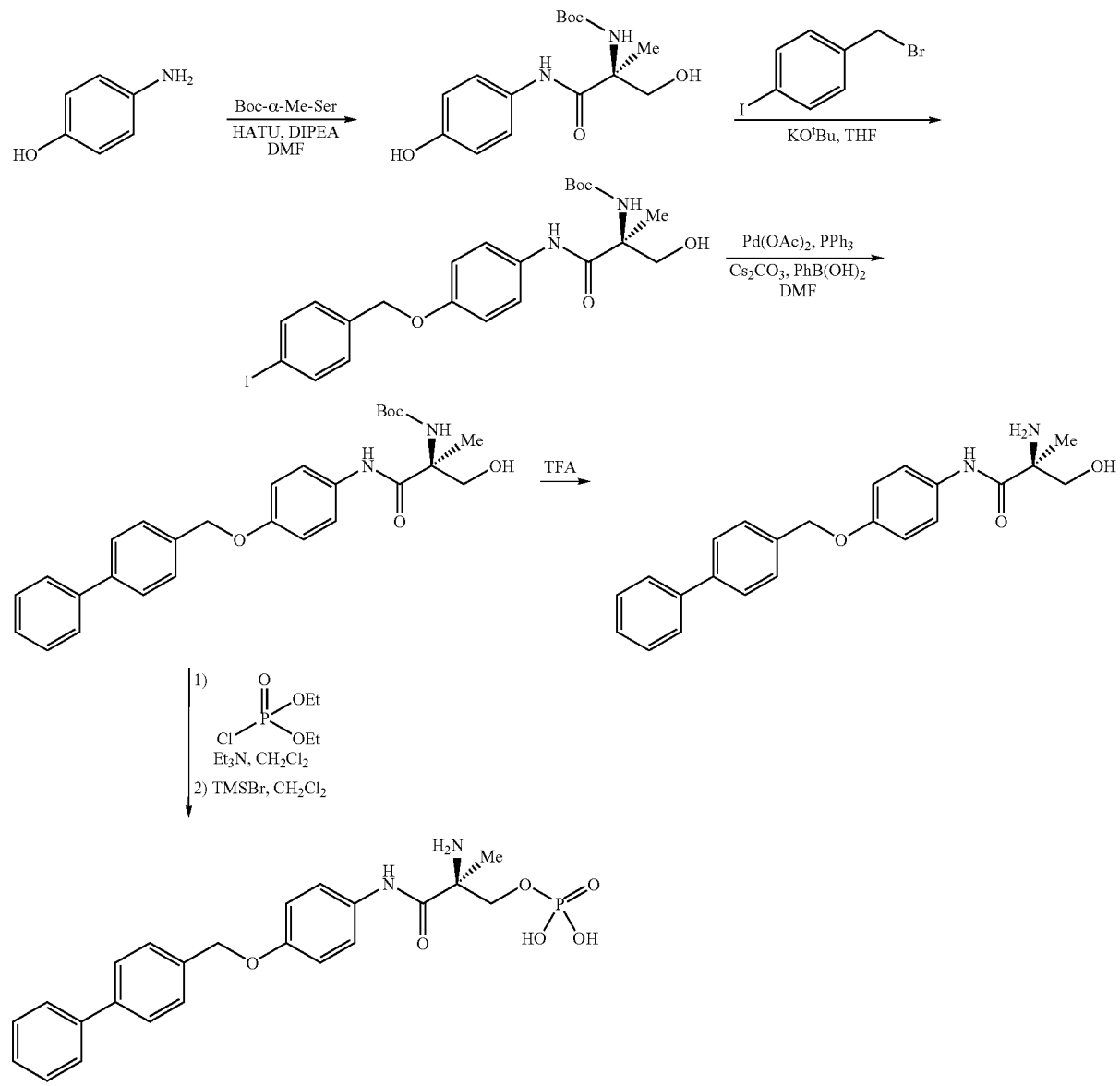

Scheme 11 tert-Butyl (S)-2-(4-(4-iodobenzyloxy)phenylcarbamoyl)-1-hydroxypropan-2-ylcarbamate To a solution of N-acylated 4-aminophenol (300 mg, 1.0 equiv) in dry THF (6 mL) at room temperature was added a 1.0 M solution of KOtBu in THF (0.97 mL, 1.0 equiv) and stirred for 10 minutes before addition of 4-iodobenyl bromide (290 mg, 1.0 equiv). The solution was stirred for 3 hours and subsequently the solvent was removed in vacuo. The crude product was purified by silica gel column chromatography using Combi-Flash system (Hex:EtOAc). The product was obtained as a white foam in 40% (203 mg) yield.

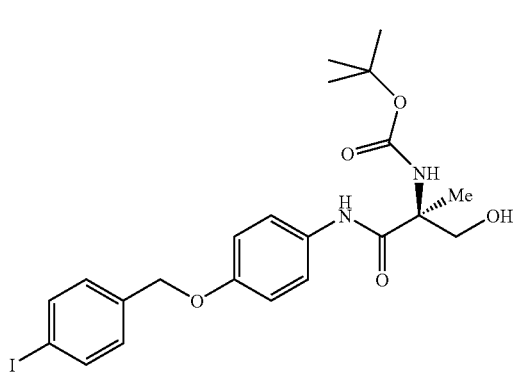

$^1$H NMR (400 MHz, CDCl$_3$) δ 9.50 (br s, 1H), 7.70 (d, 2H, J=8.6 Hz), 7.41 (d, 2H, J=8.6 Hz), 7.18 (d, 2H, J=8.6 Hz), 6.90 (d, 2H, J=8.6 Hz), 5.60 (br s, 1H), 4.99 (s, 2H), 4.08 (br s, 1H), 3.55 (br s, 1H), 3.22 (br s, 1H), 1.58 (s, 3H), 1.46 (s, 9H).

tert-Butyl (S)-2-(4-(4-phenylbenzyloxy)phenylcarbamoyl)-1-hydroxypropan-2-ylcarbamate To a mixture of a substituted aryl iodide (120 mg, 1.0 equiv), phenyl boronic acid (35 mg, 1.2 equiv), Pd(OAc)$_2$ (5 mg, 0.1 equiv), triphenylphosphine (12 mg, 0.2 equiv), and cesium carbonate (74 mg, 1.0 equiv) was added DMF (4 mL). The mixture was heated at 50° C. for an hour. The reaction was then diluted with EtOAc (20 mL) and washed with H$_2$O (2×25 mL) then the solvent was removed in vacuo. The crude product was purified by silica gel column chromatography using Combi-Flash system (Hex:EtOAc) as required. The product was obtained as a white solid in 79% (85 mg) yield.

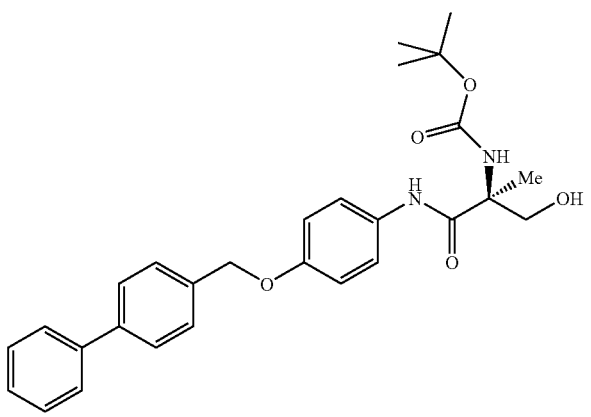

$^1$H NMR (400 MHz, CDCl$_3$) δ 9.46 (br s, 1H), 7.57–7.63 (m, 4H), 7.40–7.52 (m, 6H), 7.32–7.38 (m, 1H), 6.98 (d, 2H, J=8.6 Hz), 5.61 (br s, 1H), 5.09 (s, 2H), 4.09 (br s, 1H), 3.56 (br s, 1H), 3.27 (br s, 1H), 1.58 (s, 3H), 1.47 (s, 9H).

(S)-N-(4-(4-Phenylbenzyloxy)phenyl)-2-amino-3-hydroxy-2-methylpropanamide

The product was obtained as a white solid in 45% (9.0 mg) yield. MS (ESI, M+H$^+$)=377.4; $^1$H NMR (400 MHz, DMSO-d$_6$) δ 9.76 (br s, 1H), 8.12 (br s, 1H), 7.63–7.69 (m, 4H), 7.42–7.53 (m, 6H), 7.32–7.38 (m, 1H), 7.02 (d, 2H, J=8.6 Hz), 5.74 (t, 1H, J=5.1 Hz), 5.13 (s, 2H), 3.94 (dd, 1H, J=11.8 Hz, J=4.7 Hz), 3.61 (dd, 1H, J=11.8 Hz, J=4.7 Hz), 1.46 (s, 3H).

(S)-2-(4-(4-Phenylbenzyloxy)phenylcarbamoyl)-2-aminopropyl dihydrogen phosphate The product was obtained as a white solid in 36% (18.0 mg) yield over two steps. MS (ESI, M+H$^+$)=457.1.

Thiazole Linker:

The thiazole-biphenyl analogs were synthesized using the process described in Scheme 12. Substituted benzamide was converted to thiobenzamide using Lawesson's reagent. Reaction of thioamide with bromoketone afforded the thiazole intermediate. Reduction of the nitro group followed by acylation provided an orthogonally protected intermediate, which was further modified by a mild Suzuki cross-coupling process using aryl boronic acid. The protecting Boc and the oxazolidine groups were removed using p-TsOH and the product was then phosphorylated to obtain the final phosphate product.

Scheme 12
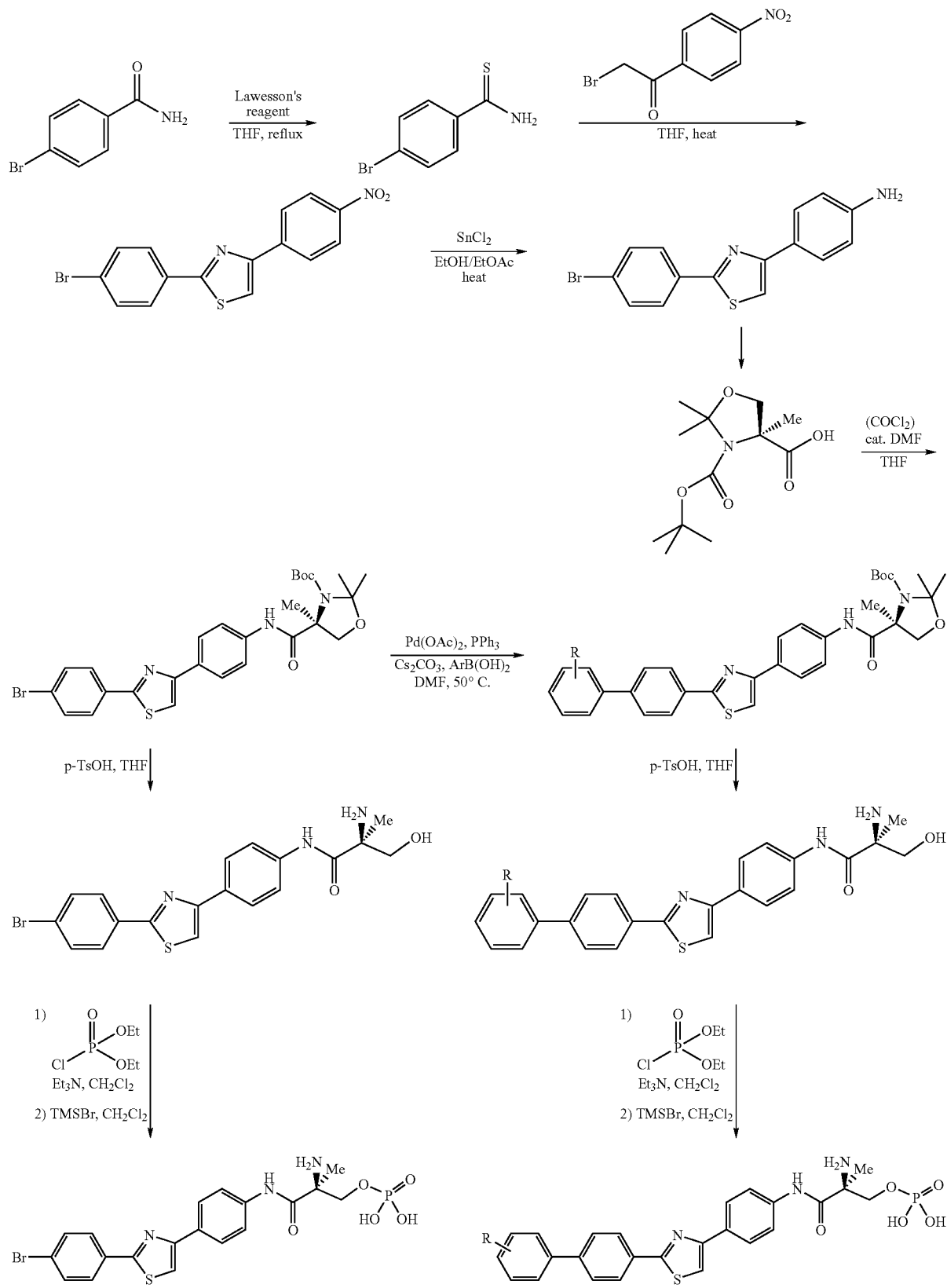

4-(2-(4-Bromophenyl)thiazol-4-yl)benzenamine

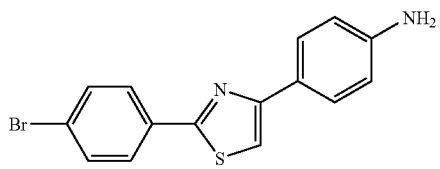

To a mixture of Lawesson's reagent (6.07 g, 1.5 equiv) and 4-bromobenzamide (2.00 g, 1.0 equiv) was added dry THF (20 mL). The reaction mixture was refluxed overnight under nitrogen atmosphere. The reaction was allowed to cool to room temperature, then diluted with EtOAc (50 mL) and washed with 5% NaHCO$_3$ (2×50 mL) and saturated NaCl (1×25 mL). The organic layer was dried over anhydrous MgSO$_4$ then the solvent removed in vacuo. The crude product was purified by silica gel column chromatography using Combi-Flash system (Hex:EtOAc). The product was obtained as white solid in 99% (2.16 g) yield.

To a mixture of 4-bromothiobenzamide (2.16 g, 1.0 equiv) and 4-nitrobromoacetophenone (2.43 g, 1.0 equiv) was added dry THF (20 mL) and heated at 60° C. for 3 hours. The solvent was removed in vacuo and the crude product was purified by silica gel column chromatography using Combi-Flash system (Hex:EtOAc). The product was obtained as yellow solid in 84% (3.00 g) yield.

To a mixture of the nitro intermediate (1.10 g, 1.0 equiv) and SnCl$_2$ (3.02 g, 5.0 equiv) was added EtOH (30 mL) then heated at 80° C. for 3 hours. The reaction mixture was diluted with H$_2$O (50 mL) then basified to pH 10 using saturated NaOH solution. The reaction mixture was then extracted with EtOAc (2×100 mL). The organic layers were combined and removed in vacuo. The crude product was purified by silica gel column chromatography using Combi-Flash system (Hex:EtOAc). The product was obtained as yellow solid in 63% (0.63 g) yield.

$^1$H NMR (400 MHz, CDCl$_3$) δ 7.90 (d, 2H, J=8.6 Hz), 7.79 (d, 2H, J=8.6 Hz), 7.58 (d, 2H, J=8.6 Hz), 7.26 (d, 1H, J=0.8 Hz), 6.75 (d, 2H, J=8.6 Hz), 3.80 (br s, 2H).

(S)-tert-Butyl 4-(4-(2-(4-bromophenyl)thiazol-4-yl)phenylcarbamoyl)-2,2,4-trimethyloxazolidine-3-carboxylate

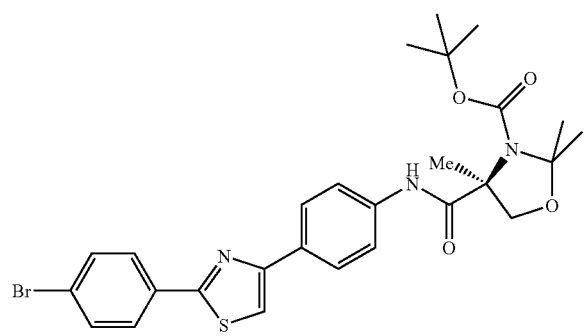

To a solution of (S)-3-(tert-butoxycarbonyl)-2,2,4-trimethyloxazolidine-4-carboxylic acid (100 mg, 1.0 equiv) in dry THF (5 mL) was added a 2.0 M solution of oxalyl chloride in CH$_2$Cl$_2$ (0.23 mL, 1.2 equiv) and catalytic amount of DMF (2 drops). The reaction was allowed to stir at room temperature for 30 minutes. To the reaction mixture was then added the desired aniline (solid or solution in THF, 128 mg, 1.0 equiv). The reaction was allowed to stir overnight. The solvent removed in vacuo and the crude product was purified by silica gel column chromatography using Combi-Flash system (Hex:EtOAc). The product was obtained as a white solid in 74% (164 mg) yield.

$^1$H NMR (400 MHz, CDCl$_3$) δ 7.88–7.97 (m, 4H), 7.56–7.63 (m, 4H), 7.43 (s, 1H), 3.90 (br s, 2H), 1.70 (br s, 6H), 1.60 (br s, 3H), 1.50 (br s, 9H).

(S)-2-Amino-N-(4-(2-(4-bromophenyl)thiazol-4-yl)phenyl)-3-hydroxy-2-methylpropanamide

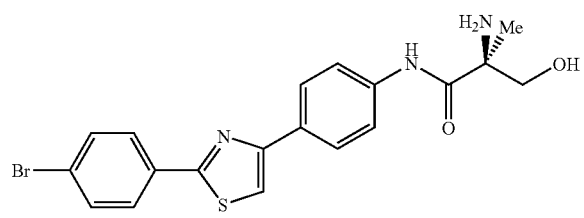

The product was obtained as a white solid in 75% (20.0 mg) yield. MS (ESI, M+H$^+$)=432.6 and 434.1; $^1$H NMR (400 MHz, DMSO-d$_6$) δ 10.01 (br s, 1H), 8.18 (br s, 2H), 8.14 (s, 1H), 8.04 (d, 2H, J=8.6 Hz), 7.96 (d, 2H, J=8.6 Hz), 7.70–7.76 (m, 4H), 5.60 (br s, 1H), 4.00 (br d, 1H), 3.65 (br d, 1H), 1.50 (s, 3H).

(S)-2-Amino-3-hydroxy-2-methyl-N-(4-(2-(4-phenylphenyl)thiazol-4-yl)phenyl)propanamide

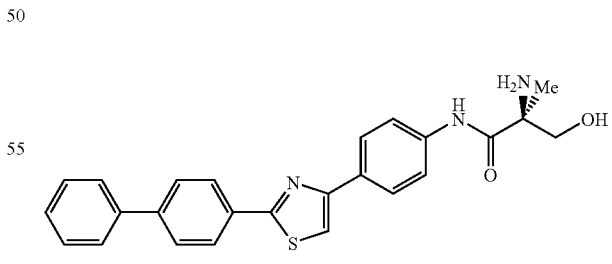

The product was obtained as a white solid in 58% (15.0 mg) yield over two steps. MS (ESI, M+H$^+$)=430.4; $^1$H NMR (400 MHz, DMSO-d$_6$) δ 10.01 (br s, 1H), 8.18 (br s, 2H), 8.04–8.14 (m, 5H), 7.84 (d, 2H, J=8.6 Hz), 7.72–7.78 (m, 4H), 7.50 (t, 2H, J=8.6 Hz), 7.37–7.47 (m, 2H), 5.80 (br s, 1H), 4.01 (br d, 1H), 3.65 (br d, 1H), 1.51 (s, 3H).

137

(S)-2-Amino-N-(4-(2-(4-(benzo[d][1,3]dioxol-6-yl)phenyl)thiazol-4-yl)phenyl)-3-hydroxy-2-methylpropanamide

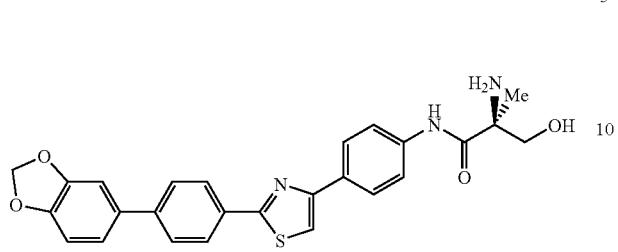

The product was obtained as a white solid in 42% (15.0 mg) yield over two steps. MS (ESI, M+H$^+$)=474.3; $^1$H NMR (400 MHz, DMSO-d$_6$) δ 10.05 (br s, 1H), 8.25 (br s, 2H), 7.98–8.11 (m, 5H), 7.76–7.82 (m, 4H), 7.36 (d, 1H, J=1.6 Hz), 7.26 (dd, 1H, J=8.2 Hz, J=2.0 Hz), 7.04 (d, 1H, J=8.2 Hz), 6.09 (s, 2H), 5.05 (br s, 1H), 3.78 (br d, 1H), 3.30 (br d, 1H), 1.20 (s, 3H).

(S)-2-(4-(2-(4-Bromophenyl)thiazol-4-yl)phenylcarbamoyl)-2-aminopropyl dihydrogen phosphate

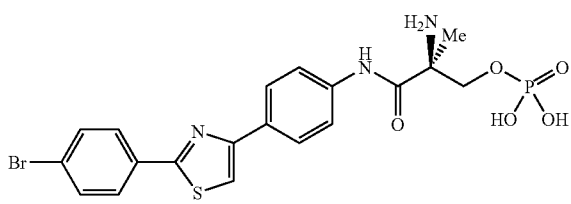

The product was obtained as a white solid in 83% (5.0 mg) yield over two steps. MS (ESI, M+H$^+$)=512.6 and 514.3.

138

(S)-2-(4-(2-(4-Phenylphenyl)thiazol-4-yl)phenylcarbamoyl)-2-aminopropyl dihydrogen phosphate

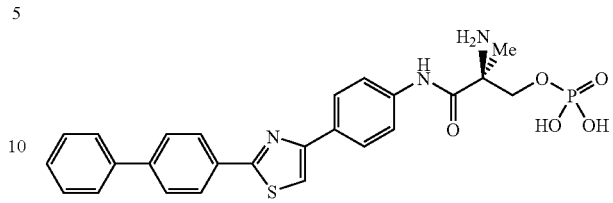

The product was obtained as a white solid in 65% (3.0 mg) yield over two steps. MS (ESI, M+H$^+$)=510.2.

(S)-2-(4-(2-(4-(Benzo[d][1,3]dioxol-6-yl)phenyl)thiazol-4-yl)phenylcarbamoyl)-2-aminopropyl dihydrogen phosphate

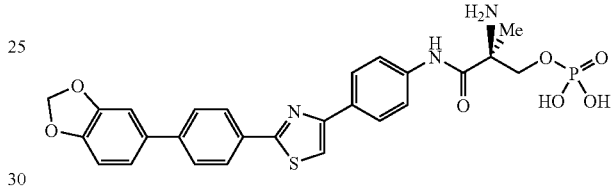

The product was obtained as a white solid in 45% (3.0 mg) yield over two steps. MS (ESI, M+H$^+$)=554.1.

Acetophenone-Based Linker:

Synthesis of the acetophenone-based linker was achieved using the process described in Scheme 13. Reaction of protected 4-aminobenzoyl chloride with 4-ethynylbiphenyl followed by hydrogenation of the alkyne provided the Boc-protected 4-aminoacetophenone. Acylation of the amino group after removal of the Boc protecting group afforded an orthogonally protected oxazolidine intermediate, which could be removed using p-TsOH. The free alcohol could then be rapidly converted into the final phosphate product.

Scheme 13.

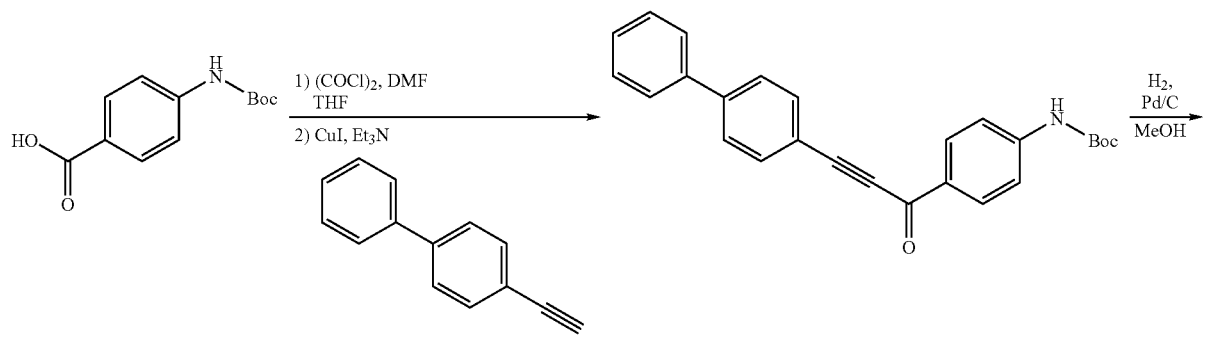

-continued

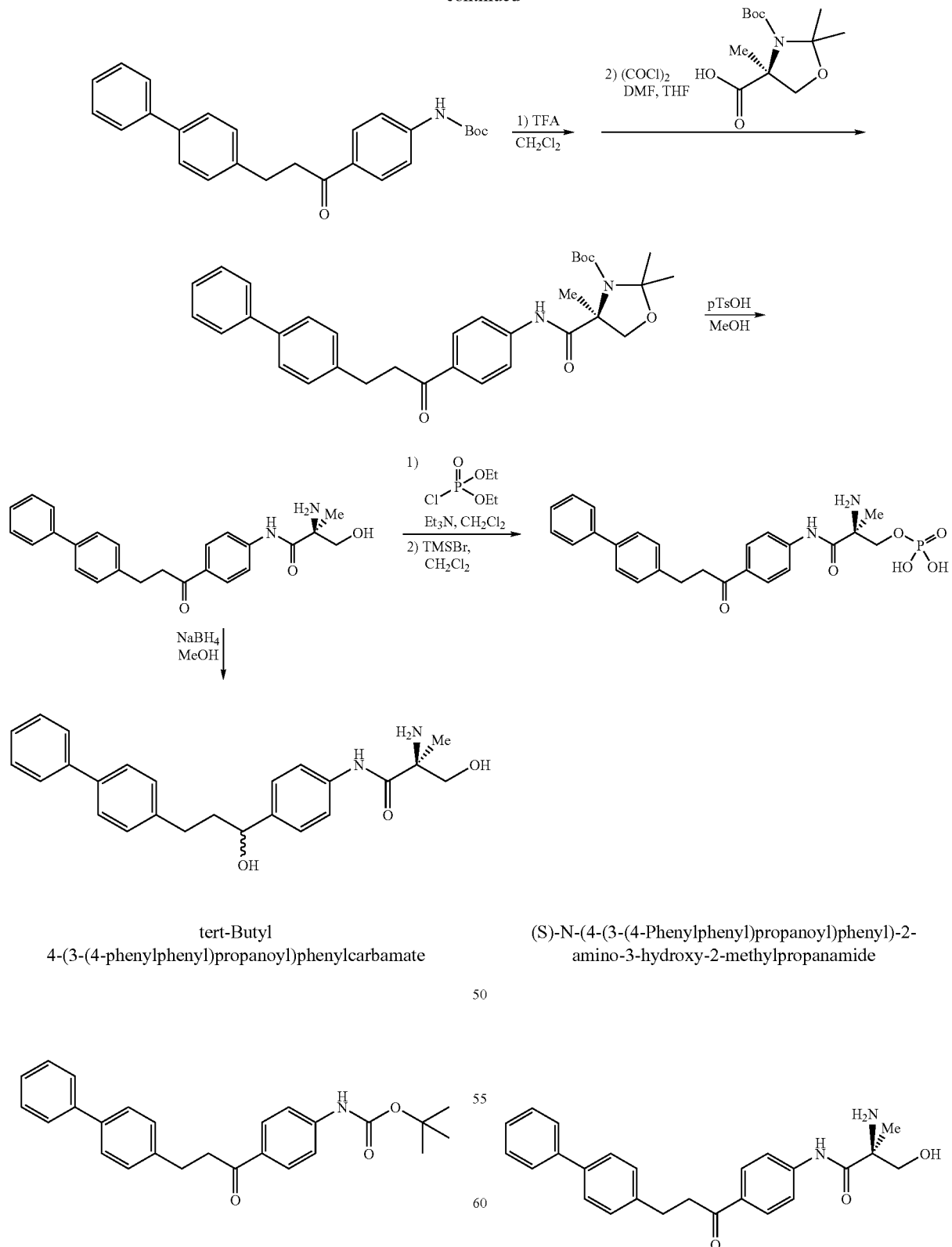

tert-Butyl
4-(3-(4-phenylphenyl)propanoyl)phenylcarbamate (S)-N-(4-(3-(4-Phenylphenyl)propanoyl)phenyl)-2-amino-3-hydroxy-2-methylpropanamide The product was obtained as a yellow solid in 25% (185 mg) yield over three steps. $^1$H NMR (400 MHz, CDCl$_3$) δ 7.90 (d, 2H, J=8.6 Hz), 7.50–7.60 (m, 4H), 7.40–7.46 (m, 4H), 7.30–7.36 (m, 3H), 6.66 (br s, 1H), 3.29 (t, 2H, J=7.0 Hz), 3.10 (t, 2H, J=7.0 Hz), 1.54 (s, 9H).

The product was obtained as a white solid in 66% (111 mg) yield over four steps. MS (ESI, M+H$^+$)=403.3; $^1$H NMR (400 MHz, DMSO-d$_6$) δ 7.95 (d, 2H, J=8.6 Hz), 7.80

(d, 2H, J=8.6 Hz), 7.52–7.63 (m, 4H), 7.43 (t, 2H, J=8.6 Hz), 7.29–7.38 (m, 3H), 4.99 (br t, 1H, J=5.1 Hz), 3.72 (dd, 1H, J=10.2 Hz, J=5.2 Hz), 3.35 (t, 2H, J=6.8 Hz), 3.20 (dd, 1H, J=10.2 Hz, J=5.2 Hz), 2.96 (t, 2H, J=6.8 Hz), 1.15 (s, 3H).

(S)-2-(4-(3-(4-Phenylphenyl)propanoyl)phenylcarbamoyl)-2-aminopropyl dihydrogen phosphate

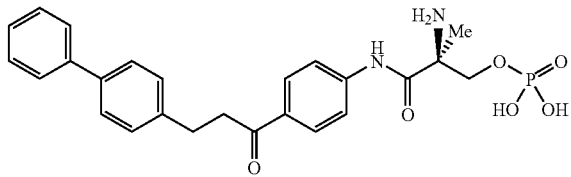

The product was obtained as a white solid in 62% (5.0 mg) yield over two steps. MS (ESI, M+H⁺)=483.5.

(S)-2-Amino-3-hydroxy-N-(4-(1-hydroxy-3-(4-phenylphenyl)propyl)phenyl)-2-methylpropanamide

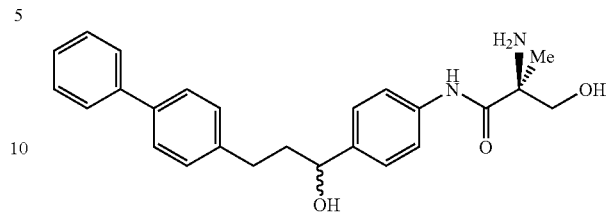

The product was obtained as a white solid in 80% (5.0 mg) yield. MS (ESI, M+H⁺)=405.2.

Thioether Linker:

Synthesis of the thioether, sulfoxide and sulfone linkers was achieved using the process described in Scheme 14. Reduction of biphenyl acetic acid to alcohol followed by conversion of the alcohol to bromo leaving group allowed conversion of the functional group to a thioether. The nitro group was then reduced and acylated to afford oxazolidine intermediate. The thioether could then be further functionalized before deprotection of the Boc and oxazolidine protecting groups. The free alcohol was then converted into the desired final phosphate product.

Scheme 14

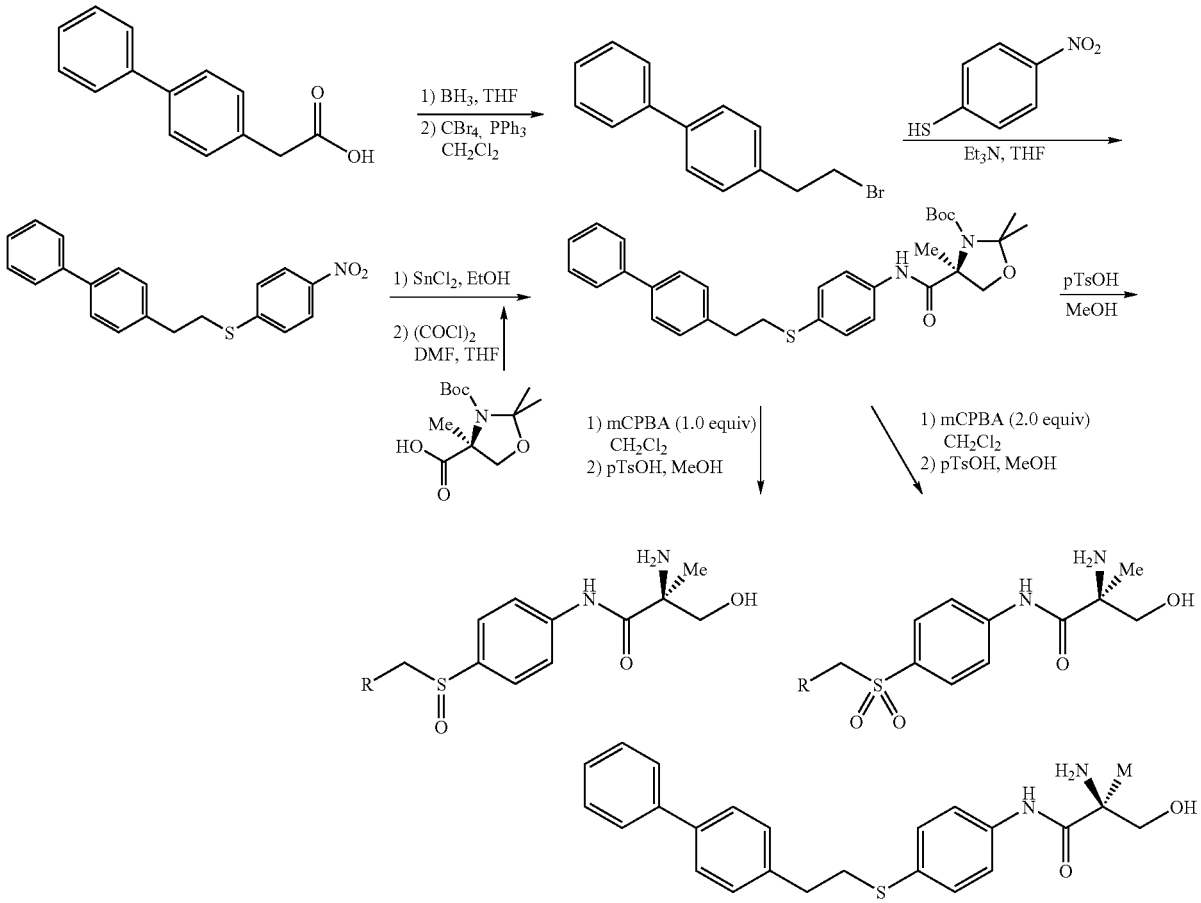

4-(2-(4-Nitrophenylthio)ethyl)biphenyl

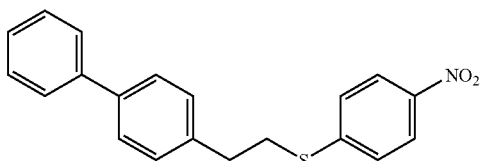

The product was obtained as a yellow solid in 73% (0.72 g) yield over three steps. $^1$H NMR (400 MHz, CDCl$_3$) δ 8.14 (d, 2H, J=8.6 Hz), 7.53–7.62 (m, 6H), 7.44 (t, 2H, J=8.6 Hz), 7.28–7.38 (m, 3H), 3.32 (t, 2H, J=7.4 Hz), 3.06 (t, 2H, J=7.4 Hz).

(S)-tert-Butyl 4-(4-(4-phenylphenethylthio)phenylcarbamoyl)-2,2,4-trimethyloxazolidine-3-carboxylate

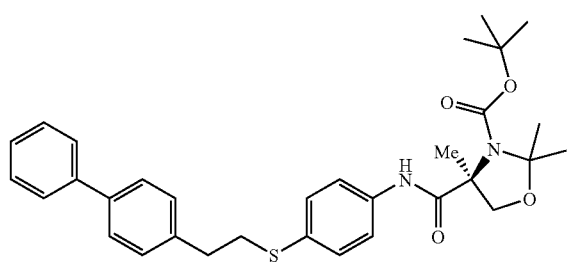

The product was obtained as a white solid in 42% (160 mg) yield over three steps. $^1$H NMR (400 MHz, CDCl$_3$) δ 7.48–7.52 (m, 2H), 7.45 (d, 2H, J=8.6 Hz), 7.41 (d, 2H, J=8.8 Hz), 7.36 (t, 2H, J=8.6 Hz), 7.22–7.32 (m, 3H), 7.29–7.38 (m, 3H), 7.12 (d, 2H, J=8.8 Hz), 3.70 (br s, 2H), 3.08 (t, 2H, J=7.0 Hz), 2.86 (d, 2H, J=7.0 Hz), 2.96 (t, 2H, J=6.8 Hz), 1.62 (s, 6H), 1.48 (s, 3H), 1.43 (br s, 9H).

(S)-N-(4-(4-Phenylphenethylthio)phenyl)-2-amino-3-hydroxy-2-methylpropanamide

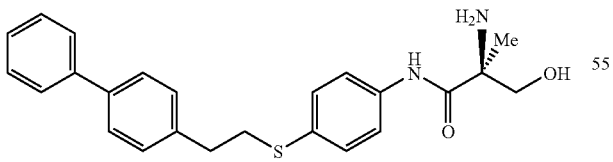

The product was obtained as a white solid in 42% (160 mg) yield over three steps. MS (ESI, M+H$^+$)=407.3; $^1$H NMR (400 MHz, DMSO-d$_6$) δ 9.94 (br s, 1H), 8.16 (br s, 2H), 7.54–7.64 (m, 6H), 7.44 (d, 2H, J=8.6 Hz), 7.28–7.40 (m, 5H), 5.76 (br s, 1H), 3.99 (br dd, 2H), 3.63 (br dd, 1H), 3.22 (t, 2H, J=7.0 Hz), 2.87 (t, 2H, J=6.8 Hz), 1.49 (s, 3H).

(2S)-N-(4-(4-Phenylphenethylsulfinyl)phenyl)-2-amino-3-hydroxy-2-methylpropanamide

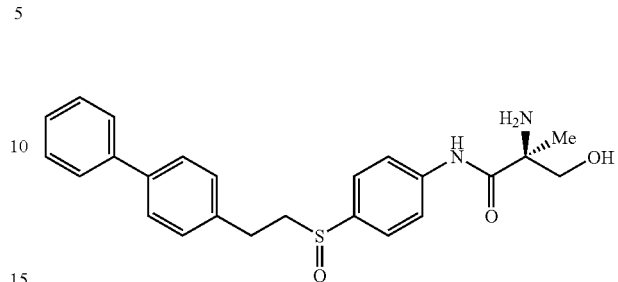

The product was obtained as a white solid in 90% (40 mg) yield over two steps. MS (ESI, M+H$^+$)=423.7; $^1$H NMR (400 MHz, DMSO-d$_6$) δ 10.23 (br s, 1H), 8.23 (br s, 2H), 7.88 (d, 2H, J=8.6 Hz), 7.68 (d, 2H, J=8.6 Hz), 7.61 (dd, 2H, J=8.6 Hz, J=1.6 Hz), 7.56 (d, 2H, J=8.6 Hz), 7.43 (t, 2H, J=8.6 Hz), 7.27–7.36 (m, 3H), 5.78 (br s, 1H), 4.05 (br d, 2H), 3.53 (br d, 1H), 3.20–3.43 (m, 1H), 2.90–3.10 (m, 2H), 2.67–2.78 (m, 1H), 1.48 (s, 3H).

(S)-N-(4-(4-Phenylphenethylsulfonyl)phenyl)-2-amino-3-hydroxy-2-methylpropanamide

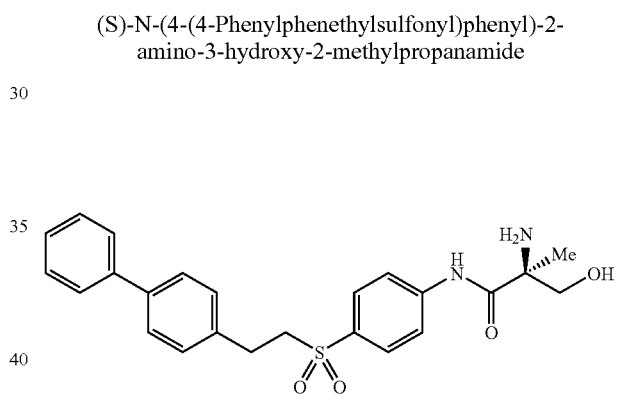

The product was obtained as a white solid in 91% (52 mg) yield over two steps. MS (ESI, M+H$^+$)=439.4; $^1$H NMR (400 MHz, DMSO-d$_6$) δ 10.41 (br s, 1H), 8.25 (br s, 2H), 7.86–7.99 (m, 4H), 7.59 (d, 2H, J=8.6 Hz), 7.52 (d, 2H, J=8.6 Hz), 7.42 (t, 2H, J=8.6 Hz), 7.32 (tt, 1H, J=8.4 Hz, J=1.2 Hz), 7.27 (d, 2H, J=8.6 Hz), 5.80 (br t, 1H), 4.06 (dd, 1H, J=11.6 Hz, J=4.7 Hz), 3.58–3.69 (m, 3H), 2.85–2.93 (m, 2H), 1.52 (s, 3H).

(S)-2-(4-(4-Phenylphenethylthio)phenylcarbamoyl)-2-aminopropyl dihydrogen phosphate

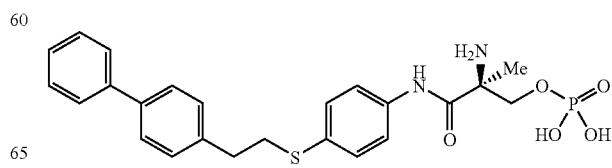

The product was obtained as a white solid in 65% (6.0 mg) yield over two steps. MS (ESI, M+H⁺)=487.3.

(S)-2-(4-(4-Phenylphenethylsulfinyl)phenylcarbamoyl)-2-aminopropyl dihydrogen phosphate

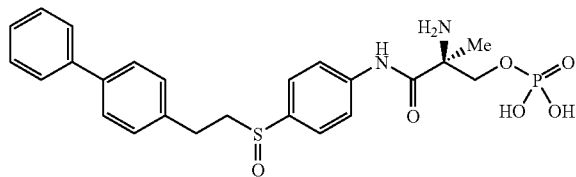

The product was obtained as a white solid in 45% (1.5 mg) yield over two steps. MS (ESI, M+H⁺)=503.1.

(S)-2-(4-(4-Phenylphenethylsulfonyl)phenylcarbamoyl)-2-aminopropyl dihydrogen phosphate

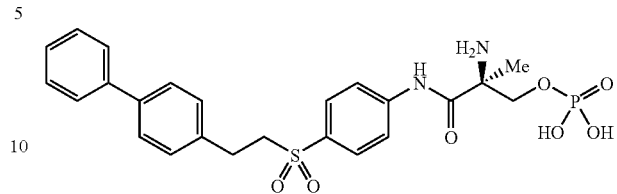

The product was obtained as a white solid in 65% (15.0 mg) yield over two steps. MS (ESI, M+H⁺)=519.7.

Benzamide Linker:

The benzamide linker based compounds were synthesized as described in Scheme 15. Acylation of 4-phenylbenzylamine followed by a one-pot, two step acylation of the aniline intermediate afforded orthogonally protected oxazolidine intermediate. The oxazolidine intermediate was then converted into free alcohol and its phosphate respectively.

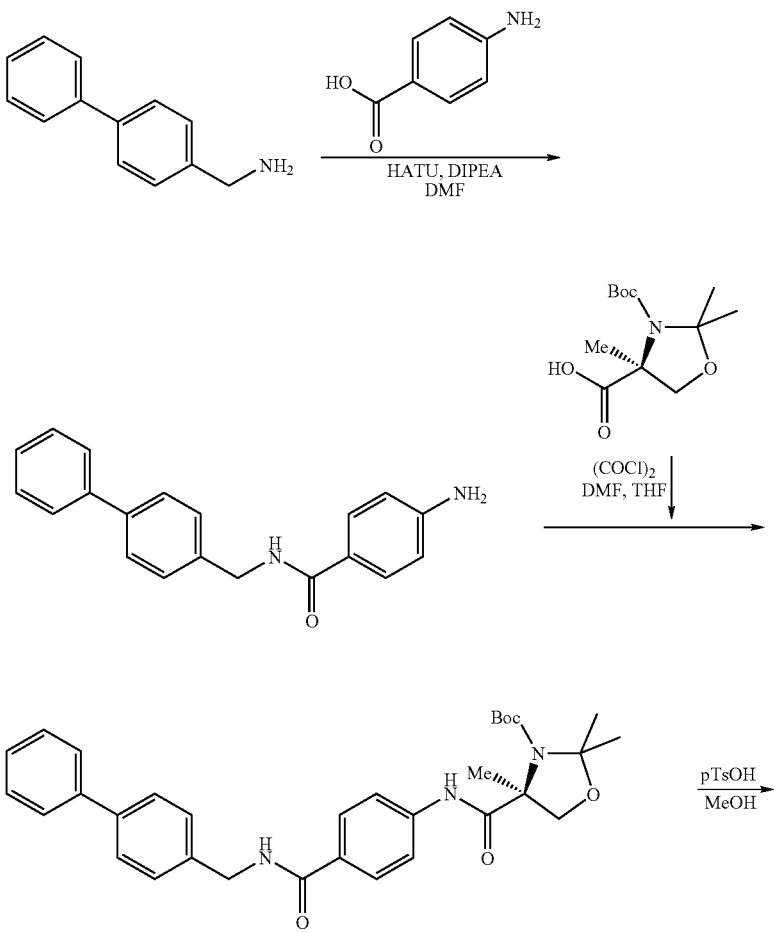

-continued

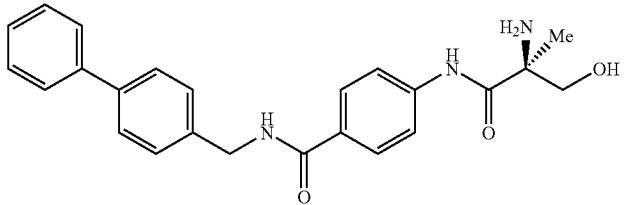

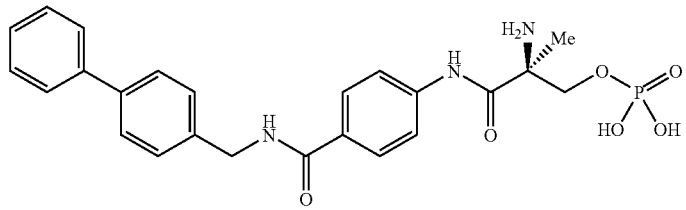

N-(4-Phenylbenzyl)-4-aminobenzamide

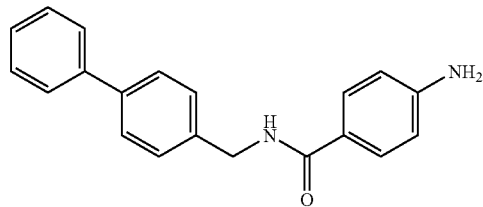

The product was obtained as a yellow solid in 60% (0.49 g) yield. ¹H NMR (400 MHz, CDCl₃) δ 7.64 (d, 2H, J=8.6 Hz), 7.55–7.60 (m, 4H), 7.40–7.47 (m, 4H), 7.35 (tt, 1H, J=8.6 Hz, J=1.2 Hz), 6.66 (d, 2H, J=8.6 Hz), 6.25 (br t, 1H), 4.67 (d, 2H, J=5.9 Hz), 3.95 (br s, 2H).

(S)-tert-Butyl 4-(4-(4-phenylbenzylcarbamoyl)phenylcarbamoyl)-2,2,4-trimethyloxazolidine-3-carboxylate

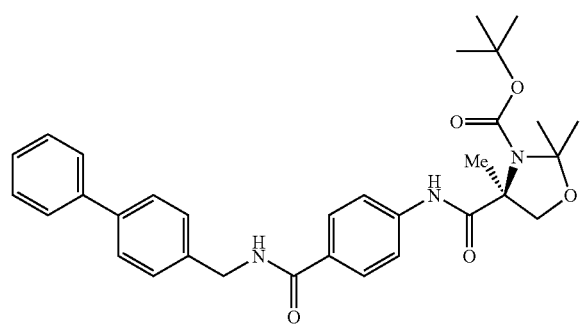

The product was obtained as a white solid in 43% (105 mg) yield. ¹H NMR (400 MHz, CDCl₃) δ 7.79 (d, 2H, J=8.8 Hz), 7.55–7.63 (m, 6H), 7.41–7.47 (m, 4H), 7.35 (tt, 1H, J=8.6 Hz, J=1.2 Hz), 6.37 (br t, 1H), 4.69 (d, 2H, J=5.5 Hz), 3.78 (br s, 2H), 1.69 (s, 6H), 1.59 (s, 3H), 1.48 (br s, 9H).

(S)-N-(4-(N'-(4-Phenylbenzyl)formamido)phenyl)-2-amino-3-hydroxy-2-methylpropanamide

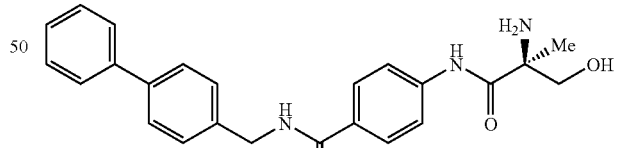

The product was obtained as a white solid in 61% (35 mg) yield. MS (ESI, M+H⁺)=404.3; ¹H NMR (400 MHz, DMSO-d₆) δ 8.98 (br 1, 1H, J=5.8 Hz), 7.87 (d, 2H, J=8.6 Hz), 7.77 (d, 2H, J=8.6 Hz), 7.60–7.66 (m, 4H), 7.32–7.48 (m, 5H), 7.10 (br d, 1H), 5.02 (br t, 1H), 4.50 (d, 2H, J=5.8 Hz), 3.75 (dd, 1H, J=10.5 Hz, J=5.5 Hz), 3.22 (dd, 1H, J=10.5 Hz, J=5.1 Hz), 1.17 (s, 3H).

(S)-2-(4-(N'-(4-Phenylbenzyl)formamido)phenylcarbamoyl)-2-aminopropyl dihydrogen phosphate

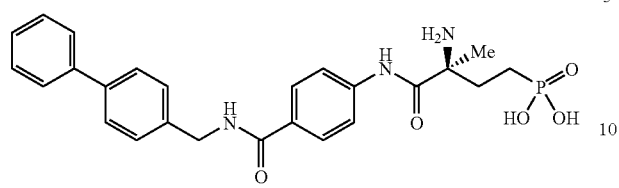

The product was obtained as a white solid in 30% (7.0 mg) yield over two steps. MS (ESI, M+H⁺)=484.7.

Biphenyl Ethanol Linker:

A number of substituted biphenyl ethanols were synthesized using a Suzuki cross-coupling protocol a described in Scheme 16.

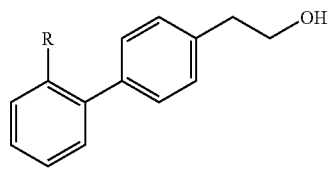

Reaction of the substituted biphenyl ethanol with substituted 4-fluoro-nitrobenzene under Williamson ether synthesis (scheme 17) conditions followed by hydrogenation and coupling with amino acid provided the Boc protected amino-alcohol which was further phosphorylated or deprotected to obtain the desired final product.

Scheme 17.

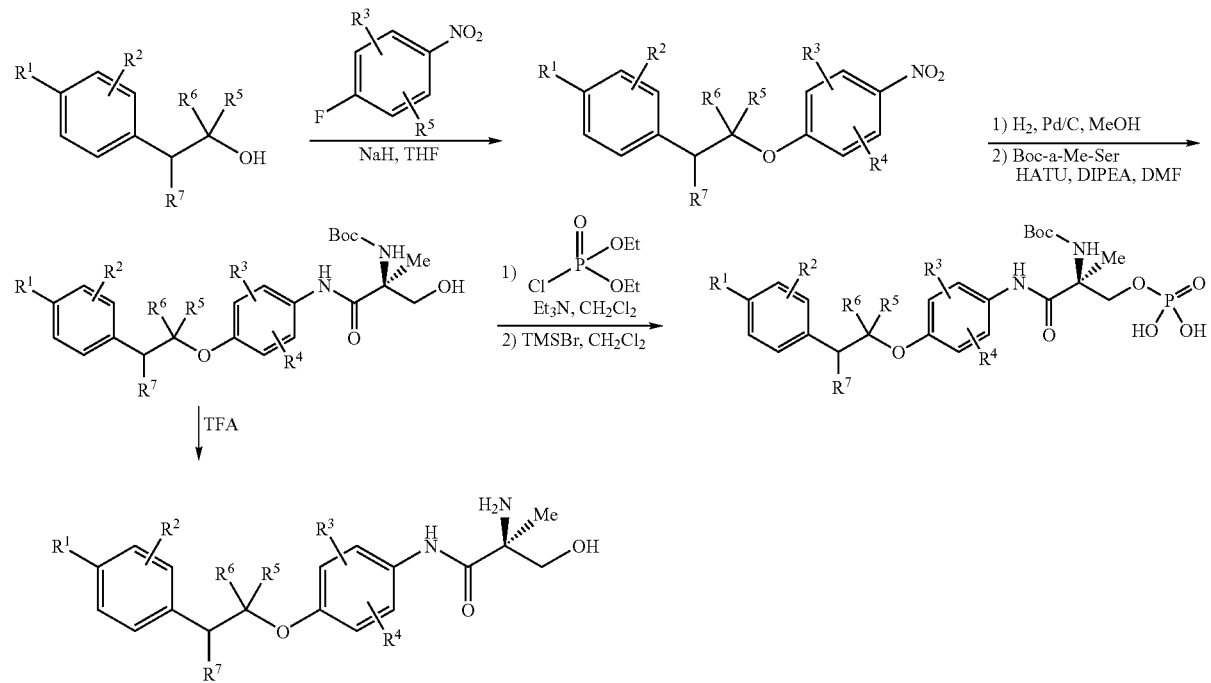

Scheme 16.

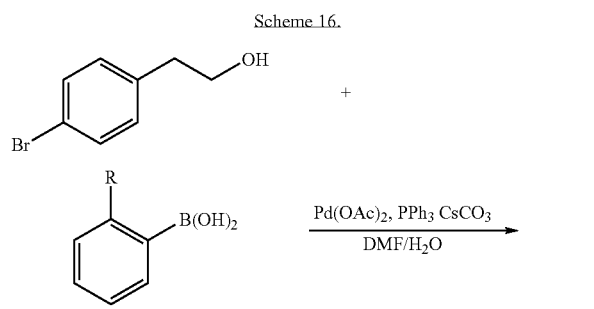

General Procedure for Synthesis of Substituted Biaryl Ethanol:

To a DMF solution of the 4-(haloaryloxy)-aniline (1.0 equiv) and substituted aryl boronic acid in a microwave tube, was added Pd(OAc)₂ (0.1 equiv), triphenyl phosphine (0.2 equiv), cesium carbonate (1.0–1.5 equiv) and TBAC (0.1 equiv). The reaction was then sealed and heated at 50–70° C. for 3–18 hours using an oil bath. The reaction mixture was diluted with EtOAc (25 mL), washed with water (2×10 mL) and then brine (1×10 mL). The organic layer was then dried over MgSO₄, and then solvent removed under reduced pressure. The crude product was purified using the Combi-Flash silica gel column chromatography, using a Hexane/EtOAc gradient.

151

2-(2'-Methyl-biphenyl-4-yl)-ethanol

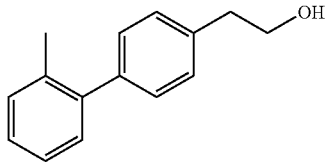

The final product was obtained as a white solid after column chromatography, in 85% yield. $^1$H NMR (400 MHz, CDCl$_3$) δ 7.28 (s, 4H), 7.26 (s, 4H), 3.93 (t, 2H, J=6.4 Hz), 2.93 (t, 2H, J=6.4 Hz), 2.28 (s, 3H).

2-(2'-Chloro-biphenyl-4-yl)-ethanol

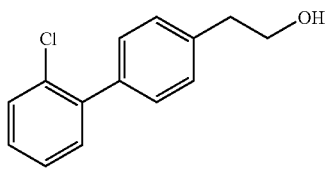

The final product was obtained as a white solid after column chromatography, in 85% yield. $^1$H NMR (400 MHz, CDCl$_3$) δ 7.45–7.48 (m, 1H), 7.405 (d, 2H, J=8.0 Hz), 7.28–7.33 (m, 4H), 3.93 (t, 2H, J=6.4 Hz), 2.94 (t, 2H, J=6.4 Hz).

2-(2-Cyano-biphenyl-4-yl)-ethanol

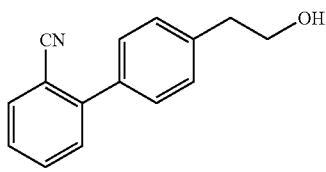

The final product was obtained as a white solid after column chromatography, in 97% yield. $^1$H NMR (400 MHz, CDCl$_3$) δ 7.76 (dd, 1H, J=8.0 and 1.2), 7.64 (m, 1H), 7.49–7.53 (m, 3H), 7.43 (m, 1H), 7.36 (d, 2H, J=8.0 Hz), 3.93 (t, 2H, J=6.8 Hz), 2.95 (t, 2H, J=6.4 Hz).

2-Methyl-4'[2-(4-nitro-phenoxy)-ethyl]-biphenyl

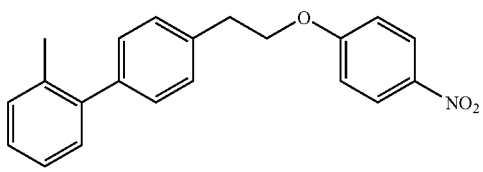

The final product was obtained as a yellow solid after column chromatography, in 88% yield. $^1$H NMR (400 MHz, CDCl$_3$) δ 8.20 (d, 2H, J=9.2 Hz), 7.2–7.316 (m, 8H), 6.97 (d, 2H, J=8.8 Hz), 4.32 (t, 2H, J=7.2 Hz), 3.19 (t, 2H, J=6.8 Hz), 2.27 (s, 3H).

152

2-Chloro-4'[2-(4-nitro-phenoxy)-ethyl]-biphenyl

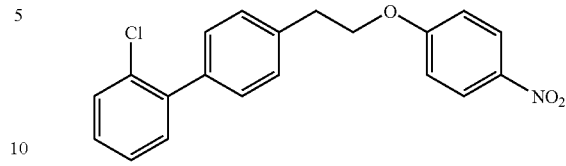

The final product was obtained as a yellow solid after column chromatography, in 88% yield. $^1$H NMR (400 MHz, CDCl$_3$) δ 8.20 (d, 2H, J=9.2 Hz), 7.41–7.48 (m, 3H), 7.27–7.36 (m, 4H), 7.24 (s, 1H), 6.97 (d, 2H, J=9.2 Hz), 4.32 (t, 2H, J=6.8 Hz), 3.20 (t, 2H, J=6.8 Hz).

4'-[2-(4-Nitro-phenoxy)-ethyl]-biphenyl-2-carbonitrile

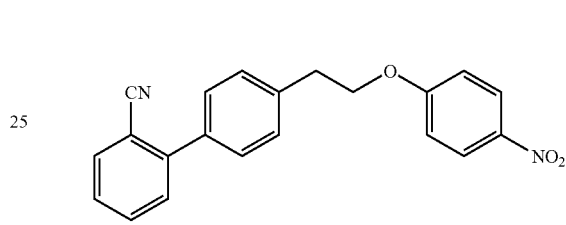

The final product was obtained as an off white solid after column chromatography, in 81% yield. $^1$H NMR (400 MHz, CDCl$_3$) δ 8.19 (d, 2H, J=9.2 Hz), 7.76 (dd, 1H, J=8.0 and 1.2), 7.66–7.62 (m, 1H), 7.54–7.49 (m, 3H), 7.40–7.46 (m, 3H), 6.96 (d, 2H, J=9.2 Hz), 4.31 (t, 2H, J=6.8 Hz), 3.21 (t, 2H, J=6.8 Hz).

4-[2-(2-Chloro-4-nitro-phenoxy)-ethyl]biphenyl

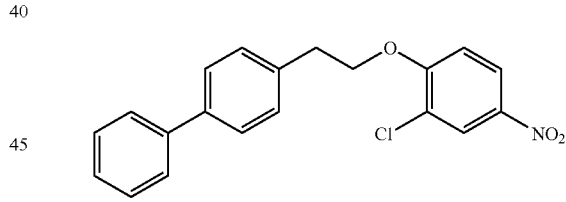

The final product was obtained as a yellow solid after column chromatography, in 50% yield. $^1$H NMR (400 MHz, CDCl$_3$) δ 8.29 (d, 1H, J=3.0 Hz), 8.13 (dd, 1H, J=2.8 and 9.2 Hz), 7.57–7.60 (m, 4H), 7.40–7.46 (m, 4H), 7.35 (m, 1H), 6.95 (d, 2H, J=9.2 Hz), 4.35 (t, 2H, J=6.4 Hz), 3.25 (t, 2H, J=6.8 Hz).

4-[2-(2-Methyl-4-nitro-phenoxy)-ethyl]biphenyl

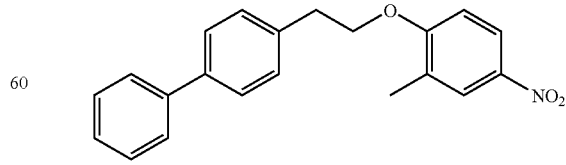

The final product was obtained as a yellow solid after column chromatography, in 78% yield. $^1$H NMR (400 MHz, CDCl$_3$) δ 8.03–8.09 (m, 2H), 7.55–7.59 (m, 4H), 7.44 (t, 2H, J=8.0), 7.37 (d, 2H, J=8.4 Hz), 6.84 (d, 2H, J=9.2 Hz), 4.30 (t, 2H, J=6.4 Hz), 3.20 (t, 2H, J=6.8 Hz), 2.27 (s, 3H).

4-(2-Biphenyl-4-ylethoxy)-3-chloro-phenylamine

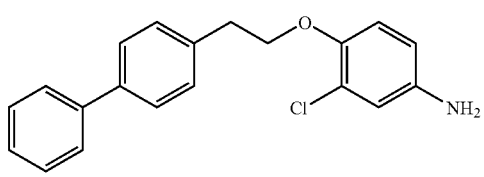

The final product was obtained as a brown oil after column chromatography, in 79% yield. $^1$H NMR (400 MHz, CDCl$_3$) δ 7.54–7.60 (m, 5H), 7.46–7.38 (m, 4H), 6.75 (m, 2H), 6.52 (dd, 1H, J=2.8 and 8.8), 4.17 (t, 2H, J=7.6 Hz), 3.15 (t, 2H, J=7.2 Hz).

4-(2-Biphenyl-4-ylethoxy)-3-methyl-phenylamine

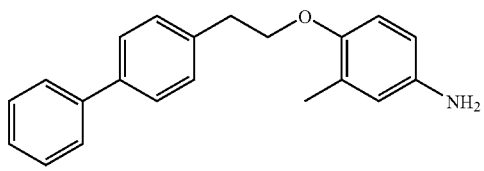

The final product was obtained as an off white solid after column chromatography, in 84%-yield. $^1$H NMR (400 MHz, CDCl$_3$) δ 7.51–7.58 (m, 4H), 7.39–7.43 (m, 2H), 7.34 (d, 3H, J=8.4 Hz), 6.64 (d, 1H, J=8.8 Hz), 6.50 (d, 1H, J=3.2 Hz), 6.50 (dd, 1H, J=2.8 and 8.4), 4.10 (t, 2H, J=7.2 Hz), 3.09 (t, 2H, J=7.2 Hz), 2.13 (s, 3H).

(2-Hydroxy-1-methyl-1-{4-[2-(2'-methyl-biphenyl-4-yl)-ethoxy]-phenyl carbamoyl}-ethyl)-carbamic acid tert-butyl ester

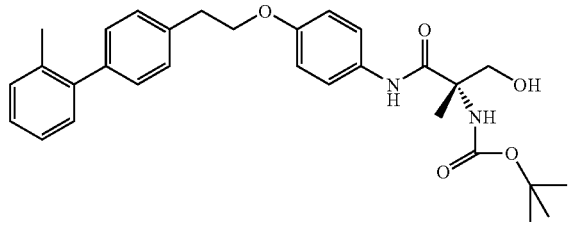

The final product was obtained as an off white solid after column chromatography, in 73% yield. $^1$H NMR (400 MHz, CDCl$_3$) δ 7.41 (dd, 2H, J=6.4 and 9.4 Hz), 7.31–7.33 (m, 2H), 7.28 (s, 2H), 7.22–7.26 (m, 4H), 6.88 (d, 1H, J=8.8 Hz), 4.2 (t, 2H, J=7.2 Hz), 3.78 (d, 1H, J=12.0 Hz), 3.56 (d, 1H, J=10.8 Hz), 3.13 (t, 2H, J=7.2 Hz), 2.28 (s, 3H), 1.58 (s, 3H), 1.46 (s, 9H).

(1-{4-[2-(2'-Chloro-biphenyl-4-yl)-ethoxy]-phenyl carbamoyl}-2-hydroxy-1-methyl-ethyl)-carbamic acid tert-butyl ester

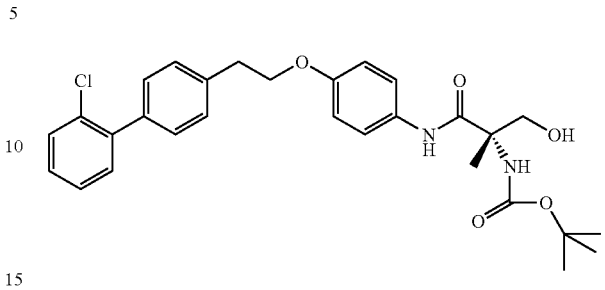

The final product was obtained as an off white oil after column chromatography, in 83% yield. $^1$H NMR (400 MHz, CDCl$_3$) δ 7.55 (m, 1H), 7.46 (dd, 1H, J=7.2 and 8.8 Hz), 7.37–7.43 (m, 3H), 7.27–7.35 (m, 4H), 7.26 (s, 1H), 6.88 (d, 2H, J=9.2 Hz), 4.21 (t, 2H, J=7.2 Hz), 4.08 (br.s, 1H), 3.557 (d, 1H, J=10.8 Hz), 3.14 (t, 2H, J=7.2 Hz), 1.58 (s, 3H), 1.46 (s, 9H).

{1-[4-(2-Biphenyl-4-yl-ethoxy)-3-chloro-phenylcarbamoyl]-2-hydroxy-1-methyl-ethyl}-carbamic acid tert-butyl ester

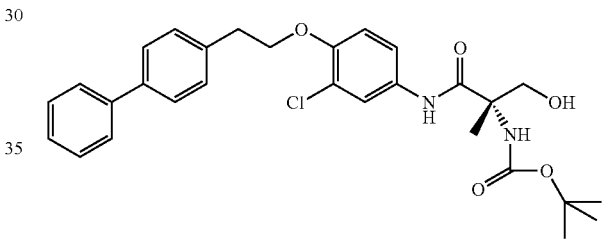

The final product was obtained as an off white solid after column chromatography, in 85% yield. $^1$H NMR (400 MHz, CDCl$_3$) δ 7.63 (s, 1H), 7.53–7.59 (m, 4H), 7.38–7.44 (m, 4H), 7.30–7.35 (m, 2H), 6.84 (d, 1H, J=8.8 Hz), 4.21 (t, 2H, J=7.2 Hz), 4.06 (br.s, 1H), 3.6 (s, 1H), 3.17 (t, 2H, J=7.2 Hz), 1.56 (s, 3H), 1.44 (s, 9H).

{1-[4-(2-Biphenyl-4-yl-ethoxy)-3-methyl-phenylcarbamoyl]-2-hydroxy-1-methyl-ethyl}-carbamic acid tert-butyl ester

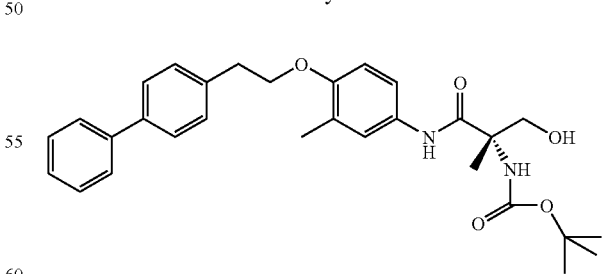

The final product was obtained as an off white solid after column chromatography, in 81% yield. $^1$H NMR (400 MHz, CDCl$_3$) δ 7.53–7.59 (m, 4H), 7.43 (t, 2H, J=7.6 Hz), 7.36 (d, 3H, J=8.4 Hz), 7.26 (br. s, 2H), 6.76 (d, 1H, J=8.4 Hz), 4.18 (t, 2H, J=6.4 Hz), 3.56 (br.s, 1H), 3.31 (s, 1H), 3.14 (t, 2H, J=6.8 Hz), 2.19 (s, 3H), 1.57 (s, 3H), 1.46 (s, 9H).

tert-Butyl (S)-2-(4-(4-phenylphenethyloxy)-3-(methylformyl)phenylcarbamoyl)-1-hydroxypropan-2-ylcarbamate

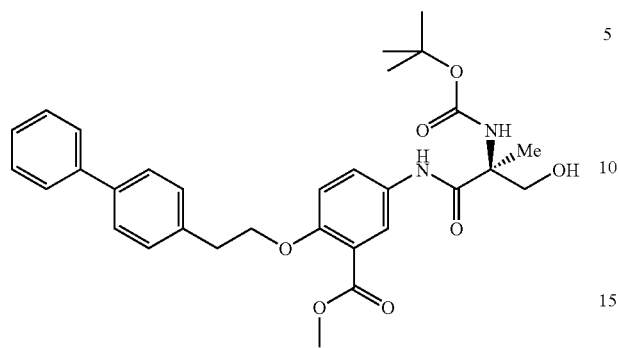

$^1$H NMR (400 MHz, CDCl$_3$) δ 7.87 (d, 1H, J=2.7 Hz), 7.65 (dd, 1H, J=8.8 Hz, J=2.7 Hz), 7.50–7.60 (m, 4H), 7.28–7.46 (m, 5H), 6.83 (d, 1H, J=8.8 Hz), 5.59 (br s, 1H), 4.53 (br t, 1H), 4.25 (t, 2H, J=6.8 Hz), 3.87 (s, 3H), 3.53–3.62 (m, 1H), 3.18 (t, 2H, J=6.8 Hz), 3.16–3.18 (m, 1H), 1.57 (s, 3H), 1.47 (s, 9H).

tert-Butyl (S)-2-(4-(4-phenylphenethyloxy)-3-(trifluoromethyl)phenylcarbamoyl)-1-hydroxypropan-2-ylcarbamate

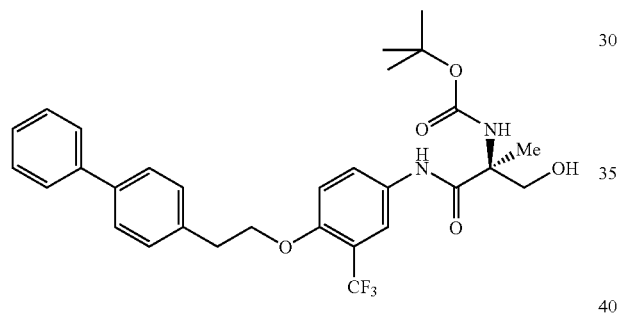

The product was obtained as a thick colorless oil in 45% (300 mg) yield over two steps from 2-biphenylethanol. $^1$H NMR (400 MHz, CDCl$_3$) δ 9.70 (br s, 1H), 7.70 (d, 1H, J=2.7 Hz), 7.64 (dd, 1H, J=8.8 Hz, J=2.7 Hz), 7.52–7.60 (m, 4H), 7.30–7.46 (m, 5H), 6.94 (d, 1H, J=8.8 Hz), 5.60 (br s, 1H), 4.25 (t, 2H, J=6.8 Hz), 4.04–4.14 (m, 1H), 3.50–3.60 (m, 1H), 3.17 (t, 2H, J=6.8 Hz), 1.57 (s, 3H), 1.47 (s, 9H).

tert-Butyl (S)-2-(4-(4-phenylphenethyloxy)-3-bromophenylcarbamoyl)-1-hydroxypropan-2-ylcarbamate

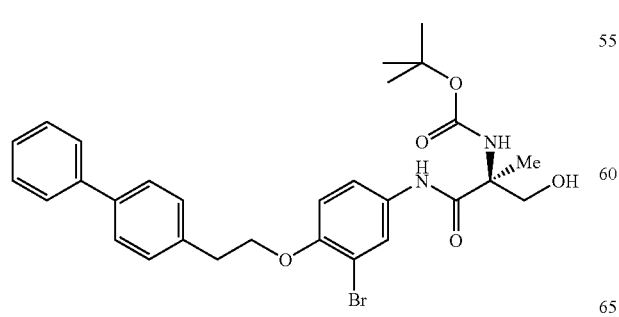

The product was obtained as a thick colorless oil in 40% (385 mg) yield over two steps from 2-biphenylethanol. $^1$H NMR (400 MHz, CDCl$_3$) δ 9.60 (br s, 1H), 7.7 8 (d, 1H, J=2.3 Hz), 7.53–7.62 (m, 5H), 7.30–7.46 (m, 5H), 6.83 (d, 1H, J=8.8 Hz), 5.60 (br s, 1H), 4.22 (t, 2H, J=6.8 Hz), 4.06–4.12 (m, 1H), 3.58 (br d, 1H), 3.20 (t, 2H, J=6.8 Hz), 1.58 (s, 3H), 1.46 (s, 9H).

2-Amino-3-hydroxy-2-methyl-N-{4-[2-(2'-methyl-biphenyl-4-yl)-ethoxy]-phenyl}-propionamide

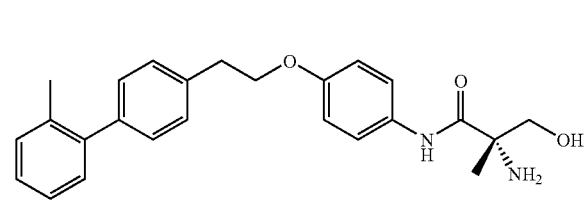

The compound was obtained as a white solid after HPLC purification. Yield: 93%, (92 mg). MS (ESI, M+H$^+$)=404.4

2-Amino-N-{4-[2-(2'-Chloro-biphenyl-4-yl)-ethoxy]-phenyl}-3-hydroxy-2-methylpropionamide

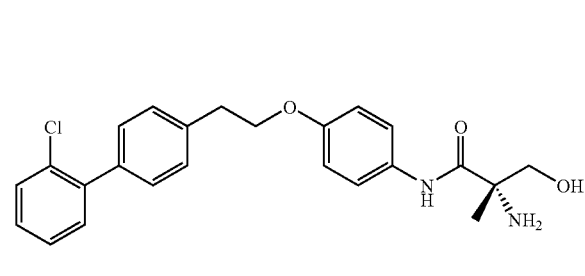

The compound was obtained as a white solid after HPLC purification. Yield: 84%, (68 mg). MS (ESI, M+H$^+$)=425.7

(1-{4-[2-(2'-Cyano-biphenyl-4-yl)-ethoxy]-phenylcarbamoyl}-2-hydroxy-1-methyl-ethyl)-carbamic acid tert-butyl ester

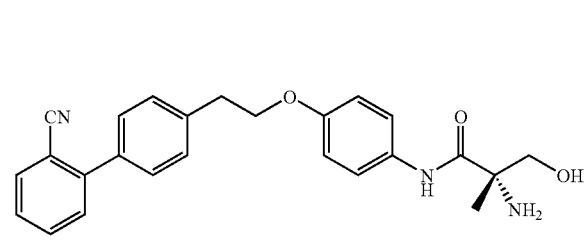

The final product was obtained as an off white oil after column chromatography, in 80% yield. MS (ESI, M+H$^+$)=416.6, $^1$H NMR (400 MHz, CDCl$_3$) δ 7.55–7.63 (m, 3H), 7.53 (br. s, 2H), 7.48–7.51 (m, 4H), 6.97 (d, 2H, J=9.2 Hz), 5.77 (t, 1H, J=5.2 Hz), 4.24 (t, 2H, J=6.8 Hz), 3.96 (dd, 1H, J=12.0 and 5.2 Hz), 3.628 (dd, 1H, J=11.6 and 4.8 Hz), 3.12 (t, 2H, J=6.8 Hz), 1.47 (s, 3H).

(S)-N-(4-(4-Phenylphenethyloxy)-3-(trifluoromethyl)phenyl)-2-amino-3-hydroxy-2-methylpropanamide

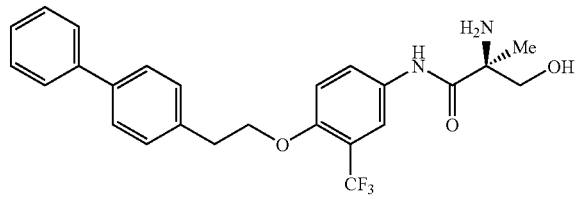

The product was obtained as a white solid in 70% (66 mg) yield. MS (ESI, M+H$^+$)=459.7; $^1$H NMR (400 MHz, DMSO-d$_6$) δ 10.01 (br s, 1H), 8.180 (br s, 2H), 7.89 (d, 1H, J=2.4 Hz), 7.82 (dd, 1H, J=8.8 Hz, J=2.4 Hz), 7.58–7.67 (m, 4H), 7.30–7.49 (m, 6H), 5.80 (br s, 1H), 4.32 (t, 2H, J=6.7 Hz), 3.95 (br d, 1H), 3.62 (br d, 1H), 3.09 (t, 2H, J=6.7 Hz), 1.48 (s, 3H).

(S)-N-(4-(4-phenylphenethyloxy)-3-bromophenyl)-2-amino-3-hydroxy-2-methylpropanamide

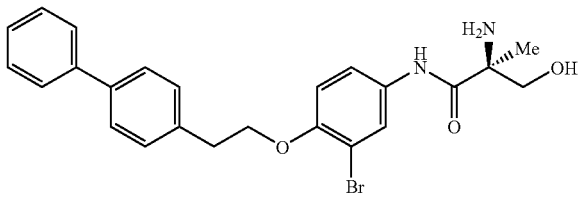

The product was obtained as a white solid in 60% (50 mg) yield. MS (ESI, M+H$^+$)=469.4 and 471.4.

(S)-N-(4-(4-(4-Ethylphenyl)phenethyloxy)phenyl)-2-amino-3-hydroxy-2-methylpropanamide

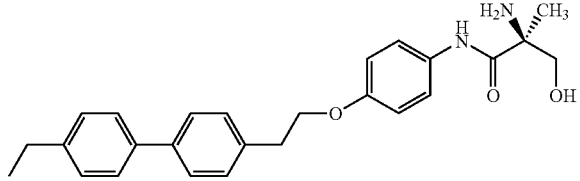

MS (ESI, M+H$^+$)=419; $^1$H NMR (400 MHz, DMSO-d$_6$) δ 9.74 (bs, 1H), 8.1 (bs, 1H), 7.55 (m, 4H), 7.47 (d, 2H), 7.37 (d, 2H), 7.26 (d, 2H), 6.93 (d, 2H), 5.74 (bs, 1H), 4.16 (t, 2H), 3.95 (bd, 1H), 3.6 (bd, 1H), 3.04 (t, 2H), 2.6 (q, 2H), 1.73 (m, 4H), 1.45 (s, 3H), 1.19 (t, 3H).

(S)-N-(4-(4-(4-Trifluoromethylphenyl)phenethyloxy)phenyl)-2-amino-3-hydroxy-2-methylpropanamide

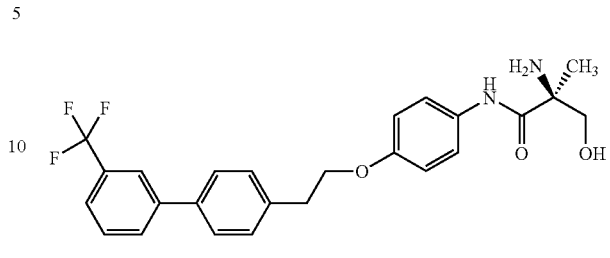

MS (ESI, M+H$^+$)=459; $^1$H NMR (400 MHz, DMSO-d$_6$) δ 9.74 (br s, 1H), 8.1 (br s, 2H), 7.95 (m, 2H), 7.68 (m, 3H), 7.47 (m, 3H), 6.93 (m, 2H), 5.74 (br s, 1H), 4.19 (t, 2H), 3.95 (m, 1H), 3.6 (m, 1H), 3.04 (t, 2H), 2.6 (q, 2H), 1.45 (s, 3H).

(S)-N-(4-(4-(4-ethoxyphenyl)phenethyloxy)phenyl)-2-amino-3-hydroxy-2-methylpropanamide

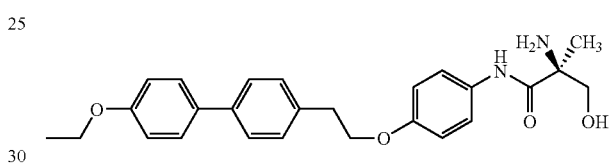

MS (ESI, M+H$^+$)=435; $^1$H NMR (400 MHz, DMSO-d$_6$) δ 9.73 (bs, 1H), 8.10 (bs, 2H), 7.57 (m, 2H), 7.46 (m, 2H), 7.32 (t, 1H), 7.22 (m, 1H), 6.94 (m, 2H), 5.75 (t, 1H), 4.19 (t, 2H), 4.04 (q, 2H), 3.93 (m, 1H), 3.61 (m, 1H), 3.07 (t, 2H), 1.45 (s, 3H), 1.32 (t, 3H).

(S)-N-(4-(4-(4-Chlorophenyl)phenethyloxy)phenyl)-2-amino-3-hydroxy-2-methylpropanamide trifluoroacetic acid salt

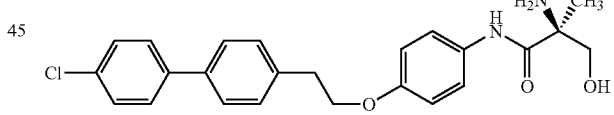

MS (ESI, M+H$^+$)=424; $^1$H NMR (400 MHz, DMSO-d$_6$) δ 9.73 (s, 1H), 8.10 (bs, 2H), 7.69 (m, 2H), 7.61 (s, 1H), 7.49 (m, 3H), 7.37 (t, 1H), 7.33 (m, 1H), 6.94 (d, 2H), 5.75 (t, 1H), 4.20 (t, 2H), 4.04 (q, 2H), 3.93 (m, 1H), 3.61 (m, 1H), 3.08 (t, 2H), 1.45 (s, 3H).

(S)-N-(4-(4-(4-Isopropylphenyl)phenethyloxy)phenyl)-2-amino-3-hydroxy-2-methylpropanamide

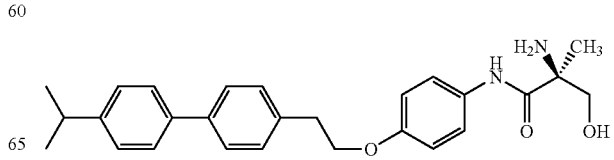

MS (ESI, M+H⁺)=433; ¹H NMR (400 MHz, DMSO-d₆) δ 9.73 (s, 1H), 8.11 (br s, 2H), 7.59 (d, 1H), 7.41–7.34 (m, 3H), 7.2 (d, 1H), 6.9 (d, 2H), 5.65 (br s, 1H), 4.18 (t, 2H), 3.93 (d, 1H), 3.61 (d, 1H), 3.04 (t, 2H), 2.95 (q, 1H), 1.45 (s, 3H), 1.24 (d, 6H).

(S)-N-(4-(2-(4-Phenyl-3-fluorophenyl)propoxy)phenyl)-2-amino-3-hydroxy-2-methylpropanamide

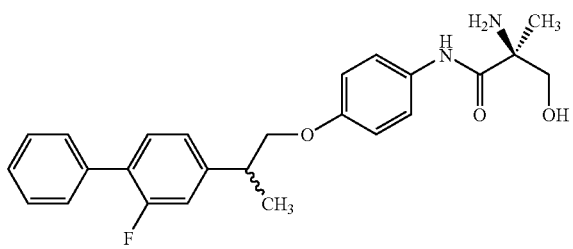

MS (ESI, M+H⁺)=423; ¹H NMR (400 MHz, DMSO-d₆) δ 9.74 (br s, 1H), 8.1 (br s, 1H), 7.5 (m, 6H), 7.40 (m, 2H), 7.28 (m, 2H), 6.93 (d, 2H), 5.74 (br s, 1H), 4.1–4.0 (m, 2H), 3.9 (m, 1H), 3.65 (m, 1H), 3.28 (m, 2H), 1.47 (s, 3H), 1.33 (d, 3H).

(S)-N-(4-(4-(Thiophen-2-yl)phenethyloxy)phenyl)-2-amino-3-hydroxy-2-methylpropanamide

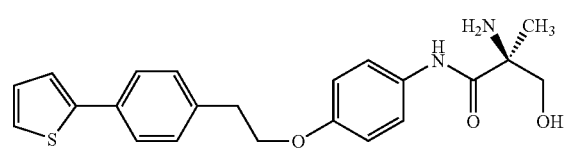

MS (ESI, M+H⁺)=397; ¹H NMR (400 MHz, DMSO-d₆) δ 9.74 (br s, 1H), 8.1 (br s, 2H), 7.60 (d, 2H), 7.50 (m, 4H), 7.36 (d, 2H), 7.12 (m, 1H), 6.95 (d, 2H), 5.74 (br s, 1H), 4.18 (t, 2H), 3.95 (br d, 1H), 3.6 (br d, 1H), 3.04 (t, 2H), 1.45 (s, 3H).

(S)-N-(4-(4-(3,5-Dimethylisoxazol-4-yl)phenethyloxy)phenyl)-2-amino-3-hydroxy-2-methylpropanamide

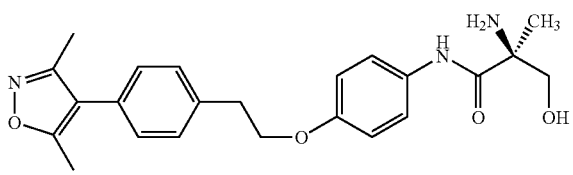

MS (ESI, M+H⁺)=410; ¹H NMR (400 MHz, DMSO-d₆) δ 9.75 (br s, 1H), 8.13 (br s, 2H), 7.50 (d, 2H), 7.41 (d, 2H), 7.3 (d, 2H), 6.9 (d, 2H), 4.22 (t, 2H), 3.94 (d, 1H), 3.6 (d, 1H), 3.07 (t, 2H), 2.4 (s, 3H), 2.2 (s, 2H), 1.48 (s, 3H).

(S)-N-(4-(4-(Furan-3-yl)phenethyloxy)phenyl)-2-amino-3-hydroxy-2-methylpropanamide

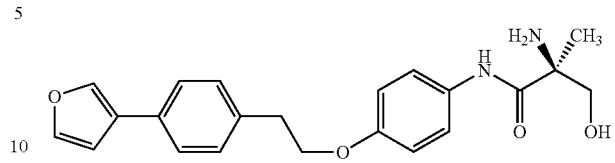

MS (ESI, M+H⁺)=424; ¹H NMR (400 MHz, DMSO-d₆) δ 9.73 (s, 1H), 8.10 (br s, 2H), 7.69 (m, 2H), 7.61 (s, 1H), 7.49 (m, 3H), 7.37 (t, 1H), 7.33 (m, 1H), 6.94 (d, 2H), 5.75 (t, 1H), 4.20 (t, 2H), 4.04 (q, 2H), 3.93 (m, 1H), 3.61 (m, 1H), 3.08 (t, 2H), 1.45 (s, 3H).

(S)-N-(4-(4-(3-Phenyl)phenethyloxy)phenyl)-2-amino-3-hydroxy-2-methylpropanamide

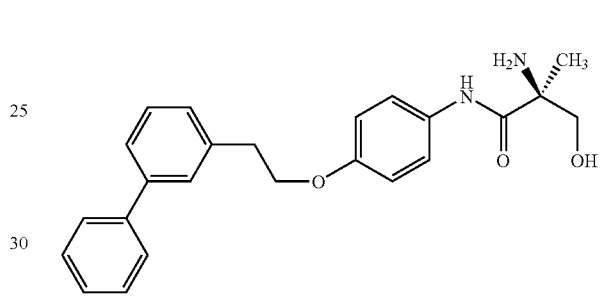

MS (ESI, M+H⁺)=391; ¹H NMR (400 MHz, DMSO-d₆) δ 9.73 (s, 1H), 8.10 (br s, 2H), 7.66 (d, 2H), 7.61 (s, 1H), 7.55–7.30 (m, 4H), 6.94 (d, 2H), 5.75 (bs, 1H), 4.25 (t, 2H), 3.93 (d, 1H), 3.65 (d, 1H), 3.08 (t, 2H), 1.45 (s, 3H).

(S)-N-(4-(4-(Pyridin-4-yl)phenethyloxy)phenyl)-2-amino-3-hydroxy-2-methylpropanamide

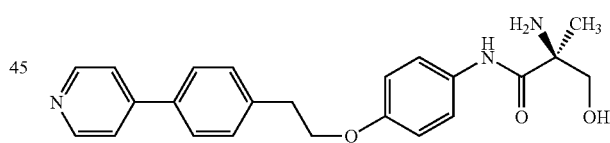

MS (ESI, M+H⁺)=392; ¹H NMR (400 MHz, DMSO-d₆) δ 9.74 (br s, 1H), 8.67 (br s), 8.19 (br s, 2H), 8.12 (br s, 2H), 7.8 (m, 2H), 7.5 (m, 4H), 6.9 (m, 2H), 6.95 (d, 2H), 5.74 (br s, 1H), 4.2 (t, 2H), 3.95 (br d, 1H), 3.04 (t, 2H), 1.45 (s, 3H).

(S)-N-(4-(4-(Pyridin-3-yl)phenethyloxy)phenyl)-2-amino-3-hydroxy-2-methylpropanamide

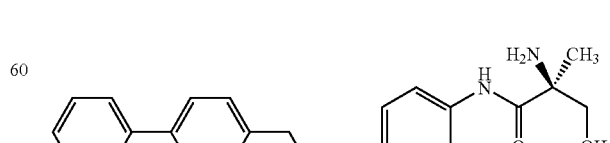

MS (ESI, M+H⁺)=392; ¹H NMR (400 MHz, DMSO-d₆) δ 9.69 (s, 1H), 9.0 (s, 1H), 8.65 (m, 1H), 8.3 (d, 2H), 8.07

(br s, 2H), 7.75 (m, 2H), 7.50 (m, 4H), 6.95 (d, 2H), 4.2 (t, 2H), 3.95 (d, 1H), 3.6 (d, 2H), 3.1 (t, 2H), 1.45 (s, 3H).

(S)-Phosphoric acid mono-(2-amino-2-{4-[2-(2'-methyl-biphenyl-4-yl)-ethoxy]-phenylcarbamoyl}-propyl)ester

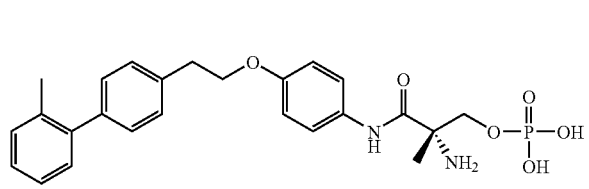

The compound was obtained as a white solid after HPLC purification. Yield: 65%, (41 mg). MS (ESI, M+H$^+$)=485.5

(S)-Phosphoric acid mono-(2-amino-2-{4-[2-(2'-chloro-biphenyl-4-yl)-ethoxy]-phenylcarbamoyl}-propyl)ester

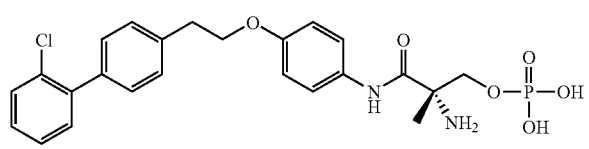

The compound was obtained as a white solid after HPLC purification. Yield: 79%, (25 mg). MS (ESI, M+H$^+$)=505.2

(S)-Phosphoric acid mono-(2-amino-2-{4-[2-(2'-cyano-biphenyl-4-yl)-ethoxy]-phenylcarbamoyl}-propyl)ester

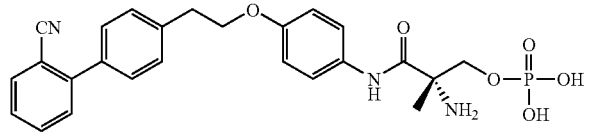

The compound was obtained as a white solid after HPLC purification. Yield: 22%, (4 mg). MS (ESI, M+H$^+$)=496.6

(S)-Phosphoric acid mono-(2-amino-2-[4-(2-biphenyl-4-yl-ethoxy)-3-chloro-phenylcarbamoyl]-propyl}ester

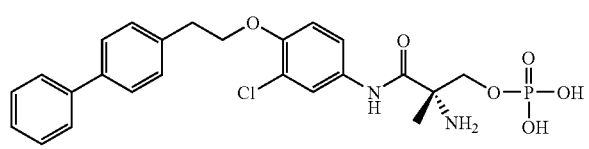

The compound was obtained as a white solid after HPLC purification. Yield: 30%, (70 mg). MS (ESI, M+H$^+$)=504.9

(S)-Phosphoric acid mono-(2-amino-2-[4-(2-biphenyl-4-yl-ethoxy)-3-methyl-phenylcarbamoyl]-propyl}ester

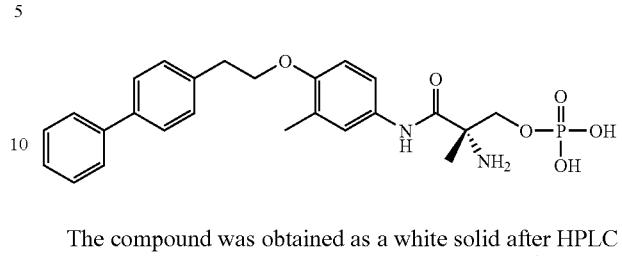

The compound was obtained as a white solid after HPLC purification. Yield: 10%, (28 mg). MS (ESI, M+H$^+$)=484.2

(S)-2-(4-(4-Phenylphenethyloxy)-3-(methylformyl)phenylcarbamoyl)-2-aminopropyl dihydrogen phosphate

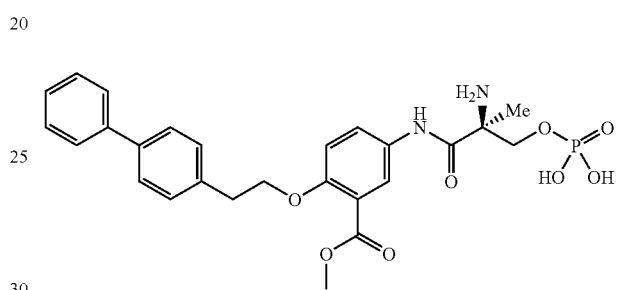

The product was obtained as a white solid in 72% (10.0 mg) yield over two steps. MS (ESI, M+H$^+$)=529.1.

(S)-2-(4-(4-Phenylphenethyloxy)-3-(formyl)phenylcarbamoyl)-2-aminopropyl dihydrogen phosphate

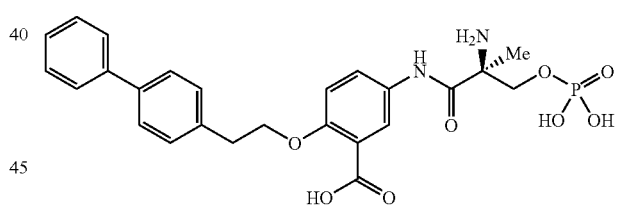

The product was obtained as a white solid in 90% (6.0 mg) yield over two steps. MS (ESI, M+H$^+$)=515.0

(S)-2-(4-(4-Phenylphenethyloxy)-3-(carbamoyl)phenylcarbamoyl)-2-aminopropyl dihydrogen phosphate

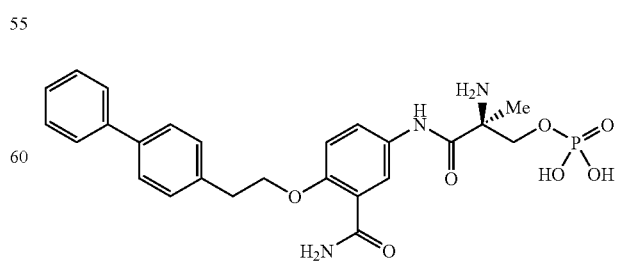

The product was obtained as a white solid in 20% (1.0 mg) yield over four steps. MS (ESI, M+H$^+$)=514.6

163

(S)-2-(4-(4-Phenylphenethyloxy)-3-(methylcarbamoyl)phenylcarbamoyl)-2-aminopropyl dihydrogen phosphate

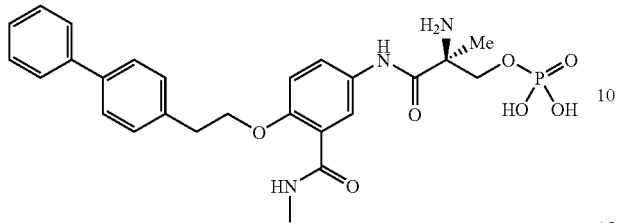

The product was obtained as a white solid in 25% (1.0 mg) yield over four steps. MS (ESI, M+H$^+$)=528.6

(S)-2-(4-(4-Phenylphenethyloxy)-3-(trifluoromethyl)phenylcarbamoyl)-2-aminopropyl dihydrogen phosphate

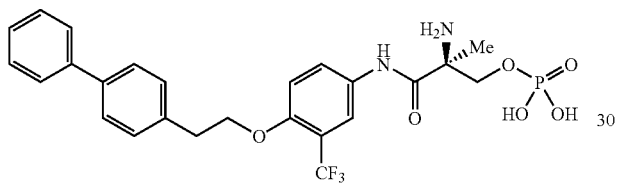

The product was obtained as a white solid in 70% (65.0 mg) yield over four steps. MS (ESI, M+H$^+$)=539.7

(S)-2-(4-(4-Phenylphenethyloxy)-3-bromophenylcarbamoyl)-2-aminopropyl dihydrogen phosphate

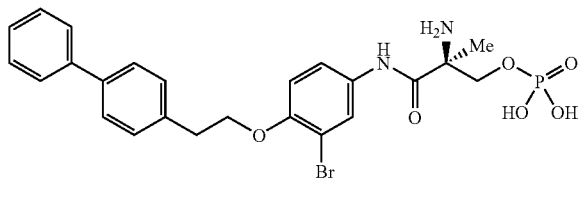

The product was obtained as a white solid in 69% (65.0 mg) yield over four steps. MS (ESI, M+H$^+$)=548.9 and 550.9

164

(S)-2-(4-(4-(4-Ethylphenyl)phenethyloxy)phenylcarbamoyl)-2-aminopropyl dihydrogen phosphate

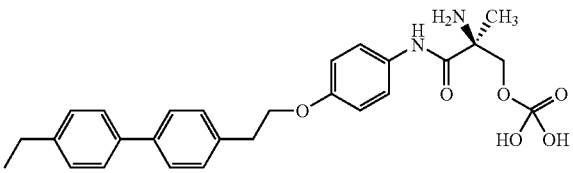

This compound was synthesized from tert-butyl (S)-2-(4-(4-(4-ethylphenyl)phenethyloxy)phenylcarbamoyl)-1-hydroxypropan-2-ylcarbamate (65 mg) to yield 21 mg solid product over two steps. MS (ESI, M+H$^+$)=499; $^1$H NMR (400 MHz, DMSO-d$_6$) δ 9.98 (br s, 1H), 7.54 (m, 6H), 7.37 (d, 2H), 7.26 (d, 2H), 6.92 (d, 2H), 4.21 (m, 1H), 4.17 (t, 2H), 4.1 (m, 1H), 3.75 (s, 3H), 3.04 (t, 2H), 2.58 (q, 2H), 1.45 (s, 3H), 1.17 (t, 3H).

(S)-2-(4-(4-(4-Trifluoromethylphenyl)phenethyloxy)phenylcarbamoyl)-2-aminopropyl dihydrogen phosphate

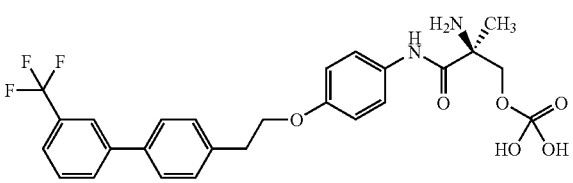

This compound was synthesized from tert-butyl (S)-2-(4-(4-(4-trifluoromethylphenyl)phenethyloxy)phenylcarbamoyl)-1-hydroxypropan-2-ylcarbamate (70 mg) to yield 27 mg solid product over two steps. MS (ESI, M+H$^+$)=539; $^1$H NMR (400 MHz, DMSO-d$_6$) δ 9.98 (br s, 1H), 7.95 (m, 2H), 7.69 (d, 4H), 7.5 (d, 2H), 7.4 (d, 2H), 6.9 (d, 2H), 4.21+4.19 (overlapping signals, 3H), 4.05 (m, 1H), 3.06 (t, 2H), 1.45 (s, 3H).

(S)-2-(4-(4-(4-Ethoxyphenyl)phenethyloxy)phenylcarbamoyl)-2-aminopropyl dihydrogen phosphate

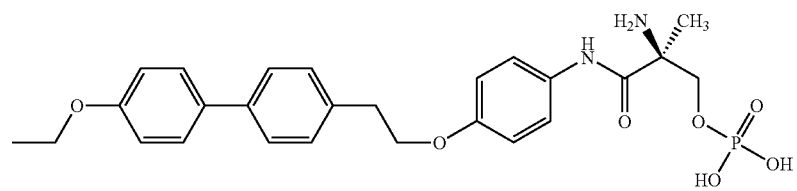

MS (ESI, M+H⁺)=515; ¹H NMR (400 MHz, DMSO-d₆) δ 9.95 (br s, 1H), 7.57 (m, 2H), 7.50 (m, 2H), 7.30 (m, 2H), 6.97 (d, 1H), 6.91 (t, 2H), 4.2–4.0 (m, 2H), 4.10 (t, 2H), 3.1 (m, 2H), 3.0 (m, 2H), 1.45 (s, 3H), 1.32 (t, 3H).

(S)-2-(4-(4-(4-Chlorophenyl)phenethyloxy)phenyl-carbamoyl)-2-aminopropyl dihydrogen phosphate

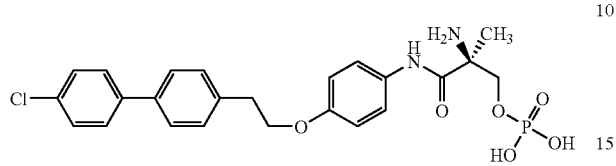

MS (ESI, M+H⁺)=505.7; ¹H NMR (400 MHz, DMSO-d₆) δ 9.95 (s, 1H), 7.69 (m, 2H), 7.61 (s, 1H), 7.49 (m, 3H), 7.37 (t, 1H), 7.33 (m, 1H), 6.94 (d, 2H), 4.3–4.0 (m overlapping signals, 4H), 3.08 (t, 2H), 3.00 (m, 2H), 1.45 (s, 3H).

(S)-2-(4-(2-(4-Phenyl-3-fluorophenyl)propoxy)phenylcarbamoyl)-2-aminopropyl dihydrogen phosphate

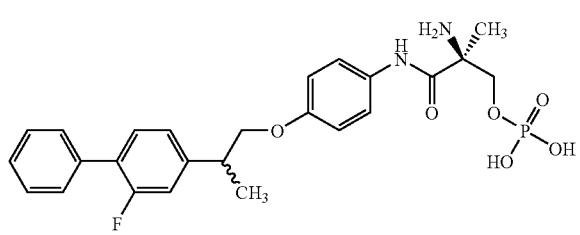

This compound was synthesized from tert-butyl (S)-2-(4-(2-(4-phenyl-3-fluorophenyl)propoxy)phenylcarbamoyl)-1-hydroxypropan-2-ylcarbamate (135 mg) to yield 72 mg solid product over two steps. MS (ESI, M+H⁺)=503; ¹H NMR (400 MHz, DMSO-d₆) δ 9.98 (br s, 1H), 8.6 (br s, 2H), 7.54–7.26 (m, 10H), 6.92 (d, 2H), 4.28 (t, 1H), 4.1–3.9 (m, 3H), 4.1 (m, 1H), 3.28 (m, 2H), 1.49 (s, 3H), 1.35 (d, 3H).

(S)-2-(4-(4-(Thiophen-3-yl)phenethyloxy)phenylcarbamoyl)-2-aminopropyl dihydrogen phosphate

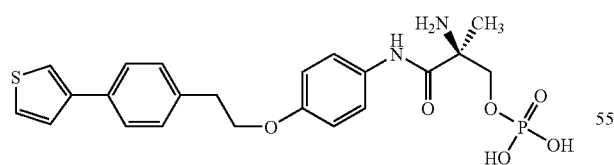

The starting material, 2-(4-(thiophen-3-yl)phenyl)ethanol, was synthesized as follows: In a sealed vessel was combined 2-(4-bromophenyl)ethanol (70 μL), 4,4,5,5-tetramethyl-2-(thiophen-3-yl)-1,3,2-dioxaborolane (126 mg), K₂CO₃ (207 mg), catalytic Pd(PPh₃)₄, 4.5 mL THF, and 0.5 mL H₂O. The vessel was heated in an oil bath at 60° C. overnight. The reaction mixture was diluted with water and DCM. The organic layer was concentrated to yield 2-(4-(thiophen-3-yl)phenyl)ethanol (80 mg) as a solid white product. 80 mg tert-butyl (S)-2-(4-(4-(thiophen-3-yl)phenethyloxy)phenylcarbamoyl)-1-hydroxypropan-2-ylcarbamate was synthesized following the general procedure employing 2-(4-(thiophen-3-yl)phenyl)ethanol (200 mg), N-(Boc)-α-methylserine (175 mg), HATU (375 mg), and DIPEA (430 uL). MS (ESI, M+Na⁺)=519. 2.6 mg of the phosphate was then synthesized from the carbamate (40 mg) as a solid white solid. MS (ESI, M+H⁺)=477; ¹H NMR (400 MHz, DMSO-d₆), 9.96 (br s, 1H), 7.81 (m, 1H), 7.65 (m, 3H), 7.5 (m, 3H), 7.3 (m, 2H), 6.9 (m, 2H), 4.28 (m, 1H), 4.17 (m, 2H), 4.06 (m, 1H), 3.04 (t, 2H), 1.48 (s, 3H).

(S)-2-(4-(4-(Thiophen-2-yl)phenethyloxy)phenylcarbamoyl)-2-aminopropyl dihydrogen phosphate

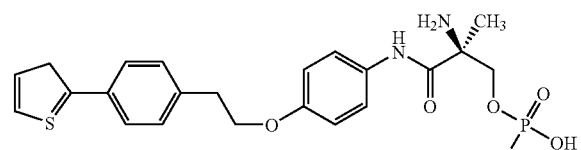

¹H NMR (400 MHz, DMSO-d₆) δ 9.98 (br s, 1H), 8.64 (br s, 3H), 7.84 (s, 1H), 7.65 (m, 3H), 7.52 (m, 3H), 7.36 (d, 2H), 6.9 (d, 2H), 4.21 (overlapping signals, 3H), 4.17 (m, 1H), 3.04 (t, 2H), 2.58 (q, 2H), 1.45 (s, 3H).

(S)-2-(4-(3-Phenylphenethyloxy)phenylcarbamoyl)-2-aminopropyl dihydrogen phosphate

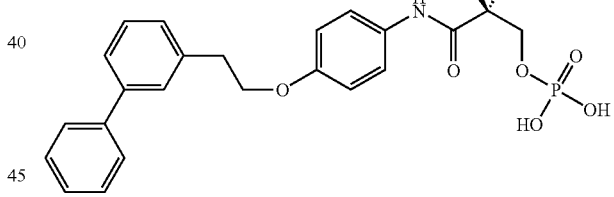

¹H NMR (400 MHz, DMSO-d₆) δ 9.9 (s, 1H), 7.66 (d, 2H), 7.61 (s, 1H), 7.55–7.30 (m, 4H), 6.94 (d, 2H), 4.25 (t, 2H), 4.2 (m, 1H), 4.05 (m, 1H), 3.08 (t, 2H), 1.45 (s, 3H).

(S)-2-(4-(4-(Pyridin-4-yl)phenethyloxy)phenylcarbamoyl)-2-aminopropyl dihydrogen phosphate

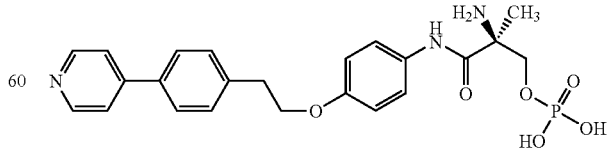

¹H NMR (400 MHz, D₂O+CD₃OD) δ 8.7 (m), 8.2 (m), 7.84 (d, 2H), 7.55 (d, 2H), 7.4 (d, 2H), 6.9 (d, 2H), 4.30 (t, 2H), 4.05 (m, 1H), 3.92 (m, 1H), 3.15 (t, 2H), 1.42 (s, 3H).

(S)-2-(4-(4-(Pyridin-3-yl)phenethyloxy)phenylcar-bamoyl)-2-aminopropyl dihydrogen phosphate

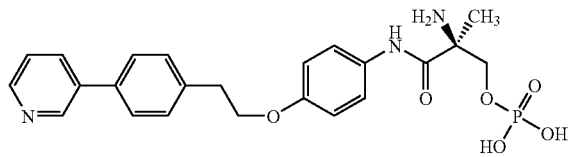

$^1$H NMR (400 MHz, DMSO-$d_6$) δ 9.95 (s, 1H), 8.95 (s, 1H), 8.65 (br s, 1H), 8.28 (d, 2H), 7.75 (m, 2H), 7.60 (m, 1H), 7.5 (t, 3H), 6.95 (d, 2H), 4.2 (m, 3H), 3.95 (m, 1H), 3.10 (m, 2H), 1.45 (s, 3H).

Example 10

Lymphopenia Assay

Several of the compounds described herein were evaluated for the ability to induce lymphopenia in mice. Male C57B1/6 mice were divided into groups of three. A control group received the 3% BSA vehicle only. The other groups received a single dose of either a specified dose of test compound in vehicle administered orally (PO). After 6 hours, the mice were anesthesized with isoflurane and approximately 250 μL of blood was removed from the retroorbital sinus and collected in an EDTA microtainer, mixed with an anticoagulant and placed on a tilt table until complete blood count (CBC) analysis. FIG. 1 shows the results of the analysis for total lymphocyte count for different doses of compounds 10, 13 and 14. The results show that all three compounds, when dosed orally, are able to induce lymphopenia in mice relative to control.

Example 11

Binding to S1P1 or S1P3 Receptors

The ability of several of the compounds described herein to bind to the S1P1 or S1P3 receptor was also tested as follows.

For the membrane preparation, plasmid DNA was transfected into HEK 293 T cells using the FuGENE 6 transfection protocol (publicly available by Roche). Briefly, subconfluent monolayers of HEK 293 T cells were transfected with the DNA mixture containing FuGENE 6 (using a 1:3 ratio). The dishes containing the cells were then placed in a tissue culture incubator (5% $CO_2$, 37° C.). The cells were harvested 48 hours after addition of the DNA by scraping in HME buffer (in mM: 20 HEPES, 5 $MgCl_2$, 1 EDTA, pH 7.4, 1 mM PMSF) containing 10% sucrose on ice, and disrupted using a Dounce homogenizer. After centrifugation at 800×g, the supernatant was diluted with HME without sucrose and centrifuged at 17,000×g for 1 hour. This crude membrane pellet was resuspended in HME with sucrose, aliquoted, and snap-frozen by immersion in liquid nitrogen. The membranes were stored at −70 C. Protein concentration was determined spectroscopically by Bradford protein assay.

For the binding assay, [$^{33}$P]sphingosine 1-phosphate (obtained from American Radiolabeled Chemicals, Inc) was added to membranes in 200 μl in 96-well plates with assay concentrations of 2.5 pM [$^{33}$P]sphingosine 1-phosphate, 4 mg/ml BSA, 50 mM HEPES, pH 7.5, 100 mM NaCl, 5 mM $MgCl_2$, and 5 μg of protein. Binding was performed for 60 minutes at room temperature with gentle mixing and terminated by collecting the membranes onto GF/B filter plates. After drying the filter plates for 10 minutes, 50 μl of Microscint 40 was added to each well, and filter-bound radionuclide was measured on a Packard Top Count. Nonspecific binding was defined as the amount of radioactivity remaining in the presence of excess of unlabeled S1P. The results fo the foregoing binding assays are presented in Table 1 provided below.

TABLE 1

| IC50 Values for Binding to S1P1 or S1P3 Receptors | | |
|---|---|---|
| COMPOUND No. | S1P1 $IC_{50}$ (nM) | S1P3 $IC_{50}$ (nM) |
| 34 | 1000 | >10000 |
| 45 | 2.4 | 343 |
| 59 | 3.5 | 50 |
| 105 | 2000 | >10000 |
| 46 | 250 | 5000 |
| 49 | 240 | 8000 |
| 42 | 32 | 1000 |
| 47 | 23 | 5000 |
| 9 | 8.7 | 511 |
| 110 | 23 | 2150 |
| 124 | 15 | 164 |
| 122 | 105 | 1100 |
| 120 | 2.2 | 135 |
| 127 | 56 | 59 |
| 125 | 2000 | 10000 |
| 123 | 3000 | >10000 |
| 130 | 90 | >10000 |
| 128 | 0.84 | 160 |
| 133 | 650 | >10000 |
| 131 | 218 | 833 |
| 129 | 17.9 | 6333 |
| 136 | 0.65 | 50 |
| 126 | >10000 | >10000 |
| 134 | 114 | 1200 |
| 132 | 167 | 3500 |
| 139 | 2.5 | 220 |
| 137 | 4000 | >10000 |
| 135 | 22.1 | 2500 |
| 142 | 8 | 315 |
| 140 | 2200 | >10000 |
| 138 | 3800 | >10000 |
| 145 | 3.4 | 2000 |
| 141 | 12 | 1040 |
| 148 | >10000 | >10000 |
| 118 | 4500 | >10000 |
| 144 | 2400 | >10000 |
| 147 | 166 | 130 |
| 154 | 21 | >10000 |
| 152 | >10000 | >10000 |
| 150 | 0.55 | 5025 |
| 157 | 1.3 | 1000 |
| 155 | >10000 | >10000 |
| 153 | 0.8 | 285 |
| 158 | 150 | >1000 |
| 160 | 500 | >1000 |
| 156 | 6 | 3250 |
| 347 | 1000 | >10000 |
| 348 | 6.5 | 500 |
| 349 | 3.5 | 50 |

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A compound of Formula IV:

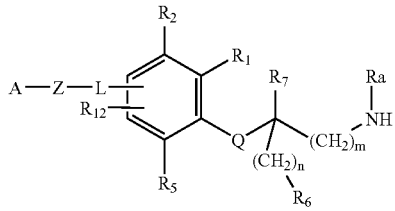

(IV)

wherein:
L is alkoxy, a covalent bond, substituted or unsubstituted alkyl, alkylcarbonyl, thioether, alkylsulfonyl, alkylcarbonylamino, alkylaminocarbonyl, alkyloxycarbonyl, alkylcarbonyloxy, or substituted or unsubstituted heteroaryl;

Z and A are each independently substituted or unsubstituted aryl, wherein Z and A may be linked by a covalent bond, substituted or unsubstituted alkyl, NH, alkyloxy, O, thioether, S, aminocarbonyl, carbonylamino, carbonyloxy, or oxycarbonyl;

$R^1$, $R^2$, $R^5$ and $R^{12}$ are each independently selected from the group consisting of hydrogen, halogen, cyano, substituted or unsubstituted aryl, straight chain or branched substituted or unsubstituted $C_1$–$C_6$-alkyl, straight chain or branched substituted or unsubstituted $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-$SO_2$ or N(R)R', wherein R and R' are each independently hydrogen, straight chain or branched substituted or unsubstituted $C_1$–$C_6$-alkyl, straight chain or branched substituted or unsubstituted $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl or $C_1$–$C_6$-alkyl-$SO_2$;

Q is —NH(CO)—;

$R^6$ is —$OPO_3R^{10}R^{11}$, where $R^{10}$ and $R^{11}$ are each independently H, straight chain or branched substituted or unsubstituted $C_1$–$C_6$-alkyl, a substituted or unsubstituted aryl group or selected from the prodrugs listed below:

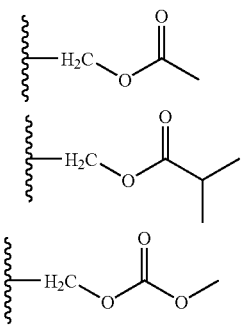

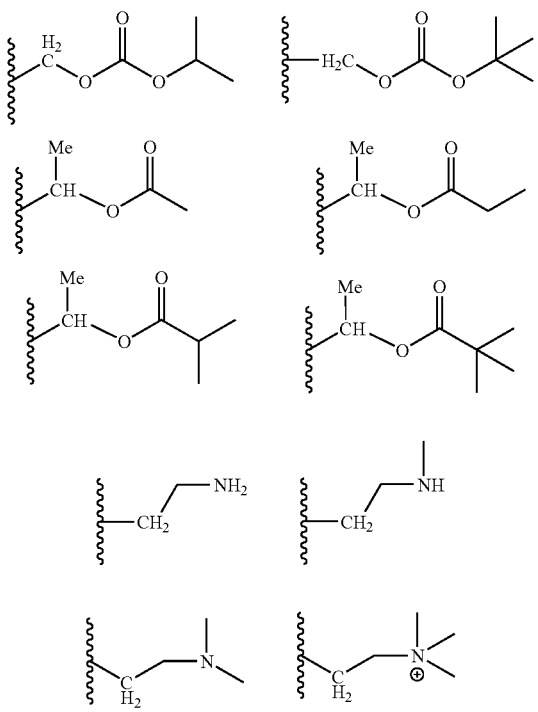

$R^7$ is H, substituted or unsubstituted $C_1$–$C_6$-alkyl, hydroxy-$C_1$–$C_6$-alkyl, aryl, or together with $R^8$ form a $C_2$–$C_5$-alkylene or a $C_2$–$C_5$-alkenylene group;

$R^8$ is H or substituted or unsubstituted $C_1$–$C_6$-alkyl; and m and n are each, independently, an integer from 0 to 3; and pharmaceutically acceptable salts thereof.

2. The compound of claim 1, wherein $R^1$ is hydrogen.

3. The compound of claim 1, wherein $R^2$ is hydrogen.

4. The compound of claim 1, wherein $R^2$ is $C_1$-$C_6$-alkyl.

5. The compound of claim 1, wherein $R^2$ is a halogen.

6. The compound of claim 1, wherein $R^5$ is hydrogen.

7. The compound of claim 1, wherein $R^5$ is a substituted or unsubstituted $C_1$–$C_6$-alkyl group or a halogen.

8. The compound of claim 1, wherein $R^7$ is hydrogen, or a substituted or unsubstituted $C_1$–$C_6$-alkyl group.

9. The compound of claim 1, wherein $R^8$ is a substituted or unsubstituted $C_1$–$C_6$-alkyl.

10. The compound of claim 1, wherein $R^{12}$ is meta to Q.

11. The compound of claim 10, wherein $R^{12}$ is cyano, hydrogen, trifluoroalkyl, or halogen.

12. The compound of claim 1, wherein $R^{12}$ is para to Q.

13. The compound of claim 12, wherein $R^{12}$ is hydrogen.

14. The compound of claim 1, wherein L is $C_1$–$C_5$ alkoxy.

15. The compound of claim 1, wherein Z is substituted or unsubstituted phenyl.

16. The compound of claim 1, wherein A is selected from the group consisting of substituted or unsubstituted phenyl and a substituted or unsubstituted heteroaryl.

17. The compound of claim 1, wherein A is linked to Z through a single covalent bond.

18. A compound selected from the group consisting of:
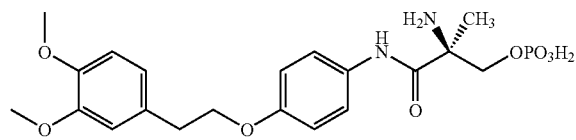
76
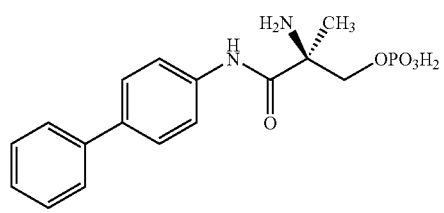
80
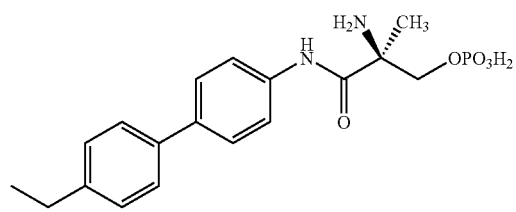
81
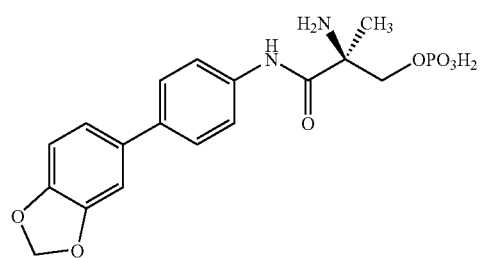
83
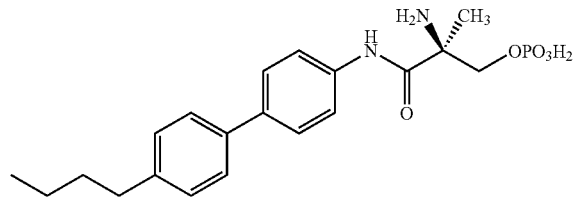
84
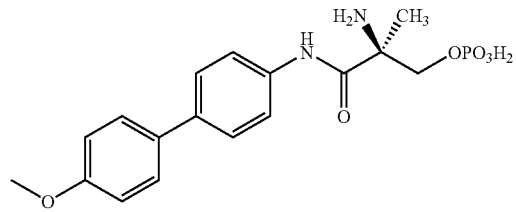
82
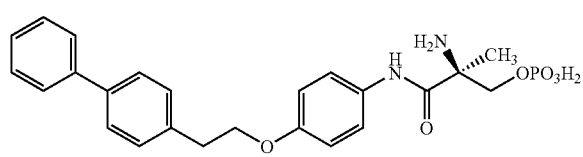
86
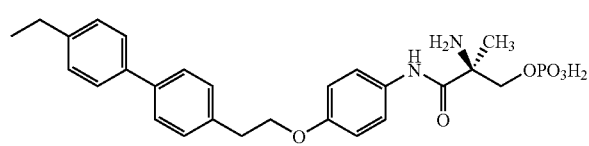
87

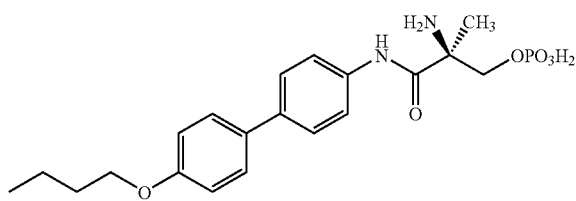
85
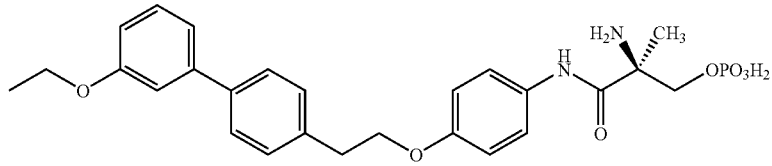
89
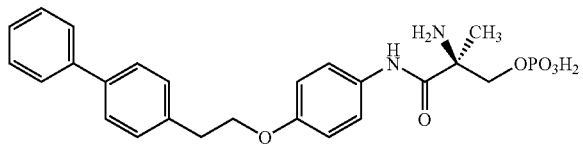
90
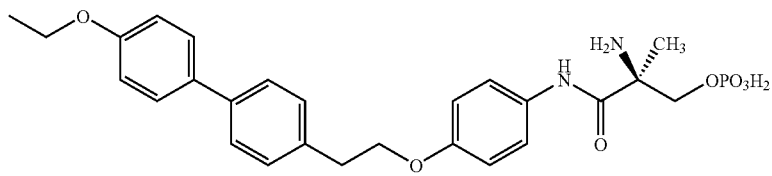
88
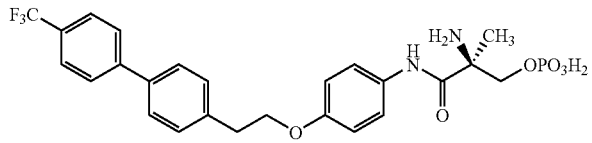
92
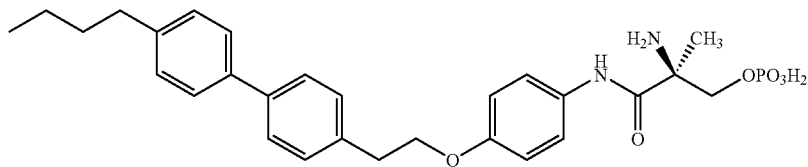
93
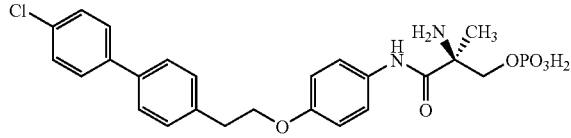
91
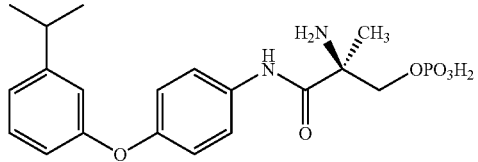
95
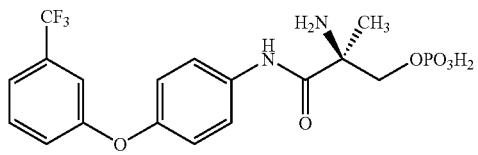
96

-continued
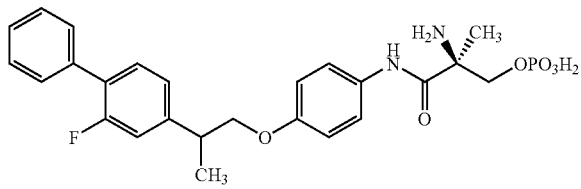 94
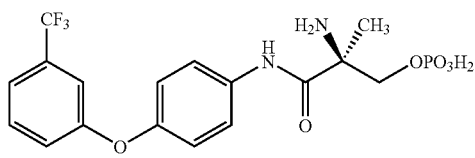 98
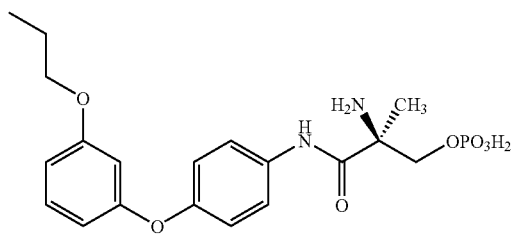 99
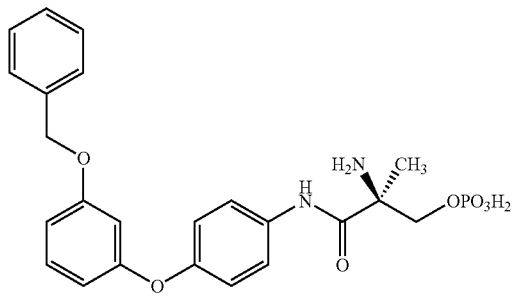 97
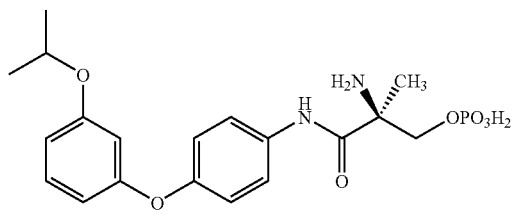 101
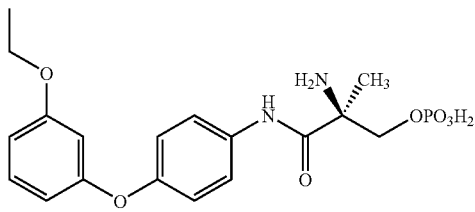 102
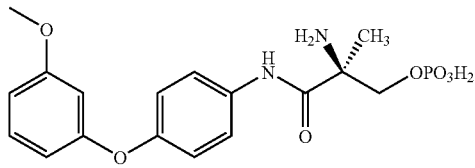 100

-continued
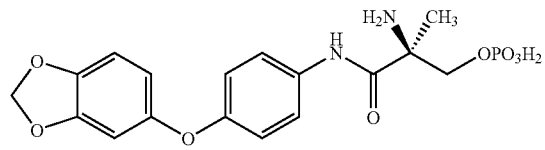
107
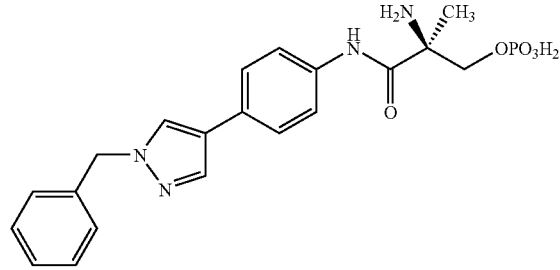
105
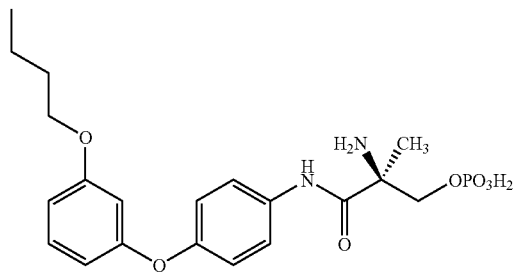
103
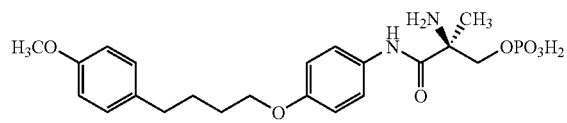
110
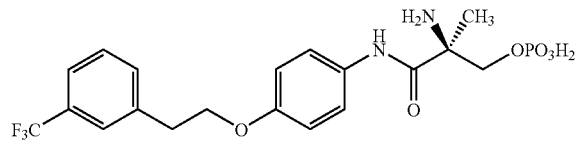
112
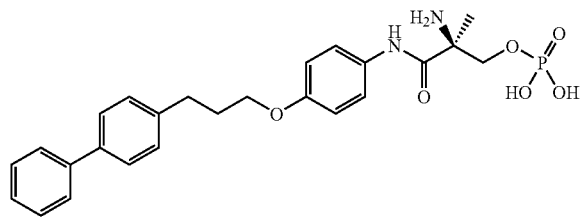
186
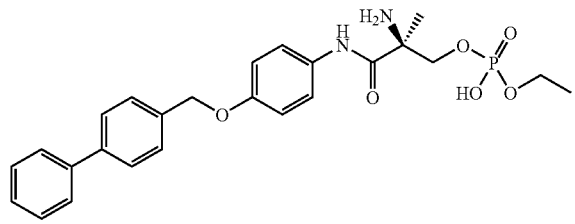
185

189
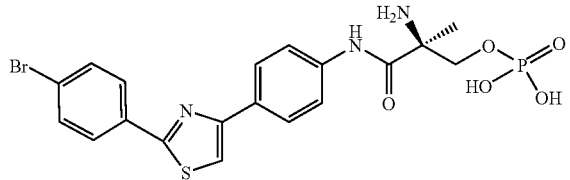
184
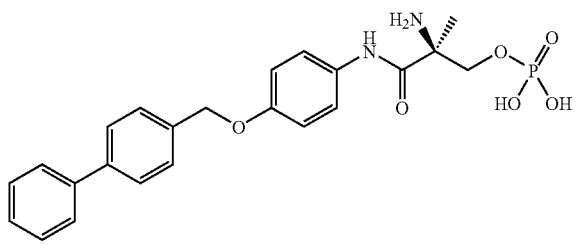
188
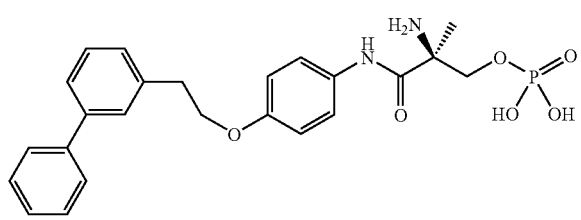
192
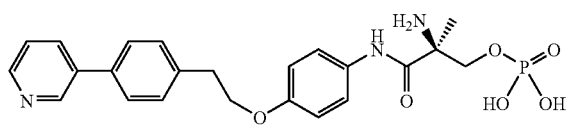
187
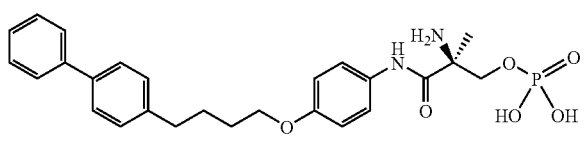
191
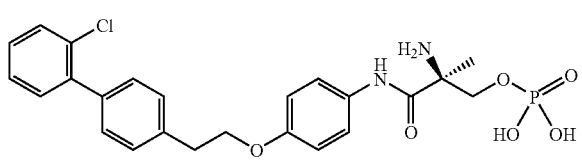
195
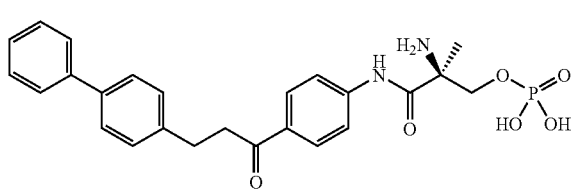
190
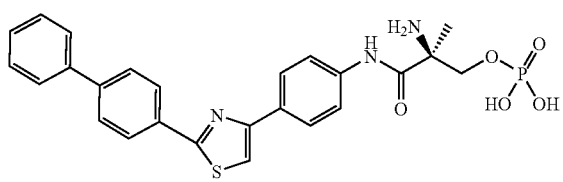
194
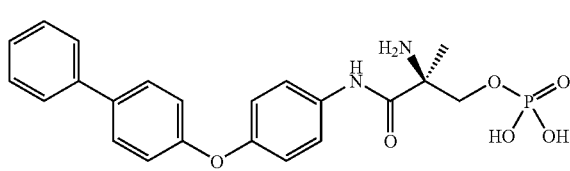

-continued
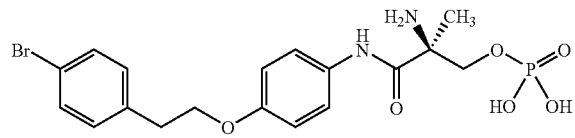
198
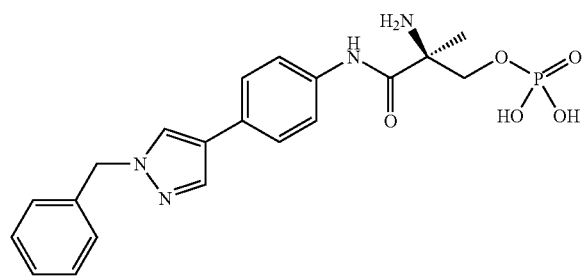
193
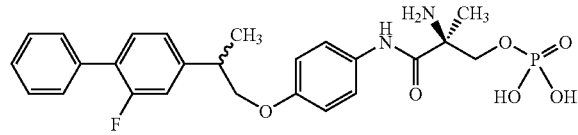
197
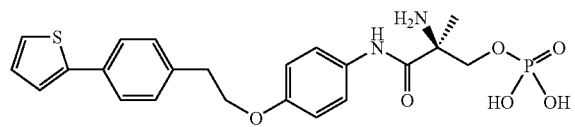
201
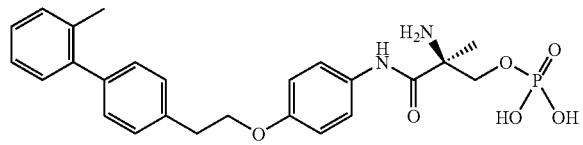
196
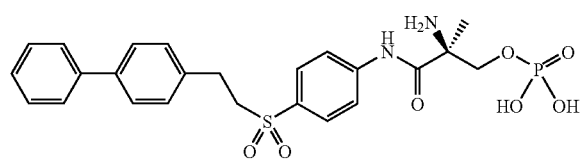
204
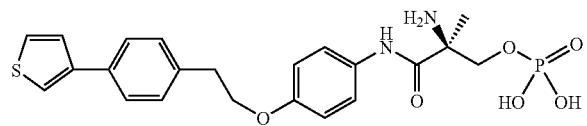
199
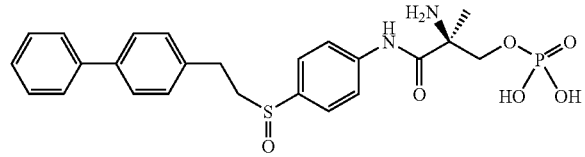
203
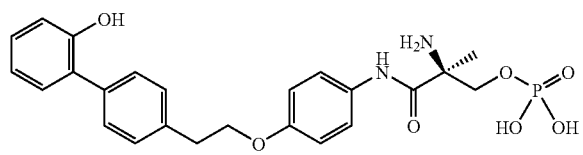
207
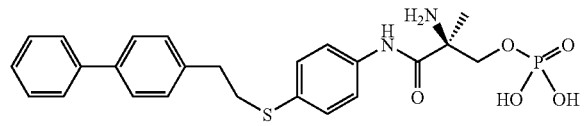
202

-continued
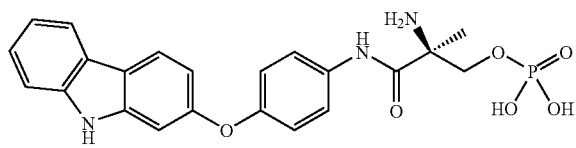
206
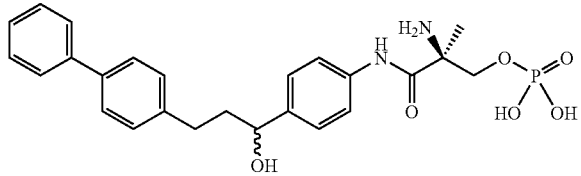
210
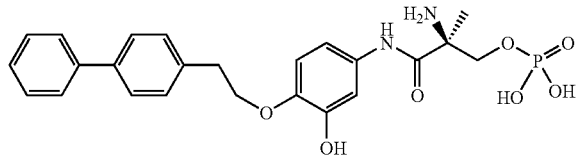
205
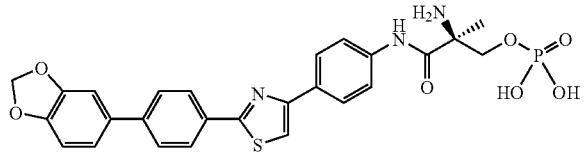
209
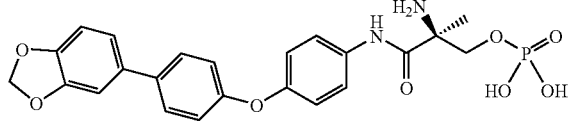
213
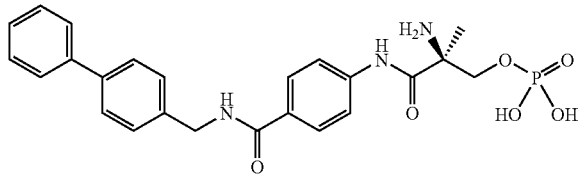
208
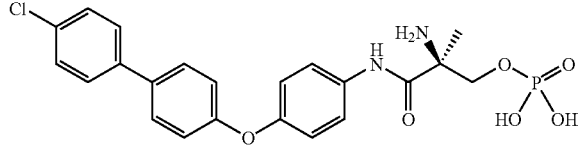
212
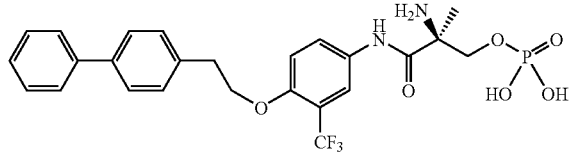
216
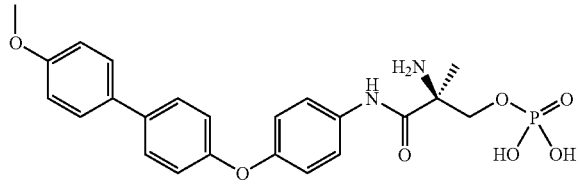
211

-continued
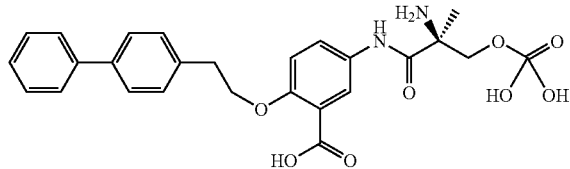
215
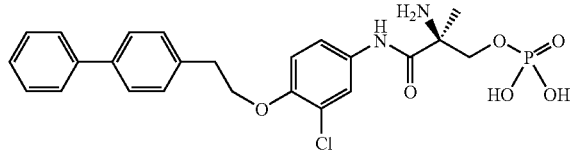
219
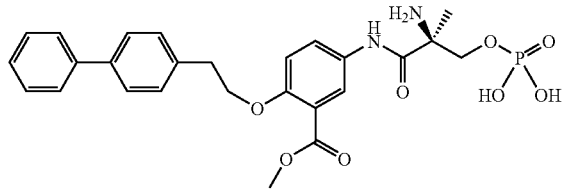
214
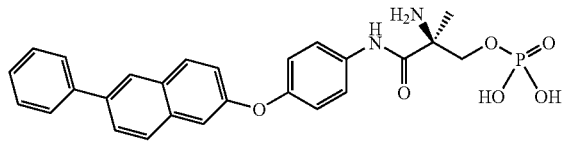
218
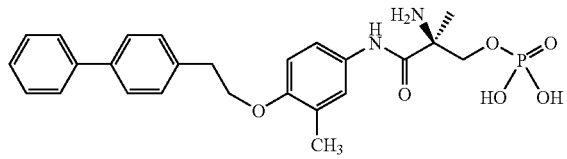
222
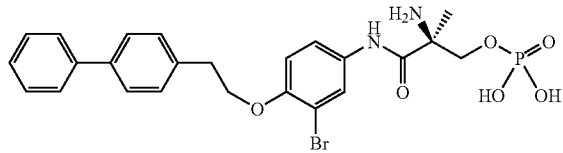
217
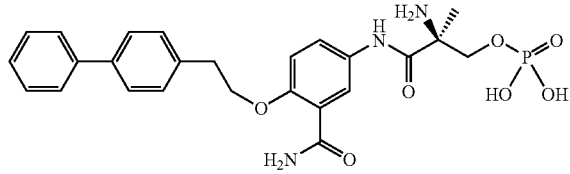
221
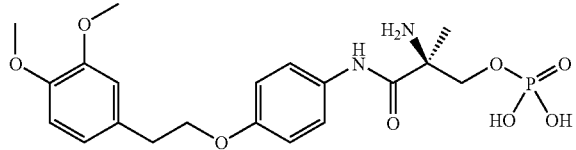
225
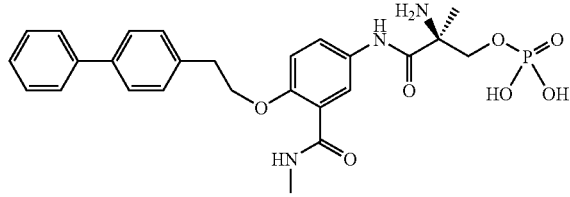
220

-continued

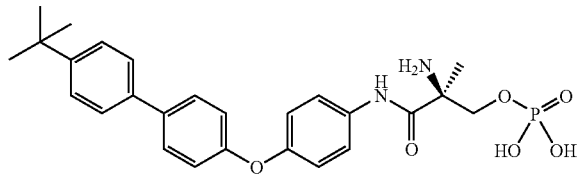

224

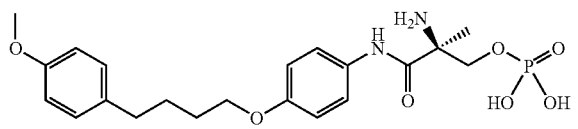

228

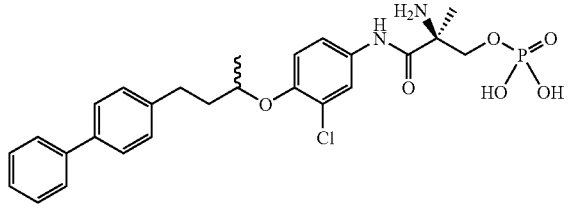

223

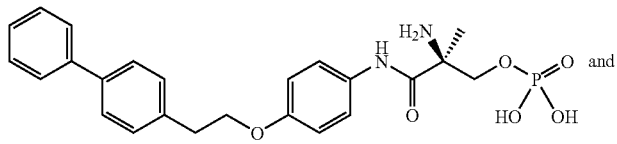 and

226

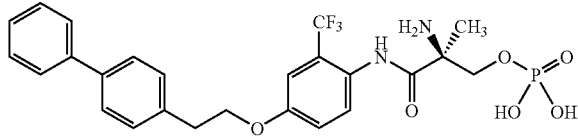

233

19. A method for treating a sphingosine 1-phosphate associated disorder in a subject, comprising administering to said subject an effective amount of a compound of formula (IV), such that said subject is treated for said sphingosine 1-phosphate associated disorder, wherein said sphingosine 1-phosphate associated disorder is a disorder selected from the group consisting of transplant rejection, graft versus host disease, systemic lupus erythematosus, rheumatoid arthritis, multiple sclerosis, type 1 diabetes, active chronic autoimmune hepatitis, psoriasis, and chronic inflammation, and wherein said compound of formula (IV) is.

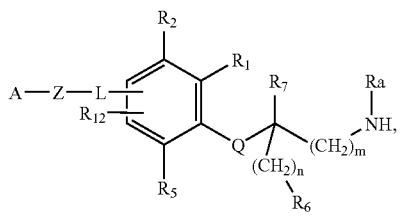

(IV)

wherein:

L is alkoxy, a covalent bond, substituted or unsubstituted alkyl, alkylcarbonyl, thioether, alkylsulfonyl, alkylcarbonylamino, alkylaminocarbonyl, alkyloxycarbonyl, alkylcarbonyloxy, or substituted or unsubstituted heteroaryl;

Z and A are each independently substituted or unsubstituted aryl, wherein Z and A may be linked by a covalent bond, substituted or unsubstituted alkyl, NH, alkyloxy, O, thioether, S, aminocarbonyl, carbonylamino, carbonyloxy, or oxycarbonyl;

$R^1$, $R^2$, $R^5$ and $R^{12}$ are each independently selected from the group consisting of hydrogen, halogen, cyano, substituted or unsubstituted aryl, straight chain or branched substituted or unsubstituted $C_1$–$C_6$-alkyl, straight chain or branched substituted or unsubstituted $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl, $C_1$–$C_6$-alkyl-SO$_2$ or N(R)R', wherein R and R' are each independently hydrogen, straight chain or branched substituted or unsubstituted $C_1$–$C_6$-alkyl, straight chain or branched substituted or unsubstituted $C_1$–$C_6$-alkoxy, straight chain or branched halo-$C_1$–$C_6$-alkyl, straight chain or branched halo-$C_1$–$C_6$-alkoxy, $C_1$–$C_6$-alkoxy-$C_1$–$C_6$-alkyl, hydroxyl-$C_1$–$C_6$-alkyl, carboxy-$C_1$–$C_6$-alkyl or $C_1$–$C_6$-alkyl-SO$_2$;

Q is —NH(CO)—;

$R^6$ is —OPO$_3$R$^{10}$R$^{11}$, where $R^{10}$ and $R^{11}$ are each independently H, straight chain or branched substituted or unsubstituted $C_1$–$C_6$-alkyl, a substituted or unsubstituted aryl group or selected from the prodrugs listed below:

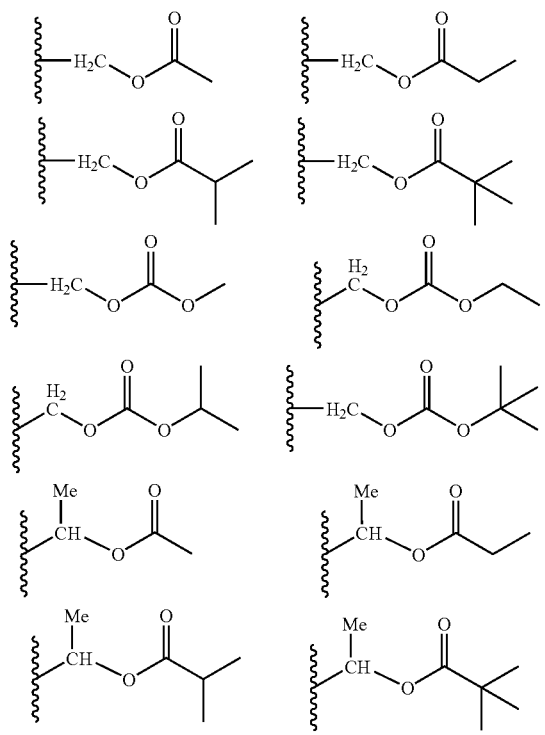

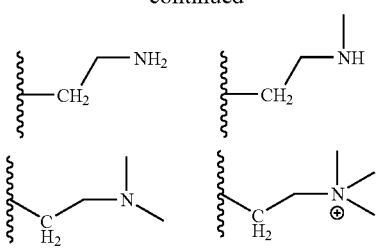

R⁷ is H, substituted or unsubstituted $C_1$–$C_6$-alkyl, hydroxy-$C_1$–$C_6$-alkyl, aryl, or together with R⁸ form a $C_2$–$C_5$-alkylene or a $C_2$–$C_5$-alkenylene group;

R⁸ is H or substituted or unsubstituted $C_1$–$C_6$-alkyl; and m and n are each, independently, an integer from 0 to 3; and pharmaceutically acceptable salts thereof.

20. A pharmaceutical composition comprising a therapeutically effective amount of a compound of claim 1 and a pharmaceutically acceptable carrier.

21. The method of claim 19, wherein the disorder is rheumatoid arthritis.

22. The method of claim 19, wherein the disorder is multiple sclerosis.

\* \* \* \* \*